(12) United States Patent
Janda et al.

(10) Patent No.: US 9,394,371 B2
(45) Date of Patent: Jul. 19, 2016

(54) ANTIBODY-MEDIATED DISRUPTION OF QUORUM SENSING IN BACTERIA

(75) Inventors: Kim D. Janda, San Diego, CA (US); Gunnar F. Kaufmann, San Diego, CA (US); Junguk Park, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 691 days.

(21) Appl. No.: 12/734,273

(22) PCT Filed: Oct. 24, 2008

(86) PCT No.: PCT/US2008/012151
§ 371 (c)(1),
(2), (4) Date: Jul. 26, 2010

(87) PCT Pub. No.: WO2009/055054
PCT Pub. Date: Apr. 30, 2009

(65) Prior Publication Data
US 2010/0291093 A1    Nov. 18, 2010

Related U.S. Application Data

(60) Provisional application No. 60/982,593, filed on Oct. 25, 2007.

(51) Int. Cl.
*C07K 17/00* (2006.01)
*C07K 16/44* (2006.01)
*C07K 16/12* (2006.01)
*A61K 39/00* (2006.01)

(52) U.S. Cl.
CPC ............ *C07K 16/44* (2013.01); *C07K 16/1271* (2013.01); *A61K 2039/505* (2013.01); *C07K 2317/21* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,248,329 B1 * | 6/2001 | Chandrashekar et al. . 424/191.1 |
| 2003/0078207 A1 | 4/2003 | Qiu |
| 2004/0180829 A1 | 9/2004 | Bassler et al. |
| 2005/0107585 A1 | 5/2005 | Murray et al. |

FOREIGN PATENT DOCUMENTS

WO    WO 2004/014423    2/2004

OTHER PUBLICATIONS

The Dictionary of Immunology, Herbert et al eds, Academic Press, 1995, definition of vaccine.*
Feng et al (Infection and Immunity, 64(1):363-365, 1996).*
The American Heritage Dictionary (http://www.bartleby.com/61/70/I0127000.html) defines infection as invasion, 2010.*
Stedman's Online Medical Dictionary (http://www.stedmans.com/section.cfm/45) defines invasion, 2010.*
Dorland's Medical Dictionary for Healthcare Consumers (http://www.mercksource.com/pp/us/cns/cns_hl_dorlands_split.jsp?pg=/ppdocs/us/common/dorlands/dorland/four/000053439.htm) defines-infection, 2010.*
Lowery, et al., "Quorum sensing in *Vibrio harveyi*: probing the specificity of the LuxP binding site ", *Bioorganic & Medicinal Chemistry Letters 15* (9): 2395-2398 (2005).
Meijler, et al., "Synthesis and Biological Validation of a Ubiquitous Quorum-Sensing Molecule", *Angew. Chem. Int. Ed. 43*(16): 2106-2108.
Janda, "Antibody and Peptide Inhibitors of Quorum Sensing" Abstract.
Scott, et al., "Side-Chain-to-Tail Thiolactone Peptide Inhibitors of the Staphylococcal Quorom-Sensing system", *Bioorg. Med. Chem. Lett. 13*: 2449-2453 (2003).

\* cited by examiner

*Primary Examiner* — Patricia Duffy
(74) *Attorney, Agent, or Firm* — Hugh Wang; Thomas Fitting; Jeffrey Oster

(57) ABSTRACT

The invention provides an immunogenic molecular entity, a supramolecular assembly, and an antibody that can be used to inhibit Gram-positive bacterial quorum sensing, prevent infection or development of a disease condition associated with a Gram-positive bacterial infection. The invention also provides methods of inhibiting Gram-positive bacterial quorum sensing, and methods of preventing infection or development of a disease condition associated with a Gram-positive bacterial infection.

9 Claims, 16 Drawing Sheets

ANTIBODY-MEDIATED DISRUPTION OF QUORUM SENSING IN BACTERIA

GOVERNMENT FUNDING

This invention was made with government support under AI055778 awarded by the National Institutes of Health. The government has certain rights in the invention.

BACKGROUND OF THE INVENTION

Bacterial infections are becoming increasingly deadly as many strains that cause diseases are developing resistance to the array of antibiotics used to control them. *Staphylococcus aureus*, for example, is a common cause of hospital-acquired infections resulting in various diseases or conditions raging from skin infections and food poisoning to life-threatening nosocomial infections. Increasing resistance of *S. aureus* isolates to glycopeptide antibiotics, most prominently vancomycin, is a major concern in today's intensive care units. Therefore, an alternative strategy to combat bacterial infections is urgently needed.

SUMMARY OF THE INVENTION

The invention relates to the discovery of an immunopharmacotherapeutic approach for the attenuation of quorum sensing. In particular, the invention involves the discovery of a monoclonal antibody elicited against a rationally-designed hapten that can inhibit quorum sensing, suppress bacterial pathogenicity in an abscess formation mouse model in vivo, and provide protection against a lethal bacterial challenge.

In one embodiment, the invention provides an immunogenic molecular entity comprising at least one hapten, the hapten being covalently linked to an macromolecular carrier, optionally via a linker moiety, the hapten comprising a cyclic peptide or an analog thereof, the cyclic peptide or analog thereof comprising a macrocyclic ring, wherein the cyclic peptide or analog thereof comprises about four to about nineteen amino acid residues, the cyclic peptide or analog thereof having a structure represented by Formula I:

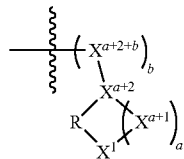

wherein each X is independently any amino acid residue; $X^1$ is an amino acid residue that is covalently bonded to R by a respective carbonyl group; $X^{a+2}$ is an internal amino acid, a respective carbon atom of which is covalently bonded to R; R is a macrocyclizing moiety that covalently connects $X^1$ and $X^{a+2}$ thereby forming the macrocyclic ring, wherein R comprises an ester, thioester, amide, carbamide, semicarbazide, or other amide-surrogate group, or any combination thereof; a is 1 to about 9; b is 1 to about 8; and a bond transected by a wavy line indicates a point of attachment of an N-terminal amino acid residue of the cyclic peptide or analog thereof to the macromolecular carrier, optionally via the linker moiety.

In some embodiments, the immunogenic molecular entity has the structure shown above, wherein a is 2-8, and R includes an alkyloxy or alkaryloxy, alkylthio, or alkylamino group covalently bonding $X^{a+2}$ to the $X^1$ carbonyl group, thereby providing an ester, thioester, or amide bond, respectively, to form a lactone, thiolactone, or lactam macrocyclic ring, respectively. In some embodiments, the immunogenic molecular entity has the structure shown above, wherein R includes —CH$_2$O—, —CH$_2$CH$_2$O—, —CH$_2$CH(CH$_3$)O—, —CH$_2$-phenyl-O—, —CH$_2$S—, —CH$_2$CH$_2$S—, or —(CH$_2$)$_n$NH—, wherein n is 1 to about 4. In some embodiments, the immunogenic molecular entity has the structure shown above, wherein a is 2-8, and R includes at least one amide, urea, or semicarbazide group, or at least one amide-surrogate bond.

In some embodiments, R is represented by Formula (IIa) or Formula (IIb):

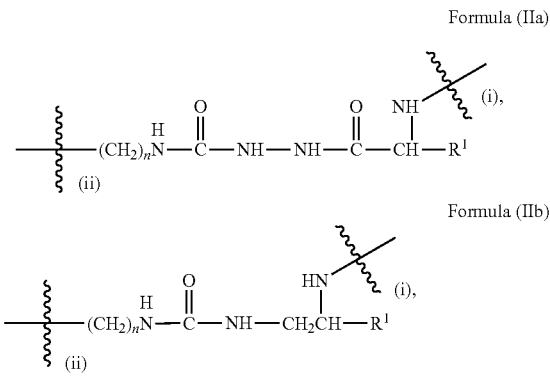

wherein n is 1 to about 4, $R^1$ is the sidechain of a naturally occurring amino acid or an analog thereof, a bond transected by a wavy line indicates a point of attachment, wherein the point of attachment designated (i) is bonded to the carbonyl group of $X^1$ and the point of attachment designated (ii) is bonded to the alpha-carbon of $X^{a+2}$.

In some embodiments, R has the formula (IIa):

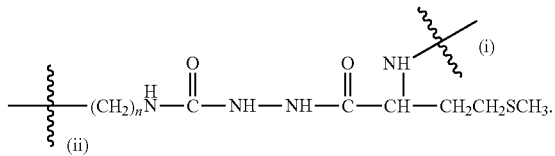

In some embodiments, R has the formula (IIb):

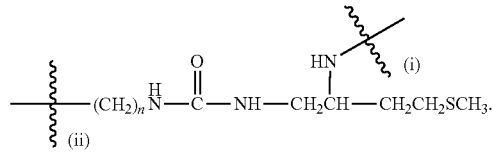

In some embodiments, the immunogenic molecular entity has the structure shown above, wherein $X^1$ and $X^2$ are hydrophobic amino acid residues, and in some embodiments, $X^1$ and $X^2$ are independently selected from the group of amino acid residues consisting of alanine, valine, leucine, isoleucine, methionine, phenylalanine, tyrosine, or tryptophan, or analogs thereof. In some embodiments each of $X^1$ and $X^2$ is independently methionine, leucine, phenylalanine, tyrosine, alanine, isoleucine, or tryptophan.

In some embodiments, the cyclic peptide or analog of the immunogenic molecular entity has the amino acid sequence YST($X^{a+2}$)DFIM (SEQ ID NO: 92), YST($X^{a+2}$)YFIM (SEQ ID NO: 93), IN($X^{a+2}$)DFLL (SEQ ID NO: 94), GVNA($X^{a+2}$)SSLF (SEQ ID NO: 95), GVNP($X^{a+2}$)GGWF (SEQ ID NO: 96), KAKT($X^{a+2}$)TVLY (SEQ ID NO: 97), KTKT($X^{a+2}$)TVLY (SEQ ID NO: 98), GANP($X^{a+2}$)OLYY (SEQ ID NO: 99), GANP($X^{a+2}$)ALYY (SEQ ID NO: 100), GYST($X^{a+2}$)SYYF (SEQ ID NO: 101), GYRT($X^{a+2}$)NTYF (SEQ ID NO: 102), YNP($X^{a+2}$)VGYF (SEQ ID NO: 103), GGKV($X^{a+2}$)SAYF (SEQ ID NO: 104), SVKP($X^{a+2}$)TGFA (SEQ ID NO: 105), DSV($X^{a+2}$)ASYF (SEQ ID NO: 106), KYNP($X^{a+2}$)SNYL (SEQ ID NO: 107), KYNP($X^{a+2}$)ASYL (SEQ ID NO: 108), KYNP($X^{a+2}$)ANYL (SEQ ID NO: 109), RIPT($X^{a+2}$)TGFF (SEQ ID NO: 110), DI($X^{a+2}$)NAYF (SEQ ID NO: 111), DM($X^{a+2}$)NGYF (SEQ ID NO: 112), KYNP($X^{a+2}$)LGFL (SEQ ID NO: 113), KYYP($X^{a+2}$)FGYF (SEQ ID NO: 114), GARP($X^{a+2}$)GGFF (SEQ ID NO: 115), GAKP($X^{a+2}$)GGFF (SEQ ID NO: 116), YSP($X^{a+2}$)TNFF (SEQ ID NO: 117), YSP($X^{a+2}$)TNF (SEQ ID NO: 118), or QN($X^{a+2}$)PNIFGQWM (SEQ ID NO: 119), wherein the last amino acid residue of each sequence is $X^1$, and ($X^{a+2}$) is the internal amino acid to which the carbonyl group of $X^1$ is covalently bonded via R.

In some embodiments, the macromolecular carrier includes a protein, a polymer or a nanoparticle. In some embodiments, the polymer is a dendrimer. In some embodiments, the dendrimer is a MAP dendrimer. In some embodiments, the macromolecular carrier comprises a protein. In some embodiments, the protein is selected from the group consisting of keyhole limpet hemocyanin (KLH), bovine serum albumin (BSA), rabbit serum albumin (RSA), human serum albumin (HSA), *Concholepas concholepas* hemocyanin (CCH), cholera toxin B subunit, *E. coli* labile toxin B subunit, Diphtheria toxoid, tetanus toxoid, tetanus toxin C-fragment, recombinant *Pseudomonas aeruginosa* exoprotein A, CRM197 (cross-reactive material), cationized bovine serum albumin (cBSA), Thyroglobulin (Tg), avidin, bovine thyroglobulin (BTG), bovine G globulin, bovine immunoglobulin G (BIgG), conalbumin (CONA), colloidal gold, edestin, *Paralithodes camtschatica* heamocyanin (HC), *helix promatia* haemocyanin (HPH), soybean kunitz trypsin inhibitor (KTI), *Limulus polyphemus* heamocyanin (LPH), ovalbumin (OA), Pam3Cys-Th (lipopeptide/Th cell epitope), polylysine, porcine thyroglobulin (PTG), purified protein derivative (PPD), soybean trypsin inhibitor (STI), or sunflower globulin (SFG).

In some embodiments, the cyclic peptide analog is covalently linked to the macromolecular carrier via an amino group of an N-terminal amino acid residue of the cyclic peptide analog or a thiol group of an N-terminal cysteine or homocysteine residue of the cyclic peptide analog.

In some embodiments, the molecular entity of the invention further includes a linker moiety that covalently links the cyclic peptide analog to the macromolecular carrier. In some embodiments, the cyclic peptide analog is bonded to the linker moiety via an amino group of an N-terminal amino acid residue of the cyclic peptide analog, or via a thiol group of an N-terminal cysteine or homocysteine residue of the cyclic peptide analog, the linker moiety being covalently bonded to the macromolecular carrier. In some embodiments, the linker moiety includes a moiety produced by reaction of MBS, sulfo-MBS, SMCC, or sulpho-SMCC. In some embodiments, the linker moiety includes adipic acid dihydrazide (ADH), a spacer peptide, hydroxymethyl hemisuccinate, or a polyethyleneglycol derivative.

In some embodiments, the molecular entity has the structure:

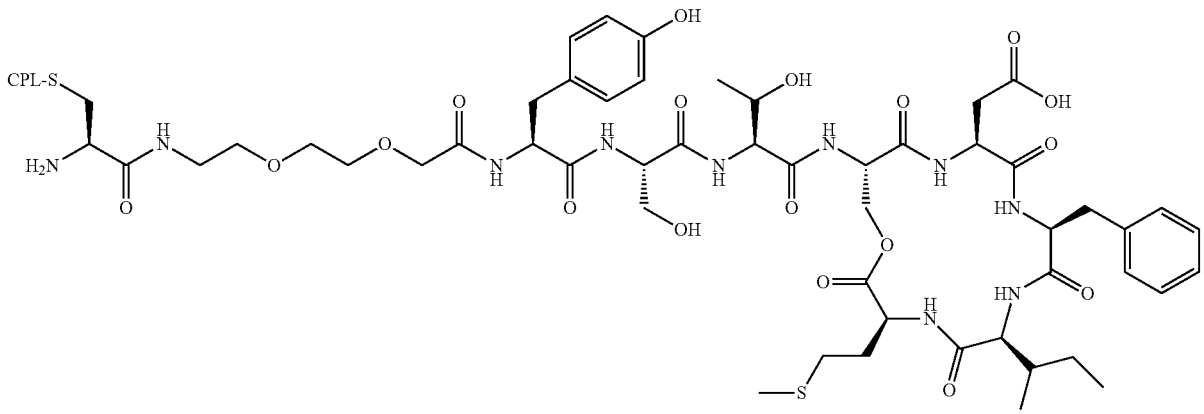

SEQ ID NO: 3 (YSTSDFIM, not including protecting groups),

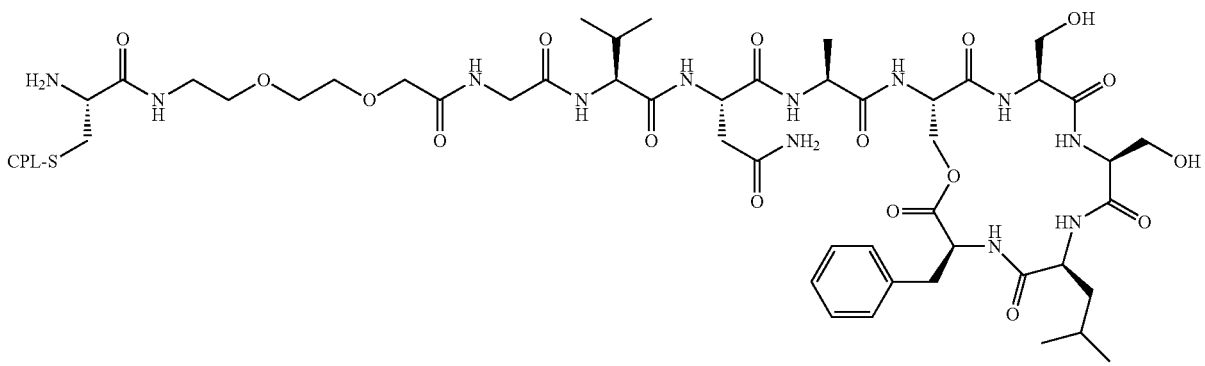

SEQ ID NO: 4 (GVNASSSLY, not including protecting groups),

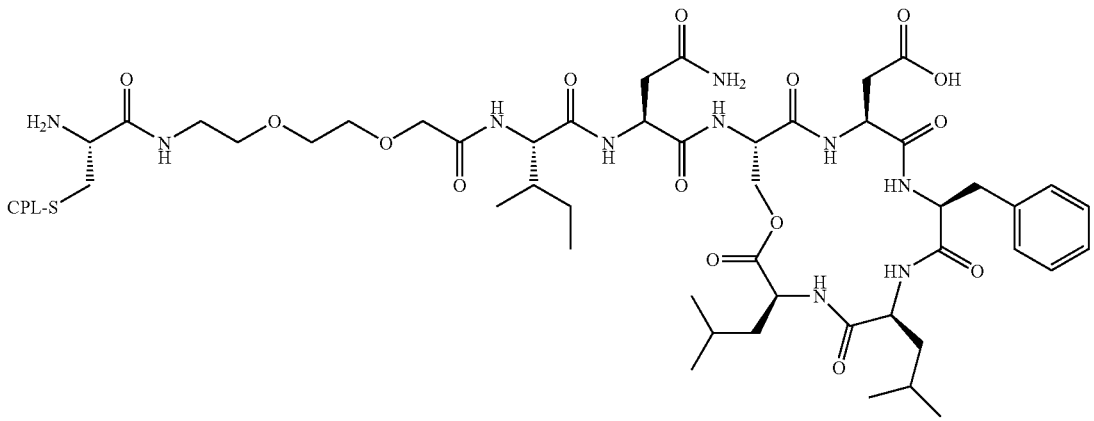

SEQ ID NO: 2 (INSDFLL, not including protecting groups), or

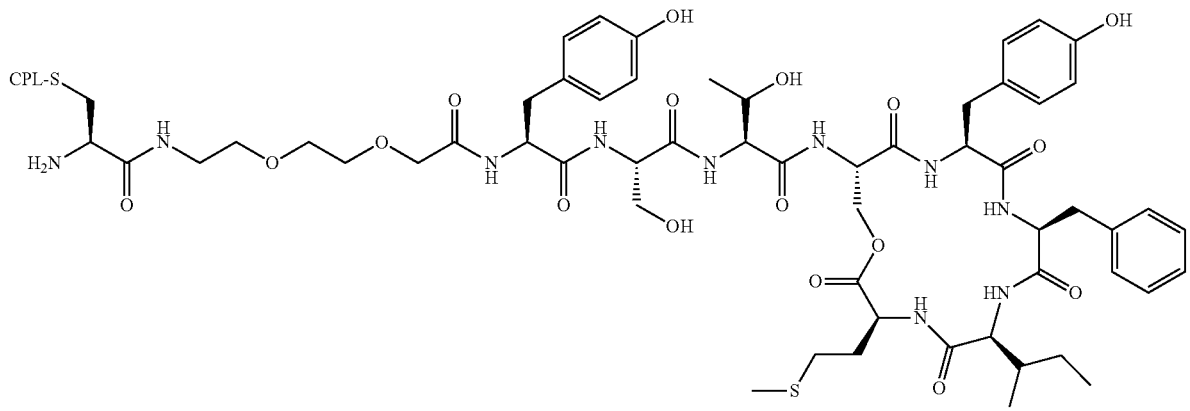

SEQ ID NO: 1 (YSTSYFLM, not including protecting groups), wherein CPL is a macromolecular carrier with optional linker covalently bonded to a cysteine thiol group.

In another aspect, the invention provides a supramolecular assembly that includes an immunogenic molecular entity of the invention. In some embodiments, the supramolecular assembly includes a liposome, a virosome, a bacteriophage, a viral particle, or a polymeric nanoparticle delivery system.

In another aspect, the invention provides an antibody that binds specifically with a cyclic peptide having the amino acid sequence YST($X^{a+2}$)DFIM (SEQ ID NO: 92), YST($X^{a+2}$)YFIM (SEQ ID NO: 93), IN($X^{a+2}$)DFLL (SEQ ID NO: 94), GVNA($X^{a+2}$)SSLF (SEQ ID NO: 95), GVNP($X^{a+2}$)GGWF (SEQ ID NO: 96), KAKT($X^{a+2}$)TVLY (SEQ ID NO: 97), KTKT($X^{a+2}$)TVLY (SEQ ID NO: 98), GANP($X^{a+2}$)OLYY (SEQ ID NO: 99), GANP($X^{a+2}$)ALYY (SEQ ID NO: 100), GYST($X^{a+2}$)SYYF (SEQ ID NO: 101), GYRT($X^{a+2}$)NTYF (SEQ ID NO: 102), YNP($X^{a+2}$)VGYF (SEQ ID NO: 103), GGKV($X^{a+2}$)SAYF (SEQ ID NO: 104), SVKP($X^{a+2}$)TGFA (SEQ ID NO: 105), DSV($X^{a+2}$)ASYF (SEQ ID NO: 106), KYNP($X^{a+2}$)SNYL (SEQ ID NO: 107), KYNP($X^{a+2}$)ASYL (SEQ ID NO: 108), KYNP($X^{a+2}$)ANYL (SEQ ID NO: 109), RIPT($X^{a+2}$)TGFF (SEQ ID NO: 110), DI($X^{a+2}$)NAYF (SEQ ID NO: 111), DM($X^{a+2}$)NGYF (SEQ ID NO: 112), KYNP($X^{a+2}$)LGFL (SEQ ID NO: 113), KYYP($X^{a+2}$)FGYF (SEQ ID NO: 114), GARP($X^{a+2}$)GGFF (SEQ ID NO: 115), GAKP($X^{a+2}$)GGFF (SEQ ID NO: 116), YSP($X^{a+2}$)TNFF (SEQ ID NO: 117), YSP($X^{a+2}$)TNF (SEQ ID NO: 118), or QN($X^{a+2}$)PNIFGQWM (SEQ ID NO: 119); wherein the last amino acid residue of each sequence is $X^1$, and ($X^{a+2}$) is the internal amino acid to which the carbonyl group of $X^1$ is covalently bonded via R, wherein R is the sidechain moiety of $X^{a+2}$ covalently bonded to the carbonyl group of $X^1$; and wherein R comprises —$CH_2O$—, —$CH_2CH_2O$—, —$CH_2CH(CH_3)O$—, —$CH_2$-phenyl-O—, —$CH_2S$—, —$CH_2CH_2S$—, or —$(CH_2)_nNH$—, wherein n is 1 to about 4.

In another aspect, the invention provides an antibody that binds specifically with a cyclic peptide signaling molecule of a Gram-positive bacterium.

In some embodiments, the antibody binds specifically with a cyclic peptide signaling molecule having the sequence YSTCDFI<u>M</u> (SEQ ID NO: 120); GVNACSSL<u>F</u> (SEQ ID NO: 121); INCDFL<u>L</u> (SEQ ID NO: 122); YSTCYFI<u>M</u> (SEQ ID NO: 123); GVNPCGGW<u>F</u> (SEQ ID NO: 124); KAKTCTVL<u>Y</u> (SEQ ID NO: 125); KTKTCTVL<u>Y</u> (SEQ ID NO: 126); GANPCOLY<u>Y</u> (SEQ ID NO: 127); GANPCALY<u>Y</u> (SEQ ID NO: 128); GYSTCSYY<u>F</u> (SEQ ID NO: 129); GYRTCNTY<u>F</u> (SEQ ID NO: 130); YNPCVGY<u>F</u> (SEQ ID NO: 131); GGKVCSAYF (SEQ ID NO: 132); SVKPCTGFA (SEQ ID NO: 133); DSVCASYF (SEQ ID NO: 134); KYN-PCSNYL (SEQ ID NO: 135); KYNPCASYL (SEQ ID NO: 136); KYNPCANYL (SEQ ID NO: 137); RIPTSTGFF (SEQ ID NO: 138); DICNAYF (SEQ ID NO: 139); DMCNGYF (SEQ ID NO: 140); KYNPCLGFL (SEQ ID NO: 141); KYYPCFGYF (SEQ ID NO: 142); VGARPCGGFF (SEQ ID NO: 143); GAKPCGGFF (SEQ ID NO: 144); YSPCTNFF (SEQ ID NO: 145); or QNSPNIFGQWM (SEQ ID NO: 146); wherein the alpha-carbonyl group of the underlined residue forms a thiolactone or lactone bond with the sulfhydryl or hydroxyl group of the bolded internal cysteine or serine residue, respectively.

In some embodiments, the antibody is a neutralizing antibody, e.g. a cross-neutralizing antibody. In some embodiments, it is a single chain variable fragment (scFv), a Fab or F(ab')$_2$ fragment. In some embodiments, the antibody comprises the amino acid sequence of any one of SEQ ID NOs: 35-53. In some embodiments, the antibody is a monoclonal antibody. In some embodiment, the antibody comprises the amino acid sequence of any one of SEQ ID NOs: 19-26 and 147-154. In some embodiments, the antibody comprises an amino acid sequence of any one of SEQ ID NOs: 19-26 in covalent interaction with an amino acid sequence of any one of SEQ ID NOs: 147-154. In some embodiments, the antibody is a murine, bovine, or human antibody. In some embodiments, the antibody is a humanized or chimeric antibody. In some embodiments, the antibody is AP4-24H11.

In another aspect, the invention provides a composition that includes at least one antibody of the invention and a pharmaceutically-acceptable carrier. In some embodiments, the composition includes two to four antibodies that bind specifically with two to four cyclic peptide signaling molecules having the sequences YSTCDFIM (SEQ ID NO: 120), GVNACSSLF (SEQ ID NO: 121), INCDFLL (SEQ ID NO: 122), and YSTCYFIM (SEQ ID NO: 123); wherein the alpha-carbonyl group of the underlined residue forms a thiolactone bond with the sulfhydryl group of the bolded internal cysteine residue.

In another aspect, the invention provides a composition includes at least one immunogenic molecular entity of the invention and a pharmaceutically-acceptable carrier. In some embodiments, the immunogenic molecular entity includes a cyclic peptide having the sequence YST($X^{a+2}$)DFIM (SEQ ID NO: 92), YST($X^{a+2}$)YFIM (SEQ ID NO: 93), IN($X^{a+2}$)DFLL (SEQ ID NO: 94), GVNA($X^{a+2}$)SSLF (SEQ ID NO: 95), GVNP($X^{a+2}$)GGWF (SEQ ID NO: 96), KAKT($X^{a+2}$)TVLY (SEQ ID NO: 97), KTKT($X^{a+2}$)TVLY (SEQ ID NO: 98), GANP($X^{a+2}$)OLYY (SEQ ID NO: 99), GANP($X^{a+2}$)ALYY (SEQ ID NO: 100), GYST($X^{a+2}$)SYYF (SEQ ID NO: 101), GYRT($X^{a+2}$)NTYF (SEQ ID NO: 102), YNP($X^{a+2}$)VGYF (SEQ ID NO: 103), GGKV($X^{a+2}$)SAYF (SEQ ID NO: 104), SVKP($X^{a+2}$)TGFA (SEQ ID NO: 105), DSV($X^{a+2}$)ASYF (SEQ ID NO: 106), KYNP($X^{a+2}$)SNYL (SEQ ID NO: 107), KYNP($X^{a+2}$)ASYL (SEQ ID NO: 108), KYNP($X^{a+2}$)ANYL (SEQ ID NO: 109), RIPT($X^{a+2}$)TGFF (SEQ ID NO: 110), DI($X^{a+2}$)NAYF (SEQ ID NO: 111), DM($X^{a+2}$)NGYF (SEQ ID NO: 112), KYNP($X^{a+2}$)LGFL (SEQ ID NO: 113), KYYP($X^{a+2}$)FGYF (SEQ ID NO: 114), GARP($X^{a+2}$)GGFF (SEQ ID NO: 115), GAKP($X^{a+2}$)GGFF (SEQ ID NO: 116), YSP($X^{a+2}$)TNFF (SEQ ID NO: 117), YSP($X^{a+2}$)TNF (SEQ ID NO: 118), or QN($X^{a+2}$)PNIFGQWM (SEQ ID NO: 119); wherein the last amino acid residue of each sequence is $X^1$, and ($X^{a+2}$) is the internal amino acid to which the carbonyl group of $X^1$ is covalently bonded via R; and wherein R comprises —CH$_2$O—, —CH$_2$CH$_2$O—, —CH$_2$CH(CH$_3$)O—, —CH$_2$-phenyl-O—, —CH$_2$S—, —CH$_2$CH$_2$S—, or —(CH$_2$)$_n$NH—, wherein n is 1 to about 4.

In some embodiments, the composition includes two to four immunogenic molecular entities, the cyclic peptides of which have the sequence YST($X^{a+2}$)DFIM (SEQ ID NO: 92), YST($X^{a+2}$)YFIM (SEQ ID NO: 93), IN($X^{a+2}$)DFLL (SEQ ID NO: 94), GVNA($X^{a+2}$)SSLF (SEQ ID NO: 95), GVNP($X^{a+2}$)GGWF (SEQ ID NO: 96), KAKT($X^{a+2}$)TVLY (SEQ ID NO: 97), KTKT($X^{a+2}$)TVLY (SEQ ID NO: 98), GANP($X^{a+2}$)OLYY (SEQ ID NO: 99), GANP($X^{a+2}$)ALYY (SEQ ID NO: 100), GYST($X^{a+2}$)SYYF (SEQ ID NO: 101), GYRT($X^{a+2}$)NTYF (SEQ ID NO: 102), YNP($X^{a+2}$)VGYF (SEQ ID NO: 103), GGKV($X^{a+2}$)SAYF (SEQ ID NO: 104), SVKP($X^{a+2}$)TGFA (SEQ ID NO: 105), DSV($X^{a+2}$)ASYF (SEQ ID NO: 106), KYNP($X^{a+2}$)SNYL (SEQ ID NO: 107), KYNP($X^{a+2}$)ASYL (SEQ ID NO: 108), KYNP($X^{a+2}$)ANYL (SEQ ID NO: 109), RIPT($X^{a+2}$)TGFF (SEQ ID NO: 110), DI($X^{a+2}$)NAYF (SEQ ID NO: 111), DM($X^{a+2}$)NGYF (SEQ ID NO: 112), KYNP($X^{a+2}$)LGFL (SEQ ID NO: 113), KYYP($X^{a+2}$)FGYF (SEQ ID NO: 114), GARP($X^{a+2}$)GGFF (SEQ ID NO: 115), GAKP($X^{a+2}$)GGFF (SEQ ID NO: 116), YSP($X^{a+2}$)TNFF (SEQ ID NO: 117), YSP($X^{a+2}$)TNF (SEQ ID NO: 118), or QN($X^{a+2}$)PNIFGQWM (SEQ ID NO: 119); wherein the last amino acid residue of each sequence is $X^1$, and ($X^{a+2}$) is the internal amino acid to which the carbonyl group of $X^1$ is covalently bonded via R; and wherein R comprises —CH$_2$O—, —CH$_2$CH$_2$O—, —CH$_2$CH(CH$_3$)O—, —CH$_2$-phenyl-O—, —CH$_2$S—, —CH$_2$CH$_2$S—, or —(CH$_2$)$_n$NH—, wherein n is 1 to about 4.

In some embodiments, the composition includes four immunogenic molecular entities, the cyclic peptides of which have the sequences YSTCDFIM (SEQ ID NO: 120), GVNACSSLF (SEQ ID NO: 121), INCDFLL (SEQ ID NO: 122), and YSTCYFIM (SEQ ID NO: 123); wherein the alpha-carbonyl group of the underlined residue forms a thiolactone bond with the sulfhydryl group of the bolded internal cysteine residue.

In some embodiments, the composition includes at least one additional immunogen. In some embodiments, the at least one additional immunogen elicits an immune response against hepatitis B, *Haemophilus influenzae* type b bacteria, diphtheria, measles, mumps, pertussis, polio, rubella, tetanus, tuberculosis, varicella, or any combination thereof.

In another aspect, the invention provides an article of manufacture comprising the immunogenic molecular entity, supramolecular assembly, antibody or composition of the invention, and instructions for its use.

In another aspect, the invention provides a method of eliciting an immune response in a mammal that involves administering to the mammal a composition that includes the immunogenic molecular entity or the supramolecular assembly of the invention in an amount effective to elicit an immune response in the mammal. In some embodiments, the mammal is a goat, rabbit, sheep, pig, mouse, rat, guinea pig, hamster, cow, horse, monkey or human. In some embodiments, the composition is administered to the mammal by intravenous, intraperitoneal, subcutaneous, intradermal, or intramuscular injection. In some embodiments, the method further involves obtaining a biological sample from the mammal, wherein the biological sample comprises an antibody that binds specifically with a cyclic peptide signaling molecule and/or with the cyclic peptide of the immunogenic molecular entity. In some embodiments, the method further involves isolating an antibody-producing cell from the mammal, and fusing the antibody-producing cell with a myeloma cell to generate a hybridoma that produces an antibody that binds specifically with a cyclic peptide signaling molecule and/or with the cyclic peptide of the immunogenic molecular entity.

In some embodiments, the mammal is susceptible to infection by a Gram positive bacterium or is susceptible to a disease condition associated with a Gram positive bacterium. In some embodiments, the Gram positive bacterium is a *Staphylococcus*, such as *S. aureus* or *S. epidermidis*. In some embodiments, the mammal is a human.

In some embodiments, the method further includes administering to the mammal at least one additional dose of the composition that include the immunogenic entity at selected time periods.

In another aspect, the invention provides a method of inhibiting quorum sensing in a mammal that involves administering to the mammal a composition that includes the antibody of the invention in an amount effective to inhibit the quorum sensing in the mammal.

In another aspect, the invention provides a method of inhibiting quorum sensing in a mammal that involves administering to the mammal an immunogenic molecular entity or the supramolecular assembly of the invention in an amount effective to elicit an immune response and inhibit the quorum sensing in the mammal. In some embodiments of the invention, the mammal is a human.

In another aspect, the invention provides a method for preventing or treating infection of a mammal by a Gram positive bacterium that involves administering to the mammal, an immunogenic molecular entity, supramolecular assembly, or the antibody of the invention in an amount effective to prevent or treat infection of the mammal by a Gram positive bacterium. In some embodiments, the mammal is a human. In some embodiments, the immunogenic molecular entity, supramolecular assembly or antibody is administered to the mammal by intravenous, intraperitoneal, subcutaneous, intradermal, or intramuscular injection.

In another aspect, the invention provides a method of identifying an antibody that binds specifically with a cyclic peptide signaling molecule that involves contacting an immunogenic molecular entity that includes a cyclic peptide analog of the signaling molecule covalently linked to a macromolecular carrier with a recombinant combinatorial immunoglobulin library, and identifying the recombinant immunoglobulin that binds specifically with the an immunogenic molecular entity as an antibody that binds specifically with the cyclic peptide signaling molecule.

In another aspect, the invention provides a method of preventing biofilm formation that involves coating a surface including a surface of a catheter with an antibody of the invention.

In another aspect, the invention provides an isolated nucleic acid having a sequence that encodes the antibody discussed herein. In some embodiments, the nucleic acid has the sequence of any one of SEQ ID NO: 54-91, 27-34 and 155-181. The term "nucleic acid," as used herein, refers to a polymer of deoxynucleic ribose nucleic acids (DNA), as well as ribose nucleic acids (RNA). The term includes linear molecules, as well as covalently closed circular molecules. It includes single stranded molecules, as well as double stranded molecules.

The term "isolated," as used herein with reference to a nucleic acid molecule, means that the nucleic acid molecule is free of unrelated nucleic acid sequences, or those involved in the expression of such other genes, that flank it's 5' and 3' ends in the naturally-occurring genome of the organism from which the nucleic acid of the invention is derived. Accordingly, an "isolated nucleic acid" of the invention has a structure that is different from that of any naturally occurring nucleic acid or to that of any fragment of a naturally occurring genomic nucleic acid spanning more than three separate genes. Thus, the term "isolated nucleic acid molecule" includes, for example, (1) a DNA molecule that has the sequence of part of a naturally occurring genomic DNA molecule, but is not flanked by both of the coding sequences that flank that part of the molecule in the genome of the organism in which it naturally occurs; (2) a nucleic acid incorporated into a vector or into the genomic DNA of a prokaryote or eukaryote in a manner such that the resulting molecule is not identical to any naturally-occurring vector or genomic DNA; (3) a separate molecule such as a cDNA, a genomic fragment, a fragment produced by polymerase chain reaction (PCR), or a restriction fragment; and (4) a recombinant nucleotide sequence that is part of a hybrid gene, i.e. a gene encoding a fusion protein. Specifically excluded from this definition are nucleic acids present in mixtures of (1) DNA molecules, (2) transfected cells, and (3) cell clones, e.g., as these occur in a DNA library such as a cDNA or genomic DNA library.

In another aspect, the invention provides an expression vector that has a nucleic acid encoding the antibody discussed herein.

In some embodiments, the nucleic acid encoding the antibody is operably-linked to an expression control sequence. In some embodiments, the expression control sequence is a promoter. In some embodiments, the promoter is a phage, viral, bacterial or mammalian promoter.

The term "expression vector," as used herein, means a nucleic acid molecule capable of transporting and/or allowing for the expression of another nucleic acid to which it has been linked. The product of that expression is referred to as a messenger ribose nucleic acid (mRNA) transcript. Thus, expression vectors contain appropriate expression control sequences that may direct expression of a nucleic acid that is operably linked to the expression control sequence to produce a transcript. Thus, the phrase "expression control sequence" means a nucleic acid sequence sufficient to direct transcription of another nucleic acid sequence that is operably linked to the expression control sequence to produce an RNA transcript when appropriate molecules such as transcriptional activator proteins are bound the expression control sequence. And the term "operably linked" means that a nucleic acid and an expression control sequence is positioned in such a way that the expression control sequence directs expression of the nucleic acid when the appropriate molecules such as transcriptional activator proteins are bound to the expression control sequence.

In another aspect, the invention provides a cell that has a nucleic acid encoding the antibody discussed above or an expression vector discussed above. The cell can be a bacterial or mammalian cell.

Other features and advantages of the invention will be apparent from the following detailed description, and from the claims.

DESCRIPTION OF THE FIGURES

FIG. 2K: MALDI-TOF analysis of AP4-BSA conjugate.

DETAILED DESCRIPTION OF THE INVENTION

Figure 1:
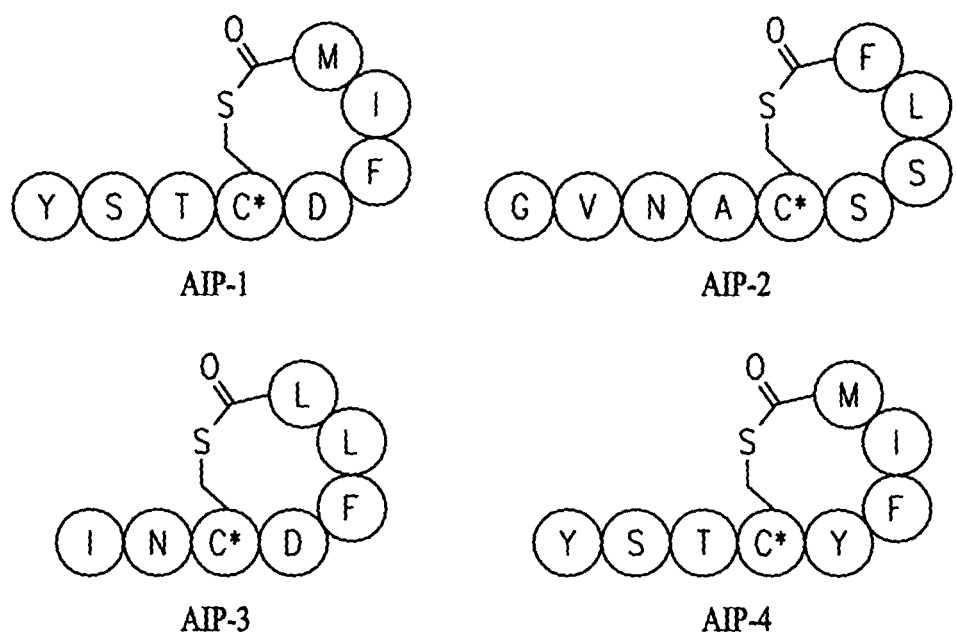
FIG. 1 illustrates the structures of the autoinducing peptides (AIPs) used by *S. aureus*. The oligopeptides are cyclized post-translationally to form a thioester linkage between the thiol moiety of the conserved $^{(*)}$Cys and the carboxyl group of the C-terminal residue (SEQ ID NOs: 120-123).

The invention relates to the discovery that an antibody specific for the *Staphylococcus aureus* AP-4 signaling peptide can block quorum sensing and prevent Staphylococcal infection in mice. Thus, the invention provides an immunogenic molecular entity that can be used to elicit the production of an immune response against a native cyclic signaling peptide produced by a Gram-positive bacterium that regulates the expression of virulence factors through quorum sensing. The immunogenic molecular entity comprising at least one hapten, the hapten being covalently linked to an macromolecular carrier, optionally via a linker moiety, wherein the linker moiety is covalently bonded to the hapten and to the macromolecular carrier, the hapten comprising a cyclic peptide or an analog thereof, the cyclic peptide or analog thereof comprising a macrocyclic ring, wherein the cyclic peptide or analog thereof comprises about four to about nineteen amino acid residues as defined in the statements of the invention.

The invention also provides an antibody that binds specifically with a cyclic peptide signaling molecule. The antibody is a neutralizing antibody that can be used to inhibit quorum sensing in a mammal. In addition, the invention provides a composition that includes the immunogenic molecular entity or the neutralizing antibody, and a pharmaceutically-acceptable carrier. Additional embodiments of the invention include a method for eliciting an immune response in a mammal against a cyclic peptide signaling molecule, and a method of inhibiting bacterial quorum sensing in a mammal.

An immunogenic molecular entity of the invention is composed of a cyclic peptide or analog thereof covalently bonded to a macromolecular carrier, optionally via a linker moiety. The immunogenic molecular entity can be further included in a supramolecular assembly, such as a viral particle. Thus, an immunogenic molecular entity of the invention can elicit an immune response from an animal that has been administered the molecular entity. The animal can be, for example, any mammal, such as a goat, pig, rabbit, mouse, rat, horse, or human.

Definitions

As used herein, the term "immunogenic" refers to the suitability of a molecular entity to generate an immune response in a vertebrate animal, for example, in a mammal including a mouse, a rat, a primate, or a human. A molecular entity is immunogenic when it is of sufficient molecular size and possesses other necessary molecular properties to generate an immune response such that antibodies are produced by the animal challenged by the molecular entity. It is well known in the art that to be immunogenic, a molecular entity such as a protein must have a molecular weight of at least about 10 kDa.

By the term "molecular entity" is meant a molecule or assembly of molecules defined by a chemical structure or assembly of chemical structures respectively. For example, a molecular entity of the invention can be a carrier protein or other immunogenically competent polymer, such as a dendrimer, covalently coupled to a hapten, optionally by a linker moiety. A "supramolecular assembly" can be an assembly of different macromolecules including the immunogenic molecular entity, such as a viral infectious particle that comprises the immunogenic molecular entity. A supramolecular assembly can also be an virosome displaying the hapten portion of the immunogenic molecular entity on its external surface.

As used herein, a "hapten" is a molecular moiety or fragment that is by itself insufficient in molecular size or weight, for example, to stimulate an immune response in an animal. When coupled to a carrier, however, antibodies can be raised that bind specifically to the hapten.

As the term is used herein, a "cyclic peptide or analog thereof" refers to an organic structure formed at least in part of multiple amino acid residues or analogous units covalently linked in a linear oligomeric form, wherein the linear chain is further internally cyclized to create a macrocyclic ring. The linear oligomeric form comprises monomeric units, each monomeric unit made up of an amino acid residue, bonded in a linear manner, but with additional formation of a loop produced by covalent attachment of the carboxy-terminal amino acid residue of the linear chain to a sidechain of an internal amino acid residue. See, for example, FIG. 1.

The term "amino acid residue" is meant an amino acid or an analog thereof as it is covalently bonded in an oligomeric chain, for example, in a natural peptide as is well known in the art. An amino acid residue is also known as an "anhydro amino acid unit" due to the formation of an amide bond between the amino group or the carboxylic acid group of the amino acid residue and the carboxylic acid group or the amino group, respectively, of an adjacent amino acid residue in the oligomer. Both the amino group and the carboxylic acid group of an amino acid or an amino acid analog can be combined in amide or amide-analogous linkages with adjacent amino acid residues in an oligomer. However the cyclic peptide or analog thereof as referred to herein need not be composed only of the residues of naturally occurring amino acids.

While a cyclic peptide, as the term is used herein, can be formed of ribosomal amino acid residues, that is, the approximately 20 L-α-amino acids that can be coded in DNA without posttranslational modification, it can include enantiomeric D-amino acid forms of these natural amino acids, as well as unnatural amino acids such as amino acids bearing sidechains other than those of the approximately 20 ribosomal amino acids. A cyclic peptide can also include amino acids of types other than α-amino acids such as β- or γ-amino acids, or amino groups wherein the carboxylic acid and amino groups are separated by larger numbers of atoms. For example, the cyclic peptide or analog can include an amino acid wherein an alkyl amino group and a carboxylic acid group are separated by various lengths of polyethyleneglycol (PEG) chains or simple alkylene chains. All of these are considered "amino acid residues" within the meaning herein. Thus, a cyclic peptide or analog thereof of the present invention can be made from genetically encoded amino acids, naturally occurring non-genetically encoded amino acids, or synthetic amino acids. The amino acid notations used herein for the twenty genetically encoded L-amino acids and some examples of non-encoded amino acids are provided in Table 1:

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Â-Alanine | | Bala |
| 2,3-Diaminopropionic acid | | Dpr |
| Â-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic | | Tic |

TABLE 1-continued

| Amino Acid | One-Letter Symbol | Common Abbreviation |
|---|---|---|
| acid | | |
| Â-2-thienylalanine | | Thi |
| Methionine sulfoxide | | MSO |
| Homoarginine | | Harg |
| N-acetyl lysine | | AcLys |
| 2,4-Diamino butyric acid | | Dbu |
| N-Aminophenylalanine | | Phe(pNH$_2$) |
| N-methylvaline | | MeVal |
| Homocysteine | | Hcys |
| Homoserine | | Hser |
| α-Amino hexanoic acid | | Aha |
| α-Amino valeric acid | | Ava |
| 2,3-Diaminobutyric acid | | Dab |

Irrespective of the amino acid make up, the structure of the cyclic peptide or analog thereof includes a macrocyclic ring. As the term is used herein, a cyclic peptide or analog thereof contains a macrocyclic ring that includes the C-terminal amino acid residue covalently bonded to the sidechain of an amino acid residue that is situated within the chain, that is, an "internal" amino acid residue. Therefore the "immunogenic molecular entity" comprising a "cyclic peptide or analog thereof" can be conceptualized as a molecule having a "lasso" like loop form, wherein the loop of the lasso is free while the tail of the lasso is bonded to the macromolecular carrier. As described below, the tail of the lasso can be bonded to the macromolecular carrier by a linker moiety, as well as directly bonded.

A cyclic peptide or analog thereof, as used herein, can also include molecular segments that do not include amino acid residues. For example, spacer segments, such as polyethyleneglycol (PEG) segments, can be included in the cyclic peptide or analog. The spacer segment, typically disposed in the tail of the lasso-like loop, can serve to hold the hapten off the surface of the macromolecular carrier to increase its accessibility to antibodies.

The loop is completed by a set of covalently bonded atoms, referred to herein as a "macrocyclizing moiety" and shown as "R" in Formula (I), intervening between a carbonyl group of the C-terminal amino acid, that is, the carbonyl group of the amino acid's carboxyl group, and a carbon atom of an internal amino acid.

The "macrocyclizing moiety" as the term is used herein refers to a group of covalently bonded atoms which can include carbon, nitrogen, oxygen, sulfur and hydrogen that forms a bridge between the carboxy-terminal carbonyl group of the C-terminal amino acid residue and an atom, such as the alpha-carbon, of an internal amino acid residue. The macrocyclizing moiety can include amide bonds; for example, the moiety may be a group that includes a carboxylic acid group, that can be covalently bonded by an amide bond to an amino group of a sidechain of an internal amino acid residue, and can also include an amino group that can be covalently bonded by an amide bond to the carbonyl of the carboxylic acid group of the C-terminal amino acid residue. The macrocyclizing moiety, designated "R" in Formula (I), can also include other group types, such as ester, thioester, ether, thioether, carbonyl, olefin or hydrocarbon groups. The macrocyclizing moiety can contain any amide-surrogate group, or several such groups, for example, as are described in "Chemistry and Biochemistry of Amino Acids, Peptides, and Proteins," volume 7, by Arno F. Spatola, (1983) Marcel Dekker, New York/Basel, which is incorporated herein by reference in its entirety. Amide surrogate groups can include ketones, amines, ethers, thioethers, sulfones, sulfoxides, sulfonamides, sulfonates, aryls, heteroaryls, alkyls, alkenyls, hydrazines, amidines, guanidines, ureas, thioureas, semicarbazides, boronates, phosphonates, and the like.

By a "macrocyclic ring" as the term is used herein is meant a ring formed entirely of covalently bonded atoms, wherein the ring size is greater than about 9 atoms. A macrocyclic ring can include up to 20 atoms, or 30 atoms, or more. The macrocyclic ring can include carbon-carbon bonds, as well as carbon-nitrogen, carbon-oxygen, carbon-sulfur, nitrogen-nitrogen, and other covalent bonds including atoms with valences greater than one. In the inventive cyclic peptide or analog thereof, the macrocyclic ring includes some atoms of at least three, and up to about 10, amino acid residues, as well as the macrocyclizing moiety described above that completes the macrocyclic ring structure.

An "macromolecular carrier" as the term is used herein refers to a macromolecular entity that is of sufficient size, in conjunction with the hapten bonded to it, to trigger the mounting of an immune response by an organism challenged by the composition. Typically, a hapten is bonded to a protein, for example, keyhole limpet hemocyanin, in order to trigger the immune response and bring about the formation of antibodies to the attached hapten by the challenged organism. Thus, the macromolecular carrier can be a protein, particularly a protein known as a good carrier for presentation of haptens, that is, where most of the antibodies raised have the hapten and not the carrier protein as their antigenic structures. However, the macromolecular carrier of the invention can be entities other than proteins. For example, the macromolecular carrier can comprise a dendrimer, such as a Multiple Antigen Peptide (MAP) dendrimer such as was developed by J. Tam et al., (see, for example Posnett, D., McGrath, H., and Tam, J. P. "A novel method for producing anti-peptide antibodies" *J. Biol. Chem.* 263, 1719-1725 (1988), and Tam, J. P. "Synthetic peptide vaccine design: synthesis and properties of a high-density multiple antigenic peptide system" PNAS USA 85, 5409-5413 (1988), which are incorporated by reference herein in their entireties) for the presentation of haptens to immune systems. Such dendrimers, which can be formed by star polymerization of multifunctional monomers such as lysine, present multiple functional groups on the surface of a globular macromolecule to which haptens can be bonded.

Further, the macromolecular entity can be a part of a supramolecular assembly of macromolecules, such as a viral particle. For example, a phage display system can be used wherein the phage surface is adapted for covalent attachment of the cyclic peptide or an analog. Or, the macromolecular carrier can include a virosome, that is, a micellar structure formed of phospholipids, wherein membrane-spanning proteins are embedded and serve as the macromolecular carrier to which the hapten is attached.

A "linker moiety" as the term is used herein refers to a molecular segment that is incorporated between the cyclic peptide or analog thereof, and the macromolecular carrier. The hapten can include the linker moiety, which is introduced as a bifunctional reagent that can serve to couple the N-terminus of the cyclic peptide or analog to the carrier by reaction with both. It is understood that in some cases, a cyclic peptide or analog thereof can be directly coupled to a macromolecular carrier, such as a protein. For example, the N-terminal amino group of a cyclic peptide can be directly linked to a protein, for example a carboxylic acid group of a protein amino acid bearing an acidic sidechain such as aspartate or glutamate, by use of a dehydrating reagent such as EDC (ethyl dimethylaminopropyl carbodiimide) to form a direct amide bond without any intervening linker moiety. However, a linker reagent, consisting of a bifunctional reagent, as is well known in the art, can carry out the same function. The atoms of this linker reagent, when incorporated into the inventive immunogenic molecular entity, form the "linker moiety" as the term is used herein.

Many types of linker reagents are known to skilled artisans. Examples include reagents that have one functional group adapted to react with thiol groups, for example N-alkylmaleimide derivatives, that can react with an N-terminal cysteine or homocysteine residue of an inventive cyclic peptide or analog thereof. The linker also has a second functional group that is adapted to react with a group present on the surface of the macromolecular carrier, for example a carboxylate group or an amino group of an amino acid sidechain in a protein. For example, an N-hydroxysuccinimide ester of an acyl group can react to form an amide bond with a protein surface lysine residue. The two functional groups of the linker reagent are covalently bonded, usually through intervening atoms, such that reaction at the two ends serves to covalently couple the reactive molecules to each other via the linker moiety. Examples of linker chemistry can be found in the catalog of Pierce, P.O. Box 117, Rockford, Ill. 61105, which may be viewed at the website http://piercenet.com/products/browse.cfm?fldID=0203, the information of which is incorporated herein by reference. Some examples of linker reagents that can react to form linker moieties include MBS, sulfo-MBS, SMCC, or sulpho-SMCC, as are well known in the art.

The term "quorum sensing" refers to the phenomenon wherein certain bacterial species detect their own population levels and, when a certain population level is reached, initiate or amplify the expression of certain traits, such as secretion of virulence factors.

The term "immunogen" refers to the active ingredient of an active vaccine and can be a polypeptide, a hapten linked to a carrier as described herein or any macromolecular entity or assembly that is capable of eliciting an immune response in a mammal that has been exposed or come into contact with the immunogen.

An Immunogenic Molecular Entity of the Invention

The invention provides an immunogenic molecular entity comprising at least one hapten, the hapten being covalently linked to an macromolecular carrier, optionally via a linker moiety, the hapten comprising a cyclic peptide or an analog thereof, the cyclic peptide or analog thereof comprising a macrocyclic ring, wherein the cyclic peptide or analog thereof comprises about four to about nineteen amino acid residues, the cyclic peptide or analog thereof having a structure represented by Formula I:

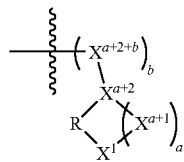

wherein each X is independently any amino acid residue; $X^1$ is an amino acid residue that is covalently bonded to R by a respective carbonyl group; $X^{a+2}$ is an internal amino acid, a respective carbon atom of which is covalently bonded to R; R is a macrocyclizing moiety that covalently connects $X^1$ and $X^{a+2}$ thereby forming the macrocyclic ring, wherein R comprises an ester, thioester, amide, carbamide, semicarbazide, or other amide-surrogate group, or any combination thereof; a is 1 to about 9; b is 1 to about 8; and a bond transected by a wavy line indicates a point of attachment of an N-terminal amino acid residue of the cyclic peptide or analog thereof to the macromolecular carrier, optionally via the linker moiety.

In one embodiment, the cyclic peptide or analog thereof includes structures of Formula (I) wherein a is 2-8, or alternatively a can be 2-4, and R comprises an alkyloxy or alkaryloxy, alkylthio, or alkylamino group covalently bonding $X^{a+2}$ to the $X^1$ carbonyl group, thereby providing an ester, thioester, or amide bond, respectively, to form a lactone, thiolactone, or lactam macrocyclic ring, respectively.

More specifically, the cyclic peptide or analog thereof includes structures of Formula (I), wherein R comprises —$CH_2O$—, —$CH_2CH_2O$—, —$CH_2CH(CH_3)O$—, —$CH_2$-phenyl-O—, —$CH_2S$—, —$CH_2CH_2S$—, or —$(CH_2)_nNH$— wherein n is 1 to about 4. In these embodiments, the cyclic peptide or analog thereof can be viewed as including a macrocyclic ring wherein the carboxy-terminal carbonyl group is bonded to the sidechain of a serine, homoserine, threonine, or tyrosine residue respectively, forming a lactone ring; or to a sidechain of a cysteine or a homocysteine residue respectively, forming a thiolactone; or to a sidechain of a diaminopropionate (n=1), diaminobutyrate (n=2), ornithine (n=3), or lysine (n=4) residue respectively, forming a lactam.

In another embodiment, the cyclic peptide or analog thereof includes structures of Formula (I), wherein a is 2-8, or alternatively a can be 2-4, and the macrocyclizing group R comprises at least one amide, urea, or semicarbazide group, or at least one amide-surrogate bond. For example, R can be represented by Formula (IIa) or Formula (IIb):

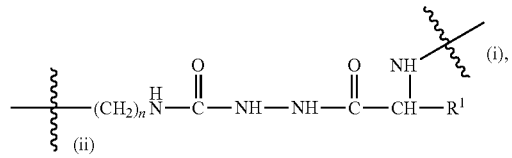

Formula (IIa)

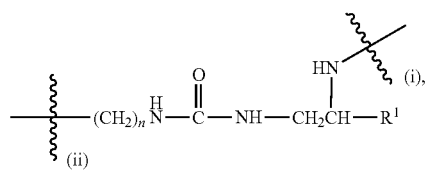

Formula (IIb)

wherein n is 1 to about 4, $R^1$ is the sidechain of a naturally occurring amino acid or an analog thereof, a bond transected by a wavy line indicates a point of attachment, wherein the point of attachment designated (i) is bonded to the carbonyl group of $X^1$ and the point of attachment designated (ii) is bonded to the alpha-carbon of $X^{a+2}$. The sidechain of a naturally occurring amino acid can be the sidechain of any of the ribosomal amino acids, or analogs thereof. Thus the sidechain represented by $R^1$ can be the sidechain of ribosomal amino acids like alanine, phenylalanine, histidine, methionine, asparagine, glutamine, tryptophan, etc. Alternatively the sidechain can be a structure analogous to these naturally occurring sidechains, for example, an ethyl group in place of an alanine methyl group, a phenethyl group in place of a phenylalanine benzyl group, and the like. An analog of an amino acid residue, or an amino acid sidechain, as the term is used herein, refers to a chemical structure that is not identical to the natural structure but differs only by addition of a short alkyl group, or addition of a substituents that does not change the fundamental physical properties of the sidechain. For example, an analog of alanine would include a fluorinated derivative of alanine such as trifluoroalanine, as the size, ionicity and hydrophobicity of the residue would not be greatly altered by the substitution.

A non-limiting example of formula (IIa) is:

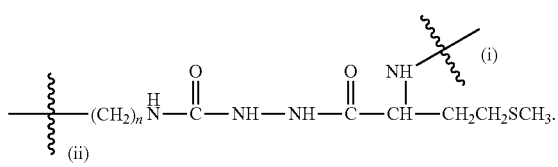

It is recognized that this R1 group corresponds to a methionine sidechain. Correspondingly, R can be a group of formula (IIb) bearing a methionine sidechain:

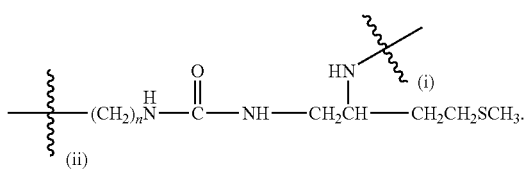

In another embodiment according to the invention, the cyclic peptide or analog thereof can include hydrophobic C-terminal amino acid residues. For example, in one embodiment, $X^1$ and $X^2$ of Formula (I) are hydrophobic amino acid residues. More specifically, $X^1$ and $X^2$ can be independently selected from the group of amino acid residues consisting of alanine, valine, leucine, isoleucine, methionine, phenylalanine, tyrosine, or tryptophan, or analogs thereof. Yet more specifically, each of $X^1$ and $X^2$ can be independently methionine, leucine, phenylalanine, tyrosine, alanine, isoleucine, or tryptophan.

In further embodiments, the cyclic peptide or analog thereof can include sequences YST($X^{a+2}$)DFIM (SEQ ID NO: 92), YST($X^{a+2}$)YFIM (SEQ ID NO: 93), IN($X^{a+2}$)DFLL (SEQ ID NO: 94), GVNA($X^{a+2}$)SSLF (SEQ ID NO: 95), GVNP($X^{a+2}$)GGWF (SEQ ID NO: 96), KAKT($X^{a+2}$)TVLY (SEQ ID NO: 97), KTKT($X^{a+2}$)TVLY (SEQ ID NO: 98), GANP($X^{a+2}$)OLYY (SEQ ID NO: 99), GANP($X^{a+2}$)ALYY (SEQ ID NO: 100), GYST($X^{a+2}$)SYYF (SEQ ID NO: 101), GYRT($X^{a+2}$)NTYF (SEQ ID NO: 102), YNP($X^{a+2}$)VGYF (SEQ ID NO: 103), GGKV($X^{a+2}$)SAYF (SEQ ID NO: 104), SVKP($X^{a+2}$)TGFA (SEQ ID NO: 105), DSV($X^{a+2}$)ASYF (SEQ ID NO: 106), KYNP($X^{a+2}$)SNYL (SEQ ID NO: 107), KYNP($X^{a+2}$)ASYL (SEQ ID NO: 108), KYNP($X^{a+2}$)ANYL (SEQ ID NO: 109), RIPT($X^{a+2}$)TGFF (SEQ ID NO: 110), DI($X^{a+2}$)NAYF (SEQ ID NO: 111), DM($X^{a+2}$)NGYF (SEQ ID NO: 112), KYNP($X^{a+2}$)LGFL (SEQ ID NO: 113), KYYP($X^{a+2}$)FGYF (SEQ ID NO: 114), GARP($X^{a+2}$)GGFF (SEQ ID NO: 115), GAKP($X^{a+2}$)GGFF (SEQ ID NO: 116), YSP($X^{a+2}$)TNFF (SEQ ID NO: 117), YSP($X^{a+2}$)TNF (SEQ ID NO: 118), or QN($X^{a+2}$)PNIFGQWM (SEQ ID NO: 119), wherein the last amino acid residue of each sequence is $X^1$, and ($X^{a+2}$) is the internal amino acid to which the carbonyl group of $X^1$ is covalently bonded via R.

In an embodiment, the cyclic peptide or analog thereof can mimic any of the sequences determined for naturally occurring cyclic peptide signaling molecule, as shown in the following Table:

| Bacterium | Native cyclic signaling peptides |
|---|---|
| S. aureus I | YSTCDFI<u>M</u> (SEQ ID NO: 120) |
| S. aureus II | GVNACSSL<u>F</u> (SEQ ID NO: 121) |
| S. aureus III | INCDFL<u>L</u> (SEQ ID NO: 122) |
| S. aureus IV | YSTCYFI<u>M</u> (SEQ ID NO: 123) |
| S. arlettae | GVNPCGGW<u>F</u> (SEQ ID NO: 124) |
| S. auricularis I | KAKTCTVL<u>Y</u> (SEQ ID NO: 125) |
| S. auricularis II | KTKTCTVL<u>Y</u> (SEQ ID NO: 126) |
| S. capitis I | GANPCOLY<u>Y</u> (SEQ ID NO: 127) |
| S. capitis II | GANPCALY<u>Y</u> (SEQ ID NO: 128) |
| S. caprae I | GYSTCSYY<u>F</u> (SEQ ID NO: 129) |
| S. caprae II | GYRTCNTY<u>F</u> (SEQ ID NO: 130) |
| S. carnosus | YNPCVGY<u>F</u> (SEQ ID NO: 131) |
| S. cohnii ssp. cohnii | GGKVCSAY<u>F</u> (SEQ ID NO: 132) |
| S. cohneii ssp. urealyticum | SVKPCTGF<u>A</u> (SEQ ID NO: 133) |
| S. epidermis I | DSVCASY<u>F</u> (SEQ ID NO: 134) |
| S. epidermis II | KYNPCSNY<u>L</u> (SEQ ID NO: 135) |
| S. epidermis III | KYNPCASY<u>L</u> (SEQ ID NO: 136) |
| S. epidermis IV | KYNPCANY<u>L</u> (SEQ ID NO: 137) |
| S. intermedius | RIPTSTGF<u>F</u> (SEQ ID NO: 138) |
| S. lugdunensis I | DICNAY<u>F</u> (SEQ ID NO: 139) |
| S. lugdunensis II | DMCNGY<u>F</u> (SEQ ID NO: 140) |
| S. simulans I | KYNPCLGF<u>L</u> (SEQ ID NO: 141) |
| S. simulans II | KYYPCFGY<u>F</u> (SEQ ID NO: 142) |
| S. gallinarum | VGARPCGGF<u>F</u> (SEQ ID NO: 143) |
| S. xylosus | GAKPCGGF<u>F</u> (SEQ ID NO: 144) |
| S. warneri (RN 833) | YSPCTNF<u>F</u> (SEQ ID NO: 145) |
| E. faecalis | QNSPNIFGQW<u>M</u> (SEQ ID NO: 146) |

NOTE:
the alpha-carbonyl group of the underlined residue forms a thiolactone bond with the sulfhydryl group of the bolded internal cysteine residue The cyclic peptides and analogs thereof of the hapten can be synthesized in linear form using standard solid phase peptide synthesis techniques, wherein the sidechain of the internal amino acid residue to which the $X^1$ carbonyl group will be bonded either directly or through a more complex macrocyclizing moiety, such as the groups of Formulas (IIa) and (IIb), is appropriately blocked, such that selective deblocking of this amino acid residue sidechain can be achieved. The selectively deblocked sidechain can then be reacted either directly with the C-terminal carboxyl group, thereby bonding the sidechain to the C-terminal carbonyl wherein the sidechain is represented by the R group of Formula (I), or can be reacted with the more complex macrocyclizing moiety to form the macrocyclic ring therethrough. Synthetic examples are provided below.

The macromolecular carrier to which the hapten is covalently bonded or coupled is of sufficient size, molecular weight, and composition to stimulate an immune response in an animal challenged with the hapten-carrier complex. The hapten, including the cyclic peptide or cyclic peptide analog, can be directly coupled to the macromolecular carrier. For example, a covalent bond can be formed between a functional group of the carrier such as a carboxylic acid and a functional group of the cyclic peptide or analog, such as between an N-terminal amino group, using an amide-forming reagent such as EDC (ethyl dimethylaminopropyl carbodiimide), optionally with N-hydroxysuccinimide. Alternatively, an N-terminal amino acid residue of the cyclic peptide can have carboxylic functionality, for example the N-terminal residue can be an aspartate or glutamate residue. In that case it can be directly coupled to an amino group on the carrier, using the same chemical synthesis approach. The amino group can be present, for example, in the sidechain of a lysine residue on the surface on a protein. Alternatively, an amino group to which the peptide carboxylate can be coupled could be on the surface of a synthetic dendrimer, such as a MAP structure. Other schemes for direct coupling of the cyclic peptide or analog thereof to a macromolecular carrier will be apparent to those of ordinary skill in the art.

The macromolecular carrier can comprise a polypeptide. For example, the macromolecular carrier can be a protein, and nonlimiting examples of such suitable carrier proteins include keyhole limpet hemocyanin (KLH), bovine serum albumin (BSA), rabbit serum albumin (RSA), human serum albumin (HAS), *Concholepas concholepas* hemocyanin (CCH), cholera toxin B subunit, *E. coli* labile toxin B subunit, Diphtheria toxoid, tetanus toxoid, tetanus toxin C-fragment, recombinant *Pseudomonas aeruginosa* exoprotein A, CRM197 (cross-reactive material), cationized bovine serum albumin (cBSA), Thyroglobulin (Tg), avidin, bovine thyroglobulin (BTG), bovine G globulin, bovine immunoglobulin G (BigG), conalbumin (CONA), colloidal gold, edestin, *Paralithodes camtschatica* heamocyanin (HC), *helix promatia* haemocyanin (HPH), soybean kunitz trypsin inhibitor (KTI), *Limulus polyphemus* heamocyanin (LPH), ovalbumin (OA), Pam3Cys-Th (lipopeptide/Th cell epitope), polylysine, porcine thyroglobulin (PTG), purified protein derivative (PPD), soybean trypsin inhibitor (STI), or sunflower globulin (SFG). Thus, in some embodiments, the immunogenic molecular entity comprises a hapten covalently linked to a polypeptide such as, without limitation, the above exemplified polypeptides.

The macromolecular carrier can be a polymer, such as a linear polymer adapted for covalent attachment of haptens, or can be another type of synthetic carrier such as, for example, a dendrimer. A dendrimer produced by star polymerization of monomers with more than two reactive groups can be adapted to provide functional groups to which a synthetic cyclic peptide or analog thereof can be coupled using chemistry known to those of skill in the art. For example, a MAP dendrimer, which provides multiple amino groups on its surface, can be coupled to a sidechain carboxyl group of an N-terminal amino acid residue of an inventive cyclic peptide. See, for example, Sakarellos-Daitsiotis et al., *Current Topics in Medicinal Chemistry* 6:1715-35 (2006); Saupe et al., *Expert Opin. Drug. Deliv.* 3:345-354 (2006); McDermott et al., *Immunology and Cell Biology* 76: 256-62 (1998); and Shahiwala et al., *Recent Patents on Drug Delivery & Formulation* 1:1-9 (2007).

In another embodiment, the immunogenic molecular entity can include a linker moiety, disposed between the cyclic peptide or analog, and the macromolecular carrier. A linker moiety can be used to physically separate the domain(s) of the hapten for which antibodies are desired to be specific, i.e., the cyclic peptide or analog, from the surface of the macromolecular carrier. A linker moiety can be derived from a linker reagent, such as MBS (m-maleimidobenzoyl N-hydroxysuccinimide ester), sulfo-MBS (m-maleimidobenzoyl N-hydroxy-2-sulfosuccinimide ester), SMCC (succinimidyl 4-(N-maleimidomethyl)-cyclohexane-1-carboxylate), sulfo-SMCC (2-sulfosuccinimidyl 4-(N-maleimidomethyl)-cyclohexane-1-carboxylate), as are well known in the art. Reaction of the linker reagent with the cyclic peptide and with the carrier yield the linker moiety coupled to both. For example, the linker reagents recited above are adapted to couple a thiol-containing N-terminal amino acid residue of the cyclic peptide and an amino group of the macromolecular carrier through addition of the thiol group to the maleimide group, and by acylation of the carrier amino group with the N-hydroxy ester group. Other linker reagents are adapted to react in different ways with different groups. Other types of structures can be included within linker moieties. For example a linker moiety can include adipic acid dihydrazide (ADH), a spacer peptide, hydroxymethyl hemisuccinate, or a polyethyleneglycol derivative. It is within ordinary skill to select a linker reagent adapted to react with the particular cyclic peptide N-terminus and with the particular macromolecular carrier in the desired manner.

The macromolecular carrier and covalently bound hapten can be included within a supramolecular assembly. The supramolecular assembly can be a liposome or virosome, that is, a micellar structure including membrane-spanning proteins. See, for example, Westerfeld & Zurbriggen, *J. Peptide Sci.* 11:707-712 (2005) and Felnerova et al., *Current Opinion in Biotechnology* 15:518-29 (2004). The supramolecular assembly can be a virus particle, such as in a phage display system, wherein a bacteriophage is adapted to express surface functional groups.

In other embodiments, the macromolecular carrier and covalently bound hapten need not be included within a supramolecular assembly to be immunogenic.

Specific examples of immunogenic molecular entities of the invention are shown below for exemplary purposes:

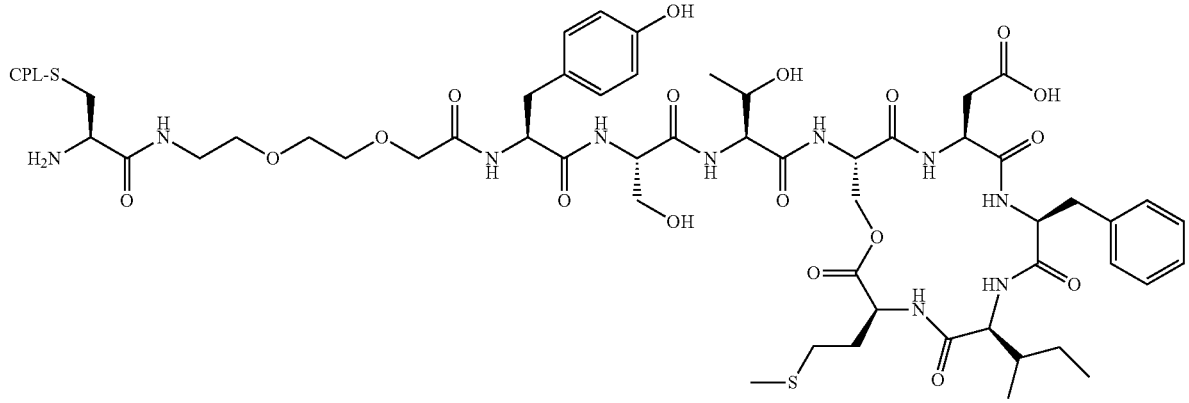

SEQ ID NO: 3 (YSTSDFIM, not including protecting groups),

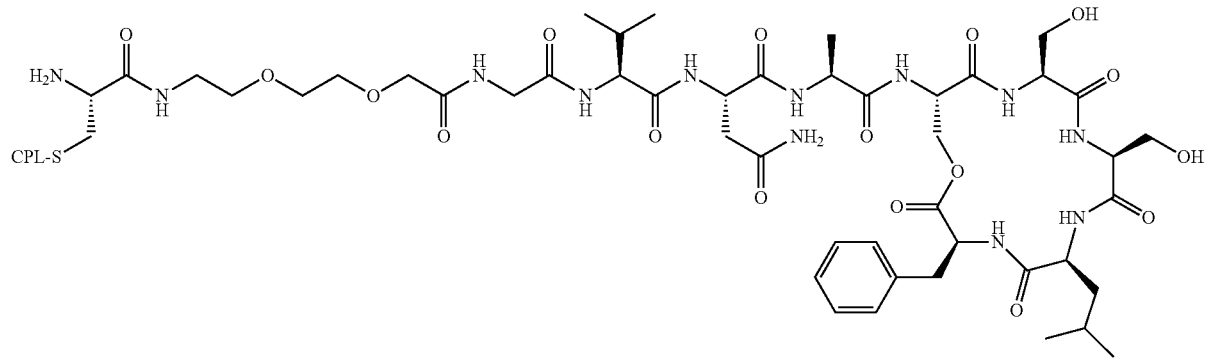

SEQ ID NO: 4 (GVNASSSLY, not including protecting groups),

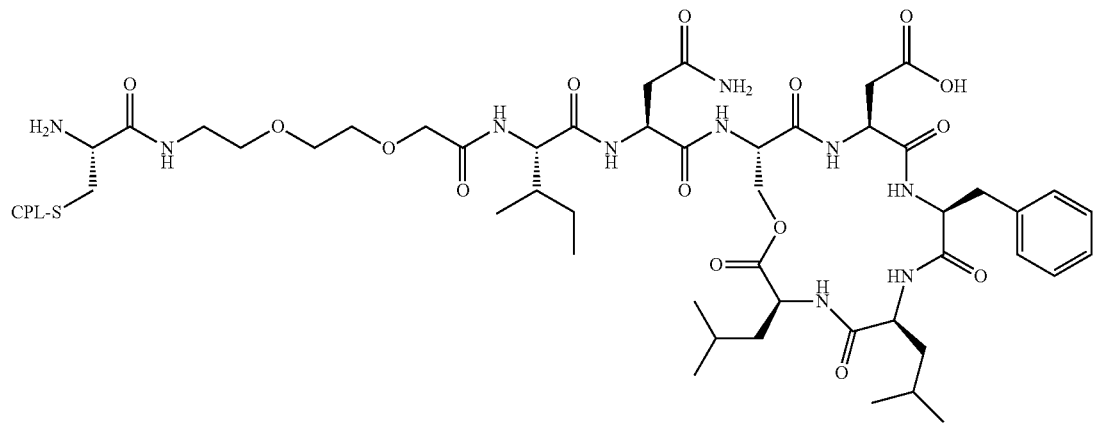

SEQ ID NO: 2 (INSDFLL, not including protecting groups), or

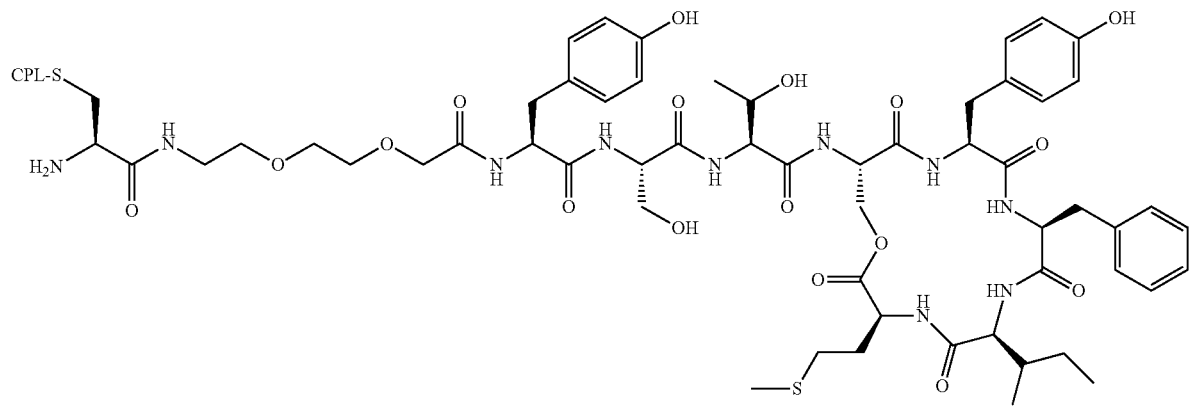

SEQ ID NO: 1 (YSTSYFLM, not including protecting groups), wherein CPL is a macromolecular carrier with optional linker covalently bonded to a cysteine thiol group. It can be seen in these examples that the macrocyclic ring includes a lactone group that is formed between an internal serine amino acid residue and the carboxy terminus, which is a methionine, phenylalanine, or leucine residue. The macrocyclic ring of each of these examples includes five amino acid residues, four additional natural amino acid residues, a synthetic amino acid residue comprising a PEG group, and an N-terminal cysteine residue bonded via an optional linker group to a macromolecular carrier, for example a macromolecular polypeptide. These compositions exemplify structures that can be used to induce antibody formation in an animal, wherein at least some of the antibodies formed in response are specific for the cyclic peptide analog of the hapten.

The immunogenic molecular entity of the invention can be used to screen a recombinant combinatorial immunoglobulin library (for example, an antibody phage display library) for an antibody specific for a native cyclic signaling peptide. For example, an immunogenic molecular entity of the invention that has a hapten corresponding to the lactone, lactam, carbamide or semicarbazide analog of the S. aureus AIP IV cyclic signaling peptide, can be used to screen a recombinant combinatorial immunoglobulin library for an antibody that will bind specifically with the AIP IV cyclic signaling peptide. Uses of an antibody that will bind specifically with a cyclic signaling peptide are discussed below.

A immunogenic molecular entity of the invention can also be used to elicit an immune response in a mammal directed against selected cyclic signaling peptide. For example, an immunogenic molecular entity of the invention that has a hapten corresponding to the lactone, lactam, carbamide or semicarbazide analog of the S. aureus AIP IV cyclic signaling peptide, can be used to elicit an immune response against the AIP-IV cyclic signaling peptide in a mammal.

The resulting mammal can be a source of antibody specific for the cyclic signaling peptide. For example, antibodies against AIP-IV can be isolated from the blood of the mammal. In addition, antibody-producing cells can be isolated and used to make antibody-producing hybridomas for the production of monoclonal antibodies as discussed below.

The immunogenic molecular entity of the invention can also be used as a vaccine in that the immune response generated in the mammal can protect the mammal from infection by a Gram positive bacteria that utilizes the selected cyclic signaling peptide in quorum sensing and expression of virulence genes or prevent the mammal from developing a disease or condition associated with infection. For example, an immunogenic molecular entity of the invention that has a hapten corresponding to the lactone, lactam, carbamide or semicarbazide analog of the S. aureus AIP IV cyclic signaling peptide can be used to elicit an immune response against the AIP-IV cyclic signaling peptide such that the mammal is protected from developing a disease condition or complications associated with S. aureus virulence.

Uses of an immunogenic molecular entity of the invention are further described below, for example, in the Methods and EXAMPLES sections.

An Antibody of the Invention

An antibody of the invention is one that binds specifically with a cyclic signaling peptide. As used herein, the term "cyclic signaling peptide" refers to a cyclic peptide produced by a Gram positive bacterium that utilizes quorum sensing to regulate the expression of virulence genes. The cyclic signaling peptide is a signaling molecule that binds to a membrane-bound histidine kinase sensor molecule, which then interacts with an intracellular response regulator.

Cyclic signaling peptides are produced by Gram-positive bacteria that employ quorum sensing including, without limitation, various Staphylococci species and Enterococcus faecalis. Non-limiting examples of cyclic signaling peptides and the producer bacteria are provided in the following table. The signaling peptide is composed of an N-terminal tail and a thiolactone- or lactone-containing ring that is formed by reaction of the alpha-carboxyl group of the "C-terminal" amino acid residue (underlined) with the sidechain sulfhydryl or hydroxyl group of an internal amino acid (bolded).

| Bacterium | Native cyclic signaling peptides |
|---|---|
| S. aureus I | YSTCDFI<u>M</u> (SEQ ID NO: 120) |
| S. aureus II | GVNACSSL<u>F</u> (SEQ ID NO: 121) |
| S. aureus III | INCDFL<u>L</u> (SEQ ID NO: 122) |
| S. aureus IV | YSTCYFI<u>M</u> (SEQ ID NO: 123) |
| S. arlettae | GVNPCGGW<u>F</u> (SEQ ID NO: 124) |
| S. auricularis I | KAKTCTVL<u>Y</u> (SEQ ID NO: 125) |
| S. auricularis II | KTKTCTVL<u>Y</u> (SEQ ID NO: 126) |
| S. capitis I | GANPCOLY<u>Y</u> (SEQ ID NO: 127) |
| S. capitis II | GANPCALY<u>Y</u> (SEQ ID NO: 128) |
| S. caprae I | GYSTCSYY<u>F</u> (SEQ ID NO: 129) |
| S. caprae II | GYRTCNTY<u>F</u> (SEQ ID NO: 130) |
| S. carnosus | YNPCVGY<u>F</u> (SEQ ID NO: 131) |
| S. cohnii ssp. cohnii | GGKVCSAY<u>F</u> (SEQ ID NO: 132) |
| S. cohneii ssp. urealyticum | SVKPCTGF<u>A</u> (SEQ ID NO: 133) |
| S. epidermis I | DSVCASY<u>F</u> (SEQ ID NO: 134) |
| S. epidermis II | KYNPCSNY<u>L</u> (SEQ ID NO: 135) |
| S. epidermis III | KYNPCASY<u>L</u> (SEQ ID NO: 136) |
| S. epidermis IV | KYNPCANY<u>L</u> (SEQ ID NO: 137) |
| S. intermedius | RIPTSTGF<u>F</u> (SEQ ID NO: 138) |
| S. lugdunensis I | DICNAY<u>F</u> (SEQ ID NO: 139) |
| S. lugdunensis II | DMCNGY<u>F</u> (SEQ ID NO: 140) |
| S. simulans I | KYNPCLGF<u>L</u> (SEQ ID NO: 141) |
| S. simulans II | KYYPCFGY<u>F</u> (SEQ ID NO: 142) |
| S. gallinarum | VGARPCGGF<u>F</u> (SEQ ID NO: 143) |
| S. xylosus | GAKPCGGF<u>F</u> (SEQ ID NO: 144) |
| S. warneri (RN 833) | YSPCTNF<u>F</u> (SEQ ID NO: 145) |
| E. faecalis | QNSPNIFGQW<u>M</u> (SEQ ID NO: 146) |

Thus, a cyclic signaling peptide can have a ring of three to eleven-amino acids and a tail of one to about nine amino acids. The ring structure is formed between the alpha-carbonyl group of the "C-terminal amino acid residue," that is the carboxy-terminal amino acid of a corresponding linear peptide, and an alkyloxy or alkylthio group on the sidechain of an internal serine or cysteine residue, in particular, the $4^{th}$, $5^{th}$, $6^{th}$, $7^{th}$, $8^{th}$ or $9^{th}$ residue from the carboxy-terminal amino acid. For example, the S. aureus AIP4 signaling molecule is a cyclic thiolactone peptide analog composed of the amino acid sequence YSTCYFIM (SEQ ID NO: 123). The cyclic thiolactone ring structure results from a bond between the alpha-carboxyl group of methionine (M), the "C-terminal amino acid residue," and the sulfhydryl group of cysteine HAS, the fifth amino acid from the "C-terminal" methionine (M) residue.

Thus, a cyclic signaling peptide can have a five-amino acid ring, for example, a thiolactone or lactone ring, and a linear two- to five-amino acid tail.

An antibody can be an immunoglobulin molecule or an immunologically-active fragment thereof that binds specifically with a particular antigen. An antibody of the invention is one that binds specifically with a native cyclic signaling peptide, or a hapten that includes the lactone, lactam, carbamide or semicarbazide analog of the cyclic signaling peptide. As used herein, the term "bind specifically" or "specifically binds" in reference to an antibody of the invention means that the antibody of the invention will bind with the cyclic signaling peptide or corresponding hapten, but does not substantially bind to other unrelated molecules including the carrier protein alone or other unrelated molecules that may be present with the immunogenic molecular entity, supramolecular assembly, or a biological sample from a mammal. For example, an antibody that binds specifically with an immunogenic molecular entity of the invention in which the hapten is a lactone, lactam, carbamide or semicarbazide analog of the S. aureus AIP IV cyclic peptide signaling molecule is one that will bind with the S. aureus AIP IV cyclic peptide, but will not bind substantially with the carrier alone or an unrelated molecule.

An antibody of the invention is also a neutralizing antibody. As used herein, the term "neutralizing antibody" refers to an antibody that will bind to a cyclic signaling peptide and prevent the binding of the cyclic signaling peptide with its membrane-associated receptor. The term "neutralizing antibody" also includes a cross-neutralizing antibody, an antibody that will bind to and prevent binding of at least two cyclic signaling peptides with their receptors, for example, cyclic signaling peptides from different agr groups. Whether an antibody is a neutralizing antibody can be determined using the methods known to those of skilled in the art including those described herein, for example, in the EXAMPLES section. The term An antibody of the invention can be a polyclonal or monoclonal antibody. Polyclonal antibodies can be obtained by immunizing a mammal with an immunogenic molecular entity of the invention, and then isolating antibodies from the blood of the mammal using standard techniques including, for example, enzyme linked immunosorbent assay (ELISA) to determine antibody titer and protein A chromatography to obtain the antibody-containing IgG fraction.

A monoclonal antibody is a population of molecules having a common antigen binding site that binds specifically with a particular antigenic epitope. A monoclonal antibody can be obtained by selecting an antibody-producing cell from a mammal that has been immunized with an immunogenic molecular entity of the invention and fusing the antibody-producing cell, e.g. a B cell, with a myeloma to generate an antibody-producing hybridoma. A monoclonal antibody of the invention can also be obtained by screening a recombinant combinatorial library such as an antibody phage display library using, for example, an immunogenic molecular entity of the invention. See, for example, Barbas, C. F., 3$^{rd}$, D. R. Burton, J. K. Scott, and G. J. Silverman, *Phage Display—A Laboratory Manual*. 2001, Cold Spring Harbor, N.Y.: Cold Spring Harbor Laboratory Press; and Kontermann, R., Dübel, S., Antibody Engineering, 2001, Berlin, Heidelberg: Springer-Verlag An immunologically-active fragment of an antibody is the biologically active fragment of an immunoglobulin molecule, for example, the F(ab) or F(ab')$_2$ fragment generated by cleavage of the antibody with an enzyme such as pepsin. An immunologically-active fragment can also be a single chain variable fragment (scFv) that results from the joining of the variable fragments of the heavy and light chains.

An antibody of the invention can also be a murine, chimeric, humanized or fully human antibody. A murine antibody is an antibody derived entirely from a murine source, for example, an antibody derived from a murine hybridoma generated from the fusion of a mouse myeloma cell and a mouse B-lymphocyte cell. A chimeric antibody is an antibody that has variable regions derived from a non-human source, e.g. murine or primate, and constant regions derived from a human source. A humanized antibody has antigen-binding regions, e.g. complementarity-determining regions, derived from a mouse source, and the remaining variable regions and constant regions derived from a human source. A fully human antibody is antibody from human cells or derived from transgenic mice carrying human antibody genes.

Methods to generate antibodies are well known in the art. For example, a polyclonal antibody of the invention can be prepared by immunizing a suitable mammal with an immunogenic molecular entity of the invention. The mammal can be, for example, a rabbit, goat, or mouse. At the appropriate time after immunization, antibody molecules can be isolated from the mammal, e.g. from the blood or other fluid of the mammal, and further purified using standard techniques that include, without limitation, precipitation using ammonium sulfate, gel filtration chromatography, ion exchange chromatography or affinity chromatography using protein A. In addition, an antibody-producing cell of the mammal can be isolated and used to prepare a hybridoma cell that secretes a monoclonal antibody of the invention. Techniques for preparing monoclonal antibody-secreting hybridoma cells are known in the art. See, for example, Kohler and Milstein, *Nature* 256:495-97 (1975) and Kozbor et al. *Immunol Today* 4: 72 (1983). A monoclonal antibody of the invention can also be prepared using other methods known in the art, such as, for example, expression from a recombinant DNA molecule, or screening of a recombinant combinatorial immunoglobulin library using an immunogenic molecular entity of the invention as discussed above.

Methods to generate chimeric and humanized monoclonal antibodies are also well known in the art and include, for example, methods involving recombinant DNA technology. A chimeric antibody can be produced by expression from a nucleic acid that encodes a non-human variable region and a human constant region of an antibody molecule. See, for example, Morrison et al., *Proc. Nat. Acad. Sci. U.S.A.* 86: 6851 (1984). A humanized antibody can be produced by expression from a nucleic acid that encodes non-human antigen-binding regions (complementarity-determining regions) and a human variable region (without antigen-binding regions) and human constant regions. See, for example, Jones et al., *Nature* 321:522-24 (1986); and Verhoeven et al., *Science* 239:1534-36 (1988). Completely human antibodies can be produced by immunizing engineered transgenic mice that express only human heavy and light chain genes. In this case, therapeutically useful monoclonal antibodies can then be obtained using conventional hybridoma technology. See, for example, Lonberg & Huszar, *Int. Rev. Immunol.* 13:65-93 (1995). Nucleic acids and techniques involved in design and production of antibodies are well known in the art. See, for example, Batra et al., *Hybridoma* 13:87-97 (1994); Berdoz et al., *PCR Methods Appl.* 4: 256-64 (1995); Boulianne et al. *Nature* 312:643-46 (1984); Carson et al., *Adv. Immunol.* 38:274-311 (1986); Chiang et al., *Biotechniques* 7:360-66 (1989); Cole et al., *Mol. Cell. Biochem.* 62:109-20 (1984); Jones et al., *Nature* 321: 522-25 (1986); Larrick et al., *Biochem Biophys. Res. Commun.* 160:1250-56 (1989); Morrison, *Annu. Rev. Immunol.* 10:239-65 (1992); Morrison et al., *Proc. Nat'l Acad. Sci. USA* 81: 6851-55 (1984); Orlandi et al., *Pro. Nat'l Acad. Sci. U.S.A.* 86:3833-37 (1989); Sandhu, *Crit. Rev. Biotechnol.* 12:437-62 (1992); Gavilondo & Larrick, *Biotechniques* 29: 128-32 (2000); Huston & George, *Hum. Antibodies.* 10:127-42 (2001); Kipriyanov & Le Gall, *Mol. Biotechnol.* 26: 39-60 (2004).

Examples of monoclonal antibodies and single chain variable fragments of the invention are shown below, as well as their coding nucleotide sequences.

| Amino Acid Sequences of the Variable Heavy and Light Chains of Murine Monoclonal Antibodies | | |
|---|---|---|
| Antibody | Variable Heavy Chain | Variable Light Chain |
| AP1-15B4 | EVHLVESGGDLVKPGGSLKLS CAASGFAFSDFAMSWVRQTPE KRLEWVAIIKSDDSYTYYPDS VRDRFTISRDNARNTLYLQMT SLRSEDTALYYCTKIYDAYFY AMDYWGQGTSVTVSS (SEQ ID NO: 19) | DIVRTQSPLSLSVSLGDQASISC RSSQSLLHSNGNTYLHWYLQKPG QSPKLLIYKVSNRFSGVPDRFSG SGSGTDFTLKISILEAEDLGIYF CSQSTHFPTFGGGTKLEIK (SEQ ID NO: 147) |
| AP4-24H11 | EVKPQESGPGLVKPSQSLSLT CTVTGYSITSNYAWNWIRQFP GNKLEWMGFISSYGTTTYNPS LKSRFSITRDTSKNQFFLQLH SVTIEDTGTYFCTREGDYWGQ GTTLTVSS (SEQ ID NO: 20) | DIVMTQATLSLPVSLGDQASISC RSSQRLVPSNGNIYLHWFLQKPG QSPKLLIYKLSSRFSGVPDRFSG SGSGTDFTLKISRVESEDLGIYF CSQTTHVPYTFGGGTKLEIK (SEQ ID NO: 148) |
| AP4-29E10-1 | EVQLQQSGPELEKPGASVKIS CKASGHSFTGYNMNWVKQSND KSLEWIGNIAPYYGVTAYNQK FKGKATLTGDKSSSTAYMQLK SLASEDSAVYYCVLDTSGYAS WGQGTLVTVSA (SEQ ID NO: 21) | DIVMTQATASLTVSLGQRATISC RASKSVSTSGYSYMHWYQQKPGQ PPKLLIYLASNLESGVPARFSGS GSGTDFTLNIHPVEEEDAATYYC QHSREVPYTFGGGTKLELK (SEQ ID NO: 149) |
| AP4-29E10-2 | QVQLQQSGPELEKPGASVKIS CKASGHSFTGYNMNWVKQSND KSLEWIGNIAPYYGVTAYNQK FKGKATLTGDKSSSTAYMQLK SLTSEDSAVYYCVLDTSGYAS WGQGTLVTVSA (SEQ ID NO: 22) | DIEMTQITASLTVSLGQRATISC RASKSVSTSGYSYMHWYQQKPGQ PPKLLIYLASNLESGVPARFSGS GSGTDFTLNIHPVEEEDAATYYC QHSREVPYTFGGGTKLELK (SEQ ID NO: 150) |
| AP1-15B4-Δ | GGDLVKPGGSLKLSCAASGFA FSDFAMSWVRQTPEKRLEWVA IIKSDDSYTYYPDSVRDRFTI SRDNARNTLYLQMTSLRSEDT ALYYCTKIYDAYFYAMDYWGQ GTS (SEQ ID NO: 23) | PLSLSVSLGDQASISCRSSQSLL HSNGNTYLHWYLQKPGQSPKLLI YKVSNRFSGVPDRFSGSGSGTDF TLKISILEAEDLGIYFCSQSTHF PTFGGGT (SEQ ID NO: 151) |
| AP4-24H11-Δ | GPGLVKPSQSLSLTCTVTGYS ITSNYAWNWIRQFPGNKLEWM GFISSYGTTTYNPSLKSRFSI TRDTSKNQFFLQLHSVTIEDT GTYFCTREGDYWGQGTT (SEQ ID NO: 24) | TLSLPVSLGDQASISCRSSQRLV PSNGNIYLHWFLQKPGQSPKLLI YKLSSRFSGVPDRFSGSGSGTDF TLKISRVESEDLGIYFCSQTTHV PYTFGGGT (SEQ ID NO: 152) |
| AP4-29E10-1-Δ | GPELEKPGASVKISCKASGHS FTGYNMNWVKQSNDKSLEWIG NIAPYYGVTAYNQKFKGKATL TGDKSSSTAYMQLKSLASEDS AVYYCVLDTSGYASWGQGTL (SEQ ID NO: 25) | TASLTVSLGQRATISCRASKSVS TSGYSYMHWYQQKPGQPPKLLIY LASNLESGVPARFSGSGSGTDFT LNIHPVEEEDAATYYCQHSREVP YTFGGGT (SEQ ID NO: 153) |
| AP4-29E10-2-Δ | GPELEKPGASVKISCKASGHS FTGYNMNWVKQSNDKSLEWIG NIAPYYGVTAYNQKFKGKATL TGDKSSSTAYMQLKSLTSEDS AVYYCVLDTSGYASWGQGTL (SEQ ID NO: 26) | TASLTVSLGQRATISCRASKSVS TSGYSYMHWYQQKPGQPPKLLIY LASNLESGVPARFSGSGSGTDFT LNIHPVEEEDAATYYCQHSREVP YTFGGGT (SEQ ID NO: 154) |

Nucleic Acid Sequences Encoding the Variable Heavy and Light Chains of
Murine Monoclonal Antibodies

| Antibody | Variable Heavy Chain | Variable Light Chain |
| --- | --- | --- |
| AP1-15B4 | gaggtgcacctggtggagtctgggggagacttagtgaa gcctggggggtccctcaaactctcctgtgcagcctctgg attcgctttcagtgactttgccatgtcttgggttcgcca gactccggagaagaggctggagtgggtcgcaatcattaa aagtgatgattcttacacctactatccagacagtgtga gggaccgattcaccatctccagagacaatgccagg aacacccttacctgcaaatgaccagtctgaggtctg aagacacggccttgtattactgtacaaaaatctatgat gcttacttctatgctatggactactggggtcaaggaac ctcagtcaccgtctcctcg (SEQ ID NO: 27) | gacattgtgaggacacagtctccactctccctgtctgtcagtcttggag atcaagcctccatctcttgtagatctagtcagagccttttacacagtaa tggaaacacctatttacattggtacctgcagaagccaggccagtctcca aaactcctgatctacaaagtttccaaccgattttctggggtcccagaca ggttcagtggcagtggatcagggacagatttcacactcaagatcagcat attggaggctgaggatctgggaatttatttctgctctcaaagtacacat tttccgacgttcggtggaggcaccaagctggaaataaaa (SEQ ID NO: 155) |
| AP4-24H11 | gaggtgaagcctcaggagtcaggacctggcctggtgaaa ccttctcagtctctgtccctcacctgcactgtcactgg ctactcaatcaccagtaattatgcctggaactggat ccggcagtttccaggaaacaaactggagtggatg ggcttcataagttcctatggaaccactacctacaac ccttctctcaaaagtcgattctctatcactcgagaca catccaagaaccagttcttcctgcaattgcattctgtg actattgaggacacaggcacatatttctgtacaaga gagggtgactactggggccaaggcaccactctca cagtctcctca (SEQ ID NO: 28) | gacattgtgatgactcaggctacactctccctgcctgtcagtcttggag accaagcctccatctcttgcagatccagtcagcgccttgttcccagtaa tggaaacatttatttacattggttcctgcagaagccaggccagtctcca aagctcctgatctacaaactttccagtcgattttctggggtcccagaca ggttcagtggcagtggatcagggacagatttcacactcaagatcagcag agtggagtctgaggatctgggaatttatttctgctctcaaactacacat gttccatacacgttcggagggggggaccaagctggaaatcaaa (SEQ ID NO: 156) |
| AP4-29E10-1 | gaggtccagctgcaacagtccggacctgagctggaga agcctggcgcttcagtgaagatatcctgcaaggcttct ggtcattcattcactggctacaacatgaactgggtgaa gcagagcaatgacaagagccttgagtggattggaaa tattgctccttactatggtgttactgcctacaaccagaag ttcaagggcaaggccacattgactggagacaaatcctcc agcactgcctacatgcagctcaagagcctggcatctga ggactctgcagtctattactgtgtcctagacacctcgggct acgcttcctggggccaagggactctggtaactgtctctg ca (SEQ ID NO: 29) | gacattgtgatgactcaggctactgcttccttaactgtatctctggggc agagggccaccatctcatgcagggccagcaaaagtgtcagtacatctgg ctatagttatatgcactggtaccaacagaaaccaggacagccacccaaa ctcctcatctatcttgcatccaacctagaatctggggtccctgccaggt tcagtggcagtgggtctgggacagacttcaccctcaacatccatcctgt ggaggaggaggatgctgcaacctattactgtcagcacagtagggaggtt ccgtacacgttcggaggggggaccaagctggagctgaaa (SEQ ID NO: 157) |
| AP4-29E10-2 | caggtccagctgcagcagtctgggcctgagctggagaag cctggcgcttcagtgaagatatcctgcaaggcttctg gtcattcattcactggctacaacatgaactgggtgaaa gcagagcaatgacaagagccttgagtggattggaaa atattgctccttactatggtgttactgcctacaaccag aagttcaagggcaaggccacattgactggagaca aatcctccagcactgcctacatgcagctcaagagcc tgacatctgaggactctgcagtctattactgtgtcctag acacctcgggctacgcttcctggggccaagggact ctggtcactgtctctgca (SEQ ID NO: 30) | gacattgagatgacccagattactgcttccttaactgtatctctggggc agagggccaccatctcatgcagggccagcaaaagtgtcagtacatctgg ctatagttatatgcactggtaccaacagaaaccaggacagccacccaaa ctcctcatctatcttgcatccaacctagaatctggggtccctgccaggt tcagtggcagtgggtctgggacagacttcaccctcaacatccatcctgt ggaggaggaggatgctgcaacctattactgtcagcacagtagggaggtt ccgtacacgttcggaggggggaccaagctggagctgaaa (SEQ ID NO: 158) |
| AP1-15B4-Δ | ggggagacttagtgaagcctgggggtccctcaaact ctcctgtgcagcctctggattcgctttcagtgactt cgccatgtcttgggttcgccagactccggagaa gaggctggagtgggtcgcaatcattaaaagtg atgattcttacacctactatccagacagtgtgagg gaccgattcaccatctccagagacaatgccagg aacacccttacctgcaaatgaccagtctgaggtc tgaagacacggccttgtattactgtacaaaaatcta tgatgcttacttctatgctatggactactggggtcaa ggaacctca (SEQ ID NO: 31) | ccactctccctgtctgtcagtcttggagatcaagcctccatctcttgta gatctagtcagagccttttacacagtaatggaaacacctatttacattg gtacctgcagaagccaggccagtctccaaaactcctgatctacaaagtt tccaaccgattttctggggtcccagacaggttcagtggcagtggatcag ggacagatttcacactcaagatcagcatattggaggctgaggatctggg aatttatttctgctctcaaagtacacattttccgacgttcggtggaggc acc (SEQ ID NO: 159) |
| AP4-24H11-Δ | ggacctggcctggtgaaaccttctcagtctctgtccct cacctgcactgtcactggctactcaatcaccagtaatt atgcctggaactggatccggcagtttccaggaaaca aactggagtgggtgggcttcataagttcctatggaacc actaccaaccttctctcaaaagtcgattctctatca ctcgagacacatccaagaaccagttcttcctgcaattg cattctgtgactattgaggacacaggcacatatttctgta caagagagggtgactactggggccaaggcaccact (SEQ ID NO: 32) | acactctccctgcctgtcagtcttggagaccaagcctccatctcttgca gatccagtcagcgccttgttcccagtaatggaaacatttatttacattg gttcctgcagaagccaggccagtctccaaagctcctgatctacaaactt tccagtcgattttctggggtcccagaggttcagtggcagtggatcag ggacagatttcacactcaagatcagcagaggtggagtctgaggatctggg aatttatttctgctctcaaactacacatgttccatacacgttcggaggg gggacc (SEQ ID NO: 160) |
| AP4-29E10-1-Δ | ggacctgagctggagaagcctggcgcttcagtgaagat atcctgcaaggcttctggtcattcattcactggctaca acatgaactgggtgaagcagagcaatgacaaga gccttgagtggattggaaatattgctccttactatggtg ttactgcctacaaccagaagttcaagggcaaggcc acattgactggagacaaatcctccagcactgcctac atgcagctcaagagcctggcatctgaggactctgca gtctattactgtgtcctagacacctcgggctacgcttcc tggggccaagggactctg (SEQ ID NO: 33) | actgcttccttaactgtatctctggggcagagggccaccatctcatgca gggccagcaaaagtgtcagtacatctggctatagttatatgcactggta ccaacagaaaccaggacagccacccaaactcctcatctatcttgcatcc aacctagaatctggggtccctgccaggttcagtggcagtgggtctggga cagacttcaccctcaacatccatcctgtggaggaggaggatgctgcaac ctattactgtcagcacagtagggaggttccgtacacgttcggaggggggg acc (SEQ ID NO: 161) |

Nucleic Acid Sequences Encoding the Variable Heavy and Light Chains of Murine Monoclonal Antibodies

| Antibody | Variable Heavy Chain | Variable Light Chain |
|---|---|---|
| AP4-29E10-2-Δ | gggcctgagctggagaagcctggcgcttcagtgaagata tcctgcaaggcttctggttcattcattcactggctacaac atgaactgggtgaagcagagcaatgacaagagcc ttgagtggattggaaatattgctccttactatggtgttact gcctacaaccagaagttcaagggcaaggccacatt gactggagacaaatcctccagcactgcctacatgca gctcaagagcctgacatctgaggactctgcagtctatt actgtgtcctagacacctcgggctacgcttcctgggc caagggactctg (SEQ ID NO: 34) | actgcttccttaactgtatctctggggcagagggccaccatctcatgca gggccagcaaaagtgtcagtacatctggctatagttatatgcactggta ccaacagaaaccaggacagccacccaaactcctcatctatcttgcatcc aacctagaatctggggtccctgccaggttcagtggcagtgggtctggga cagacttcaccctcaacatccatcctgtggaggaggaggatgctgcaac ctattactgtcagcacagtaggggggtccgtacacgttcggaggggg acc (SEQ ID NO: 162) |

Amino Acid Sequences of Human scFv Antibodies

AP1-2   QVQLVQSGAEVKKPGESLRISCKGSGYSFTSHWISWVRQMPGKGLEWMGRIDPSDSYSNYSPSFQGHVIISVDKSISTAYLQWSSLKASDTAIYY
        CARQLIVVVPAAPYYYYYGMDVWGQGTLVTVSSGGGGSGGGGSSGGGSEIVLTQSPGTLSLSPGERATLSCRASQTVNSYLAWYQKPGQAPRLL
        IYGASSRATGIPDRFSGSGSGTDFTLTISRLEPEDFAVYYCQQYGSSHPWTFGQGTKVEIK (SEQ ID NO: 35)

AP1-6   QVQLVQSGAEVKKPGSSVKVSCKASGGTFSSYAISWVRQAPGQGLEWMGGIIPIFGTANYAQKFQGRVTITADESTSTAYMELSSLRSEDTAIYY
        CARVFGSESQDPSDIWSGYYGMEVWGQGTLVTVSSGGGGSGGGGSGGGGSDIQMTQSPSSVSASVGDRVTITCRASQGISSWLAWYQQKPGKAPK
        LLIYAASSLQSRVPSRFSGSGSGTDFTLTISSLQPEDFATYYCQQANSFPYTFGQGTKLEIK (SEQ ID NO: 36)

AP1-8   QVQLVESGAEAKKPGSSVKVSCKASGGTFSSYAISWVRQAPGQGLEWMGGIIPIFGTANYAQKFQGRVTITADESTSTAYMELSSLRSEDTAVYYC
        ARAGITGTTAPPDYWGQGTLVTVSSGGGGSGGGGSGGGGSVIWMTQSPSSLSASVGDRVTITCRASQSISSYLNWYQRKPGKAPKLLIYAASSLQS
        GVTSRFSGSGSGTDFTLTISSLQPEDFATYYCQQSYSTPPTFGQGTKLEIK (SEQ ID NO: 37)

AP1-11  QVQLVQSGSELKKPGASVKLSCRASGYTFTSYSMVWVRQAPGEGLEWMGGINTNTGNPTYAQGFTERFVFSFDSSVSTAYLQISSSLKAEDTAVYY
        CARDWAYSGSWPLGQNPSDHWGQGTLVTVSSGGGGSGGGGSGGGGSEIVMTQSPATLSVSPGERATLSCRASQSVSRNLAWYQQKPGQAPRLLIY
        DTSTRATGIPARFSGSGSGTEFTLTISSLQSEDSAVYYCQQYNIWPPLTFGGGTKVEIK (SEQ ID NO: 38)

AP1-15  QVQLQQWGAGLLKPSETLSLTCAVYGGSFSGYYRTWIRQSPVKGLEWIGEVNDRGSPNYNPSFKSRLTISIDTSKNLSLKLRFMTAADTAVYSCA
        RIRPRYGMDVWGQGTMVTVSSGGGGSGGGGSSGGGSDIVMTQTPLSSPVTLGQPASISCRSSQSLVHSDGNTYLTWFHQRPGQPPRVLIHKVSNL
        FSGVPDRFSGSGAGTDFTLKISRVEAEDVGVYYCMQATQLYTFGQGTKVEIK (SEQ ID NO: 39)

AP1-16  EVQLVQSGAEVKKPGASVKVSCKVSGYTLTELSMHWVRQAPGKGLEWMGGFDPEDGETISAQKFQGRVTMTEDTSTDTAYMDLSSLRSEDTAVYYC
        ATQRLCSGGRCYSHFDYWGQGTTVTVSSGGGGSGGGGSGGGGSETTLTQSPAIMSASPGERVTMTCSASSSIRYIYWYQQKPGSSPRLLIYDTSNV
        APGVPFRFSGSGSGTSYSLTINRMEAEDAATYYCQEWSGYPYTFGGGTKVEIK (SEQ ID NO: 40)

AP1-19  QMQLVQSGAEVKKPGSSVKVSCKASGGTFNTYVISWVRQAPGQGLEWMGWISAYNGNTNYAQKLQGRVTMTTDTSTSTAYMELRSLRSDDTAVYY
        CARVWSPLDYWGQGTLVTVSSGGGGSGGGGSGGGGSDIVMTQSPDSLAVSLGERATINCKSSQSVLYSSNNMNYLAWYQQKPGQPPKLLIYWAST
        RESGVPDRFSGSGSGTDFTLTISSLQAEDAAVYYCQQYYSTPPTFGQGTKLEIK (SEQ ID NO: 41)

AP3-1   QVQLVQSGAEVKKPGASVKVSCKGSGYTFTGYYMHWVPQAPGQGLEWMGWINPNNGGTNYDQKFQGRVAMTRDTSISTAYMELSRLRSDDTAVYY
        CARDNGRVTTGGYWGQGTLVTVSSGGGGSGGGGSSGGGSQSVLTQPPSLSGAPGQSVTISCAGTSSSIGAGYDVQWYQQLPGKTPKLLIYGNDNR
        PSGVPDRFSGSRSYTSASLVITRVQIEDEADYYCQSYDSSLIGPQFGGGTKLTVLG (SEQ ID NO: 42)

AP3-2   QVQLVQSGAEVKKPGESLKISCTASGYNFASYWIGWVRQMPGQGLEWMGIIYPGDSDTRYSPSFQGQVTISADKSISTAYLQWSSLKASDTATYY
        CVRRRVPLYTNNHYLDYWGQGTLVTVSSGGGGSGGGGSGGGGSAIQMTQSPSSLSASVGDRVTITCRASQGISNYLAWFQQKPGKAPKSLIYAASS
        LQSGVPSKYSGSGSGTDFTLTISSLQPEDFATYYCQQYKSYPLTFGGGTKVEIK (SEQ ID NO: 43)

AP3-3   EVQLVQSGAEVKKPGASVKVSCKASGYTFSDYFMHWVRQAPGQGLEWMGVINPTGGSTTYAQSFQGRVTMTRDTSTSIVMELSSLRSEDTAVYY
        CTRVGYYGMDVWGQGTLVTVSSGGGGSGGGGSGGGGSDIVMTQSPSSLSASVGDRVTITCRASQSTSRFLNWYQQKPGKAPKLLIYAASSLHSGV
        PSRFSGSGSGTDFTLTISSLQPEDFATYYCQQTSSYPLTFGGGTKVEIK (SEQ ID NO: 44)

AP3-5   QVQLVQSGGGVVQVGRSLRLSCAASGFTFTNFGMHWVRQAPGKGLEWVALISSDGYRQAYADSVKGRFTISGDNSKNTVYLQMNSLTSEDTAVYY
        CAIIPPVLRIFDWEFDYWGQGTLVTVSSGGGGSGGGGSSGGGSETTLTQSPGTLSLSPGERATLSCRASQSVSSPYLAWYQKPGQAPRLLIYGA
        SNRATGIPDRFSGSGSGTDFTLTISSLQAEDEAVYYCQQYNTPLTFGGGTKVEIK (SEQ ID NO: 45)

AP3-6   QVQLQQWGAGLLKPSETLSLTCAVYSGSFTRDYWGWIRQPPGKGLEWIGEINHSGSTNYNPSLKSRVTTSVDKSKNQFSLKLTSVTAADTAVYYC
        ARRRLSSDLFMRGVGGMDVWGQGTLVTVSSGGGGSGGGGSGGGGSDIVMTQTPGTLSSSPGERATLSCRASQGVSSNLAWYQQKPGQAPRLLIYD
        ASNRATGIPLRFSGSGSGTDFTLTISRLEPEDFAVYYCHQYGSSPYTFGQGTKVEIK (SEQ ID NO: 46)

AP3-8   EVQLVQSGAEVKKPGASVKVSCKASGYTFTSYGISWVRQASGQGLEWMGWISAYNGNTNYAQKLQGRVTMTTDTSTSTAYMELRSLRSDDTAVYY
        CARVPRYFDWLLYGSDYFDYWGQGTLVTVSSGGGGSGGGGSSGGGSDIQMTQSPSTLSVSVGDRVTITCRASQGISSWLAWYQQKPGKAPKLLIY
        AASSLQSGVPSRFSGSGSGTDFTLTISSLQPEDFATYYCQQANSFPLTFGGGTKLEIK (SEQ ID NO: 47)

AP3-10  QVQLVQSGAEVKEPGSSVKVSCKASGGTFSSYAIYWVRQAPGQGLEWMGWIIPILGIANYAQKFQGRVTITADKSTSTAYMELSSLRSEDTAVYYC
        ARAAGHSTNYYYYGMDVWGQGTLVTVSSGGGGSGGGGSSGGGSQTVVTQEPSLTVSLGGTVTLTCGSSTGAVTSGHYPYWFQQKPGQAPRTLIYDT
        SNKHSWTPARFSGSLLGGKAALTLSGAQPEDEAEYYCLLSYSGTRVFGGGTKLTVLG (SEQ ID NO: 48)

AP3-13  EVQLVQSGAEVKKPGASVKVSCKASGYTFTNYYMHWVRQAPGQGLEWMGIINPSGGSTSYAQKFQGRVTMTRDTSTSTVMELSSLRSEDTAVYY
        CARDFKEYSRTGYFDYWGQGTLVTVSSGGGGSGGGGSSGGGSSYELMQPSSVSVSPGQTARITCSGDVLAKKCARWFQQKPGQAPVLVIYKDSER
        PSGIPERFSGSSSGTTVTLTISGAQVEDEADYYCYSAADNNLGVFGGGTKVTVLG (SEQ ID NO: 49)

| Amino Acid Sequences of Human scFv Antibodies |
| --- |
| AP3-20 QITLKESGPALVKPTQTLTLTCNFSGFSLSTYGGGVGWLRQPPGKALEWLAVIYWSDGKRYSPSVKNRLTITKDTSKNHVVLTMTNMDPVDTATY<br>YCAHLMMDTSITTHWFDPWGQGTLVTVSSGGGGSGGGGSGGGGSAIRMTQSPSSLSASVGDRVTITCRASQGISNYLAWYQQKPGKVPKLLIYAA<br>STLQSGVPSRFSGSGSGTDFTLTISSLQPEDVATYYCQKYNSAPGTFGQGTKVEIK (SEQ ID NO: 50) |
| AP4-8 QVQLVQSGAEVKKPGSSVKVSCKASGYTFTNYFIHWVRQAPGQGLEWMGLLNPTDSGTLYAQNFQGRITMTSDTSTNTVYMELSSLRSDDTAMYY<br>CAREGGADTTRVHSSFDYWGQGTLVTVSSGGGGSGGGGSGGGGSQAVLTQPPSVSGSPGQSITISCTGTSSDVEAYNYVSWYQQHPGKAPKLMIY<br>DVSNRPSGVSNRFSGSKSGNTASLTISGLQAEDEADYYCSSYTSSRTWVFGGGTKVIVL (SEQ ID NO: 51) |
| AP4-14 QVQLQESGGGLVQPGRSLRLSCAASGFTEDDYALHWVRQAPGKGLEWVSGISWNSVTVKYAVSVKGRFTISRDNAKNSLFLQMNALRSEDTALYYC<br>AKARGALLEAADTPSDDWGQGTLVTVSSGGGGSGGGGSGGGGSDIVMTQSPSSLSASVGDRVTITCRASQSISSYLNWYQQKPGKAPKLLIYAASS<br>LQSGVPSRFSGSGSGTDFTLTISSLQPEDVATYYCQKYNSAPWTFGQGTKVDIK (SEQ ID NO: 52) |
| AP4-20 QVQLQQSGAGLLRPSETLSLTCGLYGGSFSGHYWNWIRQSPEKGLVWIGEITHSGTTNYNPSLKSRVITSVDTSKNQYSLKLSFVTPADTAVYYCA<br>RGDYYGYWYFDLWGRGTLVTVSSGGGGSGGGGSGGGGSQSVLTQPPSVPVAPGQKVTISCSGSSSNIGNNYVSWYQQLPGTAPKLLIYDTNKRPSG<br>IPDRFAGSKSGTSATLGITGLQTGDEADYYCGTWDSSLSAGVFGGGTKLTVL (SEQ ID NO: 53) |

| Nucleotide Sequences Encoding the Heavy and Light Chains of Human scFv Antibodies | | |
| --- | --- | --- |
| Antibody | Variable Heavy Chain | Variable Light Chain |
| AP1-2 | caggtgcagctggtgcagtctggagcagaggtgaaaaagcccgggga<br>gtctctgaggatctcctgcaaggggtctggatacagctttaccagcc<br>actggatcagctgggtgcgacagatgcccgggaaaggcctggagtgg<br>atggggaggattgatcctagtgactcttatagcaactacagcccctc<br>cttccaaggccacgtcatcatctcagttgacaagtccatcagcactg<br>cctacttgcagtggagcagcctgaaggcctcggacaccgcatatat<br>tactgtgcgagacagctcattgtagtagtaccagctgctccctatta<br>ctactactactacgatatggacgtctggggccaaggaaccctggtca<br>ccgtctcctca (SEQ ID NO: 163) | gaaattgtgttgacgcagtctccaggcaccctgtctttgtctccagg<br>ggaaagagccaccctctcctgcagggccagtcagactgttaacagct<br>acttagcctggtaccagcagaaacctggccaggctcccaggctcctc<br>atctatggtgcatccagcagggccactggcatcccagacaggttcag<br>tggcagtgggtctgggacagacttcactctcaccatcagcagactgg<br>agcctgaagattttgcagtgtattactgtcagcagtatggtagctca<br>catccgtggacgttcggccaagggaccaaggtggagatcaaacgtgg<br>cctcggggggcctggtcgactacaaagatgacgatgacaaa (SEQ ID NO: 73) |
| AP1-6 | caggttcagctggtgcagtctggggctgaggtgaagaagcctgggtc<br>ctcggtgaaggtctcctgcaaggcttctggaggcaccttcagcagct<br>atgctatcagctgggtgcgacaggcccctggacaagggcttgagtgg<br>atggggagggatcatccctatctttggtacagcaaaactacgcacagaa<br>gttccagggcagagtcacgattaccgcggacgaatccacgagcacag<br>cctacatggagctgagcagcctgagatctgaggacacggccgtgtat<br>tactgtgcgagagtctttggttccgagtcgcaagatccgtccgatat<br>ttggagtggttattacggtatggaagtctggggccaaggaaccctgg<br>tcaccgtctcctca (SEQ ID NO: 164) | gacatccagatgacccagtctccgtcttccgtgtctgcatctgtagg<br>agacagagtcaccatcacttgtcgggcgagtcagggtattagcagct<br>ggttagcctggtatcagcagaaacagggaaagccccctaagctcctg<br>atctatgctgcatccagtttgcaaagtagggtcccatcaaggttcag<br>cggcagtggatctgggacagattcactctcaccatcagcagcctgc<br>agcctgaagattttgcaacttactactgtcaacaggctaacagtttc<br>ccgtacacttttggccaggggaccaagctggagatcaaacgtggcct<br>cggggggcctggtcgactacaaagatgacgatgacaaa (SEQ ID NO: 74) |
| AP1-8 | caggtgcagctggtggagtctggggctgaggcgaagaagcctgggtc<br>ctcggtgaaggtctcctgcaaggcttctggaggcaccttcagcagct<br>atgctatcagctgggtgcgacaggcccctggacaagggcttgagtgg<br>atgggagggatcatccctatctttggtacagcaaaactacgcacagaa<br>gttccagggcagagtcacgattaccgcggacgaatccacgagcacag<br>cctacatggagctgagcagcctgagatctgaggacacggccgtgtat<br>tactgtgcgagagccggtataactggaactacggctcccccagacta<br>ctggggccagggcaccctggtcaccgtctcctca (SEQ ID NO: 165) | gtcatctggatgacccagtctccatcctccctgtctgcatctgtagg<br>agacagagtcaccatcacttgccgggcaagtcagagcattagcagct<br>atttaaattggtatcagcggaaaccagggaaagccccctaagctcctg<br>atctatgctgcatccagtttgcaaagtggggtcacatcaaggttcag<br>tggcagtggatctgggacagatttcactctcaccatcagcagtctgc<br>aacctgaagattttgcaacttactactgtcaacagagttacagtacc<br>cctccgacgttcggccaagggaccaagctggagatcaaa (SEQ ID NO: 75) |
| AP1-11 | caggtgcagctggtgcagtccggatctgagttaaagaagcctggggc<br>ctcagtgaagctttcctgcagggtctctggatacaccttcactagtt<br>attccatggttgggtgcgacaggcccctggacaaagggcttgagtgg<br>atgggaggatcaacaccaacactgggaacccaacgtatgcccaggg<br>cttcacagaacgtttgtcttctccttcgacagctctgtcagcacgg<br>catatctgcaaatcagcagcctcaaaggctgaggacactgccgtgtat<br>tactgtgcgagagattgggcgtatagcggcagctggcccttaggcca<br>gaaccctcctgaccactggggccagggcaccctggtcaccgtctcct<br>ca (SEQ ID NO: 166) | gaaatagtgatgacgcagtctccagccaccctgtctgtgtctccagg<br>ggaaagagccaccctctcctgcagggccagtcagagtgttagcgca<br>acttagcctggtaccagcagaaacctggccaggctcccaggctcctc<br>atctatgatacatccaccagggccactggtatcccagcaggttcag<br>tggcagtgggtctgggacagagttcactctcaccatcagcagcctgc<br>agtctgaagattctgcagtttattactgtcagcagtataatatctgg<br>cctccactcacttttcggcggagggaccaaggtggagatcaaa (SEQ ID NO: 76) |
| AP1-15 | caggtgcagctacagcagtggggcgcaggattgttgaagccttcgga<br>gaccctgtccctcacctgcgctgtctatggtgggtccttcagtggtt<br>actaccggacctggatccgccagtcccagtgaaggggctggagtgg<br>attggggaagtcaatgatcgtggaagccccaactacaacccgtcctt<br>caagagtcgactccaccatatcaatcgacacgtccaagaacttattat<br>ccctgaagttgagatttatgaccgcgcggacacggctgtatattcg<br>tgtgcgagaattaggcctaggtacggtatggacgtctggggccaggg<br>gacaatggtcaccgtctcctcaggcggcggcggctct (SEQ ID NO: 167) | Gatattgtgatgacccagactccactctcctcacctgtcacccttgg<br>acagccggcctccatctcctgcaggtctagtcaaagcctcgtacaca<br>gtgatggaaacacctacttgacttggtttcaccagaggccaggccag<br>cctccaagagtcctcattcataagtttctaacctgttctctggggt<br>cccagacagattcagtggcagtgggacagggacagattcactctga<br>aaatcagcagggtggaagctgaggatgtcggggtttattactgcatg<br>caagctacacaattgtacacttttggccaggggaccaaggtggaaat<br>caaa (SEQ ID NO: 77) |
| AP1-16 | gaggtccagctggtacagtctggggctgaggtgaagaagcctgggc<br>ctcagtgaaggtctcctgcaaggtttccggatacacctcactgaat | gaaacgacactcacgcagtctccagcaatcatgtctgcatctccagg<br>ggagagggtcaccatgacctgcagtgccagctcaagtatacgttaca |

Nucleotide Sequences Encoding the Heavy and Light Chains of
Human scFv Antibodies

| Antibody | Variable Heavy Chain | Variable Light Chain |
|---|---|---|
| | tatccatgcactgggtgcgacaggctcctggaaaagggcttgagtgg atgggaggttttgatcctgaagatggtgaaacaatctccgcgcagaa gttccagggcagagtcaccatgaccgaggacacatctacagacacag cctacatggatctgagcagcctgagatctgaggacacggccgtttat tactgtgcaacgcagcgcttgtgtagtggtggtcgctgctactccca ctttgactactggggccagggcaccacggtcaccgtctcctca (SEQ ID NO: 168) | tatattggtaccaacagaagcctggatcctcccccagactcctgatt tatgacacatccaacgtggctcctggagtccccttttcgcttcagtgg cagtgggtctgggacctcttattctctcacaatcaaccgaatggagg ctgaggatgctgccacttattactgccaggagtggagtggttatccg tacacgttcggaggggggaccaaggtggagatcaaa (SEQ ID NO: 78) |
| AP1-19 | cagatgcagctggtgcagtctggggctgaggtgaagaagcctgggtc ctcggtgaaggtctcctgcaaggcttctggaggcaccttcaacacct atgttatcagttgggtgcgacaggcccctggacaagggcttgagtgg atgggatggatcagcgcttacaatggtaacacaaactatgcacagaa gctccagggcagagtcaccatgaccacagacacatccacgagcacag cctacatggagctgagcagcctgagatctgacgacacggccgtgtat tactgtgcgagagtttggagtccccttgactactggggccagggcac cctggtcaccgtctcctca (SEQ ID NO: 169) | gacatcgtgatgacccagtctccagactcctggctgtgtctctggg cgagagggccaccatcaactgcaagtccagccagagtgttttataca gctccaacaatatgaactacttagcttggtaccagcagaaaccagga cagcctcctaagctgctcatttactgggcatctacccgggaatccgg ggtccctgaccgattcagtggcagcgggtctgggacagatttcactc tcaccatcagcagcctgcaggctgaagatgcggcagtttattactgt cagcagtattatagtactcctccgacgttcggccaagggaccaagct ggagatcaaa (SEQ ID NO: 79) |
| AP3-1 | caggtgcagctggtgcaatctggggctgaggtgaagaagcctgggc ctcagtgaaggtctcctgcaaggtttctggatacaccttcaccggct actatatgcactgggtgccacaggcccctggacaagggcttgagtgg atgggatggatcaacccaacaatggtggcacaaactatgaccagaa gtttcagggcagggtcgccatgaccaggacacgtccatctccacag cctacatggagctgagcaggctgagatctgacgacactgccgtgtat tactgtgcgagagataatggggagggtgaccacagggggctactgggg ccagggcaccctggtcaccgtctcctca (SEQ ID NO: 170) | cagtctgtgttgacgcagcctccctcattgtctggggccccgggaca gagtgtcaccatctcctgcgctgggaccagttccagcatcggggcag gttacgatgtacagtggtaccagcaattccaggaaaaaccccctaaa ctcctcatctacgggaatgataatcggccctcagggtcctgaccg attctctggatccaggtcttacacctcagcctccctggtcatcacta gagtccagattgaggatgaggctgattattactgccagtcgtatgac agcagtctcattggtcctcaattcggcggg (SEQ ID NO: 80) |
| AP3-2 | caggtgcagctggtgcaatctggggctgaggtgaaaaagcccgggga gtctctgaagatctcctgtacggcctccggatacaactttgccagct actggatcggctgggtgcgccagatgcccgggcaagggcctgagtgg atgggatggatcatctatcctggtgactctgataccagatacagtccgtc cttccaaggccaggtcaccatctcagccgacaagtccatcagcaccg cctacctgcagtggagcagcctgaaggcctcggacaccgccacgtat tactgtgtgagacgggtcccctctacactaacaaccactaccttga ctattggggccagggcaccctggtcaccgtctcctca (SEQ ID NO: 171) | gccatccagatgacccagtctccatcctcactgtctgcatctgtagg agacagagtcaccatcacttgtcgggcgagtcagggcattagcaatt atttagcttggtttcagcagaaacagggaaagcccctaagtcccctg atctatgctgcatccagtttgcaaagtggggtcccatcaaggtacag cggcagtggatctgggacagatttcactctcaccatcagcagcctgc agcctgaagattttgcaacttattactgccaacagtataagagttac ccccctcactttcggcggagggaccaaggtggagatcaaa (SEQ ID NO: 81) |
| AP3-3 | gaggtgcagctggtgcagtctggggctgaagtgaagaagcctgggc ctcagtgaaggtttcctgtaaggcatctggatacaccttcagcgact actttatgcactgggtgcgacaggcccctggacaagggcttgagtgg atgggagtaatcaaccaactggtggttccacaactacgcacagaa cttccagggcagagtcaccatgaccagagacacgtccacgagcatag tctacatggagctgagcagcctgagatctgaagacacggccgtgtac tactgtacgcgagtcggctactacggtatggacgtctggggccaagg caccctggtcaccgtctcctca (SEQ ID NO: 172) | gacatcgtgatgacccagtctccatccaccctgtctgcatctgtagg agacagagtcaccatcacttgccgggcaagtcagagcactagcaggt ttttaaaattggtatcagcagaaacctgggaaagcccctaaactcctg atctatgctgcatccagtttgcatagtggcgtcccatcaaggttcag tggcagtggatctgggacagatttcactctcaccatcagcagtctgc aacctgaagattttgcaacttactactgtcaacgactctccagttac cctctcactttcggcggagggaccaaggtggaaatcaaa (SEQ ID NO: 82) |
| AP3-5 | caggtccagctggtacagtctggggaggcgtggtccaggttgggag gtccctgagacttttcctgtgcggcctctggattcaccttcacaaact ttggcatgcactgggtccgccaggctccaggcaaggggctggagtgg gtggcactcatctcatctgatggatatagacaggcctatgcagactc cgtgaagggccggttcaccatctccggagacaactccaagaacacg tgtatctgcaaatgaacagcctgacaagtgaggacacggctgtttat tactgtgccatcatacccctgtattacggattttttgattgggaatt tgactactggggccagggaaccctggtcaccgtctcctca (SEQ ID NO: 173) | gaaacgacactcacgcagtctccaggcaccctgtctttgtctccagg ggaaagagccaccctctcctgcagggccagtcagagtgtttccagcc cctacttagcctggtaccagcagaaacctggccaggctcccaggctc ctcatttatggtgcatctaacagggccactggcatcccagacaggtt cagtggcagtgggtctgggacagacttcactctcaccatcagcagcc tgcaggctgaagatgaggcagtttattactgtcagcaatactacaat actccgctcactttcggcggagggaccaaggtggaaatcaaa (SEQ ID NO: 83) |
| AP3-6 | caggtgcagctacagcagtggggcgcaggcctgttgaagccttcgga gaccctgtccctcacctgcgctgtctatagtgggtcttttactcgtg actactggggctggatccgccagccccccgggaaggggctggagtgg attggggaaatcaatcatagtggaagcaccaactacaacccgtccct caagagtcgagtcaccacgtcggtagacaagtccaagaatcagttct ccctgaagttgacctctgtgaccgccgcggacacggccgtctattac tgtgcgagacgccggcttttctagcgacctcttcatgcggggggttgg cggtatgacgctctggggccaagggcaccctggtcaccgtctcctca (SEQ ID NO: 174) | gatattgtgatgacccagactccaggcaccctgtcttcgtctccagg ggaaagagccaccctctcctgcagggccagtcagggtgttagcagca acttagcctggtaccagcagaaacctggccaggctcccaggctcctc atctatgatgcatccaacagggccactggcatcccactcaggttcag tggcagtgggtctgggacagacttcactctcaccatcagcagactgg aacctgaagattttgcagtgtattactgtcaccagtatggtagtca ccgtacaccttggccagggaccaaggtggaaatcaaa (SEQ ID NO: 84) |
| AP3-8 | gaggtgcagctggtgcagtctggagctgaggtgaagaagcctgggc ctcagtgaaggtctcctgcaaggcttctggttacaccttaccagct atggtatcagctgggtgcgacaggcctctggacaagggcttgagtgg atgggatggatcagcgcttacaatggtaacacaaactatgcacagaa gctccagggcagagtcaccatgaccacagacacatccacgagcacag cctacatggagctgagcagcctgagatctgacgacacggccgtgtat | gaccatccagatgacccagtctcttccaccctgtctgtatctgtagg agacagagtcaccatcacttgtcgggcgagtcagggtattagcagct ggttagcctggtatcagcagaaacagggaaagcccctaagctcctg atctatgctgcatccagtttgcaaagtggggtcccatcaaggttcag cggcagtggatctgggacagatttcactctcactatcagcagcctgc agcctgaagattttgcaacttactattgtcaacaggctaacagtttc |

Nucleotide Sequences Encoding the Heavy and Light Chains of Human scFv Antibodies

| Antibody | Variable Heavy Chain | Variable Light Chain |
|---|---|---|
| | tactgtgcgagagtaccccgatattttgactggttattatacgggag cgactactttgactactggggccagggaaccctggtcaccgtctcct ca (SEQ ID NO: 175) | ccgctcactttcggcggagggaccaagctggagatcaaa (SEQ ID NO: 85) |
| AP3-10 | caggtgcagctggtgcaatctggagctgaggtgaaggagcctgggtc ctcggtgaaggtctcctgcaaggcttctggaggcaccttcagcagct atgctatctactgggtgcgacaggcccctggacaagggcttgagtgg atgggatggatcatccctatccttggtatagcaaactacgcacagaa gttccagggcagagtcacgattaccgcggacaaatccacgagcacag cctacatggagctgagcagcctgagatctgaggacacggccgtgtat tactgtgcgagagctgccggtcatagtactaactactactactacgg tatggacgtctgggggccaagcaccctggtcaccgtctcctca (SEQ ID NO: 176) | cagactgtggtgacccaggagccctcactgactgtgtccctaggagg gacagtcactctcacctgtggctccagcactggagctgtcaccagtg gtcattatccctactggttccagcagaagcctggccaagcccccagg aacactgatttatgatacaagcaacaaacactcctggacccctgcccg gttctcaggctccctcctgggggcaaagtgccctgacccttcgg gtgcgcagcctgaggatgaggctgagtattactgcttgctctcctat agtggtactcgggtgttcggcggagggaccaagctgaccgtccta (SEQ ID NO: 86) |
| AP3-13 | gaggtgcagctggtgcagtctggggctgaggtgaagaagcctggggc ctcagtgaaggtttcctgcaaggcatctggatacaccttcaccaact actatatgcactgggtgcgacaggcccctggacaagggcttgagtgg atgggaataatcaaccctagtggtggtagcacaagctacgcacagaa gttccagggcagagtcaccatgactaggacacgtccacgagcacag tctacatggagctgagcagcctgagatctgaggacacggccgtgtat tactgtgcgagagattttcaaagagtatagccgtacgggctactttga ctactggggccagggcaccctggtcaccgtctcctca (SEQ ID NO: 177) | tcctatgagctgatgcagccatcctcagtgtcagtgtctccgggaca gacagccaggatcacctgctcaggagatgtactggcaaaaaatgtg g ctcggtggttccagcagaagccaggccaggcccctgctggtgatt tataaagacagtgagcggccctcagggatccctgagcgattctccgg ctccagctcagggaccacagtcaccttgaccatcagcggggcccagg ttgaggatgaggctgactattactgttactctgcggctgacaacaac ctgggggtgttcggcggagggaccaagctcaccgtccta (SEQ ID NO: 87) |
| AP3-20 | cagatcaccttgaaggagtctggtcctgcgctggtgaaacccacaca gaccctcacgctgacctgcaacttctctgggttctcccctcagcactt atggaggggtgtgggctggctccgtcagccccaggaaaggccctg gagtggcttgccgtcatttattggagtgatggtaaacgctacagcc ctctgtaaagaaccggctcaccatcaccaaggacacctccaaaaacc acgtggtcctgacaatgaccaacatgaccctgtggacacagccacc tattattgtgcacaccttatgatggatacatctattactacccactg gttcgaccccgggggccagggaaccctggtcaccgtctcctca (SEQ ID NO: 178) | gccatccggatgacccagtctccatcctccctgtctgcatctgtagg agacagagtcaccatcacttgccgggcgagtcagggcattagcaatt atttagcctggtatcagcagaaaccagggaaagttcctaagctcctg atctatgctgcatccactttgcaatcaggggtcccatctcggttcag cggcagtggatctgggacagatttcactctcaccatcagcagcctg cagcctgaagatgttgcaacttattactgtcaaaagtataacagtgcc cctgggacgttcggccaagggaccaaggtggagatcaaa (SEQ ID NO: 88) |
| AP4-8 | caggtgcagctggtgcaatctggggctgaggtgaagaagcctgggtc ctcggtgaaggtttcctgcaaggcatctggatacaccttcaccaact actttatacactgggtgcgacaggcccctggacaagggcttgagtgg atgggactactcaaccctactgatagtggcacactctacgcacagaa cttccagggcagaatcaccatgaccagtgacacgtccacaaacacag tctacatggagctgagcagcctgagatctgacgacacggccatgtat tactgtgcaagagagggggggccgacactacccgggtccactcttc gtttgactactggggccagggaaccctggtcaccgtctcctca (SEQ ID NO: 179) | caggctgtgctgactcagccgccttccgtgtcggggtctcctggaca gtcgatcaccatctcctgcactggaaccagcagtgacgttgaagctt acaactatgtctcctggtatcaacaacacccaggcaaagccccccaaa ctcatgatttatgtgtcagtaatcggccctcaggggttctaatcg cttctctggctccaagtctggcaacacggcctcctgaccatctctg ggctccaggctgaggacgaggctgattattactgcagctcatataca agcagcagcacttgggtgttcggcggagggaccaaggtcatcgtcct a (SEQ ID NO: 89) |
| AP4-14 | caggtgcagctgcaggagtcggggggaggcttggtacagcctggcag gtccctgagactctcctgtgcagcctctggattcacctttgatgatt atgccctccactgggtccggcaagctccagggaagggcctggagtgg gtctcaggtattagttggaatagtgttaccgtaaagtatgcggtctc tgtgaagggccggttcaccatctccagagacaacgccaagaactcc tgtttctgcaaatgaacgctctgagatctgaggacacggccttatat tactgtgcaaaagccagagggcccttagaagcagctgacacacc atctgacgactggggccagggcaccctggtcaccgtctcctca (SEQ ID NO: 180) | gacatcgtgatgacccagtctccgtcctccctgtctgcatctgtagg agacagagtcaccatcacttgccgggcaagtcagagcattagcagct atttaaattggtatcagcagaaaccagggaaagcccctaagctcctg atctatgctgcatccagtttgcaaagtggggtcccatcaaggttcag tggcagtggatctgggacagatttcactctcaccatcagcagcctgc agcctgaagatgttgcaacttattactgtcaaaagtataacagtgcc cgtggacgttcggccaagggaccaaagtggatatcaaa (SEQ ID NO: 90) |
| AP4-20 | caggtacagctgcagcagtcaggcgcaggtctattgaggcttcgga gaccctgtcctcacctgcggtctctatggtgggtccttcagtggtc actattggaactggatccgccagtcccagaaaaggggctggtgtgg attgggggaaatcactcatagtggaaccaccaattacaacccgtccct caagagtcgagtcatcacatcagtagacacgtccaagaatcagtact ccctgaagctgagctttgtgaccctgcgcacacggccgtgattac tgtgcgagaggtgattactatgggtactggtacttcgatctctgggg ccgtggcaccctggtcaccgtctcctca (SEQ ID NO: 181) | cagtctgtgttgacgcagccgccctcagttcctgtggccccaggaca gaaggtcaccatctcctgctctggaagcagctccaacattgggaata attatgtatcctggtaccagcagctcccaggaacagcccccaaactc ctcatttatgacactaataagcgaccctcagggattcctgaccgatt cgctggctccaagtctggcacgtcagccaccctgggcatcaccggac ccctgaagctgagctttgtgaccctgcgcacacggccgtattac tccagactggggacgaggccgattattactgcggaacatgggatagc agctgagtgctggcgtgttcggcggagggaccaagctgaccgtccta (SEQ ID NO: 91) |

Nucleic Acids Encoding the Human scFvs

| Antibody | Variable Heavy Chain |
|---|---|
| AP1-2 | caggtgcagctggtgcagtctggagcagaggtgaaaaagcccggggagtctctgaggatctcctgcaagggttctggatacagctttaccagcc actggatcagctgggtgcgccagatgcccgggaaaggcctggagtggatggggaggattgatcctagtgactcttatagcaactacagcccctc cttccaaggccacgtcatcatctcagttgacaagtccatcagcactgcctacttgcagtggagcagcctgaaggcctcggacaccgccatatat |

Nucleic Acids Encoding the Human scFvs

Antibody Variable Heavy Chain

```
           tactgtgcgagacagctcattgtagtagtaccagctgctcccctattactactactacggtatggacgtctggggccaaggaaccctggtca
           ccgtctcctcaggcggcggcggctctggcggaggtggcagcagcggtggcggatccgaaattgtgttgacgcagtctccaggcaccctgtctt
           gtctccaggggaaagagccaccctctcctgcagggccagtcagactgttaacagctacttagcctggtaccagtagaaacctggccaggctccc
           aggctcctcatctatggtgcatccagcagggccactggcatcccagacaggttcagtggcagtgggtctgggacagacttcactctcaccatca
           gcagactggagcctgaagattttgcagtgtattactgtcagcagatggtagctcacatccgtggacgttcggccaagggaccaaggtggagat
           caaacgtggcctcgggggcctggtcgactacaaagatgacgatgacaaa (SEQ ID NO: 54)
```

AP1-6
```
           caggttcagctggtgcagtctggggctgaggtgaagaagcctgggtcctcggtgaaggtctcctgcaaggcttctggaggcaccttcagcagct
           atgctatcagctgggtgcgacaggcccctggacaagggcttgagtggatgggagggatcatccctatctttggtacagcaaactacgcacagaa
           gttccagggcagagtcacgattaccgcgacgaatccacgagcacagcctacatggagctgagcagcctgagatctgaggacacggccatatat
           tactgtgcgagagtctttggttccgagtcgcaagatccgtccgatatttggagtggttattacggtatggaagtctggggccaaggaaccctgg
           tcaccgtctcctcaggcggtggcggctctggcggaggtggcagcggcggtggcggatccgacatccagatgacccagtctccgtcttccgtgtc
           tgcatctgtaggagacagagtcaccatcacttgtcgggcgagtcagggtattagcagctggttagcctggtatcagcagaaaccagggaaagcc
           cctaagctcctgatctatgctgcatccagtttgcaaagtaggggtcccatcaaggttcagcggcagtggatctgggacagatttcactctcacca
           tcagcagcctgcagcctgaagattttgcaacttactattgtcaacaggtaacagtttcccgtacacttttggccaggggaccaagctggagat
           caaacgtggcctcgggggcctggtcgactacaaagatgacgatgacaaa (SEQ ID NO: 55)
```

AP1-8
```
           caggtgcagctggtggagtctggggctgaggcgaagaagcctgggtcctcggtgaaggtctcctgcaaggcttctggaggcaccttcagcagct
           atgctatcagctgggtgcgacaggcccctggacaagggcttgagtggatgggagggatcatccctatctttggtacagcaaactacgcacagaa
           gttccagggcagagtcacgattaccgcggacgaatccacgagcacagcctacatggagctgagcagcctgagatctgaggcacggccgtgtat
           tactgtgcgagagccggtataactggaactacggctcccccagactactggggccagggcaccctggtcaccgtctcctcaggcggcggcggct
           ccggcggaggtggcagcggcggtggcggatccgtcatctgatgacccagtctccatcctccctgtctgcatctgtaggagacagagtcaccat
           cacttgtgccgggcaagtcagagcattagcagctatttaaattggtatcagcggaaaccagggaaagcccctaagtcctgatctatgctgcatcc
           agtttgcaaagtggggtcacatcaaggttcagtggcagtggatctgggacagatttcactctcaccatcagcagtctgcaacctgaagattttg
           caacttactactgtcaacagagttacagtacccctccgacgttcggccaagggaccaagctggagatcaaa (SEQ ID NO: 56)
```

AP1-11
```
           caggtgcagctggtgcagtccggatctgagttaaagaagcctggggcctcagtgaagctttcctgcagggcttctggatacacattcactagtt
           attccatggtttgggtgcgacaggcccctggagaagggcttgagtggatgggagggatcaacaccaacactgggaacccaacgtatgcccaggg
           cttcacagaacggtttgtcttctccttcgacagctctgtcagcacggcatatctgcaaatcagcagcctaaaggctgaggacactgccgtgtat
           tactgtgcgagagattgggcgtataacggcagctggcccttaggccagaaccctctgaccactggggccagggcaccctggtcaccgtctcct
           caggcggcggcggctctggcggaggtggcagcggcggtggcggatccgaaatagtgatgacgcagtctccagccaccctgtctgtgtctccagg
           ggaaagagccaccctctcctgcagggccagtcagagtgttagcgcaacttagcctggtaccagcagaaacctggccaggctcccaggctcctc
           atctatgatacatccaccagggccactggtatcccagccaggttcagtggcagtgggtctgggacagattcactctcaccatcagcagcctgc
           agtctgaagattctgcagtttattactgtcagcagtataatatctggcctccactcactttcggcggagggaccaaggtggagatcaaacgtgg
           cctcgggggcctggtcgactacaaagatgacgatgacaaa (SEQ ID NO: 57)
```

AP1-15
```
           caggtgcagctacagcagtggggcgcaggattgttgaagccttcggagaccctgtccctcacctgcgctgtctatggtgggtccttcagtggtt
           actaccggacctggatccgccagtccccagtgaaggggctggagtggattggggaagtcaatgatcgtggaagcccaactacaacccgtcctt
           caagagtcgactcaccatatcaatcgacacgtccaagaactagttatccccaagtttgagatttatgaccgccgcggacacgctgtatattcg
           tgtgcgagaattaggcctaggtacggtatggacgtctgggggccagggacaatggtcaccgtctcctcaggcggcggcggctctggcggaggtg
           gcagcagcggtggcggatccgatattgtgatgacccagactccactctcctcacctgtcacccttggacagccggcctccatcctgcaggtc
           tagtcaaagcctcgtacacagtgatggaaacacctactgacttggtttcaccagaggccaggccagcctccaagagtcctcattcataaggtt
           tctaacctgttctctgggtcccagacagattcagtggcagtggggcagggacagattcacactgaaaatcagcagggtggaagctgaggatg
           tcgggtttattactgcatgcaagctacacaattgtacactttggccaggggaccaaggtggaaatcaaacgtggcctcgggggcctggtcga
           ctacaaagatgacgatgacaaa (SEQ ID NO: 58)
```

AP1-16
```
           gaggtccagctggtacagtctggggctgaggtgaagaagcctggggcctcagtgaaggtctcctgcaaggtttccggatacaccctcactgaat
           tatccatgcactgggtgcgacaggctcctggaaaagggcttgagtggatgggaggttttgatcctgaagatggtgaaacaatctccgcgcagaa
           gttccagggcagagtcaccatgaccgaggacacatctacagacacagcctacatggatctgagcagcctgagatctgaggcacggccgttat
           tactgtgcaacgcagcgcttgtgtagtggtggtcgctgctactcccactttgactactggggccagggcaccacggtcaccgtctcctcaggcg
           gcggcggctctggcggaggtggcggcggcggtggcggatccgaaacagacactcagcagtctccagcaatcatgtctgcatctccaggggagg
           ggtcaccatgacctgcagtgccagctcaagtatacgttacatatattggtaccaacagaagcctggatcctcccccagactcctgatttatgac
           acatccaacgtggctcctggagtcccttttcgcttcagtggcagtgggtctgggacctcttattctctcacaatcaaccgaatggaggctgagg
           atgctgccacttattactgccaggagtggagtggttatccgtacacgttcggaggggggaccaaggtggagatcaaa (SEQ ID NO: 59)
```

AP1-19
```
           cagatgcagctggtgcagtctggggctgaggtgaagaagcctgggtcctcggtgaaggtctcctgcaaggcttctggaggcaccttcaacacct
           atgttatcagttgggtgcgacaggcccctggacaagggcttgagtggatgggatggatcagcgcttacaatggtaacacaaactatgcacagaa
           gctccaggggcagagtcaccatgaccacagacacatccacgagcacagcctacatggagctgaggagcctgagatctgacgacacggccgtgtat
           tactgtgcgagagtttggagtccccttgactactggggccagggcaccctggtcaccgtctcctcaggcggcggtggctctggcggaggtggca
           gcggcggtggcggatccgacatcgtgatgacccagtctccactccctccctgtgtctctgggcgagagggccaccatcaactgcaagtccag
           ccagagtgttttatacagctccaacaatatgaactacttagcttggtaccagcagaaaccaggacagcctcctaagctgctcatttactgggca
           tctacccgggaatccggggtccctgaccgattcagtggcagcgggtctgggacagatttcactctcaccatcagcagcctgcaggctgaagatg
           cggcagtttattactgtcagcagtattatagtactcctccgacgttcggccaagggaccaagctggagatcaaacgtggcctcgggggcctggt
           cgactacaaagatgacgatgacaaa (SEQ ID NO: 60)
```

AP3-1
```
           caggtgcagctggtgcaatctggggctgaggtgaagaagcctggggcctcagtgaagggtctcctgcaagggttctggatacacccttcaccggct
           actatatgcactgggtgccacaggcccctggacaagggcttgagtggatgggatggatcaaccctaacaatggtggcacaaactatgaccagaa
           gtttcagggcagggtcgccatgaccagggacacgtccatctccacagcctacatggagctgagcaggctgagatctgacgacactgccgtgtat
           tactgtgcgagagataatgggagggtgaccacagggggctactggggccagggcaccctggtcaccgtctcctcaggcggcggcggctctggcg
           gaggtggcagcagcggtggcggatccgtatgtgtgttgacgcagcctcccttcattgtctgggccccgggacagagtgtccaccatctctgcg
           tgggaccagttccagcatcggggcaggttacgatgtacagtggtaccaacaacttccaggaaaaccccaaactcctcatcacgggaatgat
           aatcggccctcaggggtccctgaccgattctctggatccaggtcttacacctcagcctccctggtcatcactagagtccagattgaggatgagg
           ctgattattactgccagtcgtatgacagcagtctcattggtcctcaattcggcggggggaccaagctgaccgtcctaggtggcctcgggggcct
           ggtcgactacaaagatgaccatgacaaatac (SEQ ID NO: 61)
```

-continued

Nucleic Acids Encoding the Human scFvs

Antibody Variable Heavy Chain

AP3-2 caggtgcagctggtgcaatctggggctgaggtgaaaaagcccgggggagtctctgaagatctcctgtacggcctccggatacaactttgccagct
actggatcggctgggtgcgccagatgcccgggcaaggcctggagtggatggggatcatctatcctggtgactctgataccagatacagtccgtc
cttccaaggccaggtcaccatctcagccgacaagtccatcagcaccgcctacctgcagtggagcagcctgaaggcctcggacaccgccacgtat
tactgtgtgagacgggtcccctctacactaacaaccactaccttgactattggggccagggcaccctggtcaccgtctcctcaggcggcggcg
gctctggcggaggtggcagcggcggtggcggatccgccatccagatgacccagtctccatcctcactgtctgcatctgtaggagacagagtcac
catcacttgtcgggcgagtcagggcattagcaattatttagcctggtttcagcagaaaccagggaaagccccctaagtcsctgatctatgctgca
tccagtttgcaaagtggggtcccatcaaagtacagcggcagtggatctgggacagatttcactctcaccatcagcagcctgcagcctgaagatt
ttgcaacttattactgccaacagtataagagttaccccctcactttcggcggagggaccaaggtggagatcaaa (SEQ ID NO: 62)

AP3-3 gaggtgcagctggtgcagtctggggctgaagtgaagaagcctggggcctcagtgaagggttcctgtaaggcatctggatacaccttcagcgact
actttatgcactgggtgcgacaggcccctggacaagggcttgagtggatggagtaatcaacccaactggtggttccacaacctacgcacagag
cttccagggcagagtcaccatgaccagagacacgtccacgagcatagtctacatggagctgagcagcctgagatctgaagacacggccgtgtac
tactgtacgcgagtcggctactacggtatggacgtctggggccaagggaccctggtcaccgtctcctcaggcggcggcggctctggcggaggtg
gcagcggcggtggcggatccgacatcgtgatgacccagtctccatccaccctgtctgcatctgtaggagacagagtcaccatcacttgccggtc
aagtcagagcactagcaggttttttaaattggtatcagcagaaacctgggaaagcccctaaactcctgatctatgctgcatccagtttgcatagt
ggcgtcccatcaaggttcagtggcagtggatctgggacagatttcactctcaccatcagcagtctgcaacctgaagattttgcaacttactact
gtcaacagacttccagttaccctctcactttcggcggagggaccaaggtggaaatcaaacgtggcctcgggggcctggtcgactacaaagatga
cgatgacaaa (SEQ ID NO: 63)

AP3-5 caggtccagctggtacagtctggggggaggcgtggtccaggttggggaggtccctgagactttcctgtgcggcctctggattcaccttcacaaact
ttggcatgcactgggtccgccaggctccaggcaaggggctggagtgggtggcactcatctcatctgatggatatagacaggcctatgcagactc
cgtgaagggccggttcaccatctccggagacaactccaagaacacagtgtatctgcaaatgaacagcctgacaagtgaggacacggctgtttat
tactgtgccatcatacccctgtattacggattttttgattggaatttgactactggggccagggaaccctggtcaccgtctcctcaggcggcg
gcggctctggcggaggtggcagcggcggtggcggatccgaaacgacactcacgcagtctccaggcaccctgtctttgtctccaggggaaagagc
caccctctcctgcagggccagtcagagtgtttccagcccctacttagcctggtaccagcagaaacctggccaggctcccaggctcctcatttat
ggtgcatctaacagggccactggcatcccactcaggttcagtggcagtgggtctgggacagacttcactctcaccatcagcagcctgcaggctg
aagatgaggcagtttattactgtcagcaatactacaatactccgctcactttcggcggagggaccaaggtggaaatcaaacgtggcctcggggg
cctggtcgactacaaagatgacgatgacaaa (SEQ ID NO: 64)

AP3-6 caggtgcagctacagcagtggggcgcaggcctgttgaagccttcggagaccctgtccctcacctgcgctgtctatagtgggtcttttactcgtg
actactgggctggatccgccagcccccgggaaggggctggagtggattgggaaatcaatcatagtggaagcaccaactacaacccgtccct
caagagtcgagtcaccacgtcggtagacaagtccaagaatcagttctccctgaagttgacctctgtgaccgccgcggacacggctgtctattac
tgtgcgagacgccggctttctagcgacctcttcatgcggggggttggcggtatggacgtctggggccaaggcacccctggtcaccgtctcctcag
gcggcggcggctctggcggaggtggcagcggcggtggcggatctgatattgtgatgacccagactccaggcaccctgtcttcgtctccagggga
aagagccaccctctcctgcagggccagtcagggtgttagcaacttagcctggtaccagcagaaacctggccaggctcccaggctcctcatc
tatgatgcatccaacagggccactggcatcccactcaggttcagtggcagtgggtctgggacagacttcactctcaccatcagcagactggaac
ctgaagattttgcagtgtattactgtcaccagtatggtagctcaccgtacacctttggccaggggaccaagctggagatcaaacgtggcctcgg
gggcctggtcgactacaaagatgacgatgacaaa (SEQ ID NO: 65)

AP3-8 gaggtgcagctggtgcagtctggagctgaggtgaagaagcctggggcctcagtgaaggtctcctgcaaggcttctggttacacctttaccagct
atggtatcagctgggtgcgacaggcctctggacaagggcttgagtggatgggatggatcagcgcttacaatggtaacacaaactatgcacagaa
gctccagggcagagtcaccatgaccacagacacatccacgagcacagcctacatggagctgaggagcctgagatctgacgacacggccgtgtat
tactgtgcgagatccccgatattttgactggttattatacgggaagatacttttgactactgggggccagggaaccctggtcaccgtctcct
caggcggcggcggctctggcggaggtggcagcagcggtggcggatccgacatccagatgacccagtctcctccaccctgtctgtatctgtagg
agacagagtcaccatcacttgtcgggcgagtcagggtattagcagctggttagcctggtatcagcagaaaccagggaaagcccctaagtcctg
atctatgctgcatccagtttgcaaagtggggtcccatcaaggttcagcggcagtggatctgggacagatttcactctcactatcagcagcctgc
agcctgaagattttgcaacttactattgtcaacaggctaacagtttcccgctcactttcggcggagggaccaagctggagatcaaacgtggcct
cgggggcctggtcgactacaaagatgacgatgacaaa (SEQ ID NO: 66)

AP3-10 caggtgcagctggtgcaatctggagctgaggtgaaggagcctgggtcctcggtgaaggtctcctgcaaggcttctggaggcaccttcagcagct
atgctatctactgggtgcgacaggcccctggacaagggcttgagtggatgggatggatcatccctatccttggtatagcaaactacgcacagaa
gttccagggcagagtcacgattaccgcggacaaatccacgcacgacacagcctatggagctgagcagcctgagatctgaggacacggccgtgtat
tactgtgcgagagctgccggtcatagtactaactactactactacggtatggacgtctgggggccaaggcaccctggtcaccgtctcctcaggcg
gcggcggctctggcggaggtggcagcagcggtggcggatcccagactgtggtgacccaggagccctcactgactgtgtcctaggagggacagt
cactctcacctgtggctccagcactggagctgtcaccagtggtcattatccctactggttccagcagaagcctggccaagcccccaggacactg
atttatgatacaagcaacaaacactcctggaccctgccggttctcaggctccctccttggggcaaagctgcctgacccttcgggtgcgc
agcctgaggatgaggctgagtattactgcttgctctcctatagtggtactcgggtgttcggcggagggaccaagctgaccgtcctaggt (SEQ
ID NO: 67)

AP3-13 gaggtgcagctggtgcagtctggggctgaggtgaagaagcctggggcctcagtgaagtttcctgcaaggcatctggatacaccttcaccaact
actatatgcactgggtgcgacaggcccctggacaagggcttgagtggatgggaataatcaaccctagtggtggtagcacaagctacgcacagaa
gttccagggcagagtcaccatgactagggacacgtccacgagcacagtctcatggagctgagcagcctgagatctgaggacacggccgtgtat
tactgtgcgagagatttcaaagagtatagccgtacgggctactttgactactggggccagggcaccctggtcaccgtctcctcaggcggcggcg
gctctggcggaggtggcagcagcggtggcggatcctcctgagctgatgcagccatcctcagtgtcagtgtctccgggacagacagcaggat
cacctgctcaggagatgtactgcaaaaaaatgtgctcggtggttcagcagaagccaggccaggcccctgtgctggtgattatataagacagt
gagcggccctcagggatccctgagcgattctccggctccagctcaggaccacagtcaccttgaccatcagcggggccaggttgaggatgagg
ctgactattactgttactctgcggctgacaacaacctggggggtgttcggcggagggaccaaggtcaccgtcctaggt (SEQ ID NO: 68)

AP3-20 cagatcaccttgaaggagtctggtcctgcgctggtgaaacccacacagaccctcacgctgacctgcaacttctctgggttctccctcagcactt
atgagggggtgtggctggtccgtcagcccccaggaaaggccctggagtggcttgccgtcatttattggagtgatgataaacgctacagccc
ctctgtaaagaaccggctcaccatcaccaaggacacctccaaaaaccacggtggtcctgacaatgaccaacatgaccctgtggacacagccacc
tattattgtgcacacctttatgatggatacatctattactacccactggttcgacccctggggccagggaaccctggtcaccgtctcctcaggcg
gcggcggctctggcggaggtggcagcggcggtggcggatccgccatccggatgacccagtctccatcctccctgtctgcatctgtaggagacag
agtcaccatcacttgccgggcgagtcagggcattagcaattatttagcctggtatcagcagaaaccagggaaagttcctaagctcctgatctat
gctgcatccactttgcaatcagggggtcccatctcggttcagcggcagtggatctgggacagatttcactctcaccatcagcagcctgcagcctg -continued Nucleic Acids Encoding the Human scFvs Antibody Variable Heavy Chain

```
            aagatgttgcaacttattactgtcaaaagtataacagtgccccctgggacgttcggccaagggaccaaggtggagatcaaacgtggcctcggggg
            cctggtcgactacaaagatgacgatgacaaa (SEQ ID NO: 69)

AP4-8       caggtgcagctggtgcaatctggggctgaggtgaagaagcctgggtcctcggtgaaggtttcctgcaaggcatctggatacaccttcaccaact
            actttatacactgggtgcgacaggcccctggacaagggcttgagtggatgggactactcaaccctactgatagtggcacactctacgcacagaa
            cttccagggcagaatcaccatgaccagtgacacgtccacaaacacagtctacatggagctgagcagcctgagatctgacgacacggccatgtat
            tactgtgcaagagagggggggccgacactacccgggtccactcttcgtttgactactggggccagggaaccctggtcaccgtctcctcaggcg
            gcggcggctctggcggaggtggcagcagcggtggcggatcccaggctgtgctgactcagccgccttccgtgtcggggtctcctggacagtcgat
            caccatctcctgcactggaaccagcagtgacgttgaagcttacaactatgtctcctggtatcaacaacacccaggcaaagcccccaaactcatg
            atttatgatgtcagtaatcggccctcagggggtttctaatcgcttctctggctccaagtctggcaacacggcctccctgaccatctctgggctcc
            aggctgaggacgaggctgattattactgcagctcatatacaagcagcagcacttgggtgttcggcggagggaccaaggtcatcgtccta (SEQ
            ID NO: 70)

AP4-14      caggtgcagctgcaggagtcgggggggaggcttggtacagcctggcaggtccctgagactctcctgtgcagcctctggattcacctttgatgatt
            atgccctccactgggtccggcaagctccagggaagggcctggagtgggtctcaggtattagttggaatagtgttaccgtaaagtatgcggtctc
            tgtgaagggccggttcaccatctccagagacaacgccaagaactccctgtttctgcaaatgaacgctctgagatctgaggacacggccttatat
            tactgtgcaaaagccagaggggccctcttagaagcagctgacacaccatctgacgactgggggccagggcaccctggtcaccgtctcctcaggcg
            gcggcggctctggcggaggtggcagcagcggtggcggatccgacatcgtgatgacccagtctccgtcctccctgtctgcatctgtaggagacag
            agtcaccatcacttgccgggcaagtcagagcattagcgactctatttaaattggtatcagcagaaaccagggaaagcccctaagctcctgatctat
            gctgcatccagtttgcaaagtggggtcccatcaaggttcagtggcagtggatctgggacagatttcactctcaccatcagcagcctgcagcctg
            aagatgttgcaacttattactgtcaaaagtataacagtgccccgtggacgttcggccaagggaccaaagtggatatcaaa (SEQ ID NO:
            71)

AP4-20      caggtacagctgcagcagtcaggcgcaggtctattgaggccttcggagaccctgtccctcacctgcggtctctatggtgggtccttcagtggtc
            actattggaactggatccgccagtccccagaaaaggggctggtgtggattggggaaatcactcatagtggaaccaccaattacaacccgtccct
            caagagtcgagtcatcacatcagtagacacgtccaagaatcagtactccctgaagctgagcttttgtgaccctgcggacacggccgtgtattac
            tgtgcgagaggtgattactatgggtactggtacttcgatctctggggccgtggcaccctggtcaccgtctcctcaggcggcggcggctctggcg
            gaggtggcagcggcggtggcggatcccagtctgtgttgacgcagccgccctcagttcctgtggccccaggacagaaggtcaccatctcctgctc
            tggaagcagctccaacattgggaataattatgtatcctggtaccagcagctcccaggaacagcccccaaactcctcatttatgacactaataag
            cgaccctcagggattcctgaccgattcgctggctccaagtctggcacgtcagccaccctgggcatcaccggactccagactggggacgaggccg
            attattactgcggaacatgggatagcagcctgagtgctggcgtgttcggcggagggaccaagctgaccgtccta (SEQ ID NO: 72)
```

An antibody of the invention can be used to detect the presence, or determine the amount, of a cyclic signaling peptide in a biological sample. An antibody of the invention can also be used for a prophylactic purpose to prevent a mammal from becoming infected with a Gram positive bacterium or developing a disease or condition that is caused by a Gram positive bacterium.

Pharmaceutical Compositions of the Invention

The immunogenic molecular entity, supramolecular assembly including the immunogenic molecular entity or antibody of the invention, herein "active agents" of the invention, can be incorporated into a pharmaceutical composition for administration to a mammal. A pharmaceutical composition of the invention can include one or more active agents of the invention (e.g. one or more antibodies, immunogenic molecular entities, supramolecular assemblies or combinations thereof). A pharmaceutical composition of the invention can also include one or more active agents of the invention in combination with another polypeptide or antibody vaccine.

For example, a pharmaceutical composition of the invention may include one or more immunogenic molecular entities, the haptens of which include the lactone, lactam, carbamide or semicarbazide analogs of a S. aureus AIP-I, AIP-II, AIP-III or any combination thereof. Thus, a pharmaceutical composition of the invention may include a combination of two or more immunogenic molecular entities of the invention, each of which has a hapten that includes to the lactone, lactam, carbamide or semicarbazide analog of a S. aureus AIP cyclic peptide signaling molecule.

A pharmaceutical composition of the invention can include two different immunogenic molecular entities of the invention: (1) the first having a hapten that corresponds to the lactone, lactam, carbamide or semicarbazide analog of a S. aureus AIP-I cyclic signaling peptide, and a second having a hapten that corresponds to the lactone, lactam, carbamide or semicarbazide analog of a S. aureus AIP-II, III or IV; (2) the first having a hapten that corresponds to the lactone, lactam, carbamide or semicarbazide analog of a S. aureus AIP-II cyclic signaling peptide, and a second having a hapten that corresponds to the lactone, lactam, carbamide or semicarbazide analog of a S. aureus AIP-III or IV; or (3) the first having a hapten that corresponds to the lactone, lactam, carbamide or semicarbazide analog of a S. aureus AIP-III cyclic signaling peptide, and a second having a hapten that corresponds to the lactone, lactam, carbamide or semicarbazide analog of a S. aureus AIP-IV.

A pharmaceutical composition of the invention can also include three different immunogenic molecular entities of the invention, for example: (1) a first having a hapten that corresponds to the lactone, lactam, carbamide or semicarbazide analog of a S. aureus AIP-I cyclic signaling peptide, a second having a hapten that corresponds to the lactone, lactam, carbamide or semicarbazide analog of a S. aureus AIP-II, and a third immunogenic molecular entity having a hapten that corresponds to the lactone, lactam, carbamide or semicarbazide analog of a S. aureus AIP-III; (2) a first immunogenic molecular entity having a hapten that corresponds to the lactone, lactam, carbamide or semicarbazide analog of a S. aureus AIP-I cyclic signaling peptide, a second immunogenic molecular entity having a hapten that corresponds to the lactone, lactam, carbamide or semicarbazide analog of a S. aureus AIP-II, and a third immunogenic molecular entity having a hapten that corresponds to the lactone, lactam, carbamide or semicarbazide analog of a *S. aureus* AIP-IV; (3) a first immunogenic molecular entity having a hapten that corresponds to the lactone, lactam, carbamide or semicarbazide analog of a *S. aureus* AIP-I cyclic signaling peptide, a second immunogenic molecular entity having a hapten that corresponds to the lactone, lactam, carbamide or semicarbazide analog of a *S. aureus* AIP-III, and a third immunogenic molecular entity having a hapten that corresponds to the lactone, lactam, carbamide or semicarbazide analog of a *S. aureus* AIP-IV; (4) a first immunogenic molecular entity having a hapten that corresponds to the lactone, lactam, carbamide or semicarbazide analog of a *S. aureus* AIP-II cyclic signaling peptide, a second immunogenic molecular entity having a hapten that corresponds to the lactone, lactam, carbamide or semicarbazide analog of a *S. aureus* AIP-III, and a third immunogenic molecular entity having a hapten that corresponds to the lactone, lactam, carbamide or semicarbazide analog of a *S. aureus* AIP-IV.

A pharmaceutical composition of the invention can also include four different immunogenic molecular entities of the invention, for example, a first immunogenic molecular entity having a hapten that corresponds to the lactone, lactam, carbamide or semicarbazide analog of a *S. aureus* AIP-I cyclic signaling peptide, a second immunogenic molecular entity having a hapten that corresponds to the lactone, lactam, carbamide or semicarbazide analog of a *S. aureus* AIP-II, a third immunogenic molecular entity having a hapten that corresponds to the lactone, lactam, carbamide or semicarbazide analog of a *S. aureus* AIP-III; and a fourth immunogenic molecular entity having a hapten that corresponds to the lactone, lactam, carbamide or semicarbazide analog of a *S. aureus* AIP-IV.

Similarly, a pharmaceutical composition of the invention can also include one or more antibodies that bind specifically one or more cyclic peptide signaling molecules. For example, a pharmaceutical composition of the invention can include an antibody that binds specifically to any one of the *S. aureus* AIP-I, AIP-II, AIP-III or AIP-IV cyclic signaling peptides. A pharmaceutical composition of the invention can include two or more antibodies that bind specifically to two or more cyclic signaling peptides, for example, any two, three or all four cyclic signaling peptides of the *S. aureus* AIP-I, AIP-II, AIP-III or AIP-IV cyclic signaling peptides.

A pharmaceutical composition of the invention can also include one or more immunogenic molecular entities having haptens that correspond to cyclic signaling peptides from one or more Gram positive bacteria, as well as one or more antibodies that bind specifically with one or more cyclic signaling peptides from one or more Gram positive bacteria that use quorum sensing.

A pharmaceutical composition of the invention can also include the active agent of the invention in combination with one or more vaccines directed against different infectious agents including, without limitation, hepatitis B, *Haemophilus influenzae* type b bacteria, diphtheria, measles, mumps, pertussis, polio, rubella, tetanus, tuberculosis, and varicella.

In addition to the above, a pharmaceutical composition of the invention includes a pharmaceutically-acceptable carrier. As used herein, the term "pharmaceutically-acceptable carrier" includes, without limitation, any one or more solvents, dispersion media, coatings, antibacterial or antifungal agents, antioxidants, stabilizers, isotonic agents, adjuvants and the like that are suitable for administration to a mammal. Pharmaceutically-acceptable carriers are well known in the art, and unless a conventional carrier is incompatible with the immunogenic molecular entity or antibody of the invention, or incompatible with the route of administration, use thereof in a composition of the invention is contemplated.

A pharmaceutical composition of the invention is formulated to be compatible with a selected route of administration. Examples of route of administration include any route of parenteral administration including intravenous, intradermal, subcutaneous, inhalation, transdermal, transmucosal and rectal administration.

Solutions or suspensions used for parenteral, intradermal or subcutaneous application may include (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials.

Pharmaceutical compositions suitable for injection include sterile aqueous solutions or dispersions and sterile powders for extemporaneous preparation of sterile injectable solutions or dispersions. For intravenous administration, suitable carriers include physiological saline, bacteriostatic water, or phosphate buffered saline. Compositions must be sterile and be stable under the conditions of manufacture and storage and must be preserved against contamination by microorganisms such as bacteria and fungi. The carrier may be a solvent or dispersion medium containing, for example, water, ethanol, polyol (e.g. glycerol, propylene glycol and liquid polyethylene glycol), and suitable mixtures thereof. The proper fluidity may be achieved, for example, by using a coating such as lecithin, by maintaining the required particle size in the case of dispersion and by using surfactants. Prevention of the action of microorganisms may be achieved using various antibacterial and antifungal agents such as, for example, parabens, chlorobutanol, phenol, ascorbic acid, and thimerosal. Other ingredients such as an isotonic agent or an agent that delays absorption (e.g. aluminum monostearate and gelatin) may be included.

Sterile injectable solutions may be prepared by incorporating the active agent in the required amount in an appropriate solvent with one or a combination of ingredients discussed above, as required, followed by filtered sterilization. Dispersions may be prepared by incorporating the active compound into a sterile vehicle that contains a basic dispersion medium and other required ingredients discussed above. In the case of sterile powders for the preparation of injectable solutions, the preferred methods of preparation include vacuum drying and freeze-drying which yield a powder of the active ingredient and any additional desired ingredient from a previously sterile-filtered solution.

Oral compositions may include an inert diluent or an edible carrier. They may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier. Pharmaceutically compatible binding agents and/or adjuvant materials may be included as part of the composition. The tablets, pills, capsules, troches and the like may contain any of the following ingredients or compound of a similar nature: a binder such as microcrystalline cellulose, gum tragacanth or gelatin; an excipient such as starch or lactose; a disintegrating agent such as alginic acid or corn starch; a lubricant such as magnesium stearate; a glidant such as colloidal silicon dioxide; a sweetening agent such as sucrose or saccharin; or a flavoring agent such as peppermint, methyl salicylate or orange flavoring.

For administration by inhalation, the composition may be delivered in the form of an aerosol spray from a pressurized container or dispenser which contains a suitable propellant, for example, a gas such as carbon dioxide or a nebulizer.

For transmucosal or transdermal administration, penetrants known in the art to be appropriate to the barrier to be permeated may be used. These include detergents, bile salts and fusidic acid derivatives for transmucosal administrations, which may be accomplished using nasal sprays, for example. For transdermal administration, the active agents of the invention are formulated into ointments, salves, gels or creams as generally known in the art.

The compositions of the invention may be prepared with carriers that will protect against rapid elimination from the body. Controlled release formulations such as implants and microencapsulated delivery systems, for example, permit sustained slow release of the active agents of the invention, and in some cases, release of immunostimulators as well. Examples of such formulations include active agents of the invention entrapped in liposomes, ethylene-vinyl acetate copolymer (EVAc) (see Niemi et al., *Laboratory Animal Science* 35:609-612 (1985)), and degradable polymer. The biodegradable, biocompatible polymers used for encapsulation include, without limitation, poly(DL-lactide-co-glycolide) (see Eldridge et al., *Molecular Immunology* 28: 287-294 (1991)). Additional examples of polymers that can be used include polyanhydrides, polyglycolic acid, collagen, polyorthoesters, and polylactic acid. Methods for preparation of such formulations will be apparent to those skilled in the art. Liposomal suspensions, including those targeted to infected cells with monoclonal antibodies to viral antigens may also be used as pharmaceutically acceptable carriers. These may be prepared using methods known in the art.

Thus, compositions formulated to elicit an immune response can include adjuvants, as well as other carriers and vehicles. Non-limiting examples of adjuvants, carriers and vehicles include Freund's incomplete adjuvant; Freund's complete adjuvant; aluminum salts (e.g. potassium sulfate, aluminum phosphate, aluminum hydroxide); bacterial lipopolysaccharide; synthetic polynucleotides (poly IC/poly AU); Montanide ISA Adjuvants (Seppic, Paris, France); Ribi's Adjuvants (Ribi ImmunoChem Research, Inc., Hamilton, Mont.); Hunter's TiterMax (CytRx Corp., Norcross, Ga.); Nitrocellulose-Adsorbed Protein; Gerbu Adjuvant (Gerbu Biotechnik GmbH, Gaiberg, Germany/C-C Biotech, Poway, Calif.); saponin; muramyl di- and tripeptides; monophosphoryl lipid A; *Bordetella pertussis*; cytokines; bacterial toxoids; fatty acids; living vectors; mineral oil emulsions; biodegradable oil emulsions (e.g. those containing peanut oil, squalene, or squalane); nonionic block copolymer surfactants; liposomes and biodegradable polymer microspheres. See, for example, Eldridge et al., *Mol. Immunol.* 28:287-94 (1991)). Additional examples of vaccine delivery systems are discussed in Felnerova et al., *Current Opinion in Biotechnology* 15:518-29 (2004); Saupe et al., Expert Opin. Drug Deliv. 3:345-54 (2006); Sakarellos-Daitsiotis et al., *Current Topics in Medicinal Chemistry* 6:1715-1735 (2006); Chen & Huang, Advances in Genetics 54: 315-37 (2005); Westerfeld and Zurbriggen, *J. Peptide Sci* 11: 707-712 (2005); Shahiwala et al., *Recent Patents on Drug Delivery & Formulation* 1:1-9 (2007); and McDermott et al., *Immunology and Cell Biology* 76:256-62 (1998); the contents of which are incorporated by reference herein.

Compositions may be formulated in dosage unit form for ease of administration and uniformity of dosage. The phrase "dosage unit form" refers to physically discrete units suited as unitary dosages for the subject to be treated, each unit containing a predetermined quantity of active compound calculated to produce the desired therapeutic effect in association with the required pharmaceutical carrier. The specification for the dosage unit forms is dependent on the unique characteristics of the active compound and the particular therapeutic effect to be achieved.

Kits and Articles of Manufacture

The active agents or pharmaceutical compositions of the invention may be included in a container, pack or dispenser together with instructions for their use. Such kits can include additional reagents as required for the intended use of the immunogenic molecular entities, antibodies or pharmaceutical compositions. For example, an antibody of the invention can be used for diagnostic purposes, in which case, one or more reagents that enable detection/visualization can be included in the kit, preferably in a separate container, pack or dispenser from that holding the antibody of the invention. The kit or article of manufacture can include instructions for its use in diagnostic, prophylactic and/or therapeutic purposes as described below.

Methods of the Invention

The invention provides a method for identifying a mammal susceptible to or having a disease or condition associated with a Gram-positive bacterial infection, as well as a method to prevent infection by a Gram positive bacterium or its associated disease or condition. The invention also provides a method of eliciting an immune response in the mammal and a method of preventing quorum sensing in a mammal.

In the context of the invention, a mammal is any warm-blooded vertebrate including, for example, a mouse, rat, hamster, rabbit, guinea pig, pig, cow, horse, sheep, monkey, and human. A Gram-positive bacterium is any bacterium that utilizes cyclic peptides as signaling molecules in quorum sensing and can be, for example, *Enterococcus faecalis* and a *Staphylococcus* species including, for example, *S. aureus, S. epidermidis, S. auricularis, S. capitis, S. caprae, S. carnosus, S. arlettae, S. cohnii, S. epidermis, S. intermedius, S. lugdunensis, S. simulans, S. gallinarum, S. xylosus*, and *S. warneri*. The disease or condition associated with infection by such a bacterium includes, for example, food poisoning, toxic shock syndrome, scalded skin syndrome, surgical wound infection, urinary tract infection, sepsis, and pneumonia.

Diagnostic Methods

A diagnostic method of the invention can be used to identify a mammal in need of or that may benefit from treatment using an immunogenic molecular entity or antibody of the invention. A mammal in need of or that may benefit from treatment using an immunogenic molecular entity or antibody of the invention is one that has a Gram positive bacterial infection or is susceptible to the infection or to a disease or condition associated with a Gram-positive bacterial infection. To identify such a mammal, a biological sample from the mammal can be obtained. The biological sample can be a tissue sample, a cell sample or a sample of a biological fluid such as blood, urine, or lymph. An antibody of the invention can be used to determine whether a biological sample contains a cyclic peptide signaling molecule, the presence of which indicates that the mammal has a Gram positive bacterial infection or is susceptible to or has a disease or condition associated with a Gram-positive bacterial infection. For example, an antibody of the invention that binds specifically to the S. aureus AIP-IV signaling peptide can be used to detect the presence of S. aureus AIP-IV in a biological sample from a mammal suspected of being susceptible to or of having a disease or condition associated with a S. aureus infection. The presence of S. aureus AIP-IV in the sample indicates that the mammal has an S. aureus infection or susceptible to or has a disease or condition associated with the S. aureus infection. Thus, an antibody of the invention can be used diagnostically to detect the presence of and/or determine the amount of a cyclic peptide signaling molecule in a biological sample from a mammal.

The presence or amount of the cyclic peptide signaling molecule in a biological sample from a mammal can be detected in a competitive assay using a suitably-labelled antibody of the invention. For example, an immunogenic molecular entity of the invention, e.g. hapten linked to macromolecular carrier such as a polypeptide, can be immobilized on a surface. The binding of a suitably-labelled antibody of the invention to the immobilized immunogenic molecular entity in the presence or absence of a biological sample from the mammal is determined. A decrease in binding of the labeled-antibody to the surface in the presence of the biological sample indicates the presence of a cyclic peptide signaling molecule. The biological sample can be a partially purified or processed sample in which unrelated mammalian cells have been removed. The antibody can be labeled with a detectable molecule, which can be an enzyme such as alkaline phosphatase, acetylcholinesterase, β-galactosidase or horseradish peroxidase; a prosthetic group such as streptavidin, biotin, or avidin; a fluorescent group such as dansyl chloride, dichlorotriazinylamine, dichlorotriazinylamine fluorescein, fluorescein, fluorescein isothiocyanate, phycoerythrin, rhodamine, umbelliferone; a luminescent group such as luminal; a bioluminescent group such as aequorin, luciferase, and luciferin; or a radioisotope such as $^3H$, $^{125}I$, $^{131}I$, $^{35}S$.

Therapeutic Methods

An immunogenic molecular entity or antibody of the invention can be used to prevent or treat infection of a mammal by a Gram positive bacterium such as, for example, a Staphylococcus species, that utilizes cyclic peptide signaling molecules in quorum sensing. Mammals that can benefit from treatment with an immunogenic molecular entity or antibody of the invention include: (1) a mammal at risk for or susceptible to infection by a Gram positive bacterium, (2) a mammal who has come into contact with an infectious Gram positive bacterium, or (3) a mammal who is infected by a Gram positive bacterium. To prevent or treat a Gram-positive bacterial infection, an immunogenic molecular entity of the invention can be administered to the mammal to elicit an immune response in the mammal. In addition, an antibody of the invention can be administered to inhibit the activity of a cyclic signaling peptide thereby preventing the production of virulence genes or toxins that aid in bacterial infection or development of the disease condition associated the bacterial infection.

A mammal that can benefit from treatment with the immunogenic molecular entity or antibody of the invention can be identified using the methods discussed above in which the presence and/or amount of a cyclic peptide signaling peptide is determined. Other methods of detecting the presence of a Gram positive bacterial infection such as, for example, by culturing from a sample from the mammal, e.g. a blood culture, can be used. A mammal, such as a human, who can benefit from treatment with an immunogenic molecular entity or antibody of the invention can be an individual having a weakened immune system, an individual with a suppressed immune system, an individual who has undergone or will undergo surgery, an older individual or one who is very ill, an individual who has been hospitalized or has had a medical procedure. A mammal that can benefit from treatment with an immunogenic molecular entity or antibody of the invention can be a hospital patient at risk of developing nosocomial infection or a mammal known to be infected with or having been exposed to antibiotic resistant bacteria such as, for example, Methicillin-resistant S. aureus, Vancomycin-intermediary-sensible S. aureus, Vancomycin-resistant S. aureus and other antibiotic resistant enterococci including Pneumococcus pneumoniae.

The antibody or immunogenic molecular entity of the invention can be administered prior to infection, after infection but prior to the manifestation of symptoms associated with the infection, or after the manifestation of symptoms to prevent further bacterial multiplication and to prevent further expression of virulence genes thereby hindering development of the disease or its progression. When administered to a mammal, the immunogenic molecular entity of the invention elicits the production of antibodies that prevent the disease or condition or its progression by binding to and neutralizing the cyclic peptide signaling molecules produced by the bacteria thereby preventing the production of virulence genes or toxins that aid in development of the infection or the disease condition associated with the bacterial infection. In addition, a neutralizing antibody of the invention can also be administered to the mammal. The neutralizing antibody can bind to a cyclic peptide signaling molecule produced by the bacteria and prevent its binding to its cell-associated receptor and in doing so, prevent the production of virulence genes or toxins that aid in infection or development of the disease condition associated with the bacterial infection. Accordingly, a composition that includes an immunogenic molecular entity of the invention can be used as a live vaccine, while a composition that includes an antibody of the invention can be used as a passive vaccine, to prevent the bacterial infection or a disease or condition associated with the bacterial infection.

The active agents of the invention can be administered by any route discussed herein. The dosage of the immunogenic molecular entity or supramolecular assembly to be administered to a mammal may be any amount appropriate to elicit an immune response against a cyclic signaling peptide. The dosage of the antibody to be administered to a mammal can be any amount appropriate to neutralize the activity of a cyclic signaling peptide.

The dosage may be an effective dose or an appropriate fraction thereof. This will depend on individual patient parameters including age, physical condition, size, weight, the condition being treated, the severity of the condition, and any concurrent treatment. Factors that determine appropriate dosages are well known to those of ordinary skill in the art and may be addressed with routine experimentation. For example, determination of the physicochemical, toxicological and pharmacokinetic properties may be made using standard chemical and biological assays and through the use of mathematical modeling techniques known in the chemical, pharmacological and toxicological arts. The therapeutic utility and dosing regimen may be extrapolated from the results of such techniques and through the use of appropriate pharmacokinetic and/or pharmacodynamic models.

The precise amount to be administered to a patient will be the responsibility of the attendant physician. An immunogenic molecular entity or antibody of the invention may be administered by injection at a dose of from about 0.05 to about 2000 mg/kg weight of the mammal, preferable from about 1 to about 200 mg/kg weight of the mammal. As certain agents of the invention are long acting, it may be advantageous to administer an initial dose of 80 to 4,000 mg the first day then a lower dose of 20 to 1,000 mg on subsequent days. A patient may also insist upon a lower dose or tolerable dose for medical reasons, psychological reasons or for virtually any other reasons. One or more booster doses of the immunogenic molecular entity or antibody could be administered at a selected time period after the first administration.

Treatment using an antibody or immunogenic molecular entity of the invention can be for a duration needed to elicit an effective neutralizing immune response.

Methods of Generating Antibodies of the Invention

An immunogenic molecular entity or supramolecular assembly of the invention can be used to generate antibodies directed to a cyclic signaling peptide.

An immunogenic molecular entity or supramolecular assembly of the invention can be used to screen a recombinant immunoglobulin library to identify an antibody that binds specifically with a selected cyclic signaling peptide. Methods and reagents for generating and screening a recombinant combinatorial immunoglobulin library are described in, for example, Barbas, C. F., 3$^{rd}$, D. R. Burton, J. K. Scott, and G. J. Silverman, *Phage Display—A Laboratory Manual.* 2001, Cold Spring Harbor, N.Y.: Cold Spring Harbor Laboratory Press, and Kontermann, R., Dübel, S., Antibody Engineering, 2001, Berlin, Heidelberg: Springer-Verlag An immunogenic molecular entity, or supramolecular assembly of the invention can also be used to elicit an immune response in a mammal, from which polyclonal or monoclonal antibodies can be obtained. An immunogenic molecular entity or supramolecular assembly of the invention can be administered to a mammal such as a goat, sheep, rat, mouse, or rabbit, for example. Polyclonal antibodies can be isolated from the blood of the mammal using methods known in the art. Monoclonal antibodies can be obtained by isolating antibody-producing cells from the mammal and generating antibody-producing hybridomas. Methods of producing and obtaining antibodies from a mammal are known in the art. See, for example, Harlow, D. and D. Lane, *Antibodies A laboratory manual*. Cold spring harbor laboratory, New York (1988), and Tramontano, A. and D. Schloeder, *Production of antibodies that mimic enzyme catalytic activity*. Methods Enzymol 178: p. 531-550 (1989).

The invention is further illustrated by the following non-limiting Examples.

EXAMPLES

Example 1

Materials

RN4850 was obtained from Dr. Richard P. Novick (Skirball Institute, New York University Medical Center). Purified monoclonal antibodies were obtained from TSRI Antibody Production Core Facility. The clinical isolate NRS168 was obtained through the Network on Antimicrobial Resistance in *Staphylococcus aureus* (NARSA) Program supported by NIAID/NIH (N01-AI-95359).

Example 2

Synthesis of Native AIPs 1-4

The following general procedure was used to synthesize all natural products. Batch synthesis was carried out on 0.25 mmol of MBHA resin swollen in DMF following standard Boc solid-phase peptide synthesis protocols. A solution of S-trityl-3-mercaptoproprionic acid (2 eq), HBTU (3.9 eq), and DIEA (0.5 mL) in 4 mL DMF was prepared and allowed to sit for 3 minutes for pre-activation. The cocktail was added to the resin for coupling, which is generally complete in 1 hour. The resin was then washed with DMF and subjected to trityl deprotection with 5% TIS in TFA (2×10 minutes). Once washed with DMF, the peptide sequence was completed by sequential coupling reactions using 4 eq Boc amino acid, 3.9 eq HBTU, and 0.5 mL DIEA, with 3 minute preactivation. When the synthesis was complete, the resin was washed with DMF, then $CH_2Cl_2$, and finally with ether before it was placed in the desiccator.

Cleavage:

The resin was subjected to 5-10 mL of HF for 1 hour using anisole as a scavenger. The resulting mixture was washed with ether and extracted with 1:1 water/acetonitrile. This solution was frozen and lyophilized, and the resulting solid was purified by prep-HPLC. Pure fractions were pooled, frozen, and lyophilized.

Thiolactonization:

Intramolecular thiolactonization was achieved by taking up the purified, solid linear peptide in a mixture of 80% MOPS buffer (100 mM, pH 7.0) and 20% acetonitrile, giving a peptide concentration of less than 1 mM. The reaction was monitored by ESI-MS, and was usually complete in 24-48 hour. The product was purified by prep-HPLC. Pure fractions were pooled, frozen, and lyophilized. ESI-MS: m/z calcd for AIP-1, $C_{43}H_{60}N_8O_{13}S_2$ (M+H), 961.4. found 961.8: m/z calcd for AIP-2, $C_{38}H_{58}N_{10}O_{12}S$ (M+H), 879.4. found, 879.6: m/z calcd for AIP-3, $C_{38}H_{58}N_8O_{10}S$ (M+H), 819.4. found, 819.7: m/z calcd for AIP-4, $C_{48}H_{64}N_8O_{12}S_2$, 1009.4. found 1009.7. See FIG. 2A-H.

Example 3

Synthesis of AIP4 Hapten 5-AIP4 Lactone Analog

The scheme for the synthesis of AIP4 hapten 5 is depicted in Scheme 1 below. The linear peptide YSTSYFLM (SEQ ID NO: 1, not including protecting groups) was synthesized on 2-chlorotrityl resin preloaded with Fmoc-Methionine 1 using standard Fmoc chemistry employing DIC/HOBt as coupling reagents. The N-terminal pendant cysteine was incorporated for conjugation to a carrier protein and the short flexible linker was added between the hapten and the carrier protein as spacer. The protected linear peptide was released from the resin using 4% trifluoroacetic acid in chloroform, which also selectively removed the trityl protection group from the serine. Intramolecular lactonization under dilute conditions was performed using EDC/4-DMAP, and subsequent side chain de-protections afforded the AP4 hapten 5. The details of the synthetic procedure are described in the following text.

Scheme 1 Synthesis of the AP4 Hapten 5
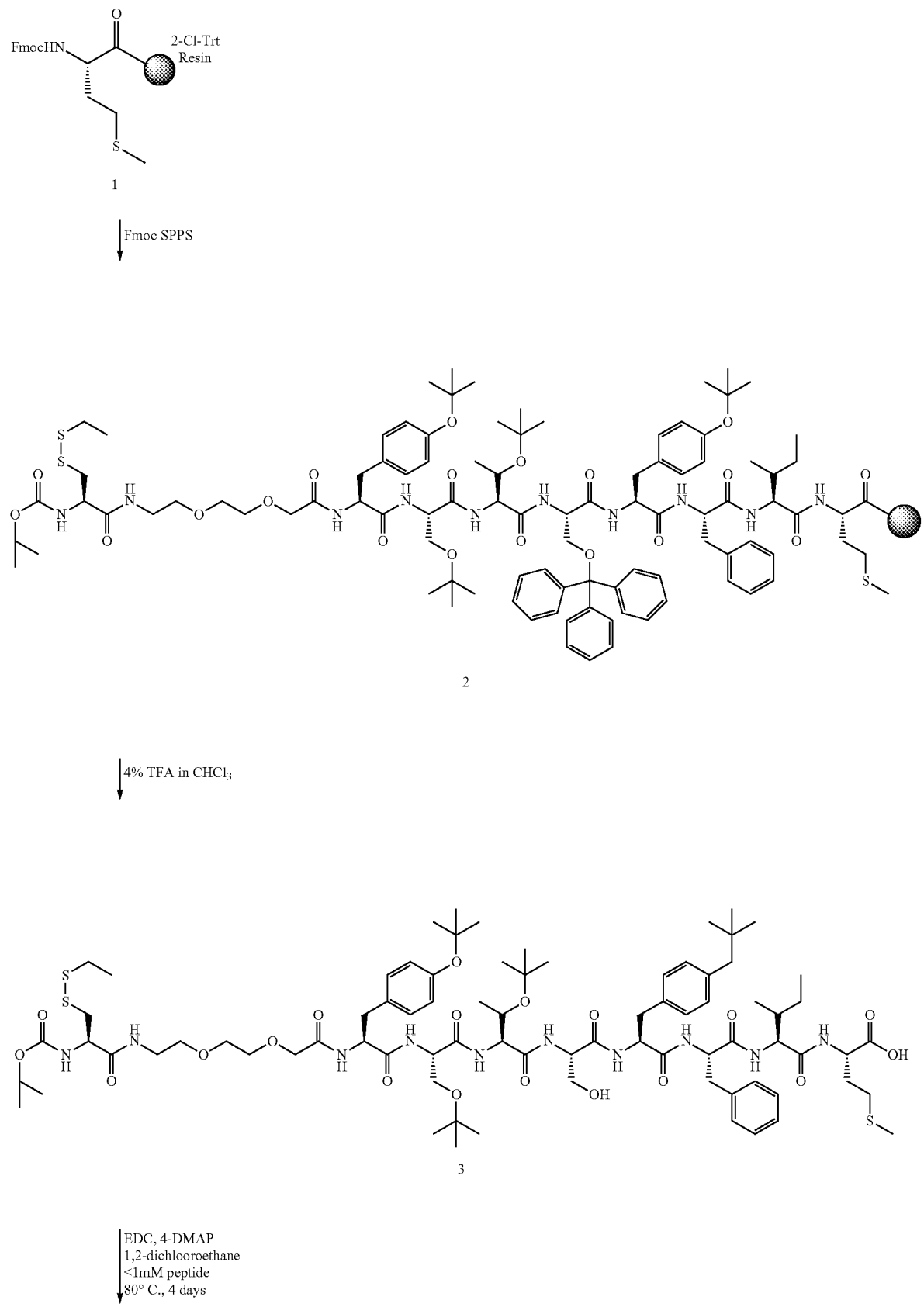

-continued

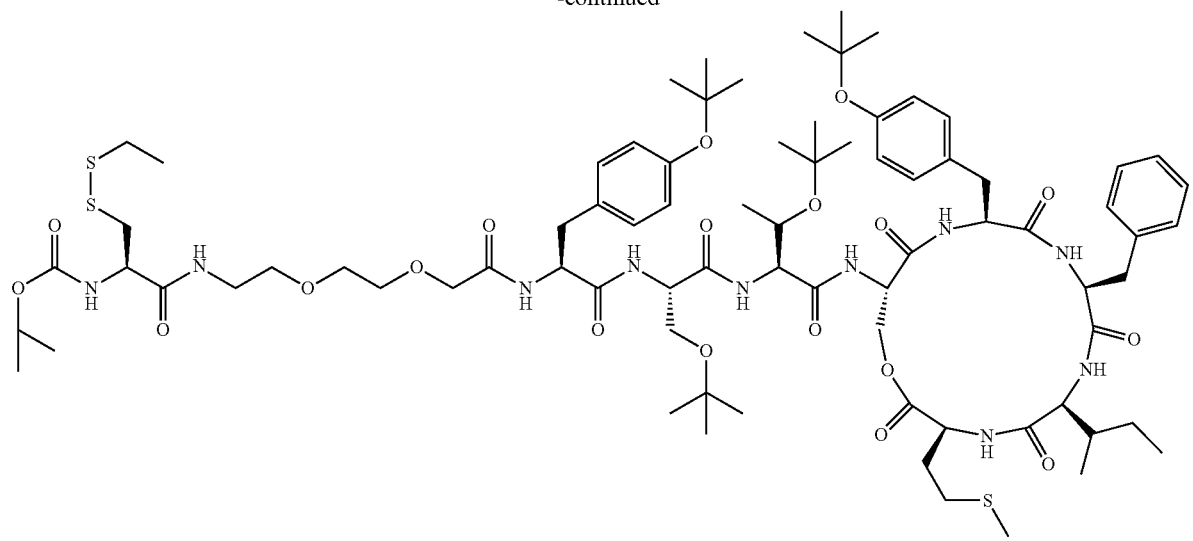

4 i. TFA
ii. TCEP in H₂O

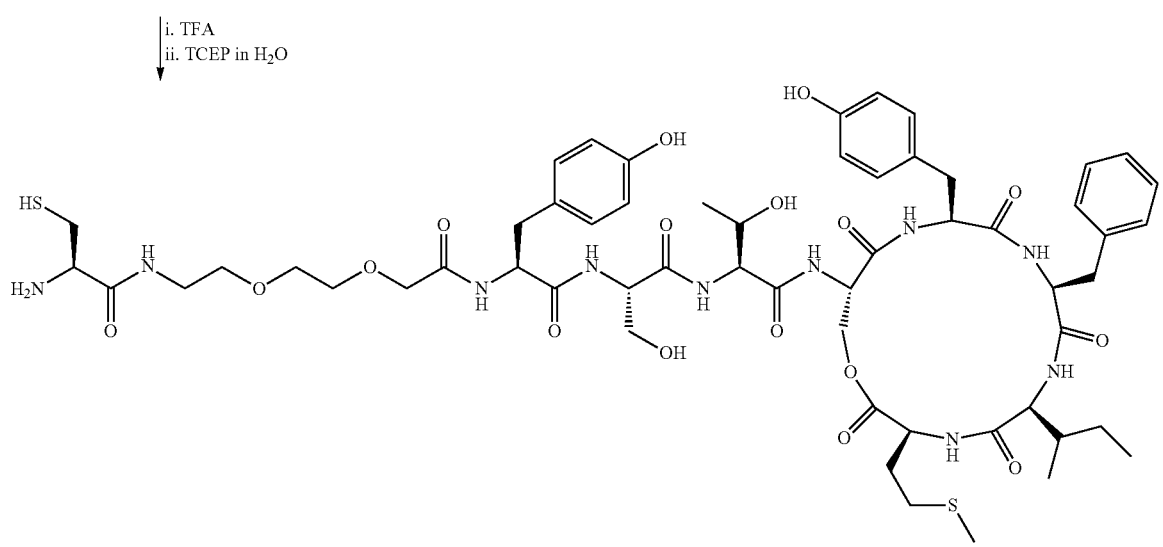

5

SEQ ID NO: 1 (YSTSYFLM, not including protecting groups)

Synthesis of the Linear Protected Peptide (3)

All N-α-Fmoc protected amino acids, coupling reagents and the resins for peptide synthesis were purchased from EMD Biosciences, Inc. (San Diego, Calif.). All other chemicals were purchased from Sigma-Aldrich Corp. (St. Louis, Mo.). ESI-MS analyses were performed with API150EX (PE SCIEX, Foster City, Calif.), and HITACHI L-7300 and SHIMADZU SCL-10A were used for analytical and preparative HPLC experiments, respectively.

The peptide was synthesized by Fmoc SPPS on 2-chlorotrityl resin preloaded with the Fmoc-Met 1. An Fmoc-Ser(Trt)-OH was incorporated at the position of lactonization. All other residues were chosen with side chain protecting groups stable to dilute TFA and labile in 95% TFA. A short flexible linker was incorporated penultimate to the N-terminus by coupling Fmoc-8-amino-3,6-dioxaoctanoic acid. The N-terminal residue was Boc-Cys(Set)-OH for eventual use in conjugation to carrier proteins.

Specific Conditions:

Batch synthesis was carried out on 1 mmol of resin swollen in DMF for at least 1 hour. A solution of the protected amino acid, DIC, and HOBt (4 equivalents each) in 5 mL DMF was prepared and allowed to sit for 5 minutes for pre-activation, followed by the addition of 0.5 mL sym-collidine. The cocktail was added to the resin for coupling, which was generally complete in 1 hour. The resin was then washed with DMF and subjected to Fmoc deprotection with 20% (v/v) piperidine in DMF (2×7 min). The resin was then washed with DMF and the next coupling reaction was carried out. When synthesis was complete, the resin was washed with DMF, then $CH_2Cl_2$, and finally with ether before it was placed in the desiccator.

Cleavage (and Trityl Deprotection):

The resin was added to a cocktail of 4% TFA, 4% triisopropylsilane (TIS) and 0.5% $H_2O$ in chloroform, and shaken for 6 hours. The mixture was filtered, allowing the filtrate to drip into cold ether to precipitate the peptide. The ether mixture was centrifuged and the supernatant was decanted. The peptide was then washed (2×) with ether by re-suspending the solid in ether, centrifugation, and decanting the supernatant. The resulting solid was placed in a desiccator.

Purification:

The fully protected peptide 3 was dissolved in methylene chloride and purified by normal phase silica gel chromatography eluted with 5% methanol in methylene chloride.

B. Lactonization of (3)

The protected linear peptide 3 was dissolved in 1,2-dichloroethane (previously dried over anhydrous $MgSO_4$) to give a final concentration of no greater than 1.0 mM. The solution was stirred and heated to 80° C. and 3 equivalents each of EDC and 4-DMAP were added; another equivalent each of EDC and 4-DMAP were added at both 24 and 48 hours into the reaction. The reaction was monitored by HPLC. After 4 days, the reaction mixture was cooled to room temperature, washed with 2×200 mL of 0.2 M $KHSO_4$ (aq), dried over anhydrous $Na_2SO_4$, and evaporated to dryness. The cyclized peptide 4 was purified by prep-HPLC. Yields range from 30-60% as determined by analytical HPLC integration.

C. Global Deprotection and Disulphide Deprotection of (4)

Figure 2A:
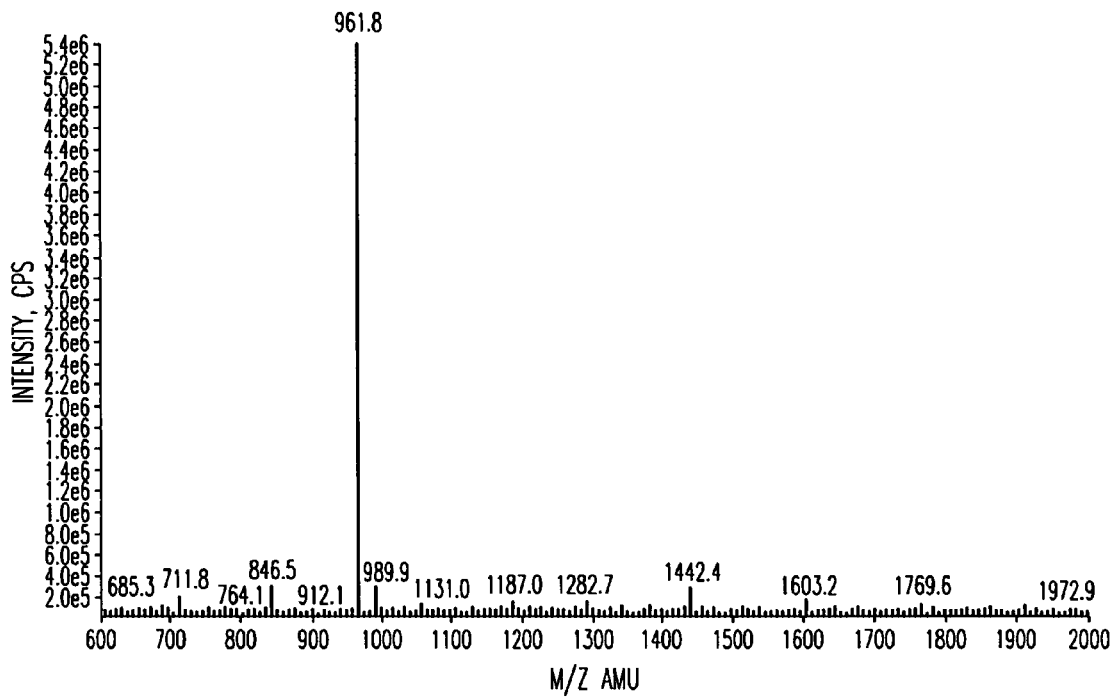
FIG. 2A-K are the ESI-MS spectra and HPLC chromatograms of the AIPs synthesized: AIP-1 (pure thiolactone) (A & B); AIP-2 (pure thiolactone) (C & D); AIP-3 (pure thiolactone) (E & F); AIP-4 (pure thiolactone) (G & H); AIP-IV (pure lactone) (I & J). HPLC was performed on a C18 column monitored at 214 nm by UV absorption using a gradient of 20% B for 3 minutes and then increasing to 50% B in 30 minutes. B is acetylnitrile run against HPLC grade water.
Figure 2B:
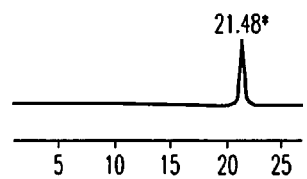
Figure 2C:
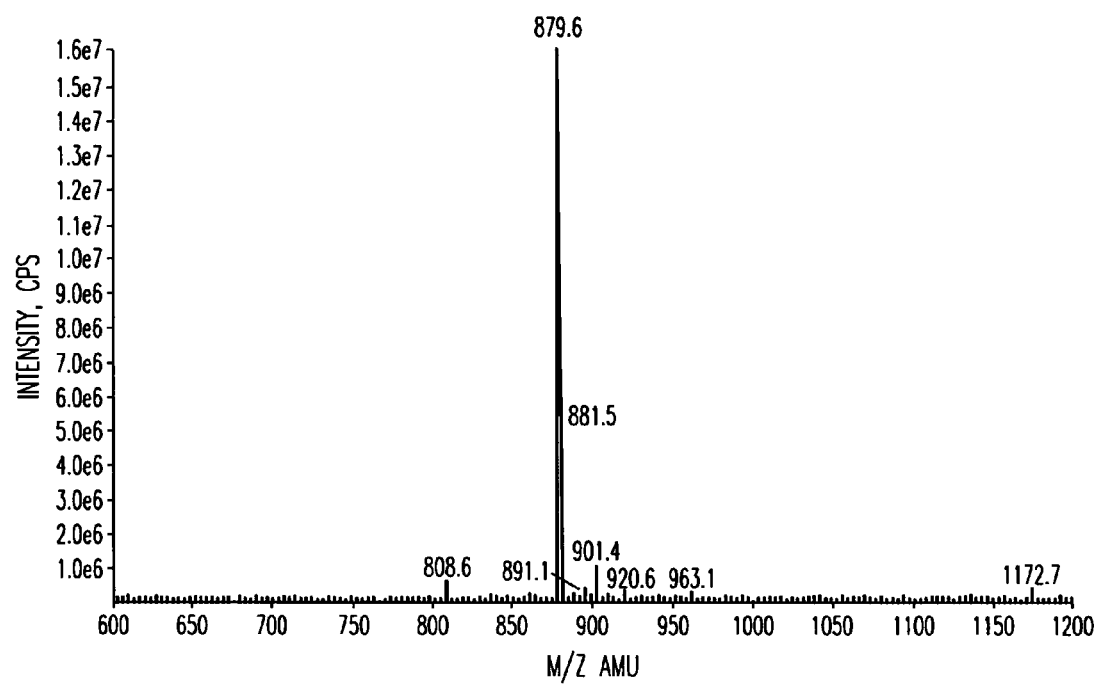
Figure 2D:
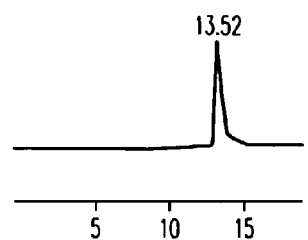
Figure 2E:
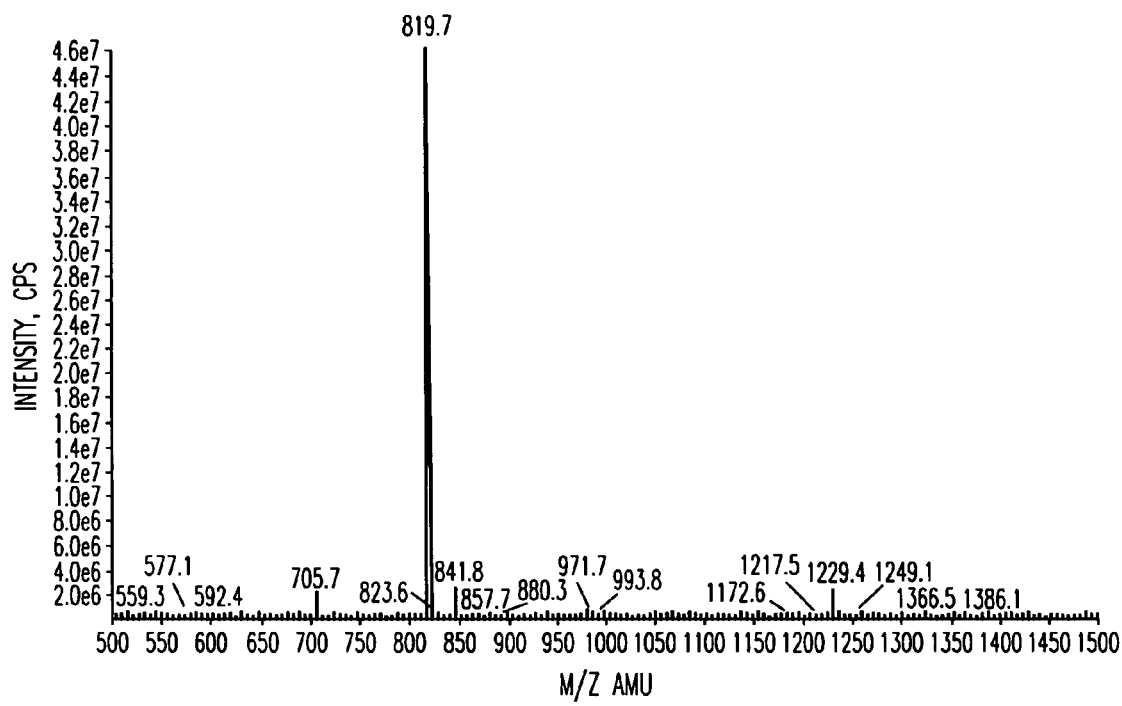
Figure 2F:
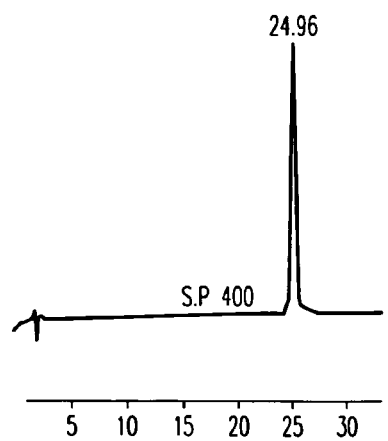
Figure 2G:
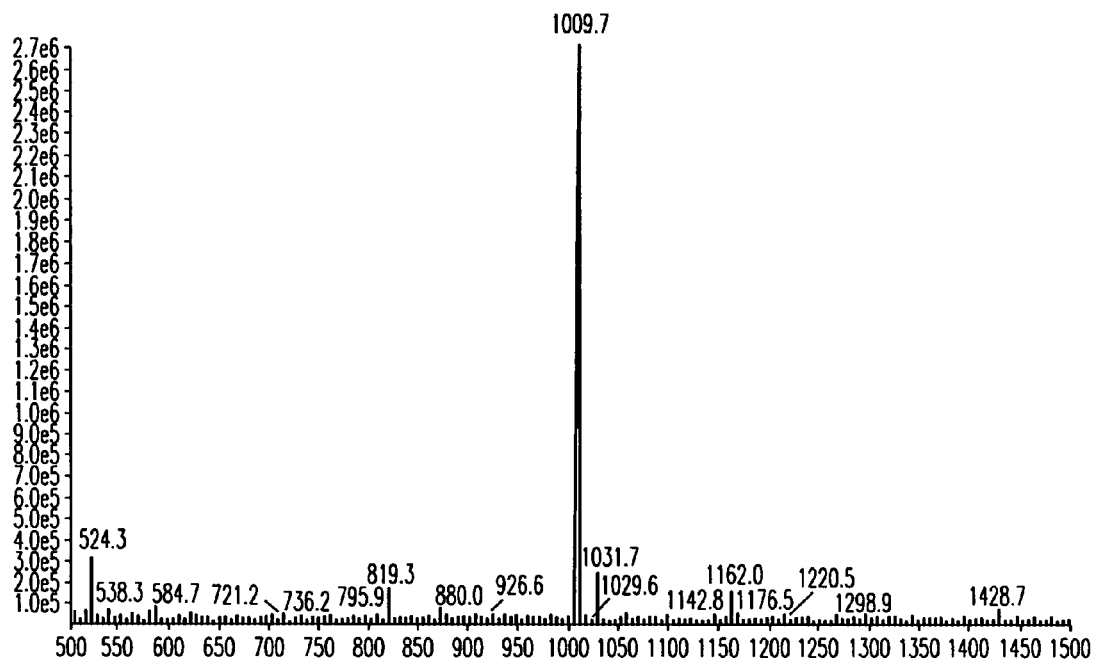
Figure 2H:
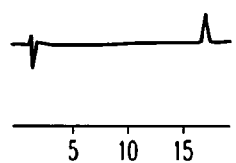
Figure 2I:
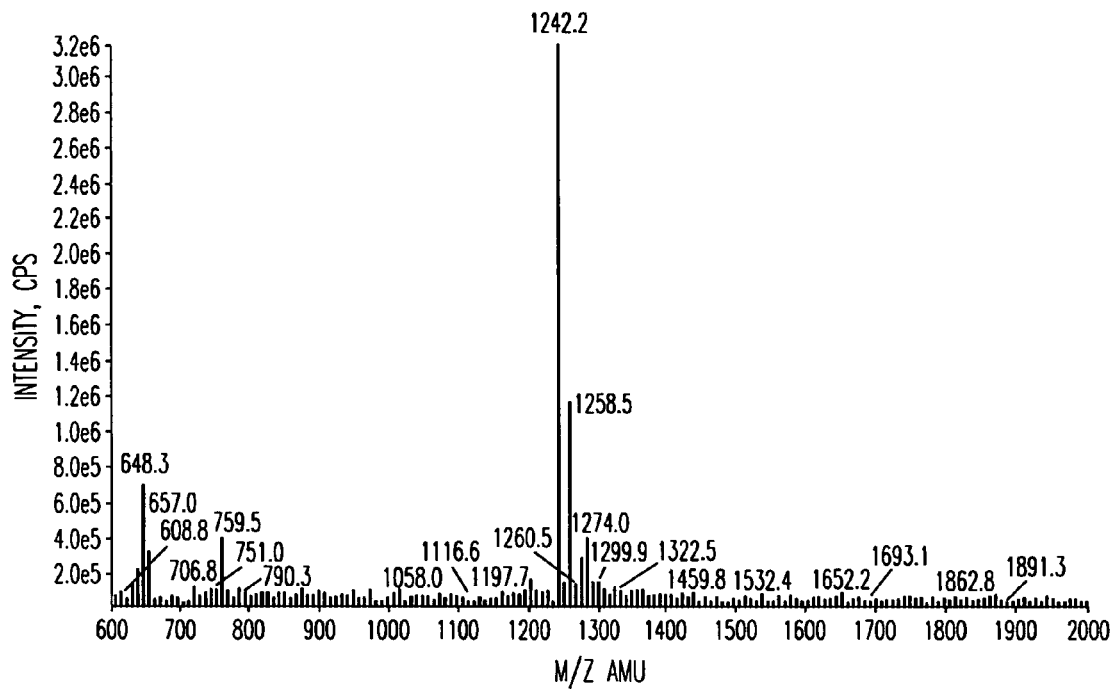
Figure 2J:
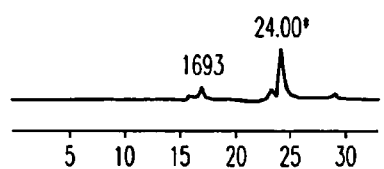

The solid, purified peptide was dissolved in TFA containing 2% TIS and stirred for 1 hour. The mixture was then evaporated to dryness. Water was added and the mixture was frozen and lyophilized. The lyophilized solid was then dissolved in $H_2O$ with tris(2-carboxyethyl)phosphine hydrochloride (TCEP). The mixture was stirred for 1 hour and injected directly into the prep-HPLC for purification yielding AP4 hapten 5. The collected pure fractions were pooled, frozen, and lyophilized. ESI-MS: m/z calcd for $C_{57}H_{80}N_{10}O_{17}S_2$ (M+H), 1241.5. found, 1242.2. See FIGS. 2I & J.

D. Conjugation of (5) to KLH/BSA

The conjugation of hapten 5 to KLH/BSA was performed as depicted in Scheme 2 below. The details of the procedure is described in the following text.

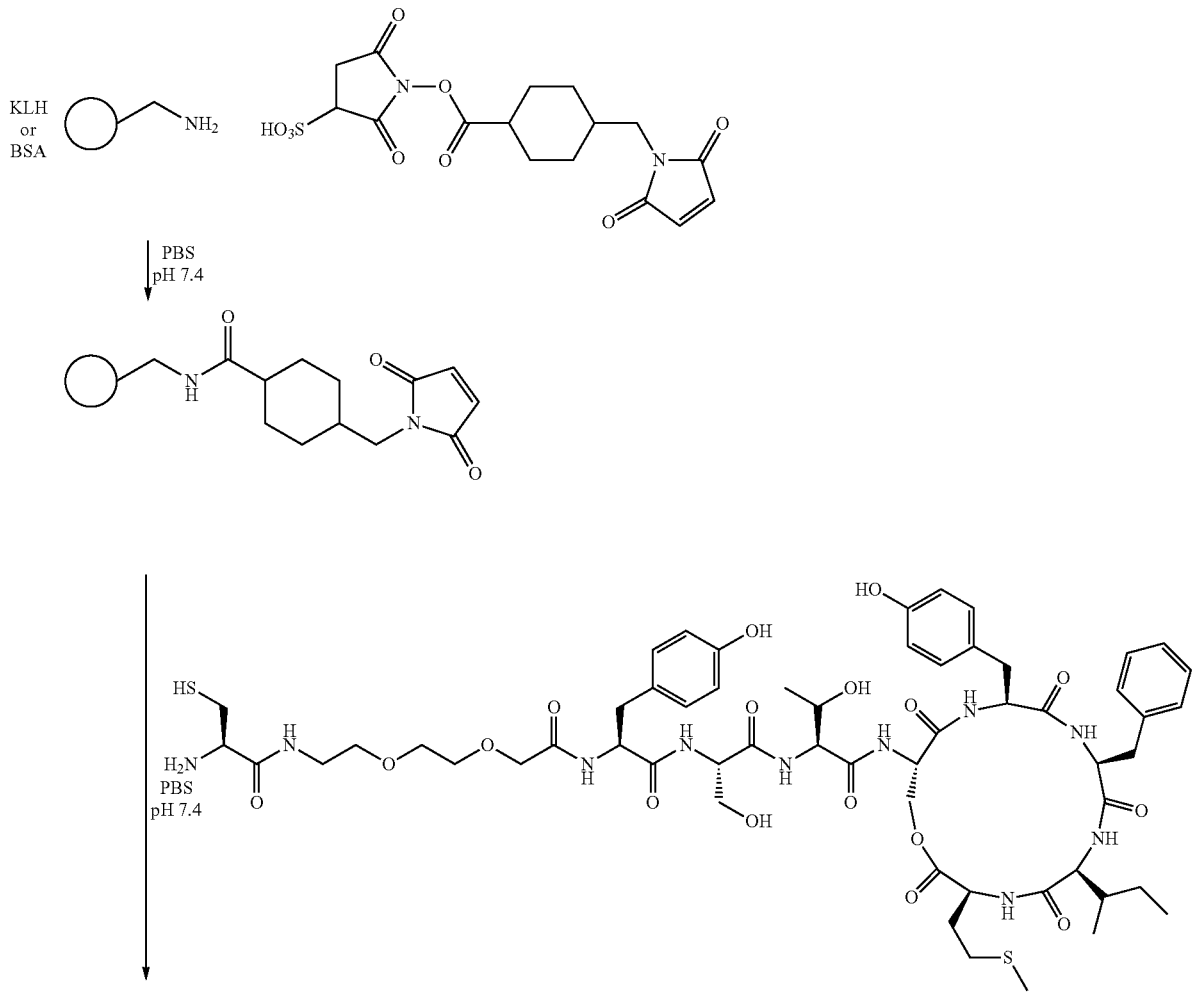

Scheme 2 Conjugation of Hapten 5 to KLH/BSA

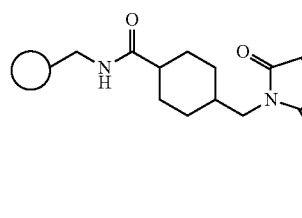
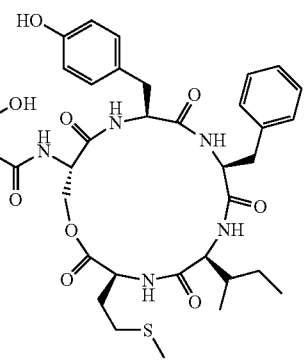

SEQ ID NO: 2 (INSDFLL, not including protecting groups)

Attachment of Sulpho-SMCC.

5 mg of the carrier protein were resuspended in 0.9 mL PBS, pH 7.4. To this solution was added 1 mg of the linker sulpho-SMCC (sulphosuccinimidyl 4-(N-maleimidomethyl)-cyclohexane-1-carboxylate). The solution was stirred for 6-8 hours and the protein-linker conjugate was purified by dialysis in PBS at 4° C.

Conjugation of the Hapten 5.

Figure 2K:
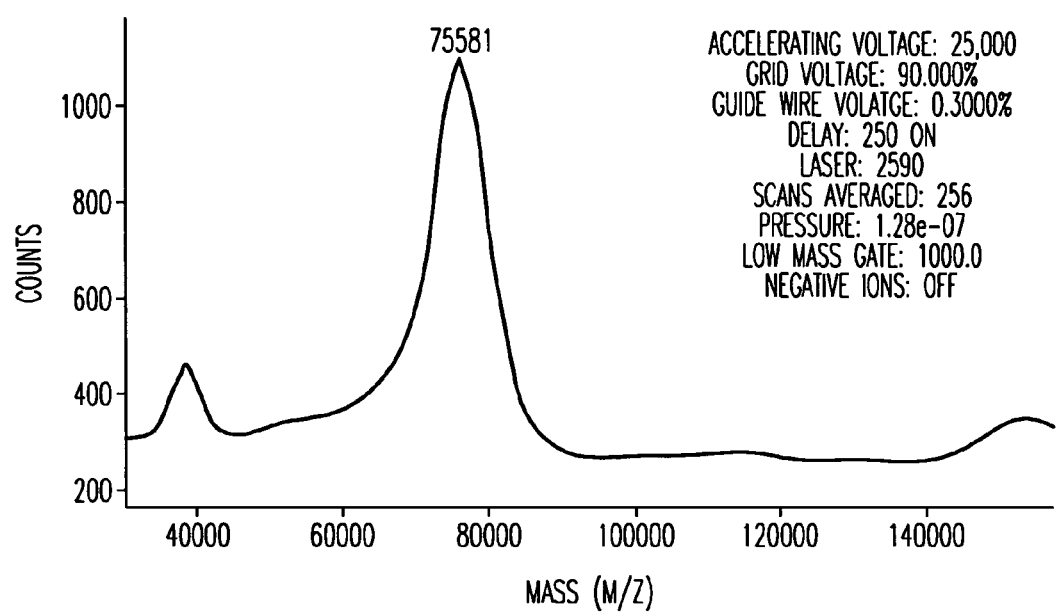

To the protein-linker conjugate in PBS were added 100 µL of DMF containing 2 mg of the hapten 5. The solution was shaken overnight and the protein-hapten conjugate was purified by dialysis. MALDI-TOF analysis confirmed the attachment on average of ≈6 haptens per BSA molecule (molecular weight of BSA-AIP4 conjugate=75581 Daltons; BSA=67000 Daltons; and hapten=1461.15 Daltons). See FIG. 2K.

Example 4

Preparation of the AP1, AP2, AP3 and AP4 Lactone Analogs as Synthetic Haptens and Hapten-Protein Carrier Conjugates For immunization and elicitation of an immune response, active vaccine, and generation of monoclonal antibodies, synthetic haptens in the form of AP1, AP2, AP3 and AP4 lactone analogs and hapten-protein carrier conjugates were prepared using procedures as described for the preparation of the AP4 hapten 5 described above. The preparation schemes are as follows.

Scheme 3

Preparation of a Synthetic Hapten (AP1) for Immunization and Elicitation of an Immune Response/Active Vaccine/Generation of Monoclonal Antibodies to AIP-1

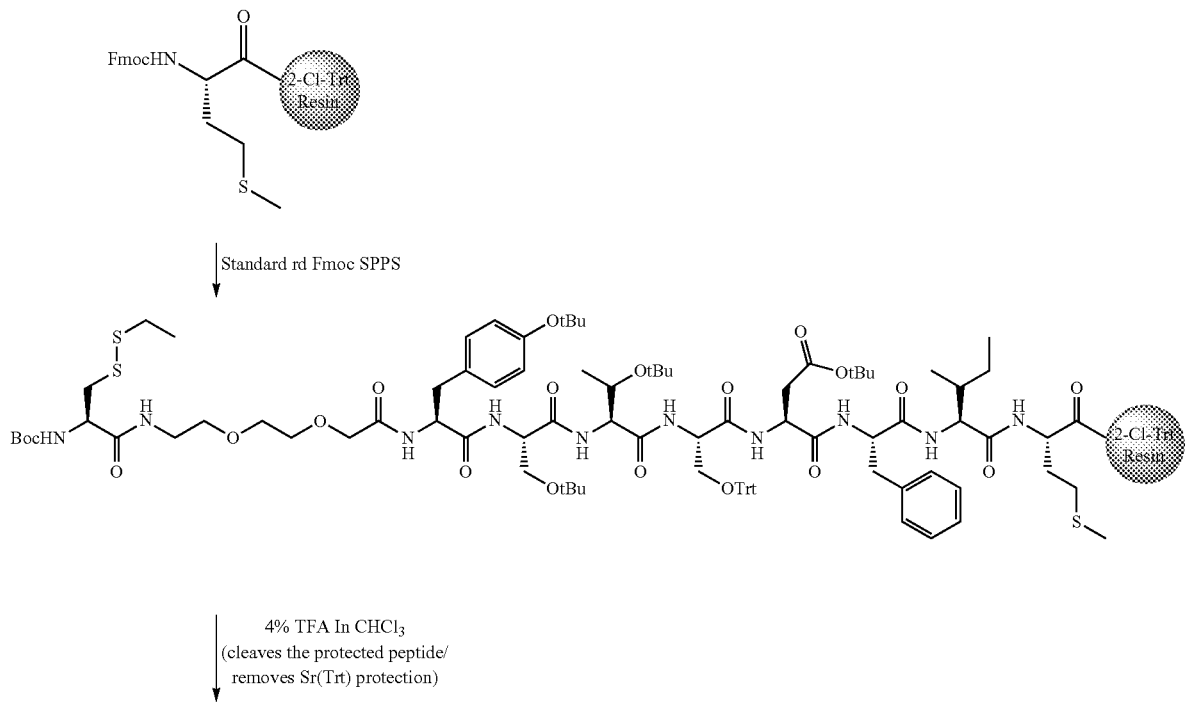

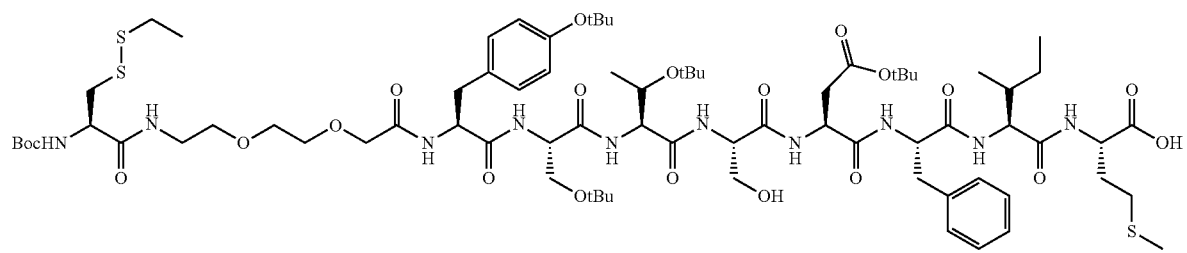
EDC, DMAP
1,2-dichloroethane
<1 mM peptide concentration
80° C., 4 days
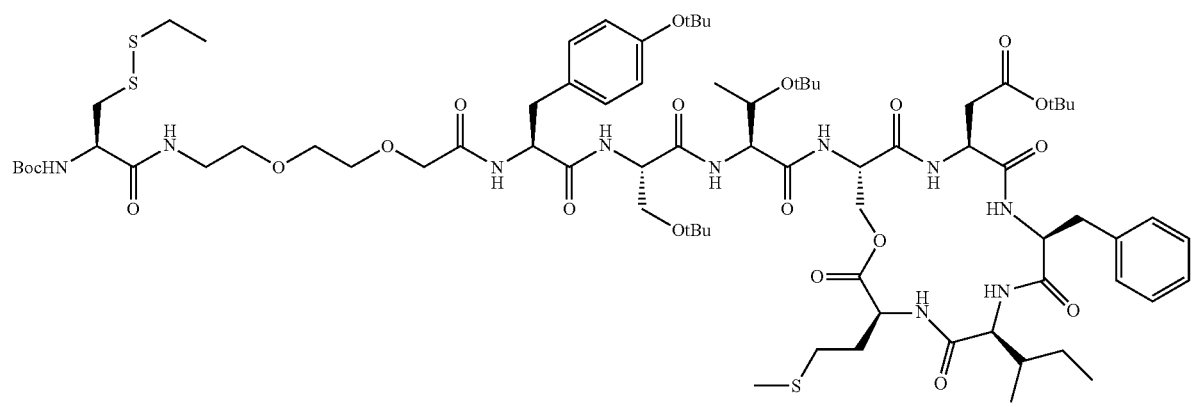
1. neat TFA
2. TCEP/water
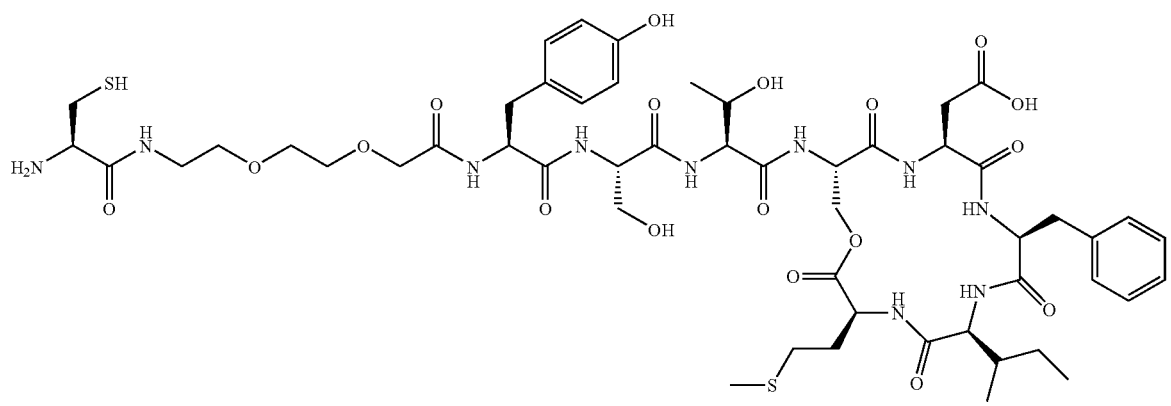 [SMILES: CCC(C)[C@@H]1NC(=O)[C@H](Cc2ccccc2)NC(=O)[C@H](CC(=O)O)NC(=O)[C@@H](NC(=O)[C@@H](NC(=O)[C@H](CO)NC(=O)[C@H](Cc2ccc(O)cc2)NC(=O)COCCOCCNC(=O)[C@@H](N)CS)C(C)O)COC(=O)[C@H](CCSC)NC1=O]

SEQ ID NO: 3 (YSTSDFIM, not including protecting groups)
Scheme 4
Preparation of a Synthetic Hapten (AP2) for Immunization and Elicitation
of an Immune Response/Active Vaccine/Generation of Monoclonal Antibodies to AIP-2
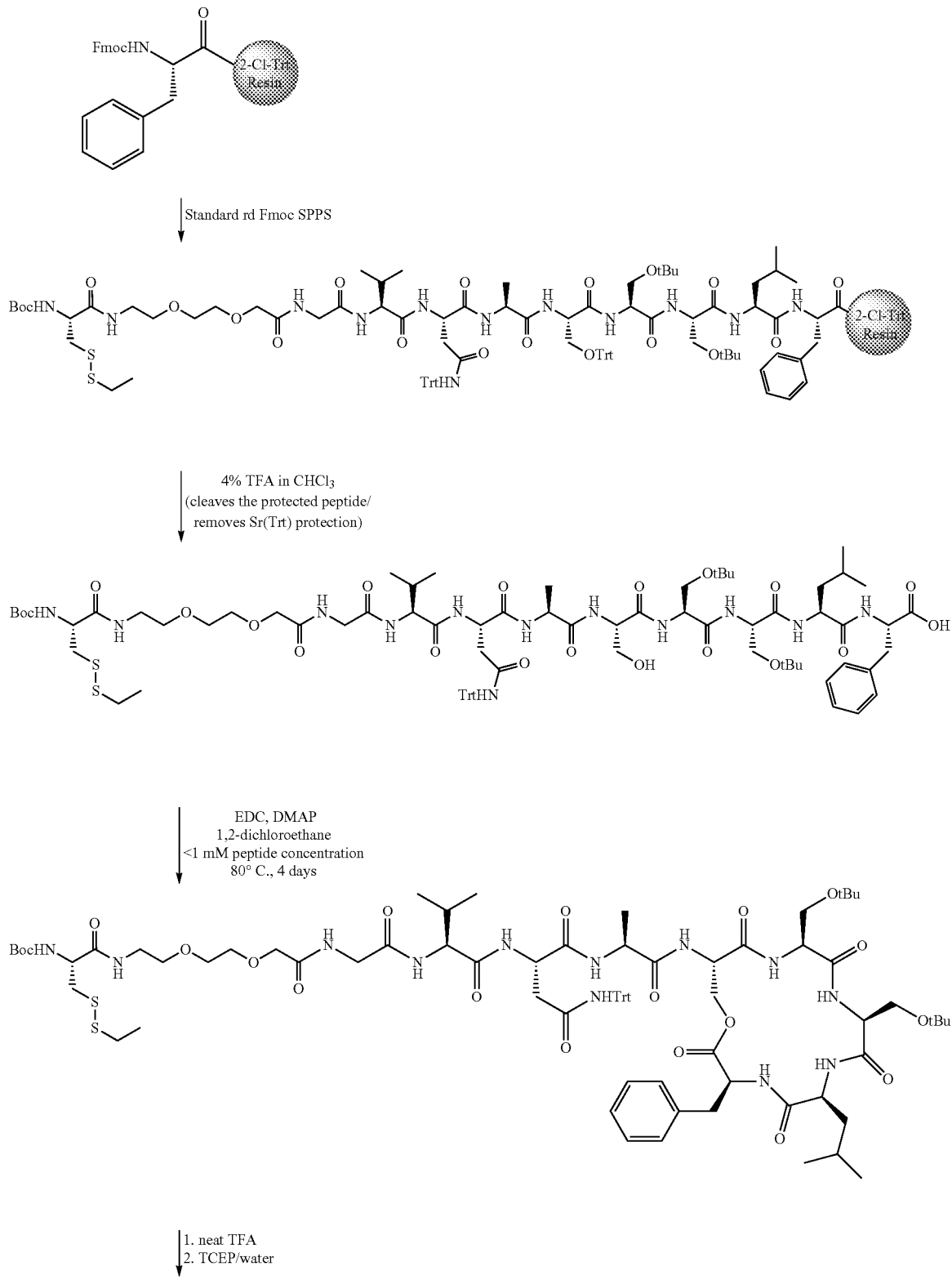

-continued
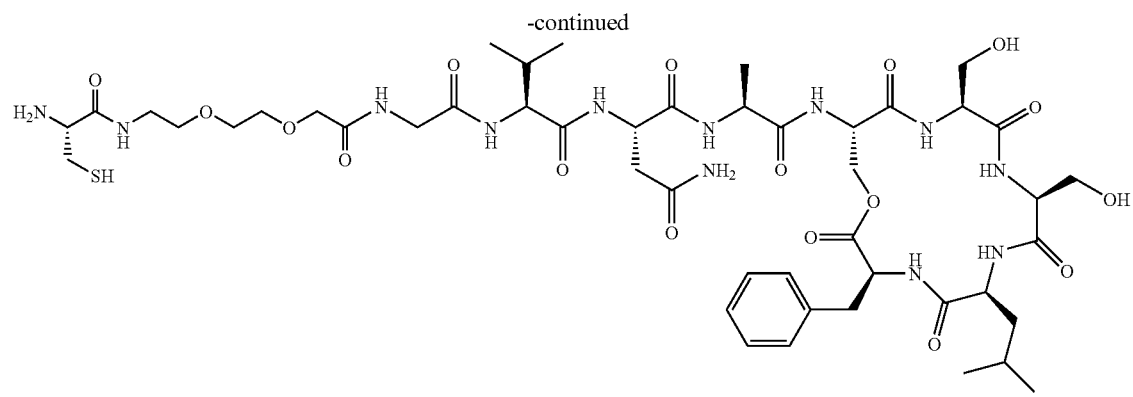
SEQ ID NO: 4 (GVNASSSLY, not including protecting groups)
Scheme 5
Preparation of a Synthetic Hapten (AP3) for Immunization and Elicitation of an Immune Response/Active Vaccine/Generation of Monoclonal Antibodies to AIP-3
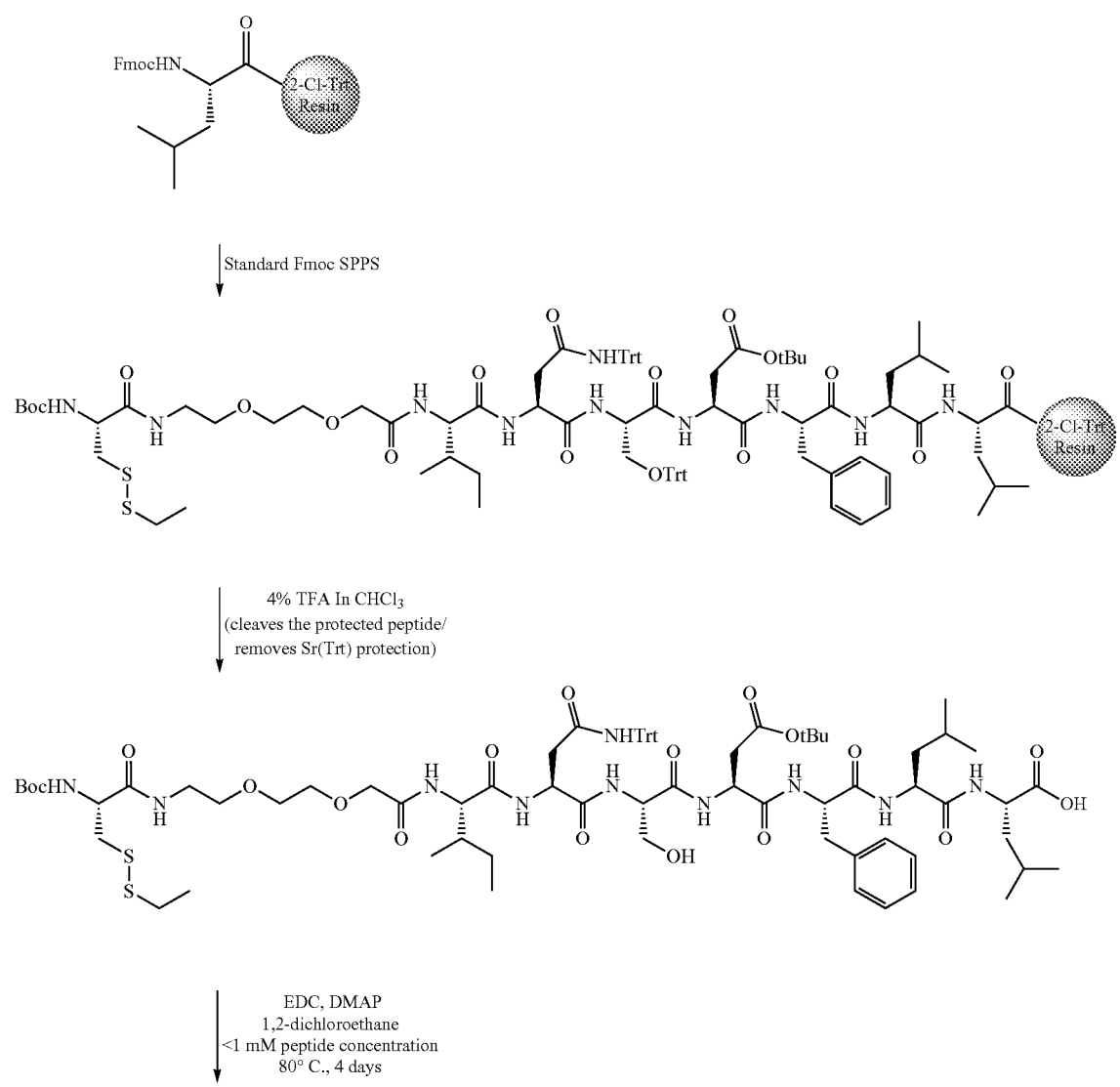

SEQ ID NO: 2 (INSDFLL, not including protecting groups)

Scheme 6

Preparation of a Synthetic Hapten (AP4) for Immunization and Elicitation of an Immune Response/Active Vaccine/Generation of Monoclonal Antibodies to AIP-4

-continued
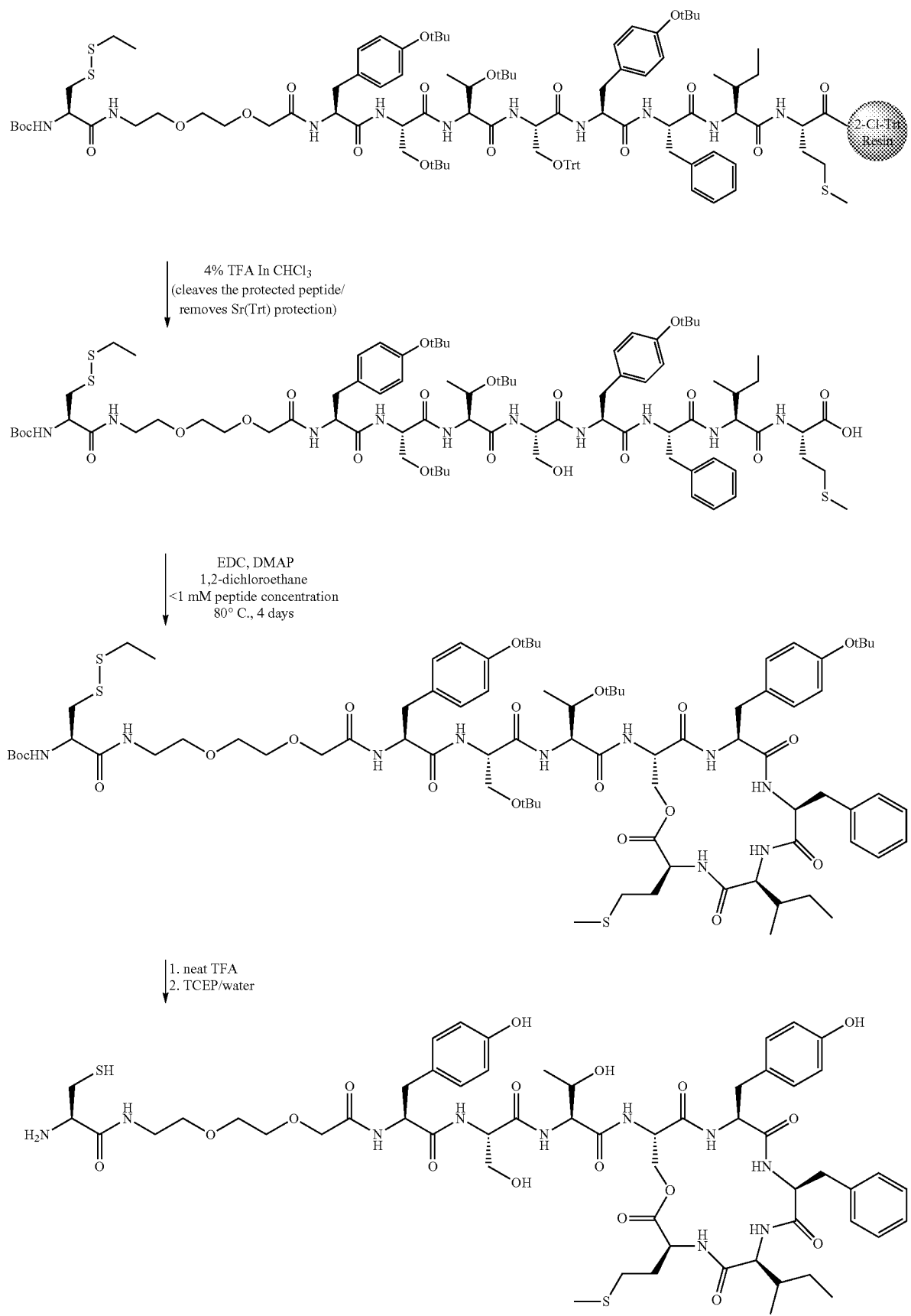

SEQ ID NO: 1 (YSTSYFLM, not including protecting groups)

cleavage of the cyclized peptide off the solid support. Osapay et al., *J. Am. Chem. Soc.* 1992, 114, 6966-6973; Taylor et al.,

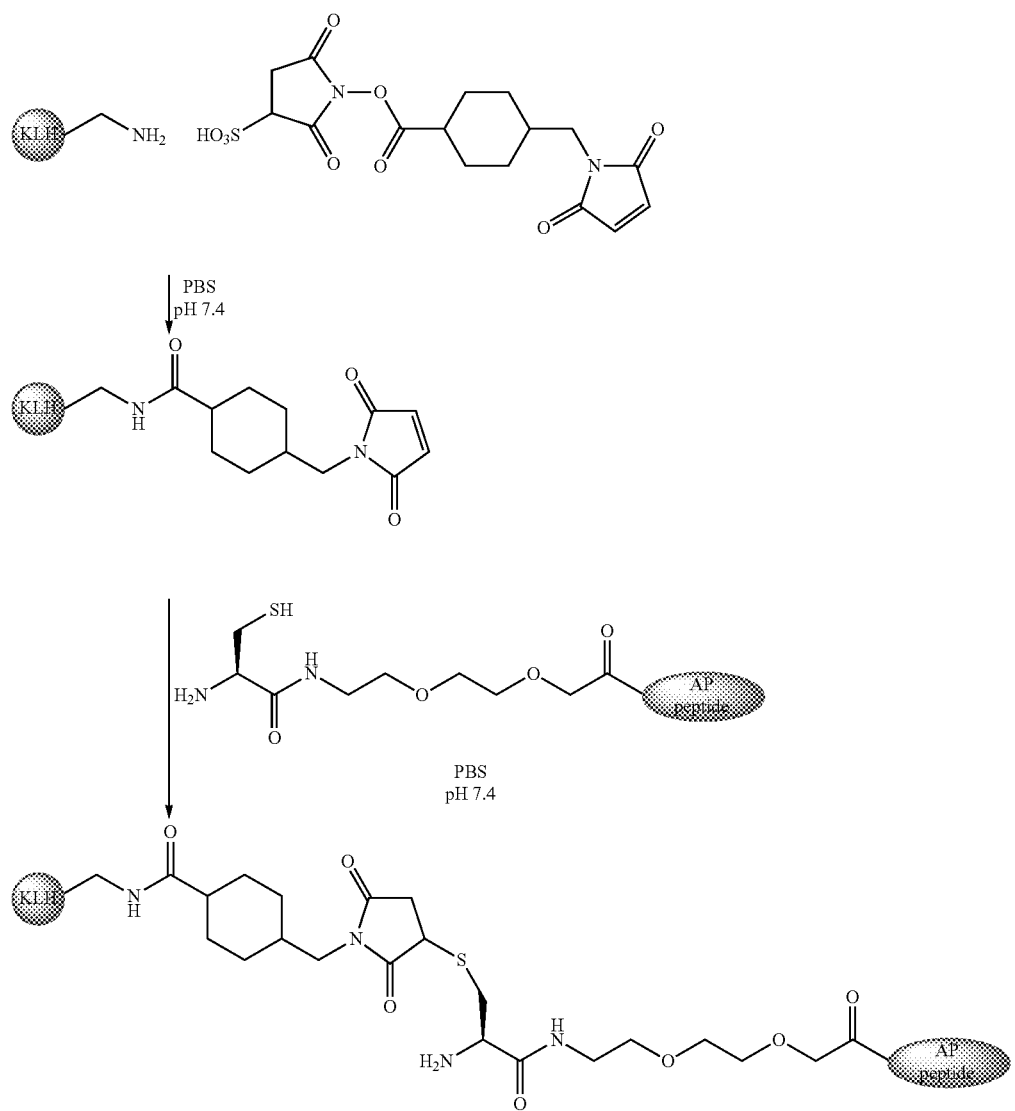

Scheme 7
Preparation of Hapten-Protein Carrier Conjugates for Immunization and Elicitation of an Immune Response/Active Vaccine/Generation of Monoclonal Antibodies to AIP-1-AIP-4

Example 5

Preparation of the AP4 Lactam, Carbamide and Semicarbazide Analogs as Synthetic Haptens The proteolytically stable cyclic lactam, carbamide and semicarbazide AIP peptide haptens are prepared using the well documented methodology of peptide cyclization on base-labile Kaiser oxime resin. See DeGrado et al., *J. Org. Chem.* 1980, 45, 1295-1300; DeGrado et al., *J. Org. Chem.* 1982, 47, 3258-3261; Nakagawa et al., *J. Org. Chem.* 1983, 48, 678-685; Nakagawa et al., *J. Am. Chem. Soc.* 1985, 107, 7087-7092; Kaiser et al., *Science* 1989, 243, 187-192. This synthetic approach is based on Boc-based solid phase peptide synthesis, where the peptide cyclization coincides with the

*Biopolymers* 2002, 66, 49-75; and Li et al., *Curr. Org. Chem.* 2002, 6, 411-440. Synthesis of the cyclic carbamide peptides requires the retro-inverso motif, as described in the literature. Chorev et al., *Biopolymers* 2005, 80, 67-84. The pre-requisite 1-N-Boc-4-(methylthio)butane-1,2-diamine building block is synthesized from the commercially available Boc-methioninol and then coupled onto the peptide chain via the nitrophenyl carbamate protocol according to a literature precedent. Vince et al., *Bioorg. Med. Chem. Lett* 1999, 9, 853-856. The following schemes outline syntheses of proteolytically stable cyclic lactam, carbamide and semicarbazide analogs of AIP-4 peptide. These synthetic methodologies can be applied to the preparation of other cyclic peptide haptens, e.g. AIP-1, AIP-2, AIP-3 as well as other Staphylococcal quorum sensing peptides.

The synthesis of the cyclic lactam AIP4 hapten is summarized in scheme 8. Schemes 9 and 10 outline the syntheses of the intermediates 1-N-Boc-4-(methylthio)butane-1,2-diamine p-nitrophenylcarbamate and N-Fmoc-Met-hydrazide p-nitrophenylcarbamate used in the syntheses of the cyclic carbamide AIP4 hapten and the cyclic semicarbazide AIP4 hapten, respectively. Synthesis of the carbamide and semicarbazide AIP4 haptens is shown in schemes 11 and 12, respectively.

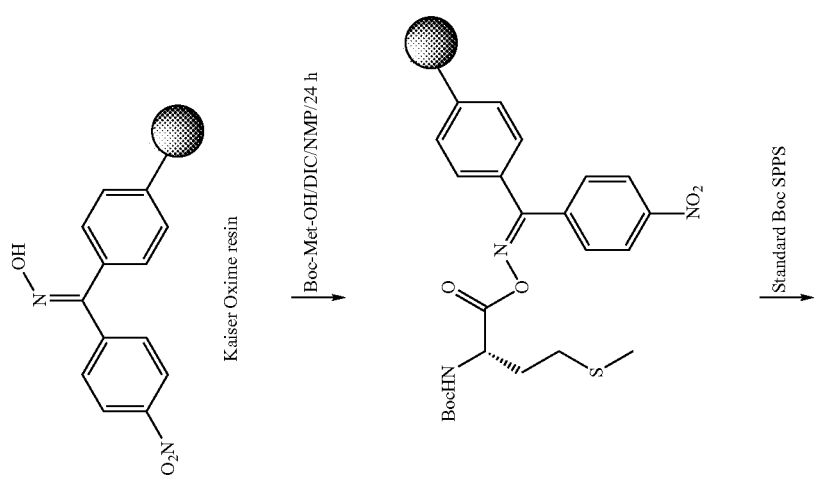
Scheme 8

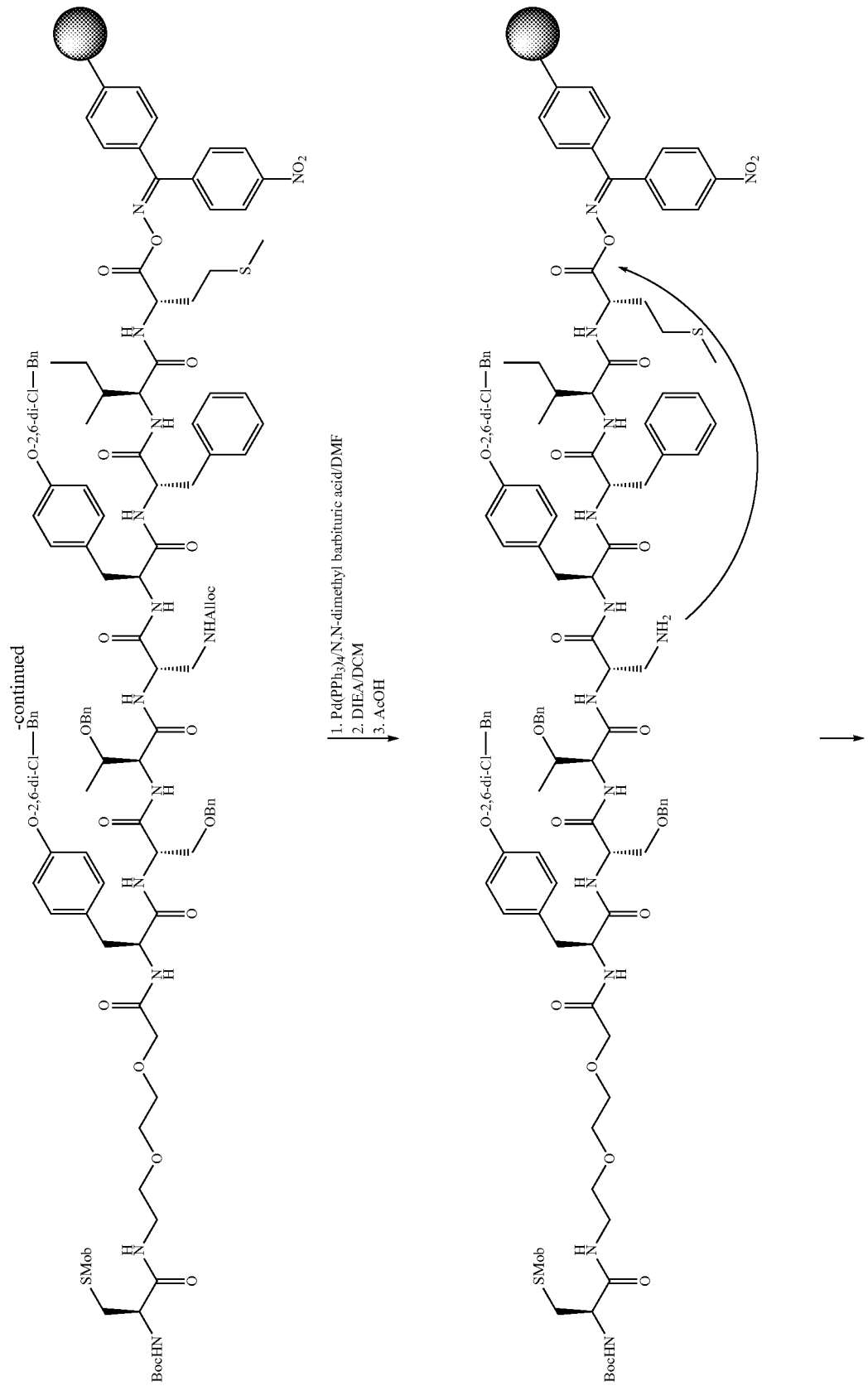

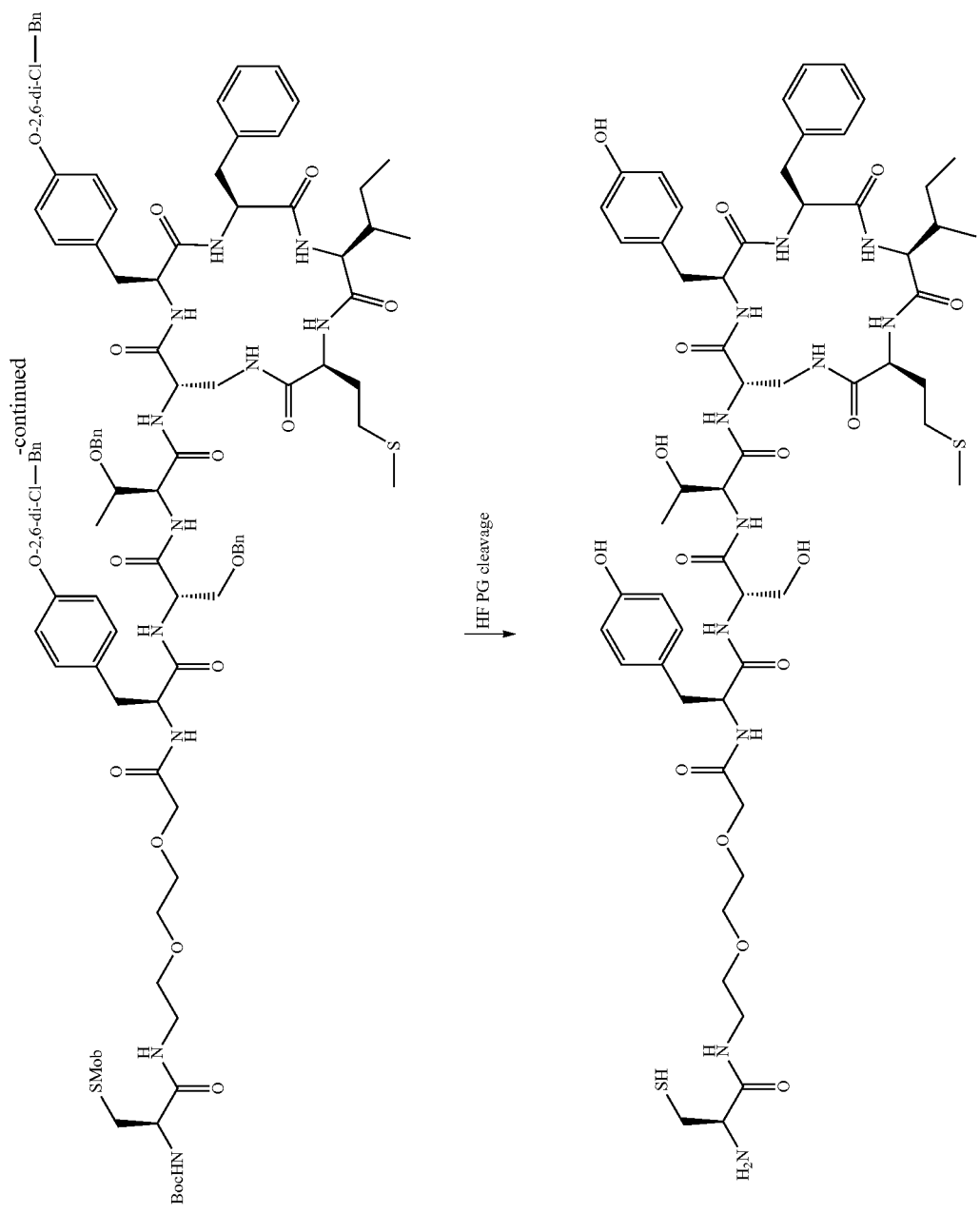

SEQ ID NO: 1 (YSTSYFLM, not including protecting groups)
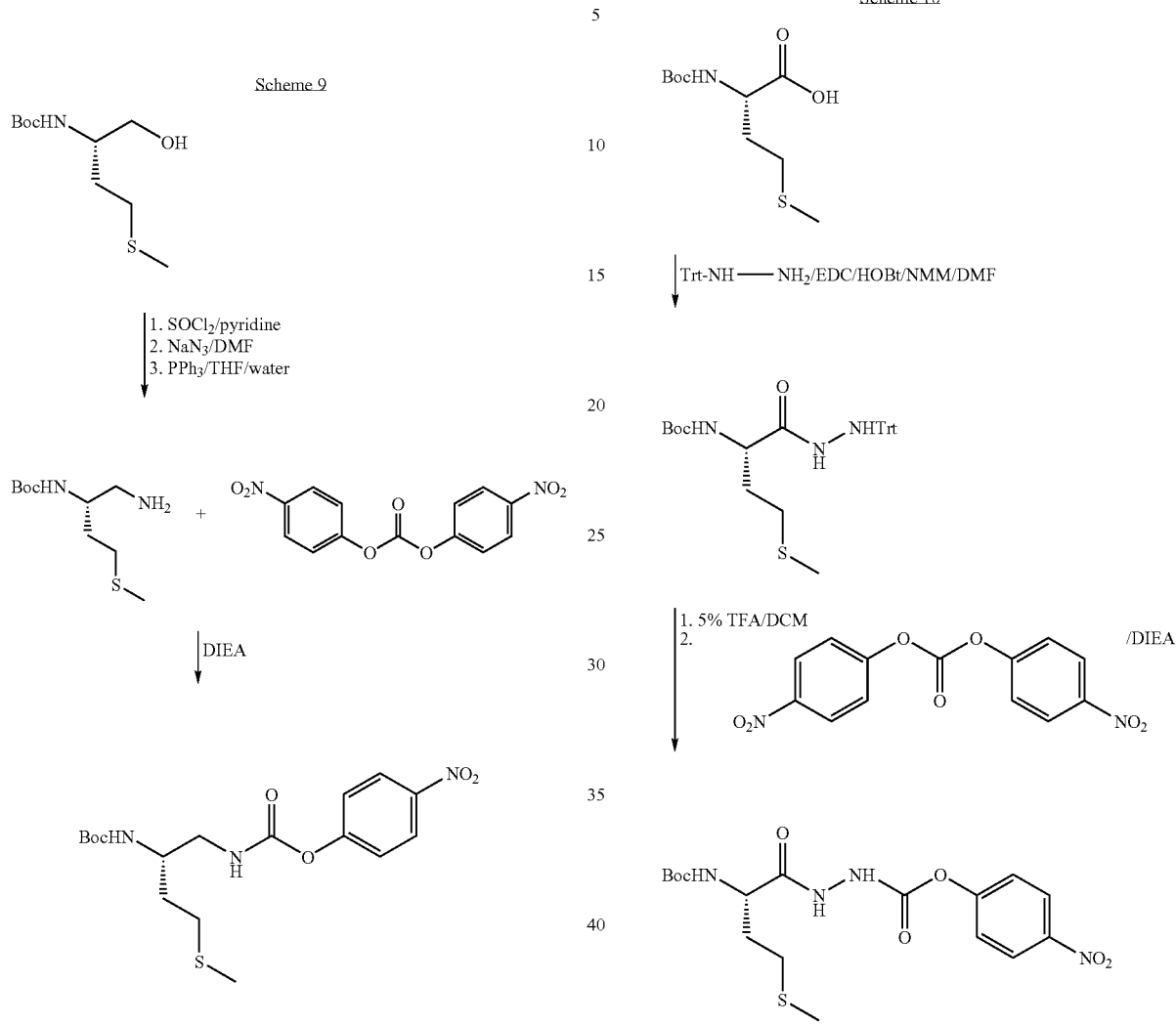
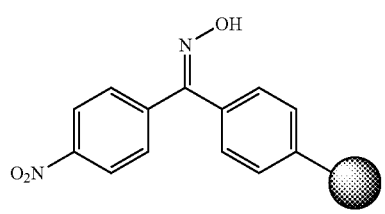
Kaiser Oxime resin
| Boc-Ilet-OH/DIC/NMP/24 h

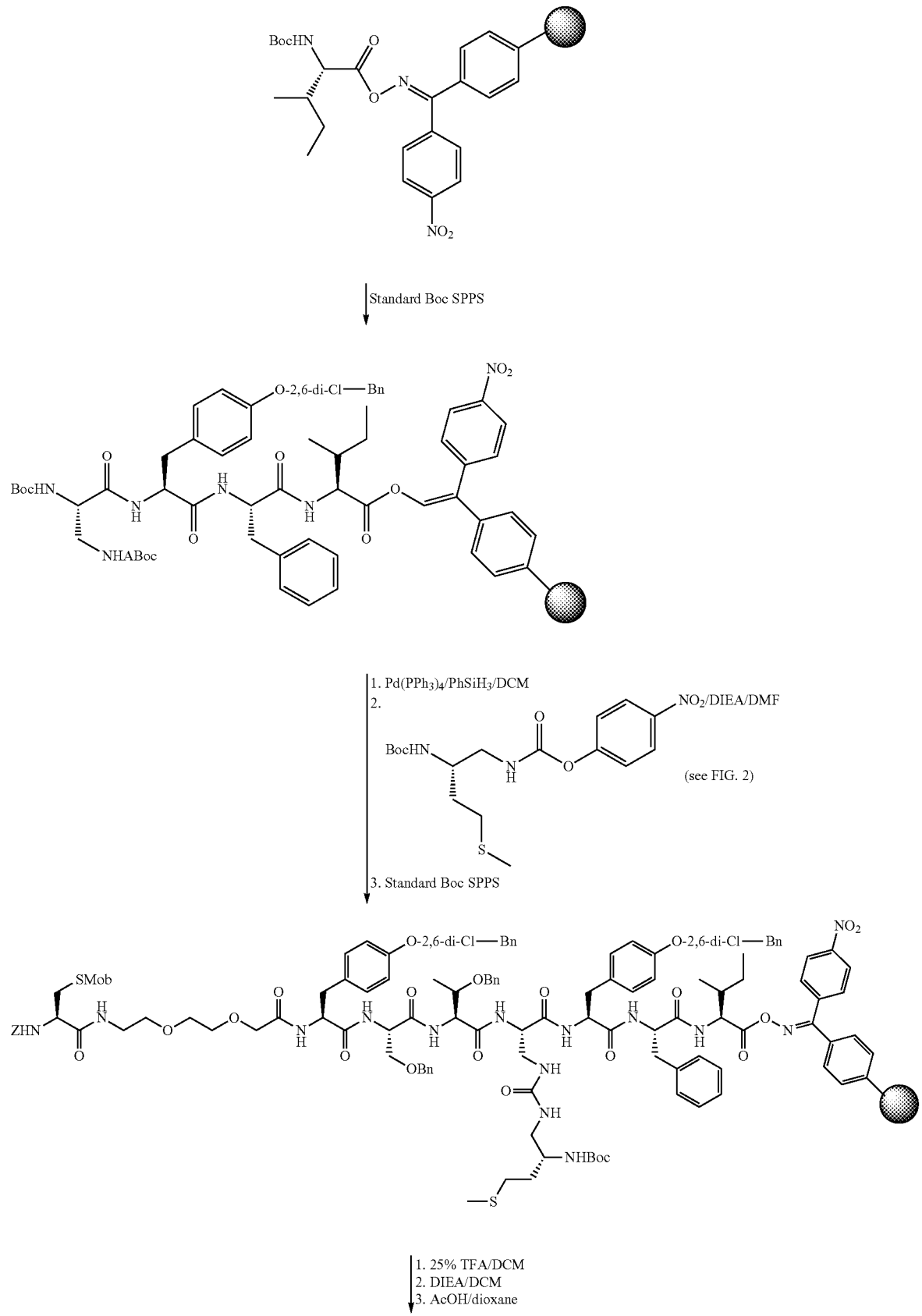

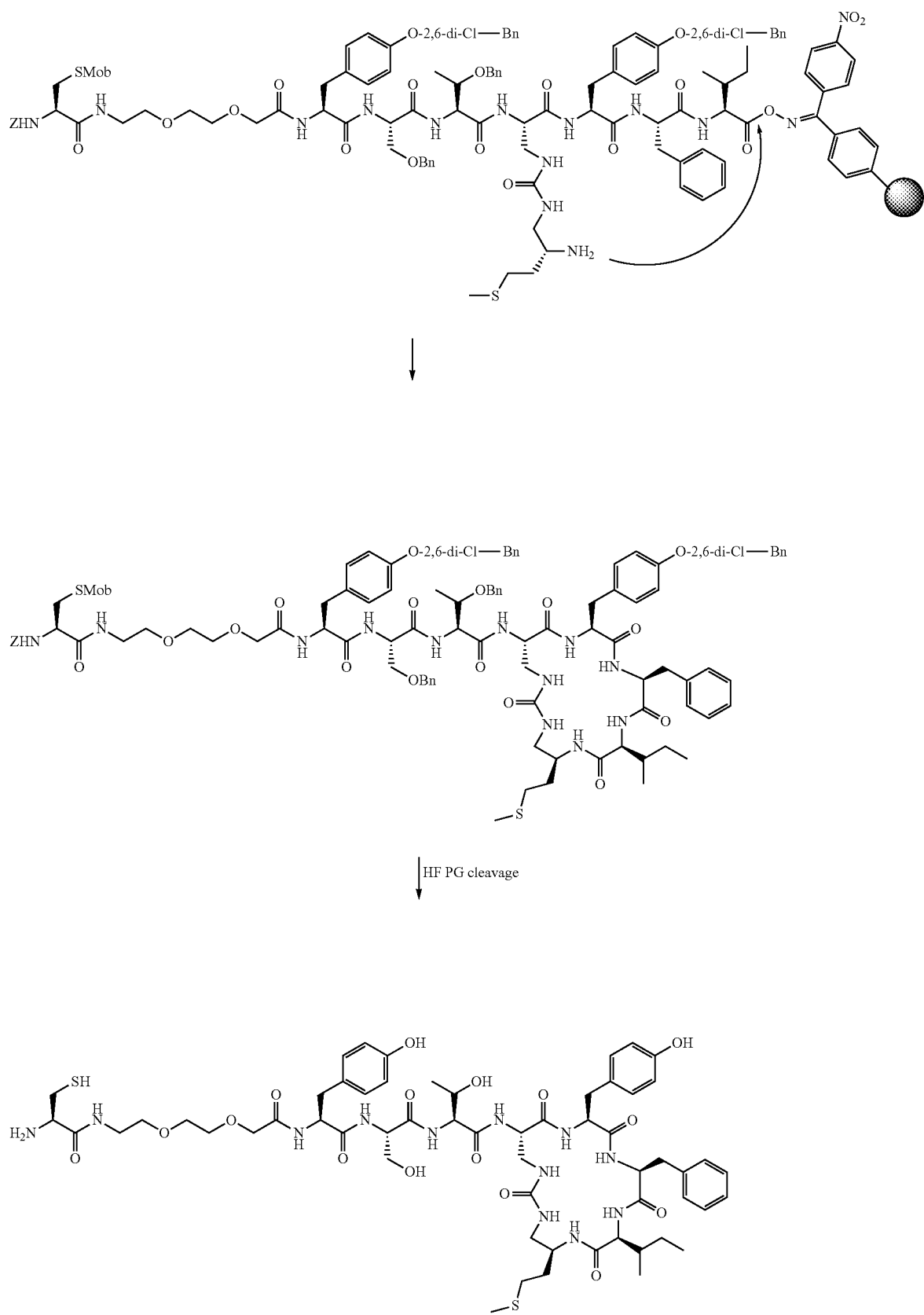

SEQ ID NO: 1 (YSTSYFLM, not including protecting groups)
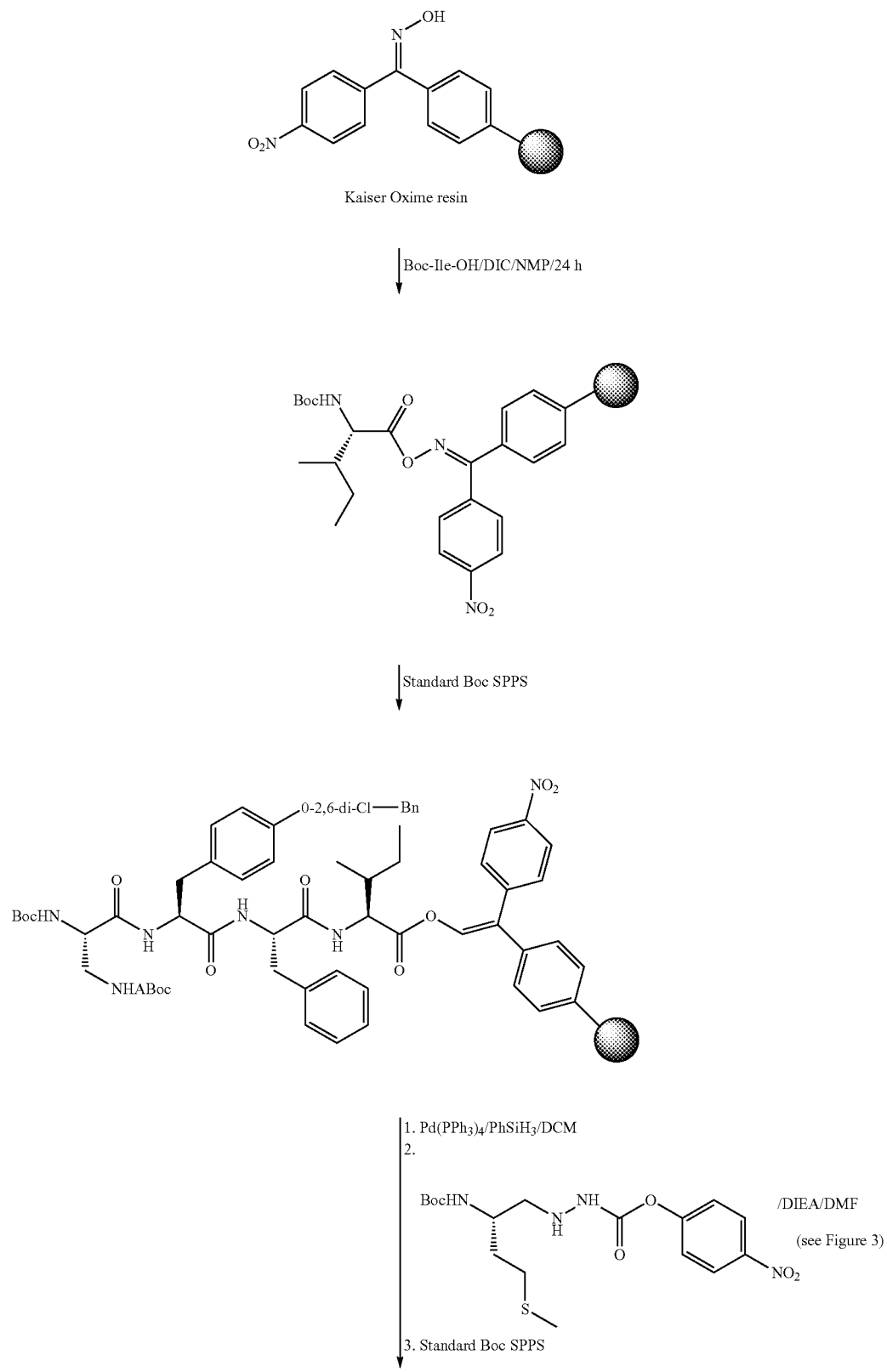
Scheme 12

-continued
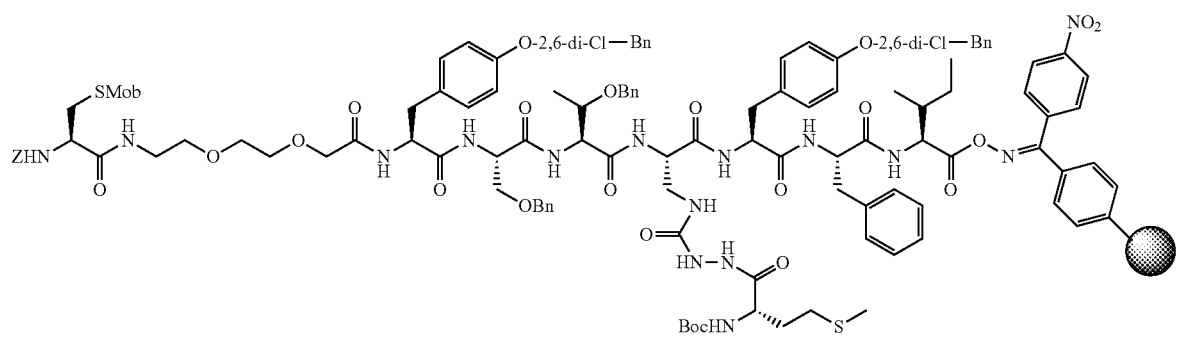
1. 25% TFA/DCM
2. DIEA/DCM
3. AcOH/dioxane
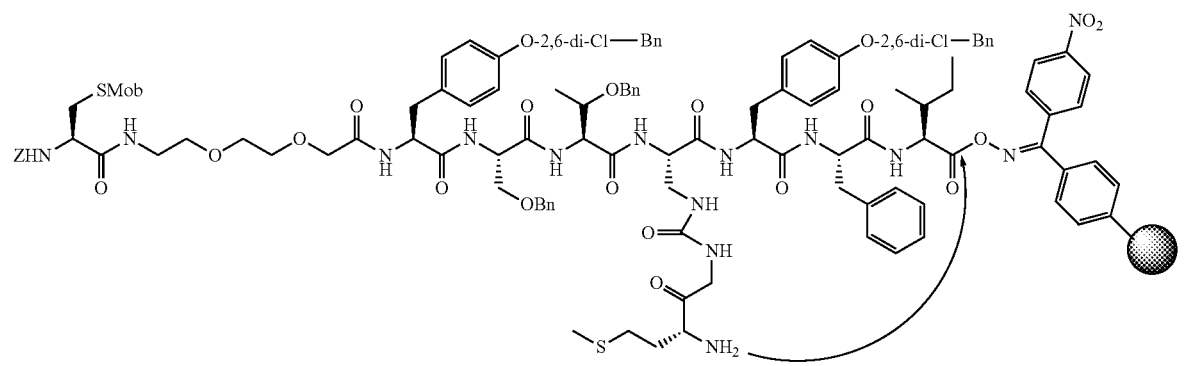
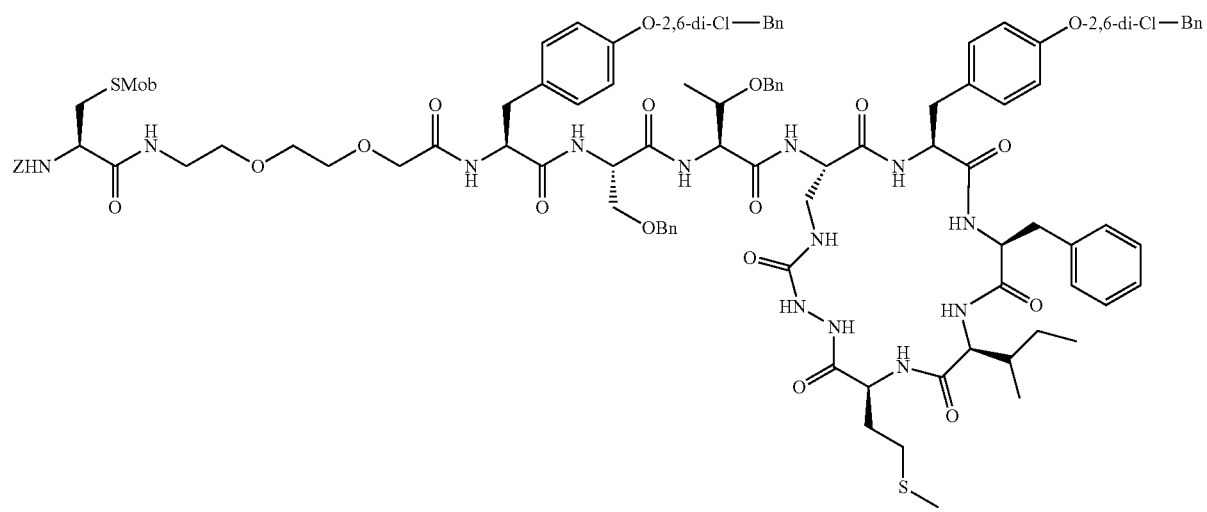
HF PG cleavage -continued

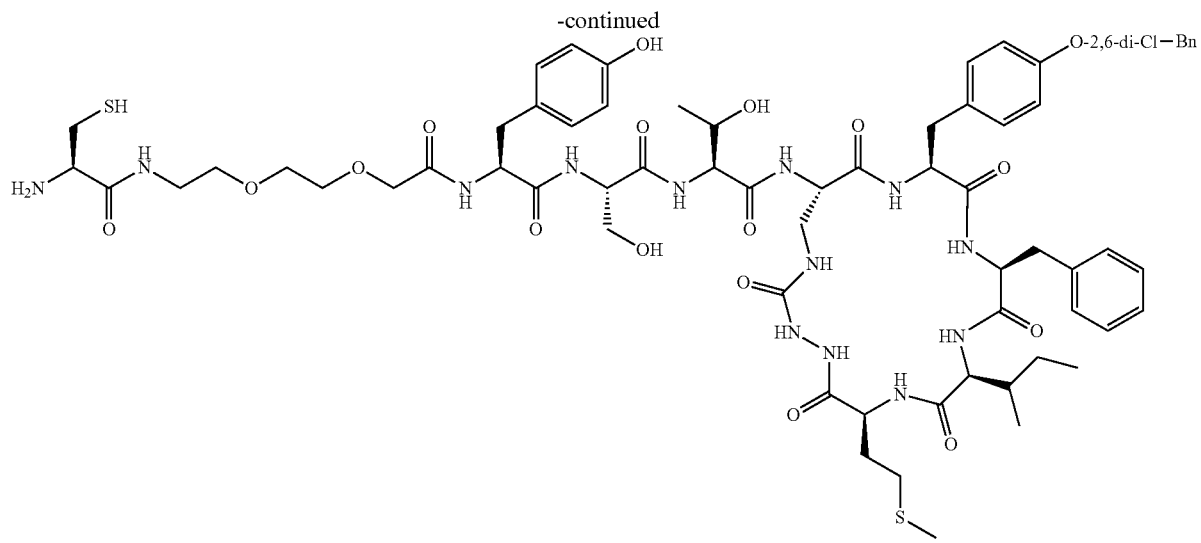

SEQ ID NO: 1 (YSTSYFLM, not including protecting groups)

Example 6

Analysis of Exoprotein Secretion in S. Aureus

After overnight growth on an agar plate at 37° C., a single colony of S. aureus (RN4850 or Wood 46) was inoculated into 3 mL CYGP medium and grown for overnight (18 hours) (see Novick, Methods Enzymol 204:587-636 (1991)). The overnight cultured cells were diluted to $OD_{600}\approx0.03$ in fresh CYGP medium, and distributed to 5 mL polystyrene cell-culturing tube, where each tube contained 0.5 mL of the diluted cells and the appropriate antibody (0.2 mg/mL). After growth for 20-24 hours at 37° C. in a humid incubator without agitation, the samples were transferred to the microcentrifuge tubes (1.5 mL) and centrifuged at 13,000 rpm for 5 minutes. The supernatants were sterilized by filtration through a Millex®-GV filter unit (0.22 µm; Millipore, Ireland), and analyzed by SDS-PAGE (10% Bis-Tris gel, Invitrogen, Carlsbad Calif.). To confirm α-hemolysin and protein A expression, Western blot analyses were performed using the HRP conjugated sheep polyclonal α-hemolysin antibody (abcam Inc., Cambridge Mass.) and anti-Protein A mouse monoclonal antibody (Sigma-Aldrich, St. Louis Mo.) and murine mAb SP2-6E11 (Park and Janda, unpublished data) was used as a control antibody. To test hemolytic activity, the S. aureus supernatants (75 µL×3) were applied onto the sheep blood agar plate, and the plates were incubated at 37° C. for 18 hours and at room temperature for another 24 hours.

Example 7

Static Biofilm Analysis

The biofilm assay was conducted by following a literature procedure with a few modifications (see O'Toole, Methods Enzymol 310:91-109 (1999)). After S. aureus cells (200 µL) were grown in tryptic soy broth (TSB) medium containing 0.2% glucose with or without the antibody (0.2 mg/mL) in the polystyrene 96-well plate for 20-24 hours without agitation, the plate was washed by submersion in water and dried. A crystal violet solution (200 µL, aq. 0.1%) was added to stain the biofilm, and then the plate was washed vigorously with water followed by adding acetic acid (250 µL, aq. 30%) to solubilize the remaining crystal violet. Absorbance was measured at 570 nm with Spectramax 250 (Molecular Devices, Sunnyvale Calif.).

Example 8

Real Time-PCR Analysis

Overnight cultured S. aureus RN4850 cells were diluted to $OD_{600}\approx0.03$ in fresh CYGP medium (1 mL) containing the antibody and grown for 20-24 hours ($OD_{600}\approx2$) at 37° C. without shaking. RNA from the cells was isolated using Rneasy® Mini Kit (QIAGEN Inc., Valencia Calif.) according to the manufacturer's instructions. Isolated RNA was further purified by treating with Rnase-Free Dnase (QIAGENE Inc.) for 30 minutes at room temperature. The first-strand DNA was synthesized using SuperScript™ First-Strand Synthesis System for RT-PCR (Invitrogen) using ≈300 ng of purified RNA. RT-PCR experiments were performed with at least two independent samples, and each experiment was set up in duplicate using LightCycler® FastStart DNA Master$^{PLUS}$ SYBR Green I (Roche Applied Science, Indianapolis, Ind.). Generic SYBR Green Protocol (Roche) was used for the PCR conditions, and relative quantification analyses were performed with LightCycler® 2.0 system (Roche Applied Science) using the housekeeping GyrA gene was a reference. The sequences of the primers used are as follows:

```
                                             (SEQ ID NO: 5)
gyrA F: 5'-TGGCCCAAGACTTTAGTTATCGTTATCC-3';
                                             (SEQ ID NO: 6)
gyrA R: 5'-TGGGGAGGAATATTTGTAGCCATACCTAC-3';

(SEQ ID NO: 7)
rnaIII F: 5'-GCACTGAGTCCAAGGAAACTAACTC-3';
                                             (SEQ ID NO: 8)
rnaIII R: 5'-GCCATCCCAACTTAATAACCATGT-3';

(SEQ ID NO: 9)
hla F: 5'-CTGAAGGCCAGGCTAAACCACTTT-3';
                                             (SEQ ID NO: 10)
hla R: 5'-GAACGAAAGGTACCATTGCTGGTCA-3';
```

-continued

```
spa F:  5'-GCGCAACACGATGAAGCTCAACAA-3';    (SEQ ID NO: 11)
spa R:  5'-ACGTTAGCACTTTGGCTTGGATCA-3';    (SEQ ID NO: 12)
eta F:  5'-GTTCCGGGAAATTCTGGATCAGGT-3';    (SEQ ID NO: 13)
eta R:  5'-GCGCTTGACATAATTCCCAATACC-3';    (SEQ ID NO: 14)
sarA F: 5'-CTGCTTTAACAACTTGTGGTTGTTTG-3'   (SEQ ID NO: 15)
sarA R: 5'-CGCTGTATTGACATACATCAGCGA-3';    (SEQ ID NO: 16)
saeR F: 5'-CGCCTTAACTTTAGGTGCAGATGAC-3';   (SEQ ID NO: 17)
saeR R: 5'-ACGCATAGGGACTTCGTGACCATT-3'.    (SEQ ID NO: 18)
```

Example 9

Dermal Infection Model in Mice

All experiments on mice were performed in accordance with TSRI guidelines and regulations. SKH1 euthymic hairless mice, 6-8 weeks old were obtained from Charles River Laboratories and housed in the biocontainment vivarium for one week before use in experiments. Brain heart infusion agar was from BBL (#211065) and CYGP broth contained 1% casamino acids (Fisher BP1424) 1% yeast extract (EMD 1.03753) 0.59% sodium chloride, 0.5% dextrose and 60 mM β-glycerol phosphate disodium salt (Fluka 50020) as described by Novick, *Methods Enzymol* 204: 587-636 (1991). Cytodex 1 beads (GE Healthcare 17-0448-01) were suspended (1 gram in 50 mL) in Dulbecco's Phosphate Buffered Saline without calcium/magnesium (Gibco) overnight at 20° C. The supernatant was decanted and the beads washed three times by suspension in DPBS and 1 G sedimentation followed by autoclaving (121° C., 15 psi, 15 minutes). *Staphylococcus aureus* RN4850 (AIP4) was grown from frozen stock (BHI+ 20% glycerol) on brain heart infusion agar plates 35° C. overnight. Three representative colonies were combined to inoculate 2 mL CYGP broth, and after overnight incubation without shaking, 0.25 mL of the culture was used to inoculate 5 mL of CYGP followed by incubation at 35° C., 200 rpm for 3 hours. The culture was centrifuged 1,300×G at 4° C. for 20 minutes, the supernatant poured off, and the bacterial pellet was suspended in 1 mL DPBS without calcium/magnesium. The SKH1 received 200 μL intradermal flank injections containing *S. aureus* ($1 \times 10^7$ or $1 \times 10^8$ bacteria), 4 μL packed volume Cytodex beads, DPBS, anti-AIP4 antibody or control IgG (0.6 or 0.06 mg). Additional control animals received 200 μL intradermal injections containing Cytodex beads or beads plus antibody. After injections were made the mice were monitored at least three times each day over a period of 4-7 days. At the conclusion of the monitoring period the mice were euthanized and tissues harvested for bacteriologic and histologic analysis.

Example 10

Passive Immunization of Mice with AP4-24H11

*S. aureus* RN4850 were stored at −80° C. in 20% glycerol/BHI medium, thawed and grown on BHI-agar plates overnight, and three separate colonies sampled to inoculate 2 mL CYGP medium. The inoculum culture was maintained 1 hour at 35° C. without shaking, followed by shaking at 200 rpm for 3 hours. Aliquots of the freshly grown inoculum culture were transferred to 5 mL CYGP medium in 50 mL conical polypropylene tubes (1/20 dilution) followed by shaking at 200 rpm, 35° C. for 3 hours. The bacteria were pelleted by centrifugation at 3,000 rpm (1300×G) for 10 minutes, 4° C. The bacterial pellets were resuspended in Dulbecco's phosphate buffered saline without calcium or magnesium (DPBS⁻), and enumerated using a Petroff-Hausser counting chamber. Final dilutions were made in DPBS⁻ so that $3 \times 10^8$ bacteria were administered i.p. in 0.5 mL. To maintain viability bacteria were administered within two hours of harvest.

Mab AP4-24H11, isotype-matched control IgG (1 mg each) or DPBS was administered i.p. in DPBS to SKH1 mice (6-9 weeks old; 6 animals per treatment group) followed two hours later by 0.5 mL DPBS⁻ i.p. containing $3 \times 10^8$ *S. aureus*. The mice were monitored several times on the day of injection and twice each day on subsequent days, observing ambulation, alertness, response to handling and skin temperature measured by infrared thermometry (Raytek MiniTemp MT4) using a 1 cm diameter infrasternal skin site. Animals showing surface temperature consistently below 30° C. and also diminished response to handling and weakened righting reflex were considered moribund and were euthanized.

Example 11

Competition ELISA Analysis

The optimal concentrations of the AP4-BSA conjugate as well as of each mAb were determined. 96 well ELISA plates were coated with the appropriate amount of AP4-BSA conjugate respectively. The plates were blocked with 4% skim milk, washed and mAbs were added at the predetermined optimal concentration. The plates were washed and free antigen, i.e. the native AIPs 1-4, was added to the wells in a concentration series starting at 100 μM. The plate was incubated for 1 hour at 37° C., thoroughly washed, and goat anti-mouse-horseradish peroxidase (HRP) conjugate (Pierce, Rockford, Ill.) was added. After an incubation period of 1 hour at RT, the plate was thoroughly washed again and the HRP substrate (TMB substrate kit; Pierce) was added, the reaction was allowed to develop for 15 minute and stopped by the addition of 2 M $H_2SO_4$. The absorbance at 450 nm was read and the values plotted using GraFit (Erithacus Software Ltd). The free antigen concentration at which the absorbance value is 50% of the maximum absorbance was considered the $K_d$ of the antibody for its antigen.

Example 12

Generation of Anti-AP4 Monoclonal Antibodies

Based on the reported structural information of AIP-4 (Mayville et al., *Proc. Natl. Acad. Sci. U.S.A.* 96:1218-1223 (1999)), the hapten AP4-5 was designed and synthesized to elicit an anti-AIP-4 antibody immune response in mice (Scheme 1). The rationale for the chemical switch from the native thiolactone to a lactone-containing hapten was based on a lactone's greater aminolytic stability. This strategy ensured that the hapten conjugates remained structurally intact during the immunization process and subsequent immune response; thus, avoiding the generation of degradation products with unknown chemical and biological properties as previously uncovered for other QS molecules. This substitution was also prevented a possible intramolecular thiol exchange between the conserved thiolactone and the pendant cysteine thiol. Therefore, Fmoc-Serine(Trt)-OH was incorporated at position 4 in place of the native cysteine residue.

The hapten 5 was conjugated to the carrier proteins keyhole limpet hemocyanin (KLH) and bovine serum albumin (BSA) via a bifunctional linker (Scheme 2). Balb/c mice were immunized with the KLH conjugate using standard protocols (see Kaufmann et al., *J. Am. Chem. Soc.* 128:2802-03 (2006)). Overall, the immunizations resulted in moderate titers (1600-3200), and based on ELISA analysis, 20 monoclonal antibodies (mAbs) were selected.

Of these, the binding affinities of three AP4-mAbs were determined. Their binding affinities, shown in the following table, were determined against all four natural AIPs using competition ELISA methodology.

| Binding Constants of Selected AP4 Monoclonal Antibodies as Measured by Competition ELISA | | | | |
|---|---|---|---|---|
| AP4-mAb | AIP-1 | AIP-2 | AIP-3 | AIP-4 |
| 23E6 | ≈6 µM | >25 µM | >25 µM | ≈390 nM |
| 24H11 | ≈5 µM | >25 µM | >25 µM | ≈90 nM |
| 29E10 | ≈3 µM | >25 µM | >25 µM | ≈24 nM |

All binding constants were measured at least twice, and the average values are shown. While AP4-29E10 possessed a higher affinity for AIP-4, it was not selected for further biological evaluation due to technical difficulties encountered during the protein production phase.

AP4-24H11, possessed strong binding affinity ($K_{d\ AIP-4} \approx 90$ nM) and high specificity to AIP-4, while displaying little cross reactivity for the other AIPs ($K_{d\ AIP-1} \approx 5$ µM, $K_{d\ AIP-2} => 25$ µM, $K_{d\ AIP-3} => 25$ µM). The ability of AP4-24H11 to discriminate between AIP1 and AIP4 is noteworthy as these two oligopeptides differ only at position 5 with an aspartic acid residue in AIP-1, and a tyrosine moiety in AIP-4. AP4-24H11 was selected for further biological evaluation.

Example 13

AP4-24H11 Alters Expression of Virulent Factors in *S. Aureus*

α-Hemolysin and protein A are two major virulence factors in *S. aureus*, and expression of these proteins is tightly regulated by *S. aureus* signaling networks including the AIP-based agr QS system. The agr QS system positively regulates expression of α-hemolysin, while protein A production is down-regulated by QS signaling.

Figure 3A:
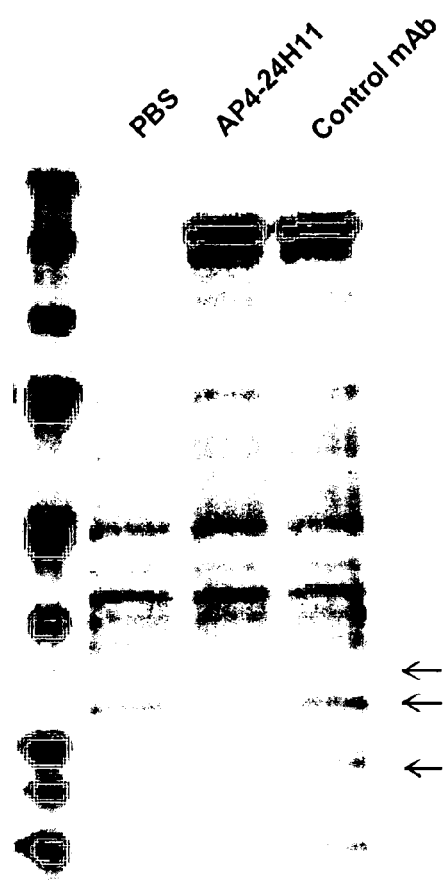
FIG. 3A-B are data illustrating the secretion of exoprotein in RN4850. (A) Analysis of exoprotein secretion in RN4850. After growth for 20-24 hours at 37° C. in the presence of the selected mAbs (200 µg/mL) as indicated, cells were centrifuged at 13,000 rpm for 2 minutes. The supernatants were analyzed by 10% SDS-PAGE. The gels were stained using GelCode® Blue Stain Reagent (Pierce, Rockford Ill.). Solid arrows denote potential difference in exoprotein levels caused by AP4-24H11. (B) Hemolytic activity of the supernatants of *S. aureus* growing medium. Supernatants (150 µL) prepared above were dropped onto the sheep blood agar plate. The plate was incubated at 37° C. for 24 hours and kept at room temperature for another 24 hours.
Figure 3B:
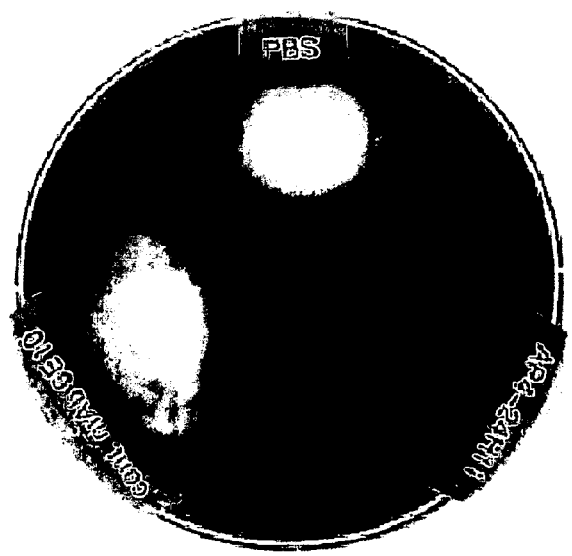
Figure 4A:
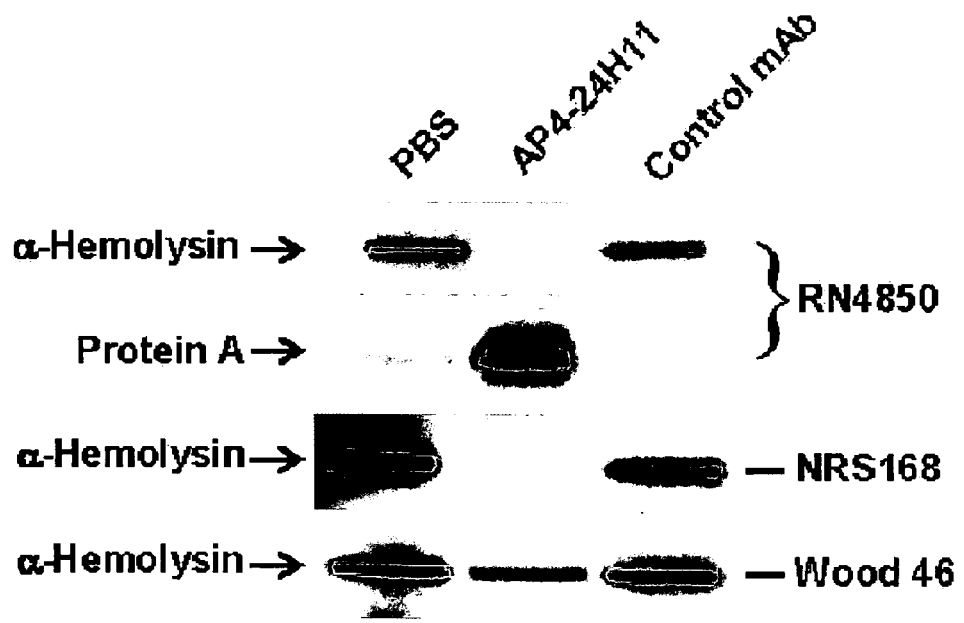
FIG. 4A-E are results illustrating the inhibition of quorum sensing signaling in *S. aureus* by AP4-24H11. (A) Western blot analyses of α-hemolysin and Protein A expression in *S. aureus* (RN4850 and Wood 46). *S. aureus* culture supernatants were prepared as described in the Examples. (B) Relative $OD_{600}$ (%) of RN4850, NRS168 and Wood 46 after 20-24 hour incubation in the presence/absence of AP4-24H11. (C) Analysis of static biofilm formation in RN4850. (D) Real-Time PCR analysis. The amounts of the selected mRNAs were measured in RN4850 grown in the presence or absence of AP4-24H11. Relative quantification was performed using gyrA as a calibrator. At least two independent experiments were carried out for each experiment in duplicate. Actual numbers of fold-change; rnaIII (−77±48), eta (−8.1±1), hla (−5.2±3.1), spa (+5.7±3.6), sarA (−2.1±0.6) and saeR (+1.4±0.4). (E) Suppression of AP4-24H11-mediated QS inhibition in *S. aureus* by AIP-4. AP4-24H11 (≈1.3 µM) was incubated with the native AIP-4 (2.5 µM) in CYPG medium for 20 minutes at room temperature. Overnight cultured *S. aureus* cells were diluted into the above medium ($OD_{600}$≈0.03) and grown for 20 to 24 hours at 37° C. under the static condition. The supernatants were prepared and analyzed. See the Examples for a detailed discussion of the experimental procedures.

To determine whether anti-AIP antibodies are able to interfere with QS signaling in *S. aureus*, whether the anti-AIP-4 mAb AP4-24H11 could modulate the expression of α-hemolysin and protein A in agr group IV strains, RN4850 and NRS168, was examined. Results in FIG. 3A indicate that AP4-24H11 affects the expression and/or secretion of *S. aureus* exoproteins, some of which might also be regulated by the agr QS circuits. As seen in FIG. 4A, mAb AP4-24H11 can successfully reduce the α-hemolysin expression in *S. aureus*, and no hemolytic activity was observed on blood agar plates with the AP4-24H11 treated supernatant as shown in FIG. 3B. In contrast, protein A expression was significantly increased by mAb AP4-24H11 in RN4850, which is also consistent with agr QS inhibition.

The only structural difference between AIP-1 and AIP-4 is position 5, and the data suggest that AP4-24H11 is able to bind to AIP-1 with moderate affinity (≈5 µM). Therefore, whether AP4-24H11 could affect QS signaling in an agr group I strain, namely Wood 46 was investigated. AP4-24H11 was not able to block α-hemolysin expression in Wood 46 as effectively as in RN4850. However, a notable decrease in α-hemolysin production in Wood 46 grown in the presence of AP4-24H11 was evident (FIG. 4A). These data suggest that it is possible to generate cross-reactive mAbs that suppress *S. aureus* QS signaling of two or more different agr groups.

Figure 4B:
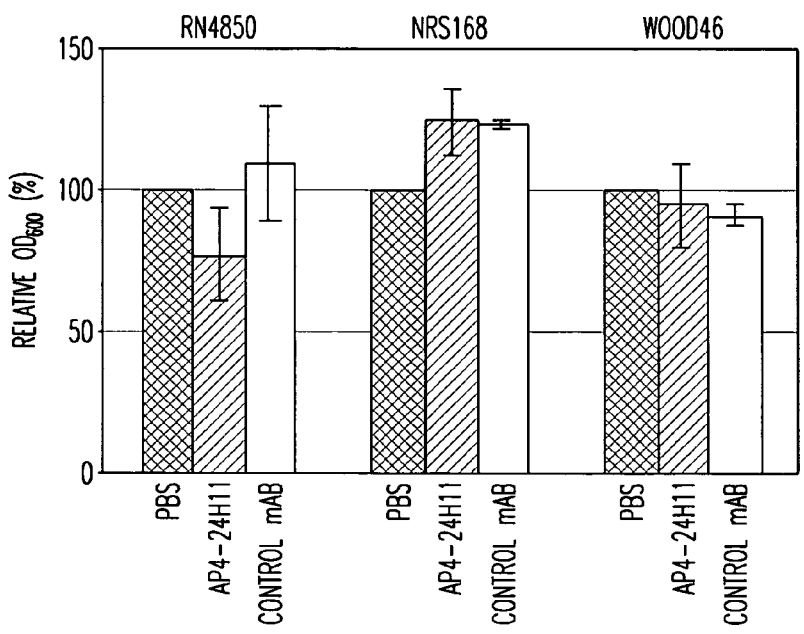

It is possible that the decrease in toxin production and overall protein secretion is caused by an antibody-mediated growth defect, results indicate that no significant growth changes of *S. aureus* were observed over a 24-hour growth period in the presence of AP4-24H11 (FIG. 4B). In addition, no discernable growth effects were observed with mAb SP2-6E11, an unrelated isotype control ($\kappa\gamma_{2a}$) for AP4-24H11.

Figure 4C:
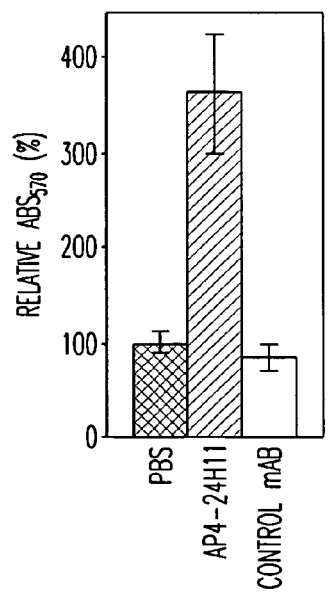

One of the important bacterial virulent factors regulated by QS is biofilm formation. In *S. aureus*, biofilm formation is negatively regulated by agr QS signaling, which is one of the problems in controlling *S. aureus* virulence through agr QS inhibition. Consistent with previous studies, AP4-24H11-mediated QS inhibition led to increased biofilm formation in RN4850 (FIG. 4C). Although the increase of biofilm formation poses a significant problem in chronic infection of *S. aureus*, it represent a lesser predicament in acute infections and thus, mAb AP4-24H11 can be an effective way to control such *S. aureus* infections.

Example 14

Figure 4D:
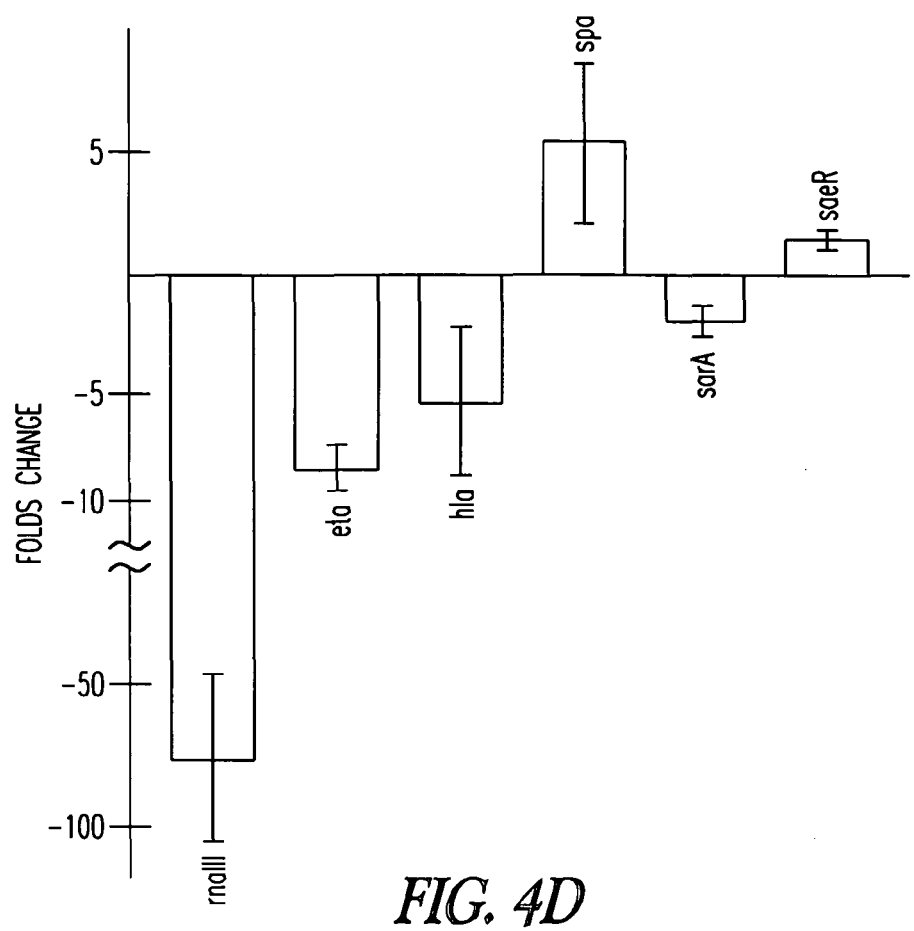

AP4-24H11 Alters Expression of Virulent Factors by Interfering with the Agr QS System To further examine agr QS inhibition by AP4-24H11, real time-polymerase chain reaction (RT-PCR) analysis was performed to evaluate if the observed changes in virulent factor expression were indeed caused by interference with the agr QS system, i.e. whether the presence of AP4-24H11 affects the transcription of rnaIII, the immediate product of agr auto-induction and the main QS effector in *S. aureus*. As expected, the rnaIII transcriptional level in RN4850 during stationary growth phase was reduced significantly (>50 fold), by AP4-24H11. Thus, the alteration of α-hemolysin and protein A expression is a direct result of the interference of AIP-4-mediated QS signaling by AP4-24H11 (FIG. 4D). Yet, the subtle changes in overall exoprotein expression (see FIG. 3) might be misconstrued to mean that AP4-24H11 does not block the QS signaling efficiently. However, the RT-PCR analysis provides evidence that AP4-24H11 significantly inhibits AIP4-based QS in *S. aureus* RN4850.

To analyze the specificity of antibody-based QS interference in *S. aureus*, the transcriptional levels of two additional virulence regulators, namely sarA (staphylococcal accessory regulator) and saeR (staphylococcal accessory protein effector), which control the response to environmental stresses as well as virulence factor expression in *S. aureus*, were investigated. Importantly, no significant changes (≤2-fold) were observed in either sarA or saeR transcription, indicating that AP4-24H11 only affects agr QS system (FIG. 4D).

The transcription of α-hemolysin and protein A was analyzed by RT-PCR as described above. As stated, (vide supra), significant changes were seen in protein expression level. In terms of transcription, the hla and spa genes were suppressed and elevated respectively ≈3 to 5 fold, again confirming that rnaIII affects not only transcription but also translation of these proteins. Finally, exofoliatin A (eta) transcription was investigated. Exofoliatin is another agr QS regulated toxin exclusively produced by AIP-4-utilizing *S. aureus* strains. The data indicated that AP4-24H11 also decreased eta transcription by ≈10 fold (FIG. 4D).

Example 15

Inactivation of AP4-24H11 by the Synthetic AIP-4

Figure 4E:
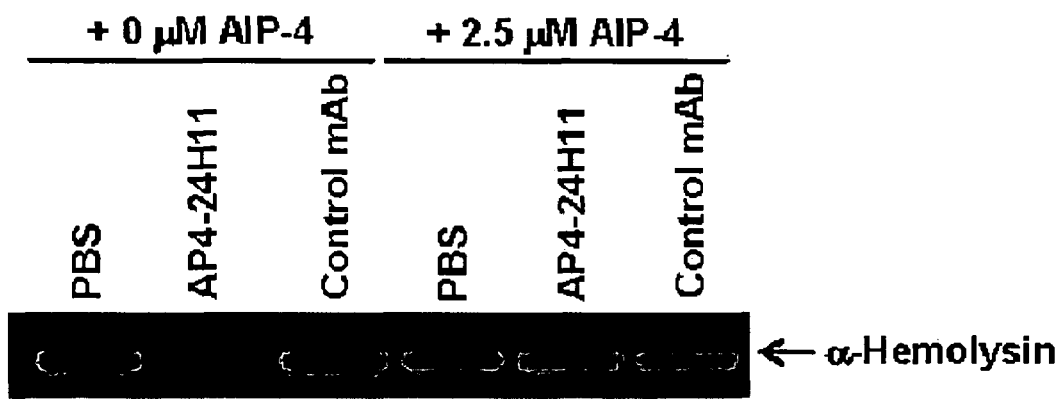

To determine whether AP4-24H11 inhibited agr QS through binding to AIP-4 and sequestering it from the cell growing medium, or whether AP4-24H11 affected other signaling systems in *S. aureus* including the linear peptide RNAIII-inhibiting peptide (RAP), which in turn affect agr QS network, the following experiment was conducted to determine whether external addition of AIP-4 could restore the agr QS signaling network in *S. aureus* RN4850 in the presence of AP4-24H11. Briefly, AP4-24H11 was treated with an equimolar amount of synthetic AIP-4 before addition to the *S. aureus* growth medium to assure saturation of the antibody binding sites with the AIP-4 peptide. As seen in FIG. 4E, the addition of synthetic AIP-4 efficiently reduced the quorum quenching effect of AP4-24H11, and as a result, fully restored expression of α-hemolysin in *S. aureus* RN4850. This finding provides additional confirmation that AP4-24H11 sequesters AIP-4 in *S. aureus* growth medium and inhibits AIP-dependent QS signaling in *S. aureus* in a strictly AIP-4-dependent manner.

Example 16

AP4-24H11 Inhibits *S. Aureus*-Induced Apoptosis in Mammalian Cells

Figure 5A:
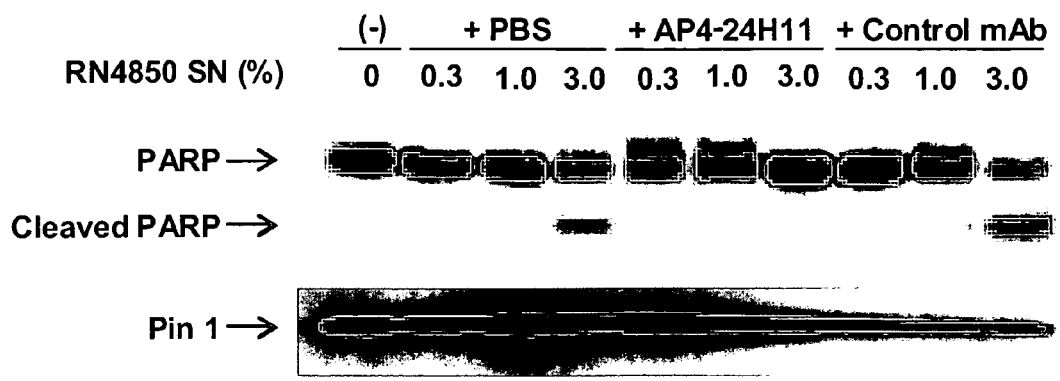
FIG. 5A-B are data illustrating the inhibition of *S. aureus*-induced PARP cleavage by AP4-24H11. PARP cleavage in Jurkat cells after treating with supernatants from *S. aureus* RN4850 (A) and Wood 46 (B). Human Jurkat leukemic T cells were maintained in RPMI 1640 supplemented with 10% heat-inactivated fatal bovine serum, 10 mM $_{(L)}$-glutamine, and 50 mg/mL of streptomycin and penicillin (GIBCO, Invitrogen Corp.). *S. aureus* supernatants were prepared as described in the Examples, and the supernatants of RN4850 were further concentrated to ⅓ of original volume using Amicon Ultra-4 (5,000 NMWL) centrifugal filter devices (MILLIPORE, Billerica Mass.). Confluent cells were distributed to 24-well plate in fresh medium (0.5 mL) and incubated for 6 hours before adding the *S. aureus* supernatants. After 4 hours incubation with the indicated amount of *S. aureus* supernatants, cell extracts were prepared and analyzed by Western blotting using anti-PARP antibody.
Figure 5B:
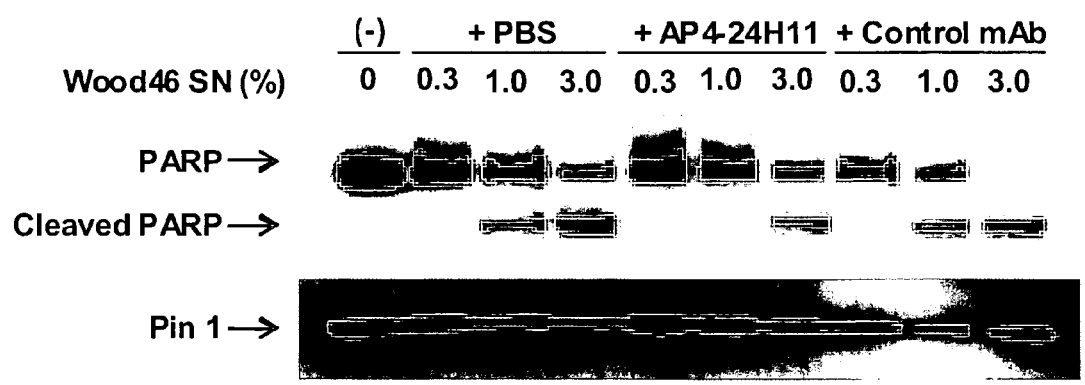

Recent studies have shown that incubation of Jurkat T cells with supernatant of *S. aureus* culture results in induction of apoptosis. Jurkat cells were treated with the supernatants of *S. aureus* (RN4850 and Wood 46) cultures grown in the presence or absence of AP4-24H11. After incubation for 4 hours with the supernatant, the cleavage of poly(ADP-ribose) polymerase (PARP), a biochemical marker indicative of apoptosis induction, was evaluated in Jurkat cell protein extracts. As shown in FIG. 5, AP4-24H11 prevented RN4850 supernatant (1%)-induced PARP cleavage in Jurkat cells, and also partially inhibited the effect of Wood 46 supernatant. The results (FIG. 4A and FIG. 5) indicate a positive correlation between expression of α-hemolysin and *S. aureus*-induced apoptosis.

Example 17

AP4-24H11 Blocks *S. Aureus*-Induced Dermal Injury in Mice

Figure 6A:
FIG. 6A-B are results showing the inhibition of *S. aureus*-induced abscess formation by AP4-24H11 in mice models. (A) *S. aureus* ($1 \times 10^7$)+PBS (upper panel); *S. aureus* ($1 \times 10^7$)+ AP4-24H11 (0.6 mg) (lower panel). (B) *S. aureus* ($1 \times 10^8$)+ Control mAb (0.6 mg) (upper panel); *S. aureus* ($1 \times 10^8$)+ AP4-24H11 (0.6 mg) (lower panel).
Figure 6B:
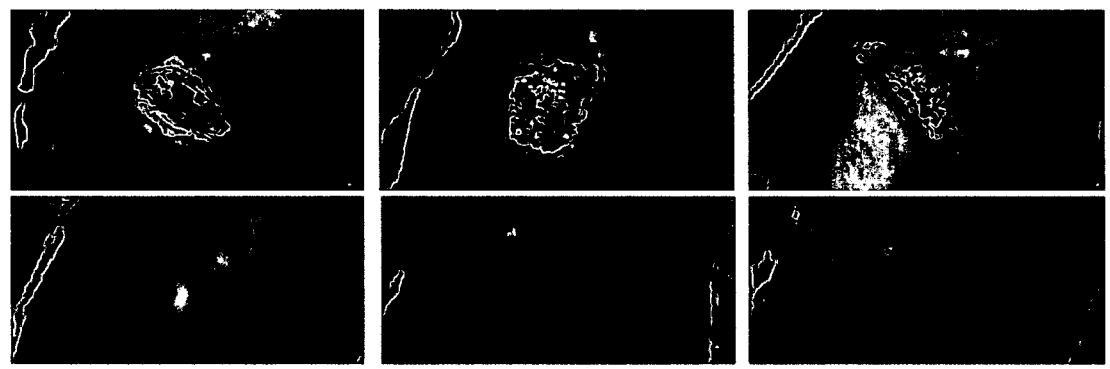
Figure 7A:
FIG. 7A-D are results illustrating the inhibition of *S. aureus*-induced abscess formation by AP4-24H11 in mice models. SKH1 euthymic hairless mice (6-8 weeks old) received 200 µL intradermal flank injections containing *S. aureus* ($1 \times 10^8$ bacteria), 4 µL packed volume Cytodex beads, DPBS, mAb AP4-24H11 or control IgG (0.06 mg or 0.6 mg). Additional control animals received 200 µL intradermal injections containing Cytodex beads or beads plus antibody. After injections were made the mice were monitored at least three times each day over a period of 4-7 days. At the conclusion of the monitoring period the mice were euthanized and tissues harvested for bacteriologic and histologic analysis. (A) *S. aureus*+PBS; (B) *S. aureus*+AP4-24H11 (0.06 mg); (C) *S. aureus*+AP4-24H11 (0.6 mg); (D) Cytodex+AP4-24H11 (0.6 mg).
Figure 7B:
Figure 7C:
Figure 7D:

Next, the potential of mAb AP4-24H11 to mitigate *S. aureus*-induced injury in vivo was investigated by employing a murine subcutaneous infection model. Freshly grown log phase *S. aureus* RN4850 were suspended in PBS containing Cytodex beads, and where indicated, AP4-24H11 or control IgG. Subcutaneous injections of bacterial suspension or vehicle control were made in the flank of SKH1 hairless mice followed by close monitoring over seven days. Doses administered were $10^7$ or $10^8$ bacteria (colony forming units; cfu) and 0.6 or 0.06 mg AP4-24H11 or control IgG. Mice receiving $10^7$ cfu developed minimal hyperemia/edema followed by limited induration over 7 days (see FIG. 6). However, as early as six hours after injection, mice receiving $10^8$ cfu suspended in saline or control IgG showed early-stage hyperemia/redness at the injection site and extending 3-5 mm horizontally and 5-10 mm vertically in a diagonal pattern along the flank (FIG. 7A). Upon reexamination at 18 hours, the same areas surrounding the injection site were devitalized, and the skin was transformed to a brittle, reddish-brown scab. Over the 7-day observation period, the hardened scab began to detach from the surrounding relatively normal appearing skin, and small amounts of purulent exudate were observed at the normal/necrotic junction. In contrast, skin injury was abrogated in mice that received $10^8$ bacteria with 0.6 mg AP4-24H11 (FIG. 7C). As anticipated, the lower dose of AP4-24H11 (0.06 mg) was not protective (FIG. 7B), and control mice receiving $10^8$ cfu with 0.6 mg control IgG were not protected (see FIG. 6). Mice that received an injection of PBS/Cytodex alone or containing 0.6 mg AP4-24H11 remained normal over the observation period with the exception of occasional local induration (FIG. 7D). Animals that had received the protective dose of 0.6 mg AP4-24H11 in combination with *S. aureus* RN4850 did not develop any significant lesions over the 7 day observation period.

Example 18

Figure 8:
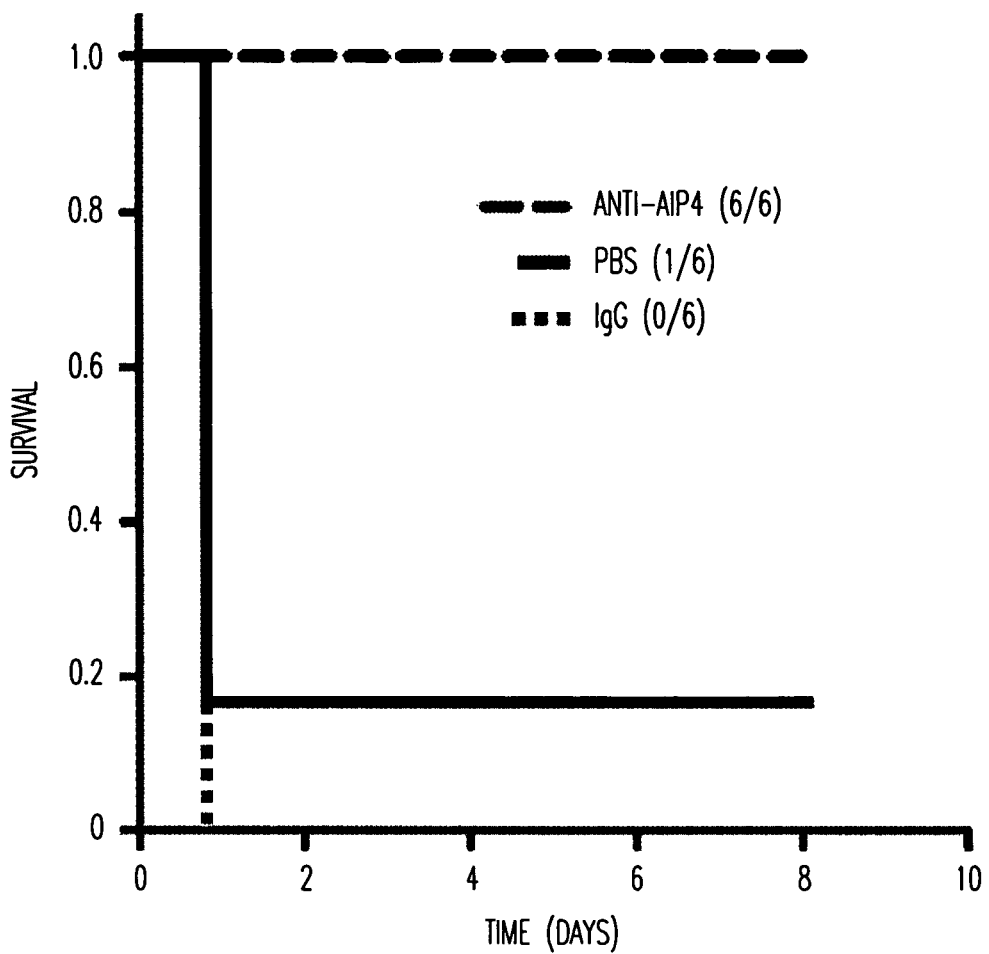
FIG. 8 illustrate survival data obtained from passive immunization of mice with AP4-24H11 against *S. aureus* infection. Survival in mice that were pretreated with mAb AP4-24H11 or control IgG followed two hours later by *S. aureus* injection ($3 \times 10^8$ i.p.). The numbers in parenthesis show number of survivors/number per group. The log rank statistic, p=0.001; n=6 for each group.

Passive Immunization with AP4-24H11 Protected Mice from *S. Aureus*-Induced Fatality To evaluate the effectiveness of a passive immunization approach using AP4-24H11 against a lethal challenge with *S. aureus*, SKH1 hairless mice received a 1 ml i.p. injection of AP4-24H11, control IgG or vehicle (DPBS) followed 2 hours later by 0.5 mL DPBS⁻ containing $3\times10^8$ *S. aureus* RN4850. As shown in FIG. 8, all of the mice receiving AP4-24H11 (6/6) survived through the 8-day observation period. In contrast, only one of the DPBS-treated control mice (1/6) and none of the control IgG-treated mice (0/6) survived longer than 24 hours. These data further validated our immunopharmcaothereutic approach for combating acute *S. aureus* infections.

Example 19

Competition ELISA Analysis of Monoclonal Antibodies Against AP-1, AP-3 and AP-4

The AP-1, AP-3 and AP-4 haptens and monoclonal antibodies specific for these haptens were prepared as described in Examples 4 and 12 above.

For the competition ELISA analysis, the optimal concentrations of the AP1-BSA, AP3-BSA, or AP4-BSA conjugate, as well as of each mAb were determined. 96 well ELISA plates were coated with the appropriate amount of AP1-BSA, AP3-BSA, or AP4-BSA conjugate respectively. The plates were blocked with 4 v % skim milk, washed and mAbs were added at the predetermined optimal concentration. The plates were washed and free antigen, i.e. the native AIPs 1-4, was added to the wells in a concentration series starting at 100 μM. The plate was incubated for 1 hour at 37° C., thoroughly washed, and goat anti-mouse-horseradish peroxidase (HRP) conjugate (Pierce, Rockford, Ill.) was added. After an incubation period of 1 hour at RT, the plate was thoroughly washed again and the HRP substrate (TMB substrate kit; Pierce) was added, the reaction was allowed to develop for 15 minutes and stopped by the addition of 2 M $H_2SO_4$. The absorbance at 450 nm was read and the values plotted using GraFit (Erithacus Software Ltd). The free antigen concentration at which the absorbance value is 50% of the maximum absorbance was considered the $K_d$ of the antibody for its antigen.

The affinity and crossreactivity data are shown in the following tables. These data demonstrate that using the hapten design strategy disclosed herein, monoclonal antibodies (mAbs) were obtained against the lactone analog of the native thiolactone peptide as hapten. The affinities of the mAbs range from low nanomolar to high micromolar, and some but not all mAbs showed crossreactivity, i.e. they recognize the native AIP based on which their original hapten was designed, as well as one or two of the other naturally-occurring AIPs.

| AP1 Sups | AIP1 wt | AIP2 wt | AIP3 wt | AIP4 wt |
|---|---|---|---|---|
| 1H11 | >25 µM | >100 µM | >25 µM | >100 µM |
| 2A9 | >25 µM | >100 µM | >25 µM | >100 µM |
| 2C2 | ~800 nM | >100 µM | ~3 µM | >100 µM |
| 2C10 | >25 µM | >100 µM | >25 µM | >100 µM |
| 2H9 | ~6 µM | >100 µM | >25 µM | ~12 µM |
| 3B1 | ~6 µM | >100 µM | >25 µM | >100 µM |
| 3B11 | ~6 µM | >100 µM | >25 µM | >100 µM |
| 3E11 | >25 µM | >100 µM | >25 µM | >100 µM |
| 4D3 | ~6 µM | >100 µM | >25 µM | >100 µM |
| 6H10 | >25 µM | >100 µM | >25 µM | >100 µM |
| 9A9 | ~6 µM | >100 µM | ~12 µM | >100 µM |
| 9B2 | ~25 µM | >100 µM | >25 µM | >100 µM |
| 9B9 | No Data | No Data | No Data | No Data |
| 9C3 | ~6 µM | >100 µM | >25 µM | >100 µM |
| 9C4 | ~6 µM | >100 µM | >25 µM | >100 µM |
| 9F9 | ~3 µM | >100 µM | ~3 µM | >100 µM |
| 10D6 | >25 µM | >100 µM | >25 µM | >100 µM |
| 10F4 | >25 µM | >100 µM | >25 µM | >100 µM |
| 11B10 | ~3 µM | >100 µM | >25 µM | >100 µM |
| 12A10 | >25 µM | >100 µM | >25 µM | >100 µM |
| 13A11 | ~12 µM | >100 µM | >25 µM | >100 µM |
| 13H3 | >25 µM | >100 µM | >25 µM | >100 µM |
| 15B4 | ~800 nM | >100 µM | ~1 µM | >100 µM |
| 15G12 | >25 µM | >100 µM | >25 µM | >100 µM |
| 16E11 | >25 µM | >100 µM | >25 µM | >100 µM |
| 16F4 | ~25 µM | >100 µM | >25 µM | >100 µM |
| 16G9 | ~12 µM | >100 µM | >25 µM | >100 µM |
| 17F5 | ~12 µM | >100 µM | >25 µM | >100 µM |

| AP3 Sups | AIP1 wt | AIP2 wt | AIP3 wt | AIP4 wt |
|---|---|---|---|---|
| 18A7 | >625 µM | >625 µM | >625 µM | >625 µM |
| 21C4 | 156 µM | >625 µM | >625 µM | >625 µM |
| 21E10 | >625 µM | >625 µM | >625 µM | >625 µM |
| 21H11 | >625 µM | >625 µM | >625 µM | >625 µM |
| 22B3 | >625 µM | >625 µM | >625 µM | >625 µM |
| 22D1 | 156-312 µM | >625 µM | 78 µM | >625 µM |
| 22E12 | >625 µM | >625 µM | >625 µM | >625 µM |
| 22H10 | 156 µM | >625 µM | 312 µM | >625 µM |
| 23C9 | >625 µM | >625 µM | >625 µM | >625 µM |
| 23H1 | >625 µM | >625 µM | >625 µM | >625 µM |
| 24H9 | >625 µM | >625 µM | >625 µM | >625 µM |
| 25A3 | >625 µM | >625 µM | >625 µM | >625 µM |
| 25E2 | >625 µM | >625 µM | >625 µM | >625 µM |
| 25E9 | 156 µM | >625 µM | >625 µM | >625 µM |
| 25F5 | 625-312 µM | >625 µM | 156-312 µM | >625 µM |
| 26A2 | >625 µM | >625 µM | >625 µM | >625 µM |
| 26G3 | >625 µM | >625 µM | >625 µM | >625 µM |
| 26G11 | >625 µM | >625 µM | >625 µM | >625 µM |
| 27E1 | >625 µM | >625 µM | >625 µM | >625 µM |
| 28H8 | >625 µM | >625 µM | >625 µM | >625 µM |
| 29A2 | ~9.8 µM | >625 µM | ~612 nM | >625 µM |
| 29B8 | >625 µM | >625 µM | >625 µM | >625 µM |
| 29D5 | >625 µM | >625 µM | >625 µM | >625 µM |
| 30C9 | 156 µM | >625 µM | >625 µM | >625 µM |
| 30H8 | >625 µM | >625 µM | >625 µM | >625 µM |
| 30H11 | 156 µM | 156 µM | 4.9-2.5 µM | >625 µM |

| AP4 Sups | AIP1 wt | AIP2 wt | AIP3 wt | AIP4 wt |
|---|---|---|---|---|
| 9G2 | >25 µM | >25 µM | >25 µM | ~700 nM |
| 12A2 | >25 µM | >25 µM | >25 µM | >25 µM |
| 13G5 | >25 µM | >25 µM | >25 µM | >25 µM |
| 15B3 | >25 µM | >25 µM | >25 µM | >25 µM |
| 15C3 | >25 µM | >25 µM | >25 µM | >25 µM |
| 15E8 | >25 µM | >25 µM | >25 µM | >25 µM |
| 16D1 | >25 µM | >25 µM | >25 µM | >25 µM |
| 17G2 | >25 µM | >25 µM | >25 µM | >25 µM |
| 18D3 | >25 µM | >25 µM | >25 µM | >25 µM |
| 18G10 | >25 µM | >25 µM | >25 µM | >25 µM |
| 22B8 | >25 µM | >25 µM | >25 µM | >25 µM |
| 22D9 | >25 µM | >25 µM | >25 µM | >25 µM |
| 22F2 | >25 µM | >25 µM | >25 µM | >25 µM |
| 22G7 | >25 µM | >25 µM | >25 µM | >25 µM |
| 23C4 | >25 µM | >25 µM | >25 µM | >25 µM |
| 23E6 | ~6 µM | >25 µM | >25 µM | ~390 nM |
| 24H11 | ~5 µM | >25 µM | >25 µM | ~98 nM |
| 26E8 | >25 µM | >25 µM | >25 µM | >25 µM |
| 27E9 | >25 µM | >25 µM | >25 µM | >25 µM |
| 29E10 | ~3 µM | >25 µM | >25 µM | ~24 nM |

All hybridomas competing were re-tested and the average is shown. AP4-29E10 was tested 5 different times showing variability ranging from 2 nM-110 nM, but most hovered around 24 nM.

The amino acid and nucleotide sequences were determined for selected monoclonal antibodies, and their sequences are shown in the Tables below.

| Amino Acid Sequences of the Variable Heavy and Light Chains of Murine Monoclonal Antibodies | | |
|---|---|---|
| Antibody | Variable Heavy Chain | Variable Light Chain |
| AP1-15B4 | EVHLVESGGDLVKPGGSLKLS CAASGFAFSDFAMSWVRQTPE KRLEWVAIIKSDDSYTYYPDS VRDRFTISRDNARNTLYLQMT SLRSEDTALYYCTKIYDAYFY AMDYWGQGTSVTVSS (SEQ ID NO: 19) | DIVRTQSPLSLSVSLGDQASISC RSSQSLLHSNGNTYLHWYLQKPG QSPKLLIYKVSNRFSGVPDRFSG SGSGTDFTLKISILEAEDLGIYF CSQSTHFPTFGGGTKLEIK (SEQ ID NO: 147) |
| AP4-24H11 | EVKPQESGPGLVKPSQSLSLT CTVTGYSITSNYAWNWIRQFP GNKLEWMGFISSYGTTTYNPS LKSRFSITRDTSKNQFFLQLH SVTIEDTGTYFCTREGDYWGQ GTTLTVSS (SEQ ID NO: 20) | DIVMTQATLSLPVSLGDQASISC RSSQRLVPSNGNIYLHWFLQKPG QSPKLLIYKLSSRFSGVPDRFSG SGSGTDFTLKISRVESEDLGIYF CSQTTHVPYTFGGGTKLEIK (SEQ ID NO: 148) |

-continued

Amino Acid Sequences of the Variable Heavy and Light Chains of Murine Monoclonal Antibodies

| Antibody | Variable Heavy Chain | Variable Light Chain |
|---|---|---|
| AP4-29E10-1 | EVQLQQSGPELEKPGASVKIS CKASGHSFTGYNMNWVKQSND KSLEWIGNIAPYYGVTAYNQK FKGKATLTGDKSSSTAYMQLK SLASEDSAVYYCVLDTSGYAS WGQGTLVTVSA (SEQ ID NO: 21) | DIVMTQATASLTVSLGQRATISC RASKSVSTSGYSYMHWYQQKPGQ PPKLLIYLASNLESGVPARFSGS GSGTDFTLNIHPVEEEDAATYYC QHSREVPYTFGGGTKLELK (SEQ ID NO: 149) |
| AP4-29E10-2 | QVQLQQSGPELEKPGASVKIS CKASGHSFTGYNMNWVKQSND KSLEWIGNIAPYYGVTAYNQK FKGKATLTGDKSSSTAYMQLK SLASEDSAVYYCVLDTSGYAS WGQGTLVTVSA (SEQ ID NO: 22) | DIEMTQITASLTVSLGQRATISC RASKSVSTSGYSYMHWYQQKPGQ PPKLLIYLASNLESGVPARFSGS GSGTDFTLNIHPVEEEDAATYYC QHSREVPYTFGGGTKLELK (SEQ ID NO: 150) |
| AP1-15B4-Δ | GGDLVKPGGSLKLSCAASGFA FSDFAMSWVRQTPEKRLEWVA IIKSDDSYTYYPDSVRDRFTI SRDNARNTLYLQMTSLRSEDT ALYYCTKIYDAYFYAMDYWGQ GTS (SEQ ID NO: 23) | PLSLSVSLGDQASISCRSSQSLL HSNGNTYLHWYLQKPGQSPKLLI YKVSNRFSGVPDRFSGSGSGTDF TLKISILEAEDLGIYFCSQSTHF PTFGGGT (SEQ ID NO: 151) |
| AP4-24H11-Δ | GPGLVKPSQSLSLTCTVTGYS ITSNYAWNWIRQFPGNKLEWM GFISSYGTTTYNPSLKSRFSI TRDTSKNQFFLQLHSVTIEDT GTYFCTREGDYWGQGTT (SEQ ID NO: 24) | TLSLPVSLGDQASISCRSSQRLV PSNGNIYLHWFLQKPGQSPKLLI YKLSSRFSGVPDRFSGSGSGTDF TLKISRVESEDLGIYFCSQTTHV PYTFGGGT (SEQ ID NO: 152) |
| AP4-29E10-1-Δ | GPELEKPGASVKISCKASGHS FTGYNMNWVKQSNDKSLEWIG NIAPYYGVTAYNQKFKGKATL TGDKSSSTAYMQLKSLASEDS AVYYCVLDTSGYASWGQGTL (SEQ ID NO: 25) | TASLTVSLGQRATISCRASKSVS TSGYSYMHWYQQKPGQPPKLLIY LASNLESGVPARFSGSGSGTDFT LNIHPVEEEDAATYYCQHSREVP YTFGGGT (SEQ ID NO: 153) |
| AP4-29E10-2-Δ | GPELEKPGASVKISCKASGHS FTGYNMNWVKQSNDKSLEWIG NIAPYYGVTAYNQKFKGKATL TGDKSSSTAYMQLKSLTSEDS AVYYCVLDTSGYASWGQGTL (SEQ ID NO: 26) | TASLTVSLGQRATISCRASKSVS TSGYSYMHWYQQKPGQPPKLLIY LASNLESGVPARFSGSGSGTDFT LNIHPVEEEDAATYYCQHSREVP YTFGGGT (SEQ ID NO: 154) |

Nucleotide Sequences of the Variable Heavy and Light Chains of Murine Monoclonal Antibodies

| Antibody | Variable Heavy Chain |
|---|---|
| AP1-15B4 | gaggtgcacctggtggagtctgggggagacttagtgaagcctgggggg tccctcaaactctcctgtgcagcctctggattcgctttcagtgactt gccatgtcttgggttcgccagactccggagaagaggctggagtgggtc gcaatcattaaaagtgatgattcttacacctactatccagacagtgtg agggaccgattcaccatctccagagacaatgccaggaacacccttac ctgcaaatgaccagtctgaggtctgaagacacggccttgtattactgt acaaaaatctatgatgcttacttctatgctatggactactggggtcaa ggaacctcagtcaccgtctcctcg (SEQ ID NO: 27) |
| AP4-24H11 | gaggtgaagcctcaggagtcaggacctggcctggtgaaaccttctcag tctctgtccctcacctgcactgtcactggctactcaatcaccagtaat tatgcctggaactggatccggcagtttccaggaaacaaactggagtgg atgggcttcataagttcctatggaaccactacctacaaccctcctctc aaaagtcgattctctatcactcgagacacatccaagaaccagttcttc ctgcaattgcattctgtgactattgaggacacaggcacatatttctgt acaagagagggtgactactggggccaaggcaccactctcacagtctcc tca (SEQ ID NO: 28) |
| AP4-29E10-1 | gaggtccagctgcaacagtccggacctgagctggagaagcctggcgct tcagtgaagatatcctgcaaggcttctggtcattcattcactggctac aacatgaactgggtgaagcagagcaatgacaagagccttgagtggatt ggaaatattgctccttactatggtgttactgcctacaaccagaagttc |

Nucleotide Sequences of the Variable Heavy and
Light Chains of Murine Monoclonal Antibodies

|  |  |
|---|---|
|  | aagggcaaggccacattgactggagacaaatcctccagcactgcctac<br>atgcagctcaagagcctggcatctgaggactctgcagtctattactgt<br>gtcctagacacctcgggctacgcttcctggggccaagggactctggta<br>actgtctctgca (SEQ ID NO: 29) |
| AP4-29E10-2 | caggtccagctgcagcagtctgggcctgagctggagaagcctggcgctt<br>cagtgaagatatcctgcaaggcttctggtcattcattcactggctacaa<br>catgaactgggtgaagcagagcaatgacaagagccttgagtggattgga<br>aatattgctccttactatggtgttactgcctacaaccagaagttcaagg<br>gcaaggccacattgactggagacaaatcctccagcactgcctacatgca<br>gctcaagagcctgacatctgaggactctgcagtctattactgtgtccta<br>gacacctcgggctacgcttcctggggccaagggactctggtcactgtct<br>ctgca (SEQ ID NO: 30) |
| AP1-15B4-Δ | gggggagacttagtgaagcctggggggtccctcaaactctcctgtgca<br>gcctctggattcgctttcagtgactttgccatgtcttgggttcgccag<br>actccggagaagaggctggagtgggtcgcaatcattaaaagtgatgat<br>tcttacacctactatccagacagtgtgagggaccgattcaccatctcc<br>agagacaatgccaggaacacccttacctgcaaatgaccagtctgagg<br>tctgaagacacggccttgtattactgtacaaaaatctatgatgcttac<br>ttctatgctatggactactggggtcaaggaacctca (SEQ ID NO:<br>31) |
| AP4-24H11-Δ | ggacctggcctggtgaaaccttctcagtctctgtccctcacctgcact<br>gtcactggctactcaatcaccagtaattatgcctggaactggatccgg<br>cagtttccaggaaacaaactggagtggatgggcttcataagttcctat<br>ggaaccactacctacaaccctctctcaaaagtcgattctctatcact<br>cgagacacatccaagaaccagttcttcctgcaattgcattctgtgact<br>attgaggacacaggcacatatttctgtacaagagagggtgactactgg<br>ggccaaggcaccact (SEQ ID NO: 32) |
| AP4-29E10-1-Δ | ggacctgagctggagaagcctggcgcttcagtgaagatatcctgcaag<br>gcttctggtcattcattcactggctacaacatgaactgggtgaagcag<br>agcaatgacaagagccttgagtggattggaaatattgctccttactat<br>ggtgttactgcctacaaccagaagttcaagggcaaggccacattgact<br>ggagacaaatcctccagcactgcctacatgcagctcaagagcctggca<br>tctgaggactctgcagtctattactgtgtcctagacacctcgggctac<br>gcttcctggggccaagggactctg (SEQ ID NO: 33) |
| AP4-29E10-2-Δ | gggcctgagctggagaagcctggcgcttcagtgaagatatcctgcaagg<br>cttctggtcattcattcactggctacaacatgaactgggtgaagcagag<br>caatgacaagagccttgagtggattggaaatattgctccttactatggt<br>gttactgcctacaaccagaagttcaagggcaaggccacattgactggag<br>acaaatcctccagcactgcctacatgcagctcaagagcctgacatctga<br>ggactctgcagtctattactgtgtcctagacacctcgggctacgcttcc<br>tggggccaagggactctg (SEQ ID NO: 34) |
| Antibody | Variable Light Chain |
| AP1-15B4 | gacattgtgaggacacagtctccactctccctgtctgtcagtcttggag<br>atcaagcctccatctcttgtagatctagtcagagccttttacacagtaa<br>tggaaacacctatttacattggtacctgcagaagccaggccagtctcca<br>aaactcctgatctacaaagtttccaaccgattttctggggtcccagaca<br>ggttcagtggcagtggatcagggacagatttcacactcaagatcagcat<br>attggaggctgaggatctgggaatttatttctgctctcaaagtacacat<br>tttccgacgttcggtggaggcaccaagctggaaataaaa (SEQ ID<br>NO: 155) |
| AP4-24H11 | gacattgtgatgactcaggctacactctccctgcctgtcagtcttggag<br>accaagcctccatctcttgcagatccagtcagcgccttgttcccagtaa<br>tggaaacatttatttacattggtcctgcagaagccaggccagtctcca<br>aagctcctgatctacaaactttccagtcgattttctggggtcccagaca<br>ggttcagtggcagtggatcagggacagatttcacactcaagatcagcag<br>agtggagtctgaggatctgggaatttatttctgctctcaaactacacat<br>gttccatacacgttcggaggggggaccaagctggaaatcaaa (SEQ<br>ID NO: 156) |
| AP4-29E10-1 | gacattgtgatgactcaggctactgcttccttaactgtatctctggggc<br>agagggccaccatctcatgcagggccagcaaaagtgtcagtacatctgg<br>ctatagttatatgcactggtaccaacagaaaccaggacagccacccaaa<br>ctcctcatctatcttgcatccaacctagaatctggggtccctgccaggt<br>tcagtggcagtgggtctgggacagacttcaccctcaacatccatcctgt<br>ggaggaggaggatgctgcaacctattactgtcagcacagtagggaggtt<br>ccgtacacgttcggaggggggaccaagctggagctgaaa (SEQ ID<br>NO: 157) |

-continued

Nucleotide Sequences of the Variable Heavy and
Light Chains of Murine Monoclonal Antibodies AP4-29E10-2  gacattgagatgacccagattactgcttccttaactgtatctctggggc
             agagggccaccatctcatgcagggccagcaaaagtgtcagtacatctgg
             ctatagttatatgcactggtaccaacagaaaccaggacagccacccaaa
             ctcctcatctatcttgcatccaacctagaatctggggtccctgccaggt
             tcagtggcagtgggtctgggacagacttcaccctcaacatccatcctgt
             ggaggaggaggatgctgcaacctattactgtcagcacagtagggaggtt
             ccgtacacgttcggaggggggaccaagctggagctgaaa (SEQ ID
             NO: 158)

AP1-15B4-Δ   ccactctccctgtctgtcagtcttggagatcaagcctccatctcttgta
             gatctagtcagagccttttacacagtaatggaaacacctatttacattg
             gtacctgcagaagccaggccagtctccaaaactcctgatctacaaagtt
             tccaaccgattttctggggtcccagacaggttcagtggcagtggatcag
             ggacagatttcacactcaagatcagcatattggaggctgaggatctggg
             aatttatttctgctctcaaagtacacattttccgacgttcggtggaggc
             acc (SEQ ID NO: 159)

AP4-24H11-Δ  acactctccctgcctgtcagtcttggagaccaagcctccatctcttgca
             gatccagtcagcgccttgttcccagtaatggaaacattttatttacattg
             gttcctgcagaagccaggccagtctccaaagctcctgatctacaaactt
             tccagtcgattttctggggtcccagacaggttcagtggcagtggatcag
             ggacagatttcacactcaagatcagcagagtggagtctgaggatctggg
             aatttatttctgctctcaaactacacatgttccatacacgttcggaggg
             gggacc (SEQ ID NO: 160)

AP4-29E10-1-Δ actgcttccttaactgtatctctggggcagagggccaccatctcatgca
             gggccagcaaaagtgtcagtacatctggctatagttatatgcactggta
             ccaacagaaaccaggacagccacccaaactcctcatctatcttgcatcc
             aacctagaatctggggtccctgccaggttcagtggcagtgggtctggga
             cagacttcaccctcaacatccatcctgtggaggaggaggatgctgcaac
             ctattactgtcagcacagtagggaggttccgtacacgttcggagggggg
             acc (SEQ ID NO: 161)

AP4-29E10-2-Δ actgcttccttaactgtatctctggggcagagggccaccatctcatgca
             gggccagcaaaagtgtcagtacatctggctatagttatatgcactggta
             ccaacagaaaccaggacagccacccaaactcctcatctatcttgcatcc
             aacctagaatctggggtccctgccaggttcagtggcagtgggtctggga
             cagacttcaccctcaacatccatcctgtggaggaggaggatgctgcaac
             ctattactgtcagcacagtagggaggttccgtacacgttcggagggggg
             acc (SEQ ID NO: 162)

Example 20

Evaluation of Other Anti-AIP Antibodies

Figure 9:
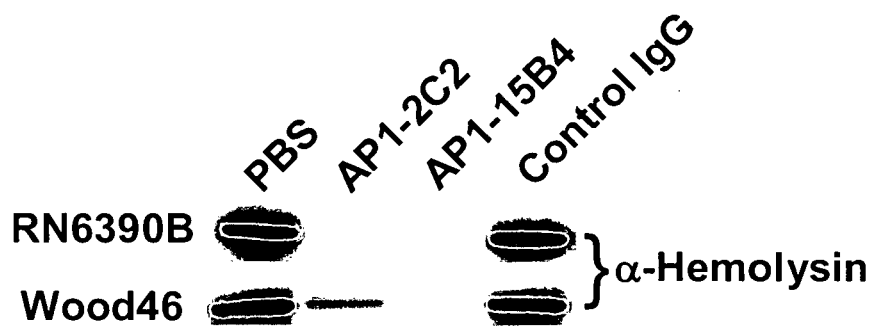
FIG. 9 is result showing the suppression of α-hemolysin expression in the agr group I strains by anti-AP1 monoclonal antibodies.

The quorum quenching ability of some of the newly obtained anti-AIP antibodies, e.g. anti-AP1 and anti-AP3 antibodies were evaluated. For the group I strains (RN6390B and Wood46), two monoclonal antibodies, AP1-2C2 and AP1-15B4, which showed high affinity toward AIP-1 in competition ELISA assay, were tested. FIG. 9 shows that the anti-AP1 antibodies also efficiently inhibit quorum sensing of the group I strains resulting in changes in the virulent factors expression. In addition, the anti-AP3 antibodies against one of the group III strains, RN8465 were also tested. Due to low exoprotein expression in RN8465, the quorum quenching effects were not determined precisely.

Example 21

Therapeutic Effects of Cyclic Peptide-Based Vaccines

To evaluate the effectiveness of cyclic peptide-based vaccines, the following experiments are conducted. Active and passive vaccination schedules are as follows:

| Active Vaccination Schedule | | |
|---|---|---|
| Initial titer: | day −1 | |
| Initial immunization: | day 0 | 50-200 μg protein |
| Titer pre-boost 1: | day 6 | |
| Boost 1: | day 7-14 (1-2 weeks after initial immunization) | 50-200 μg protein |
| Titer pre-boost 2: | day 20 | |
| Boost 2: | day 21-28 (1-2 weeks after boost 1) | 50-200 μg protein |
| Titer pre-challenge: | day X (1 day before challenge) | |
| Challenge | day X (1 week after boost 2) | |

| Passive Vaccination Schedule | | |
|---|---|---|
| Initial titer: | day −1 | |
| Immunization: | day 0 | 100-1000 μg IgG/mouse |
| Titer pre-challenge: | day 1 | |
| Challenge | day 2 | |

The vaccines are administration by intravenous, intramuscular, intraperitoneal or subcutaneous injection to male Balb/c rats of 25-30 g and between 8-12 weeks of age. Twenty animals are included in each treatment group.

To determine whether the vaccine protects the animal from a lethal system challenge, *S. aureus* strain of any with known agr group is used. About $10^8$-$10^9$ C.F.U. of the bacteria is administered by intraperitoneal injection. Body temperatures and survival every 12 hours are determined. Death or survival after 10 days represents the end point of the study. Additional details are described above.

To determine whether the vaccine protects the animal from sepsis, S. aureus strain of any with known agr group is used. About $10^7$-$10^8$ C.F.U. of the bacteria is administered by intravenous injection. Thus, S. aureus is administered directly into the blood stream and will spread hematogenously through the body. Body temperatures and survival every 12 hours are determined. Death or survival after 10 days represents the end point of the study.

To determine whether the vaccine protects the animal from septic arthritis, S. aureus strain LS-1 (a mouse-adapted strain belonging to agr group 1), or any strain with a known agr group that is capable of spontaneously causing arthritis, is used. About $10^6$-$10^7$ C.F.U. of the bacteria is administered by intravenous injection. Body temperature, survival every 12 hours, joint swelling (scoring), redness, changes in moving patterns and morbidity are determined. Death or survival at 28 days represents the end point of the study.

To determine whether the vaccine protects the animal from renal abscess, S. aureus strain of any known agr group is used. About $10^6$-$10^7$ C.F.U. of the bacteria is administered by intravenous injection. The animals are evaluated based on activity, alertness, and coat condition (scored 0-2 for normal, slightly abnormal, very abnormal). In addition, kidneys are removed aseptically and histologically evaluated (abscess formation; 0—no visible abscesses; 1—1 small abscess; 2—several abscesses; and 3—severely abscessed kidneys), and C.F.U. counts are recovered from homogenized kidneys. Death or survival at 7 days marks the end point of the study.

The same model can be used to determine whether the vaccines can block renal abscess formation, in which case, general behavior and renal abscess based on histological evaluation of the kidneys are considered.

To determine whether the vaccine protects the animal from spreading throughout the body, as well as colonize a catheter, the foreign body model is used. A piece of catheter is implanted in a subcutaneous space on the mice. After 24 hours, a suspension of S. aureus strain of any known agr group is administered by subcutaneous injection of about $10^6$-$10^8$ C.F.U. in the catheter bed. The ability of the bacteria to spread through the body and to colonize the catheter are evaluated by determining body temperature, survival every 12 hours, subcutaneous abscess formation and C.F.U. count recovered from catheter at various time points. Death or survival at 7 days marks the end point of the study. Alternatively, a colonized catheter could be used in this model.

To determine whether the vaccine protects the animal from mastitis, lactating CD1 mice are administered by intramammary injection of about $10^2$-$10^4$ C.F.U. of a S. aureus strain from any known agr group. C.F.U. counts from mammary glands are determined at various time points and expressed in C.F.U./gland or C.F.U./gram of mammary tissue. The amount of milk present in the gland and survival are also evaluated, and death or survival at 5 days marks the end point of the study. This is an established model of bovine mastitis caused by caused microbial intramammary infection that induces inflammation of the mammary gland. S. aureus provokes clinical mastitis, but more frequently causes subclinical infections that tend to become chronic and difficult to eradicate by conventional antimicrobial therapies.

Example 22

Active Vaccination with AP4-KLH Protects Mice from a Lethal Systemic S. aureus Challenge Mice were immunized i.p. with 100 µg of the immunoconjugate together with bacterial DNA containing unmethylated cytosine-guanosine dinucleotide motif-containing oligodeoxynucleotides (CpG-ODNs) as adjuvants. Chuang et al., J Leukoc Biol 71: 538-44 (2002). The animals received booster immunizations 7 days and 21 days after the initial vaccination. Serum samples were withdrawn for anti-AIP 4 antibody titer analysis from all animals prior to the infection experiment.

Results illustrating the protective effects of the vaccination in SKH1 hairless mice that had received 0.5 mL PBS i.p. containing $3 \times 10^8$ S. aureus RN4850 (Park et al., Chem Biol 14: 1119-1127 (2007)) are summarized in the following table.

| Active Vaccination Against AIP4 Protects Mice From a Lethal S. aureus Challenge | |
|---|---|
| Vaccine | Survivors |
| AIP4-KLH | 4/6 |
| KLH | 1/6 |
| PBS | 2/6 |

As shown above, 4 of the 6 mice that received the AP4-KLH conjugate survived through the 8-day observation period. In contrast, only one of the KLH-vaccinated control mice (1/6) and 2 of the PBS mock immunized mice (2/6) survived the observation period.

Analysis of the antibody titers revealed that the conjugates and immunization protocol elicited an immune response with titers in the range of 1:1000, i.e. the dilution at which 50% of the maximum signal strength is still observed as tested using standard ELISA methodology. This analysis also showed that the immunization induced an AIP4-specific immune response with cross-reactivities to AIP1 and AIP3 (anti-AIP4 titers: up to 1:6400; anti-AIP1 titers: up to 1:6400; anti-AIP3 titers: up to 1:3200).

Example 23

Evaluation of Anti-AIP1 Antibodies

Figure 10A:
FIG. 10A-B are the results of a biochemical evaluation of anti-AIP1 mAbs. A. α-hemolysin expression in agr I *S. aureus* RN6390B in the presence of anti-AIP1 mAbs (0.2 mg/mL). 1: AP1-2C2; 2: AP1-9A9; 3: AP1-9F9; 4: AP1-15B4; †: control mAb; ‡: no antibody. B. Static biofilm formation of *S. aureus* RN6390B in the presence of the anti-AIP1 mAbs.
Figure 10B:
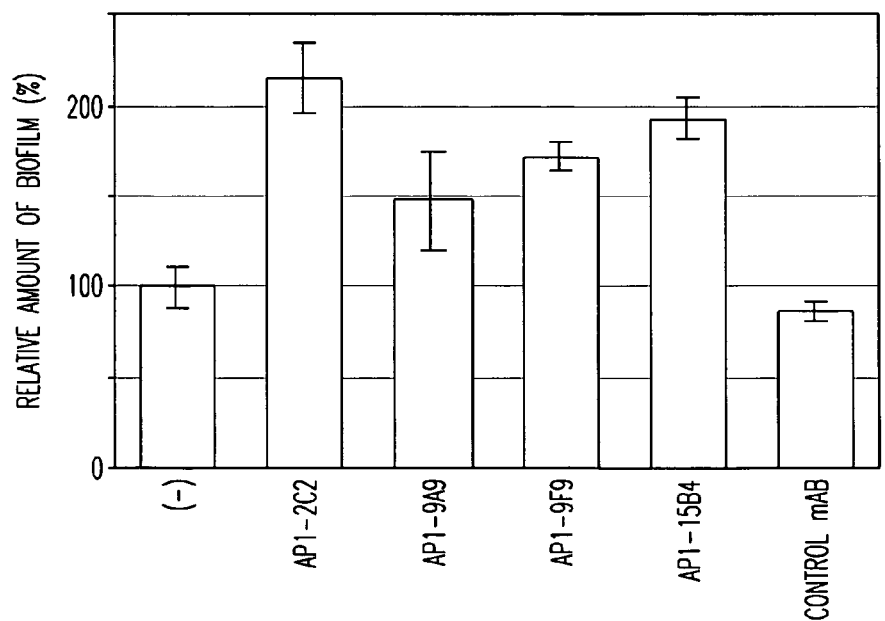

All anti-AIP1 mAbs obtained were tested against the group I S. aureus strain RN6390B. Results in FIG. 10B show that a number of anti-AP1 antibodies efficiently inhibited quorum sensing of group I S. aureus resulting in changes in hemolysin expression. The mAb AP1-15B4 (#4) exhibited the most potent activity in the immunization experiments.

Biofilm formation by S. aureus strain RN6390B was also evaluated in the presence of mAb AP1-15B4, as an increase in biofilm formation has been described in response to agr QS-signaling inhibition in S. aureus. Results in FIG. 10B show an increase in biofilm formation by S. aureus strain RN6390B in the presence of mAb AP1-15B4.

Example 24

Selection of Human scFv Antibodies Using Phage Display Technology

A phage display library generated using the method described by Gao et al. (Proc Natl Acad Sci USA. 99:12612-6

(2002)) was screened using the AP1-BSA, AP3-BSA and AP4-BSA conjugates to identify human anti-AIP-1, AIP-3 and anti-AIP-4 scFv antibodies. The antibody-displaying phage particles were subtracted against BSA first to eliminate BSA-specific clones, as well as unspecific binders. After 4 rounds of panning, selected clones were analyzed by DNA sequencing and ELISA against BSA and AP1-BSA, AP3-BSA and AP4-BSA. The amino acid sequences of the scFv antibodies, the DNA sequences encoding the variable heavy and variable light chains, as well as the DNA sequences encoding the scFv antibodies are shown in the following tables.

```
Amino Acid Sequences of Human scFv Antibodies

AP1-2    QVQLVQSGAEVKKPGESLRISCKGSGYSFTSHWISWVRQMPGKGLEWMGRIDPSDSYSNYSPSFQGHVIISVDKSISTAYLQWSSLKASDTAIYY
         CARQLIVVVPAAPYYYYYYGMDVWGQGTLVTVSSGGGGSGGGGSSGGGSEIVLTQSPGTLSLSPGERATLSCRASQTVNSYLAWYQKPGQAPRLL
         IYGASSRATGIPDRFSGSGSGTDFTLTISRLEPEDFAVYYCQQYGSSHPWTFGQGTKVEIK (SEQ ID NO: 35)

AP1-6    QVQLVQSGAEVKKPGSSVKVSCKASGGTFSSYAISWVRQAPGQGLEWMGGIIPIFGTANYAQKFQGRVTITADESTSTAYMELSSLRSEDTAIYY
         CARVFGSESQDPSDIWSGYYGMEVWGQGTLVTVSSGGGGSGGGGSGGGGSDIQMTQSPSSVSASVGDRVTITCRASQGISSWLAWYQQKPGKAPK
         LLIYAASSLQSRVPSRFSGSGSGTDFTLTISSLQPEDFATYYCQQANSFPYTFGQGTKLEIK (SEQ ID NO: 36)

AP1-8    QVQLVESGAEAKKPGSSVKVSCKASGGTFSSYAISWVRQAPGQGLEWMGGIIPIFGTANYAQKFQGRVTITADESTSTAYMELSSLRSEDTAVYYC
         ARAGITGTTAPPDYWGQGTLVTVSSGGGGSGGGGSGGGGSVIWMTQSPSSLSASVGDRVTITCRASQSISSYLNWYQRKPGKAPKLLIYAASSLQS
         GVTSRFSGSGSGTDFTLTISSLQPEDFATYYCQQSYSTPPTFGQGTKLEIK (SEQ ID NO: 37)

AP1-11   QVQLVQSGSELKKPGASVKLSCRASGYTFTSYSMVWVRQAPGEGLEWMGGINTNTGNPTYAQGFTERFVFSFDSSVSTAYLQISSLKAEDTAVYY
         CARDWAYSGSWPLGQNPSDHWGQGTLVTVSSGGGGSGGGGSGGGGSEIVMTQSPATLSVSPGERATLSCRASQSVSRNLAWYQQKPGQAPRLLIY
         DTSTRATGIPARFSGSGSGTEFTLTISSLQSEDSAVYYCQQYNIWPPLTFGGGTKVEIK (SEQ ID NO: 38)

AP1-15   QVQLQQWGAGLLKPSETLSLTCAVYGGSFSGYYRTWIRQSPVKGLEWIGEVNDRGSPNYNPSFKSRLTISIDTSKNLSLKLRFMTAADTAVYSCA
         RIRPRYGMDVWGQGTMVTVSSGGGGSGGGGSSGGGSDIVMTQTPLSSPVTLGQPASISCRSSQSLVHSDGNTYLTWFHQRPGQPPRVLIHKVSNL
         FSGVPDRFSGSGAGTDFTLKISRVEAEDVGVYYCMQATQLYTFGQGTKVEIK (SEQ ID NO: 39)

AP1-16   EVQLVQSGAEVKKPGASVKVSCKVSGYTLTELSMHWVRQAPGKGLEWMGGFDPEDGETISAQKFQGRVTMTEDTSTDTAYMDLSSLRSEDTAVYYC
         ATQRLCSGGRCYSHFDYWGQGTTVTVSSGGGGSGGGGSGGGGSETTLTQSPAIMSASPGERVTMTCSASSSIRYIYWYQQKPGSSPRLLIYDTSNV
         APGVPFRFSGSGSGTSYSLTINRMEAEDAATYYCQEWSGYPYTFGGGTKVEIK (SEQ ID NO: 40)

AP1-19   QMQLVQSGAEVKKPGSSVKVSCKASGGTFNTYVISWVRQAPGQGLEWMGWISAYNGNTNYAQKLQGRVTMTTDTSTSTAYMELRSLRSDDTAVYY
         CARVWSPLDYWGQGTLVTVSSGGGGSGGGGSGGGGSDIVMTQSPDSLAVSLGERATINCKSSQSVLYSSNNMNYLAWYQQKPGQPPKLLIYWAST
         RESGVPDRFSGSGSGTDFTLTISSLQAEDAAVYYCQQYYSTPPTFGQGTKLEIK (SEQ ID NO: 41)

AP3-1    QVQLVQSGAEVKKPGASVKVSCKGSGYTFTGYYMHWVPQAPGQGLEWMGWINPNNGGTNYDQKFQGRVAMTRDTSISTAYMELSRLRSDDTAVYY
         CARDNGRVTTGGYWGQGTLVTVSSGGGGSGGGGSSGGGSQSVLTQPPSLSGAPGQSVTISCAGTSSSIGAGYDVQWYQQLPGKTPKLLIYGNDNR
         PSGVPDRFSGSRSYTSASLVITRVQIEDEADYYCQSYDSSLIGPQFGGGTKLTVLG (SEQ ID NO: 42)

AP3-2    QVQLVQSGAEVKKPGESLKISCTASGGYNFASYWIGWVRQMPGQGLEWMGIIYPGDSDTRYSPSFQGQVTISADKSISTAYLQWSSLKASDTATYY
         CVRRVPLYTNNHYLDYWGQGTLVTVSSGGGGSGGGGSGGGGSAIQMTQSPSSLSASVGDRVTITCRASQGISNYLAWFQQKPGKAPKSLIYAASS
         LQSGVPSKYSGSGSGTDFTLTISSLQPEDFATYYCQQYKSYPLTFGGGTKVEIK (SEQ ID NO: 43)

AP3-3    EVQLVQSGAEVKKPGASVKVSCKASGYTFSDYFMHWVRQAPGQGLEWMGVINPTGGSTTYAQSFQGRVTMTRDTSTSIVYMELSSLRSEDTAVYY
         CTRVGYYGMDVWGQGTLVTVSSGGGGSGGGGSGGGGSDIVMTQSPSTLSASVGDRVTITCRASQSTSRFLNWYQQKPGKAPKLLIYAASSLHSGV
         PSRFSGSGSGTDFTLTISSLQPEDFATYYCQQTSSYPLTFGGGTKVEIK (SEQ ID NO: 44)

AP3-5    QVQLVQSGGGVVQVGRSLRLSCAASGFTFTNFGMHWVRQAPGKGLEWVALISSDGYRQAYADSVKGRFTISGDNSKNTVYLQMNSLTSEDTAVYY
         CAIIPPVLRIFDWEFDYWGQGTLVTVSSGGGGSGGGGSGGGGSETTLTQSPGTLSLSPGERATLSCRASQSVSSPYLAWYQQKPGQAPRLLIYGA
         SNRATGIPDRFSGSGSGTDFTLTISSLQAEDEAVYYCQQYYNTPLTFGGGTKVEIK (SEQ ID NO: 45)

AP3-6    QVQLQQWGAGLLKPSETLSLTCAVYSGSFTRDYWGWIRQPPGKGLEWIGEINHSGSTNYNPSLKSRVTTSVDKSKNQFSLKLTSVTAADTAVYYC
         ARRRLSSDLFMRGVGGMDVWGQGTLVTVSSGGGGSGGGGSGGGGSDIVMTQTPGTLSSSPGERATLSCRASQGVSSNLAWYQQKPGQAPRLLIYD
         ASNRATGIPLRFSGSGSGTDFTLTISRLEPEDFAVYYCHQYGSSPYTFGQGTKVEIK (SEQ ID NO: 46)

AP3-8    EVQLVQSGAEVKKPGASVKVSCKASGYTFTSYGISWVRQASGQGLEWMGWISAYNGNTNYAQKLQGRVTMTTDTSTSTAYMELRSLRSDDTAVYY
         CARVPRYFDWLLYGSDYFDYWGQGTLVTVSSGGGGSGGGGSGGGGSDIQMTQSPSTLSVSVGDRVTITCRASQGISSWLAWYQQKPGKAPKLLIY
         AASSLQSGVPSRFSGSGSGTDFTLTISSLQPEDFATYYCQQANSFPLTFGGGTKLEIK (SEQ ID NO: 47)

AP3-10   QVQLVQSGAEVKEPGSSVKVSCKASGGTFSSYAIYWVRQAPGQGLEWMGWIIPILGIANYAQKFQGRVTITADKSTSTAYMELSSLRSEDTAVYYC
         ARAAGHSTNYYYYGMDVWGQGTLVTVSSGGGGSGGGGSGGGGSQTVVTQEPSLTVSLGGTVTLTCGSSTGAVTSGHYPYWFQQKPGQAPRTLIYDT
         SNKHSWTPARFSGSLLGGKAALTLSGAQPEDEAEYYCLLSYSGTRVFGGGTKLTVLG (SEQ ID NO: 48)

AP3-13   EVQLVQSGAEVKKPGASVKVSCKASGYTFTNYYMHWVRQAPGQGLEWMGIINPSGGSTSYAQKFQGRVTMTRDTSTSTVYMELSSLRSEDTAVYYC
         CARDFKEYSRTGYFDYWGQGTLVTVSSGGGGSGGGGSSGGGSSYELMQPSSVSVSPGQTARITCSGDVLAKKCARWFQQKPGQAPVLVIYKDSER
         PSGIPERFSGSSSGTTVTLTISGAQVEDEADYYCYSAADNNLGVFGGGTKVTVLG (SEQ ID NO: 49)

AP3-20   QITLKESGPALVKPTQTLTLTCNFSGFSLSTYGGGVGWLRQPPGKALEWLAVIYWSDGKRYSPSVKNRLTITKDTSKNHVVLTMTNMDPVDTATY
         YCAHLMMDTSITTHWFDPWGQGTLVTVSSGGGGSGGGGSGGGGSAIRMTQSPSSLSASVGDRVTITCRASQGISNYLAWYQQKPGKVPKLLIYAA
         STLQSGVPSRFSGSGSGTDFTLTISSLQPEDVATYYCQKYNSAPGTFGQGTKVEIK (SEQ ID NO: 50)

AP4-8    QVQLVQSGAEVKKPGSSVKVSCKASGYTFTNYFIHWVRQAPGQGLEWMGLLNPTDSGTLYAQNFQGRITMTSDTSTNTVYMELSSLRSDDTAMYY
         CAREGGADTTRVHSSFDYWGQGTLVTVSSGGGGSGGGGSGGGGSQAVLTQPPSVSGSPGQSITISCTGTSSDVEAYNYVSWYQQHPGKAPKLMIY
         DVSNRPSGVSNRFSGSKSGNTASLTISGLQAEDEADYYCSSYTSSRTWVFGGGTKVIVL (SEQ ID NO: 51)

AP4-14   QVQLQESGGGLVQPGRSLRLSCAASGFTFDDYALHWVRQAPGKGLEWVSGISWNSVTVKYAVSVKGRFTISRDNAKNSLFLQMNALRSEDTALYY
         CAKARGALLEAADTPSDDWGQGTLVTVSSGGGGSGGGGSGGGGSDIVMTQSPSSLSASVGDRVTITCRASQSISSYLNWYQQKPGKAPKLLIYAASS
         LQSGVPSRFSGSGSGTDFTLTISSLQPEDVATYYCQKYNSAPWTFGQGTKVDIK (SEQ ID NO: 52)
```

Amino Acid Sequences of Human scFv Antibodies

AP4-20  QVQLQQSGAGLLRPSETLSLTCGLYGGSFSGHYWNWIRQSPEKGLVWIGEITHSGTTNYNPSLKSRVITSVDTSKNQYSLKLSFVTPADTAVYYCA
RGDYYGYWYFDLWGRGTLVTVSSGGGGSGGGGSGGGGSQSVLTQPPSVPVAPGQKVTISCSGSSSNIGNNYVSWYQQLPGTAPKLLIYDTNKRPSG
IPDRFAGSKSGTSATLGITGLQTGDEADYYCGTWDSSLSAGVFGGGTKLTVL (SEQ ID NO: 53)

Nucleotide Sequences Encoding the Heavy and Light Chains of Human scFv Antibodies

| Antibody | Variable Heavy Chain | Variable Light Chain |
| --- | --- | --- |
| AP1-2 | caggtgcagctggtgcagtctggagcagaggtgaaaaagcccgggga gtctctgaggatctcctgcaagggttctggatacagctttaccagcc actggatcagctgggtgcgccagatgcccgggaaaggcctggagtgg atggggaggattgatcctagtgactcttatagcaactacagcccctc cttccaaggccacgtcatcatctcagttgacaagtccatcagcactg cctacttgcagtggagcagcctgaaggcctcggacaccgccatatat tactgtgcgagacagctcattgtagtagtaccagctgctccctatta ctactactactacggtatggacgtctgggccaaggaaccctggtca ccgtctcctca (SEQ ID NO: 54) | gaaattgtgttgacgcagtctccaggcaccctgtctttgtctccagg ggaaagagccaccctctcctgcagggccagtcagactgttaacagct acttagcctggtaccagtagaaacctggccaggctcccaggctcctc atctatggtgcatccagcagggccactggcatcccagacaggttcag tggcagtgggtctgggacagacttcactctcaccatcagcagactgg agcctgaagattttgcagtgtattactgtcagcagtatggtagctca catccgtggacgttcggccaagggaccaaggtggagatcaaacgtgg cctcgggggcctggtcgactacaaagatgacgatgacaaa (SEQ ID NO: 55) |
| AP1-6 | caggttcagctggtgcagtctggggctgaggtgaagaagcctgggtc ctcggtgaaggtctcctgcaaggcttctggaggcaccttcagcagct atgctatcagctgggtgcgacaggcccctggacaagggcttgagtgg atgggagggatcatccctatctttggtacagcaaactacgcacagaa gttccagggcagagtcacgattaccgcggacgaatccacgagcacag cctacatggagctgagcagcctgagatctgaggacacggccatatat tactgtgcgagagtctttggttccgagtcgcaagatccgtccgatat ttggagtggttattacggtatggaagtctggggccaaggaaccctgg tcaccgtctcctca (SEQ ID NO: 56) | gacatccagatgacccagtctccgtcttccgtgtctgcatctgtagg agacagagtcaccatcacttgtcgggcgagtcagggtattagcagct ggttagcctggtatcagcagaaaccagggaaagcccctaagctcctg atctatgctgcatccagtttgcaaagtagggtcccatcaaggttcag cggcagtggatctgggacagatttcactctcaccatcagcagcctgc agcctgaagattttgcaacttactattgtcaacaggctaacagtttc ccgtacacttttggccaggggaccaagctggagatcaaacgtggcct cggggggcctggtcgactacaaagatgacgatgacaaa (SEQ ID NO: 57) |
| AP1-8 | caggtgcagctggtggagtctggggctgaggcgaagaagcctgggtc ctcggtgaaggtctcctgcaaggcttctggaggcaccttcagcagct atgctatcagctgggtgcgacaggcccctggacaagggcttgagtgg atgggagggatcatccctatctttggtacagcaaactacgcacagaa gttccagggcagagtcacgattaccgcggacgaatccacgagcacag cctacatggagctgagcagcctgagatctgaggacacggccgtgtat tactgtgcgagagccggtataactggaactacggctcccccagacta ctggggccagggcaccctggtcaccgtctcctca (SEQ ID NO: 58) | gtcatctggatgacccagtctccatcctccctgtctgcatctgtagg agacagagtcaccatcacttgccgggcaagtcagagcattagcagct atttaaattggtatcagcgaaaccagggaaagccccctaagctcctg atctatgctgcatccagtttgcaaagtggggtcacatcaaggttcag tggcagtggatctgggacagatttcactctcaccatcagcagtctgc aacctgaagattttgcaacttactattgtcaacagagttacagtacc cctccgacgttcggccaagggaccaagctggagatcaaa (SEQ ID NO: 59) |
| AP1-11 | caggtgcagctggtgcagtccggatctgagttaaagaagcctgggc ctcagtgaagcttcctgcagggcttctggatacacattcactagtt attccatggtttgggtgcgacaggcccctggagaagggcttgagtgg atgggagggatcaacaccaacactgggaacccaacgtatgccaggg cttcacagaacggtttgtcttctccttcgacagctctgtcagcacg catatctgcaaatcagcagcctaaaggcctgaggacactgccgtgtat tactgtgcgagagattggcgtatagcgcagctggcccttaggcca gaacccttctgaccactggggccagggcaccctggtcaccgtctcct ca (SEQ ID NO: 60) | gaaatagtgatgacgcagtctccagccaccctgtctgtgtctccagg ggaaagagccaccctctcctgcagggccagtcagagtgttagccgca acttagcctggtaccagcagaaacctggccaggctcccaggctcctc atctatgatacatccaccagggccactggtatcccagccaggttcag tggcagtgggtctgggacagagttcactctcaccatcagcagcctgc agtctgaagattctgcagtttattactgtcagcagtataatatctgg cctccactcacttttcggcggagggaccaaggtggagatcaaa (SEQ ID NO: 61) |
| AP1-15 | caggtgcagctacagcagtggggcgcaggattgttgaagccttcgga gaccctgtccctcacctgcgctgtctatggtgggtcctcagtggtt actaccggacctggatccgccagtccccagtgaaggggctggagtgg attgggaagtcaatgatcgtggaagccccaactacaaacccgtcctt caagagtcgactcaccatatcaatcgacacgtccaagaactagttat ccctgaagttgagatttatgaccgccgcggacacggctgtatattcg tgtgcgagaattaggcctaggtacggtatggacgtctggggccaggg gacaatggtcaccgtctcctcaggcggcggcggctct (SEQ ID NO: 62) | Gatattgtgatgacccagactccactctcctcacctgtcacccttgg acagccggcctccatctcctgcaggtcagtcaaagcctcgtacaca gtgatggaaacacctacttgacttggtttcaccagaggccaggccag cctccaagagtcctcattcataaggtttctaacctgttctctctgggt cccagacagattcagtgcagtggggcagggacagatttcacactga aaatcagcagggtggaagctgaggatgtcggggtttattactgcatg caagctacacaattgtacactttggccaggggaccaaggtggaaat caaa (SEQ ID NO: 63) |
| AP1-16 | gaggtccagctggtacagtctggggctgaggtgaagaagcctgggc ctcagtgaaggtctcctgcaaggtttccggatacaccctcactgaat tatccatgcactgggtgcgacaggtcctggaaaagggcttgagtgg atgggaggttttgatcctgaagtggtgaaacaatctccgcgcagaa gttccaggcagagtcaccatgaccgaggacacatctacagacacag cctacatggatctgagcagcctgagatctgaggacacggccgtttat tactgtgcaacgcagcgcttgtgtagtggtgctcgctgctactccca ctttgactactggggccagggcaccacggtcaccgtctcctca (SEQ ID NO: 64) | gaaacgacactcacgcagtctccagcaatcatgtctgcatctccagg ggagagggtcaccatgacctgcagtgccagctcaagtatacgttaca tatattggtaccaacagaagcctggatcctccccagactcctgatt tatgacacatcaactggcctctggagtccctttcgcttcagtgg cagtgggtctgggacctcttattctctcacaatcaaccgaatggagg ctgaggatgctgccacttattactgccaggagtggagtggttatccg tacacgttcggaggggggaccaaggtggagatcaaa (SEQ ID NO: 65) |
| AP1-19 | cagatgcagctggtgcagtctggggctgaggtgaagaagcctgggtc ctcggtgaaggtctcctgcaaggcttctggaggcaccttcaacacct atgttatcagttgggtgcgacaggcccctggacaagggcttgagtgg atgggatggatcagcgcttacaatggtaacacaaactatgcacagaa gctccagggcagagtcaccatgaccacagacacatccacgagcacag | gacatcgtgatgacccagtctccagactccctggctgtgtctctggg cgagagggccaccatcaactgcaagtccagccagagtgttttataca gctccaacaatatgaactactagcttggtaccagcagaaaccagga cagcctcctaagctgctcatttactgggcatctacccgggaatccgg ggtccctgaccgattcagtggcagcgggtctgggacagatttcactc |

Nucleotide Sequences Encoding the Heavy and Light Chains of Human scFv Antibodies

| Antibody | Variable Heavy Chain | Variable Light Chain |
|---|---|---|
| | cctacatggagctgaggagcctgagatctgacgacacggccgtgtat tactgtgcgagagtttggagtccccttgactactggggccagggcac cctggtcaccgtctcctca (SEQ ID NO: 66) | tcaccatcagcagcctgcaggctgaagatgcggcagtttattactgt cagcagtattatagtactcctccgacgttcggccaagggaccaagct ggagatcaaa (SEQ ID NO: 67) |
| AP3-1 | caggtgcagctggtgcaatctggggctgaggtgaagaagcctgggc ctcagtgaaggtctcctgcaagggttctggatacaccttcaccggct actatatgcactgggtgccacaggcccctggacaagggcttgagtgg atgggatggatcaaccctaacaatggtggcacaaactatgaccagaa gtttcagggcagggtcgccatgaccagggacacgtccatctccacag cctacatggagctgagcaggctgagatctgacgacactgccgtgtat tactgtgcgagagataatgggagggtgaccacaggggggctactggg ccagggcaccctggtcaccgtctcctca (SEQ ID NO: 68) | cagtctgtgttgacgcagcctccctcattgtctggggccccgggaca gagtgtcaccatctcctgcgctgggaccagttccagcatcggggcag gttacgatgtacagtggtaccagcaacttccaggaaaaacccccaaa ctcctcatctacgggaatgataatcggccctcaggggtccctgaccg attctctggatccaggtcttacacctcagcctcctggtcatcacta gagtccagattgaggatgaggctgattattactgccagtcgtatgac agcagtctcattggtcctcaattcggcggg (SEQ ID NO: 69) |
| AP3-2 | caggtgcagctggtgcaatctggggctgaggtgaaaaagcccgggga gtctctgaagatctcctgtacggcctccggatacaactttgccagct actggatcggctgggtgcgccagatgcccgggcaaggcctggagtgg atggggatcatctatcctggtgactctgataccagatacagtccgtc cttccaaggccaggtcaccatctcagccgacaagtccatcaccaccg cctacctgcagtggagcagcctgaaggcctcggacaccgccacgtat tactgtgtgagacgggtcccctctacactaacaacactaccttga ctattggggccagggcaccctggtcaccgtctcctca (SEQ ID NO: 70) | gccatccagatgacccagtctccatcctcactgtctgcatctgtagg agacagagtcaccatcacttgtcgggcgagtcagggcattagcaatt atttagcctggtttcagcagaaaccagggaaagcccctaagtccctg atctatgctgcatccagtttgcaaagtgggtcccatcaaagtacag cggcagtggatctgggacagatttcactctcaccatcagcagcctgc agcctgaagattttgcaacttattactgccaacagtataagagttac ccctcactttcggcggagggaccaaggtggagatcaaa (SEQ ID NO: 71) |
| AP3-3 | gaggtgcagctggtgcagtctggggctgaagtgaagaagcctgggc ctcagtgaaggtttcctgtaaggcatctggatacaccttcagcgact actttatgcactgggtgcgacaggcccctggacaagggcttgagtgg atgggagtaatcaacccaactggtggttccacaacctacgcacagag cttccagggcagagtcaccatgaccagagacacgtccacgagcatag tctacatggagctgagcagcctgagatctgaagacacggccgtgtac tactgtacgcgagtcggctactacggtatggacgtctggggccaagg caccctggtcaccgtctcctca (SEQ ID NO: 72) | gacatcgtgatgacccagtctccatccaccctgtctgcatctgtagg agacagagtcaccatcacttgccgggcaagtcagagcactagcaggt ttttaaattggtatcagcagaaacctgggaaagcccctaaactcctg atctatgctgcatccagtttgcatagtggcgtcccatcaaggttcag tggcagtggatctgggacagatttcactctcaccatcagcagtctgc aacctgaagattttgcaacttactactgtcaacagacttccagttac cctctcactttcggcggagggaccaaggtggaaatcaaa (SEQ ID NO: 73) |
| AP3-5 | caggtccagctggtacagtctggggggaggcgtggtccaggttggag gtccctgagactttcctgtgcggcctctggattcacctttcacaaact ttggcatgcactgggtccgccaggctccaggcaaggggctggagtgg gtggcacttcatctcatctgatggatatagacaggcctatgcagactc cgtgaagggccggttcaccatctccggagacaactccaagaacacag tgtatctgcaaatgaacgcctgacaagtgaggacacggctgtttat tactgtgccatcatacccctgtattacggattttttgattgggaatt tgactactggggccagggaaccctggtcaccgtctcctca (SEQ ID NO: 74) | gaaacgacactcacgcagtctccaggcaccctgtctttgtctccagg ggaaagagccaccctctcctgcagggccagtcagagtgtttccagcc cctacttagctggtaccagcagaaacctggccaggctcccaggctc ctcatttatggtgcatctaacagggccactggcatcccagacaggtt cagtggcagtgggtctgggacagacttcactctcaccatcagcagcc tgcaggctgaagatgaggcagtttattactgtcagcaatactacaat actccgctcactttcggcggagggaccaaggtggaaatcaaa (SEQ ID NO: 75) |
| AP3-6 | caggtgcagctacagcagtggggcgcaggcctgttgaagccttcgga gaccctgtccctcacctgcgctgtctatagtgggtcttttactcgtg actactggggctggatccgccagcccccgggaaggggctggagtgg attggggaaatcaatcatagtggaagcaccaactacaacccgtccct caagagtcgagtcaccacgtcagtagacaagtccaagaatccttct ccctgaagttgacctctgtgaccgccgggacacggctgtctattac tgtgcgagacgccggctttctagcgacctcttcatgcggggggttga cggtatggacgtctggggccaaggcaccctggtcaccgtctcctca (SEQ ID NO: 76) | gatattgtgatgacccagactccaggcaccctgtcttcgtctccagg ggaaagagccaccctctcctgcagggccagtcagggtgttagcagca acttagcctggtaccagcagaaacctggccaggctcccaggctcctc atctatgatgcatccaacagggccactggcatcccactcaggttcag tggcagtggtctgggacagactttcactctcaccatcagcagactgg aacctgaagattttgcagtgtattactgtcaccatggtagctca ccgtacaccttggccaggggaccaaggtggaaatcaaa (SEQ ID NO: 77) |
| AP3-8 | gaggtgcagctggtgcagtctggagctgaggtgaagaagcctgggc ctcagtgaaggtctcctgcaaggcttctggttacacctttaccagct atggtatcagctgggtgcgacaggcctctggacaaagggcttgagtgg atggggtggatcagcgcttacaatggtaacacaaactatgcacaag ggctccagggcagagtcaccatgaccacagacacatccacgagcacag cctacatggagctgaggagcctgagatctgacgacacggccgtgtat tactgtgcgagagtacccgatattttgactggttattatacggag cgactactttgactactggggccagggaaccctggtcaccgtctcct ca (SEQ ID NO: 78) | gacatccagatgacccagtctccttccaccctgtctgtatctgtagg agacagagtcaccatcacttgtcgggcgagtcagggtattagcagct ggttagcctggtatcagcagaaacagggaaagcccctaagtcctg atctatgctgcatccagtttgcaaagtgggtcccatcaaggttcag cggcagtggatctgggacagatttcactctcactatcagcagcctgc agcctgaagattttgcaacttactattgtcaacaggctaacagtttc ccgctcactttcggcggagggaccaagctggagatcaaa (SEQ ID NO: 79) |
| AP3-10 | caggtgcagctggtgcaatctggagctgaggtgaaggagcctgggtc ctcggtgaaggtctcctgcaaggcttctggaggcaccttcagcagct atgctatctactgggtgcgacaggcccctggacaagggcttgagtgg atgggatggatcatccctatccttggtatagcaaactacgcacagaa gttccagggcagagtcaccgattaccgcggacaaatccacgagcacag cctacatggagctgagcagcctgagatctgaggacacggccgtgtat tactgtgcgagagccggtcatagtactaactactactactacggc tatggacgtctggggccaaggcaccctggtcaccgtctcctca (SEQ ID NO: 80) | cagactgtggtgacccaggagccctcactgactgtgtcccctaggagg gacagtcactctcacctgtggctccagcactggagctgtcaccagtg gtcattatccctactggttccagcagaagcctggccaagcccccagg acactgatttatgataaagcaacaaacactcctggacccctgcccg gttctcaggctcctccttggggcaaagctgccctgaccctttcgg gtgcgcagcctgaggatgaggctgagtattactgcttgctctcctat agtggtactcgggtgttcggcggagggaccaagctgaccgtccta (SEQ ID NO: 81) |
| AP3-13 | gaggtgcagctggtgcagtctggggctgaggtgaagaagcctgggc ctcagtgaaggtttcctgcaaggcatctggatacaccttcaccaact actatatgcactgggtgcgacaggcccctggacaagggcttgagtgg | tcctatgagctgatgcagccatcctcagtgtcagtgtctccgggaca gacagccaggatcacctgctcaggagatgtactggcaaaaaatgtg ctcggtggttccagcagaagccaggccaggcccctgtgctggtgatt |

Nucleotide Sequences Encoding the Heavy and Light Chains of Human scFv Antibodies

| Antibody | Variable Heavy Chain | Variable Light Chain |
|---|---|---|
| | atgggaataatcaaccctagtggtggtagcacaagctacgcacagaa gttccagggcagagtcaccatgactagggacacgtccacgagcacag tctacatggagctgagcagcctgagatctgaggacacggccgtgtat tactgtgcgagagatttcaaagagtatagccgtacgggctactttga ctactggggccagggcaccctggtcaccgtctcctca (SEQ ID NO: 82) | tataaagacagtgagcggccctcagggatccctgagcgattctccgg ctccagctcagggaccacagtcaccttgaccatcagcggggcccagg ttgaggatgaggctgactattactgttactctgcggctgacaacaac ctgggggtgttcggcggagggaccaaggtcaccgtccta (SEQ ID NO: 83) |
| AP3-20 | cagatcaccttgaaggagtctggtcctgcgctggtgaaacccacaca gaccctcacgctgacctgcaacttctctgggttctccctcagcactt atggaggggtgtgggctggctccgtcagcccccaggaaaggccctg gagtggcttgccgtcatttattggagtgatggtaaacgctacagccc ctctgtaaagaaccggctcaccatcaccaaggacacctccaaaaacc acgtggtcctgacaatgaccaacatggacctgtggacacagccacc tattattgtgcacaccttatgatgacatctattactacccactg gttcgaccctgggccagggaaccctggtcaccgtctcctca (SEQ ID NO: 84) | gccatccggatgacccagtctccatcctccctgtctgcatctgtagg agacagagtcaccatcacttgccgggcgagtcagggcattagcaatt atttagctggtatcagcagaaaaccagggaaagttcctaagctcctg atctatgctgcatccactttgcaatcagggggtcccatctcggttcag cggcagtggatctgggacagatttcactctcaccatcagcagcctgc agcctgaagatgttgcaacttattactgtcaaaagtataacagtgcc cctgggacgttcggccaagggaccaaggtggagatcaaa (SEQ ID NO: 85) |
| AP4-8 | caggtgcagctggtgcaatctggggctgaggtgaagaagcctgggtc ctcggtgaaggtttcctgcaaggcatctggatacacctttcaccaact acttatacactgggtgcgacaggcccctggacaagggcttgagtgg atgggactactcaaccctactgatagtggcacactctacgcacagaa cttccagggcagaatcaccatgaccagtgacacgtccacaaacag tctacatggagctgagcagcctgagatctgacgacacggccatgtat tactgtgcaagagagggggggggccgacactacccgggtccactcttc gtttgactactggggccagggaaccctggtcaccgtctcctca (SEQ ID NO: 86) | caggctgtgctgactcagccgccttccgtgtcgggtctcctggaca gtcgatcaccatctcctgcactggaaccagcagtgacgttgaagctt acaactatgtctcctggtatcaacaacacccaggcaaagcccccaaa ctcatgatttatgatgtcagtaatcggccctcagggggtttctaatcg cttctctggctccaagtctggcaacacggcctccctgaccatctctg ggctccaggctgaggacgaggctgattattactgcagctcatataca agcagcagcacttgggtgttcggcggagggaccaaggtcatcgtcct a (SEQ ID NO: 87) |
| AP4-14 | caggtgcagctgcaggagtcgggggggaggcttggtacagcctggcag gtccctgagactctcctgtgcagcctctggattcacctttgatgatt atgccctccactgggtccgccaagctccagggaaggcctggagtgg gtctcaggtattagttggaatagtattaccgtaaagtatgcggtctc tgtgaagggccggttcaccatctccagagacaacgccaagaactccc tgtttctgcaaatgaacgctctgagatctgaggacacggccttatat tactgtgcaaaagccagaggggccctcttagaagcagctgacacacc atctgacgactggggccagggcaccctggtcaccgtctcctca (SEQ ID NO: 88) | gacatcgtgatgacccagtctccgtcctccctgtctgcatctgtagg agacagagtcaccatcacttgccgggcaagtcagagcattagcagct atttaaattggtatcagcagaaaccagggaaagcccctaagctcctg atctatgctgcatccagtttgcaaagtgggggtcccatcaaggttcag cggcagtggatctgggacagatttcactctcaccatcagcagcctgc agcctgaagatgttgcaacttattactgtcaaaagtataacagtgcc ccgtgacgttcggccaagggaccaaagtggatatcaaa (SEQ ID NO: 89) |
| AP4-20 | caggtacagctgcagcagtcaggcgcaggtctattgaggccttcgga gacccgtccctcacctgcggtctctatgtgggtccttcagtggtc actattggaactggatccgccagtccccagaaaaggggctggtgtgg attggggaaatcactcatagtggaaccaccaattacaacccgtccct caagagtcgagtcatcacatcagtagacacgtccaagaatcagtact ccctgaagctgagctttgtgaccctgcggacacggccgtgtattac tgtgcgagaggtgattactatgggtactggtacttcgatctctgggg ccgtggcaccctggtcaccgtctcctca (SEQ ID NO: 90) | cagtctgtgttgacgcagccgccctcagttcctgtggccccaggaca gaaggtcaccatctcctgctctggaagcagctccaacattgggaata attatgtatcctggtaccagcagctcccaggaacagcccccaaactc ctcatttatgacactaataagcgaccctcagggattcctgaccgatt cgctggctccaagtctggcacgtcagccaccctgggcatcaccggac tccagactggggacgaggccgattattactgcggaacatgggatagc agcctgagtgctggcgtgttcggcggagggaccaagctgaccgtcct a (SEQ ID NO: 91) |

Nucleic Acids Encoding the Human scFvs

| Antibody | Variable Heavy Chain |
|---|---|
| AP1-2 | caggtgcagctggtgcagtctggagcagaggtgaaaaagcccggggagtctctgaggatctcctgcaagggttctggatacagctttaccagcca ctggatcagctgggtgcgccagatgcccgggaaaggcctggagtggatggggaggattgatcctagtgactcttatagcaactacagcccctcct ccaaggccacgtcatcatctcagttgacaagtccatcagcactgcctacttgcagtggagcagcctcggacaccgccatatattac tgtgcgagacagtccattgtagtaccagctgctccctattactactactacgtatggacgtctgggggccaaggaaccctggtcaccgt ctcctcaggcggcggcggctctggcggaggtggcagcagcggtggcggatccgaattgtgttgacgcagtctccaggcaccctgtctttgtctc caggggaaagagccaccctctcctgcagggccagtcagactgttaacagctacttagcctggtaccagtagaaacctggccaggctcccaggctc ctcatctatggtgcatccagcagggccactggcatcccagacaggttcagtggcagtgggtctgggacagacttcactctcaccatcagcagact ggagcctgaagattttgcagtgtattactgtcagcagtatcacatccgtggacgttcggccaagggaccaaggtggagatcaaacgtg gcctcgggggcctggtcgactacaaagatgacgatgacaaa (SEQ ID NO: 54) |
| AP1-6 | caggttcagctggtgcagtctggggctgaggtgaagaagcctgggtcctcggtgaaggtctcctgcaaggcttctggaggcaccttcagcagcta tgctatcagctgggtgcgacaggcccctggacaagggcttgagtggatgggagggatcatccctatctttggtacgacaactacgcacagaagt tccagggcagagtcacgattaccgcggacgaatccacggacacagcctacatggagctgagcagcctgagatctgaggacacggccatatattac tgtgcgagagtctttggttccgagtcgcaagatccgtccgatatttggagtggttattacggtatggaagtctggggccaaggaaccctggtcac cgtctcctcaggcggtggcggctctggcggaggtggcagcggcggtggcggatccgacatccagatgacccagtctccgtcttccgtgtctgcat ctgtaggagacagagtcaccatcacttgtcgggcgagtcagggtattagcagctggttagcctggtatcagcagaaaccagggaaagcccctaag ctcctgatctatgctgcatccagtttgcaaagtaggggtcccatcaaggttcagcggcagtggatctgggacagatttcactctcaccatcagcag cctgcagcctgaagattttgcaacttactattgtcaacaggctaacagtttcccgtacacttttggccaggggaccaaggtggagatcaaacgtg gcctcgggggcctggtcgactacaaagatgacgatgacaaa (SEQ ID NO: 55) |

-continued

Nucleic Acids Encoding the Human scFvs

| Antibody | Variable Heavy Chain |
|---|---|
| AP1-8 | caggtgcagctggtggagtctggggctgaggcgaagaagcctggggtcctcggtgaaggtctcctgcaaggcttctggaggcaccttcagcagcta tgctatcagctgggtgcgacaggcccctggacaagggcttgagtggatgggagggatcatccctatctttggtacagcaaactacgcacagaagt tccagggcagagtcacgattaccgcggacgaatccacgagcacagcctacatggagctgagcagcctgagatctgaggacacggccgtgtattac tgtgcgagagccggtataactggaactacggctcccccagactactggggccagggcaccctggtcaccgtctcctcaggcggcggcggctccgg cggaggtggcagcggcggtggcggatccgtcatctggatgacccagtctccatcctccctgtctgcatctgtaggagacagagtcaccatcactt gccgggcaagtcagagcattagcagctatttaaattggtatcagcggaaaccagggaaagcccctaagctcctgatctatgctgcatccagtttg caaagtggggtcacatcaaggttcagtggcagtggatctgggacagatttcactctcaccatcagcagtctgcaacctgaagattttgcaactta ctactgtcaacagagttacagtacccctccgacgttcggccaagggaccaagctggagatcaaa (SEQ ID NO: 56) |
| AP1-11 | caggtgcagctggtgcagtccggatctgagttaaagaagcctggggcctcagtgaagctttcctgcagggcttctggatacacattcactagtta tttccatggctttgggtgcgacaggcccctggagaagggcttgagtggatgggagggatcaacaccaacactgggaacccaacgtatgcccagggct tcacagaacggtttgtcttctccttcgacagctctgtcagcacggcatatctgcaaatcagcagcctaaaggctgaggacactgccgtgtattac tgtgcgagagattgggcgtatagcggcagctggcccttacgtgactactggggccagggcaccctggtcaccgtctcctcagg cggcggcggctctggcggaggtggcagcggcggtggcggatccgaaatagtgatgacgcagtctccagccaccctgtctgtgtctccaggggaaa gagccaccctctcctgcagggccagtcagagtgttagccgcaacttagcctggtaccagcagaaacctggccaggctcccaggctcctcatctat gatacatccaccagggccactggtatcccagccaggttcagtggcagtgggtctgggacagagttcactctcaccatcagcagcctgcagtctga agattctgcagtttattactgtcagcagtataatatctggcctccactcactttcggcggagggaccaaggtggagatcaaacgtggcctcgggg gcctggtcgactacaaagatgacgatgacaaa (SEQ ID NO: 57) |
| AP1-15 | caggtgcagctacagcagtggggcgcaggattgttgaagccttcggagaccctgtccctcacctgcgctgtctatggtgggtccttcagtggtta ctaccggacctggatccgccagtcccccagtcaagggcctggagtggattgggaagtcaatgatcgtggaagccccaactacaaccgtccttca agagtcgactcaccatatcaatcgacacgtccaagaactagttatccctgaagttgagatttatgaccgccgcgacacggctgtatattcgtgt gcgagaattaggcctaggtacggtatggacgtctgggggcaggggacaatggtcaccgtctcctcaggcggcggcggctctggcggaggtggcag cagcggtggcggatccgatattgtgatgacccagactccactctcctcacctgtcacccttggacagccggcctccatctcctgcaggtctagtc aaagcctcgtacacagtgatggaaacacctacttgacttggtttcaccagaagccaggccagcctccaagagtcctcattcataaggtttctaac ctgttctctggggtcccagacagattcagtggcagtgggtcagggacagatttcactctgaaaatcagcagggtggaagctgaggatgtcgggt ttattactgcatgcaagctacacaattgtacacttttggccaggggaccaaggtggaaatcaaacgtggcctcggggggcctggtcgactacaaag atgacgatgacaaa (SEQ ID NO: 58) |
| AP1-16 | gaggtccagctggtacagtctggggctgaggtgaagaagcctggggcctcagtgaaggtctcctgcaaggtttccggatacaccctcactgaatt atccatgcactgggtgcgacaggctcctggaaaagggcttgagtggatgggaggttttgatcctgaagatggtgaaacaatctccgcgcagaagt tccagggcagagtcaccatgaccgaggacacatctacagacacagcctacatggatctgagcagcctgagatctgaggacacggccgtttattac tgtgcaacagcgcttgtgtagtggtggtcgctgctactcccactttgactactggggccagggcaccacggtcaccgtctcctcaggcggcgg cggctctggcggaggtggcagcggcggtggcggatccgcaaacgacacctcacgcagtctccagccaatcatgtctgcatctccagggggaggtca ccatgacctgcagtgccagctcaagtatacgttacatatattggtaccaacagaagcctggatcctcccccagactcctgatttatgacacatcc aacgtggctcctgaagtccctttcgcttcagtggcagtgggtctgggacccttattctctcacaatcaaccgaatggaggctgaggatgctgc cacttattactgccaggagtggagtggttatccgtacacgttcggaggggggaccaaggtggagatcaaa (SEQ ID NO: 59) |
| AP1-19 | cagatgcagctggtgcagtctggggctgaggtgaagaagcctggggcctcggtgaaggtctcctgcaaggcttctggaggcaccttcaacaccta tgttatcagttgggtgcgacaggcccctggacaagggcttgagtggatgggatggatcagcgcttacaatggtaacacaaactatgcacagaagc tccagggcagagtcaccatgaccacagacacatccacgagcacagcctacatggagctgaggagcctgagatctgacgacacggccgtgtattac tgtgcgagagttttggagtccccttgactactggggccagggcaccctggtcaccgtctcctcaggcggcggtggctccggcggaggttcc cggtggcggatccgacatcgtgatgacccagtctccagactccctggctgtgtctctgggcgagggccaccatcaactgcaagtccagccaga gtgttttatacagctccaacaatatgaactactagcttggtaccagcagaaaccaggacagcctcctaagctgctcatttactgggcatctacc cgggaatccggggtccctgaccgattcagtggcagcgggtctgggacagatttcactctcaccatcagcagcctgcaggctgaagatgcggcagt ttattactgtcagcagtttatagtactcctccgacgttcggccaagggaccaagctggagatcaaacgtggcctcggggggcctggtcgactaca aagatgacgatgacaaa (SEQ ID NO: 60) |
| AP3-1 | caggtgcagctggtgcaatctggggctgaggtgaagaagcctggggcctcagtgaagggtctcctgcaagggttctggatacaccttcaccggcta ctatatgcactgggtgccacaggcccctggacaagggcttggagtggatgggatggatcaacccttaacaatggtggcacaaactatgaccagaagt ttcagggcagggtcgccatgaccagggacacgtccatctccacagcctacatggagctgagcaggctgagatctgacgacactgccgtgtattac tgtgcgagagataatgggagggtgaccacaggggggctactggggccagggcaccctggtcaccgtctcctcaggcggcggcggctctggcggagg tggcagcagcggtggcggatccccagtctgtgttgacgcagcctcccctcattgtctggggccccgggacagagtgtcaccatctcctgcgctggga ccagttccagcatcggggcaggttacgatgtacagtggtaccagcaacttccaggaaaaaccccccaaactcctcatctacgggaatgataatcgg cctcaggggtccctgaccgattctctggctccaagtcttacacctcagcctccctggtcatcactagagtccagattgaggatgaggctgatta ttactgccagtcgtatgcagcagtctcattgtcctcaattcggcggggggaccaagctgaccgtcctaggtgcctcgggggcctggtcgact acaaagatgaccatgacaaatac (SEQ ID NO: 61) |
| AP3-2 | caggtgcagctggtgcaatctggggctgaggtgaaaaagcccggggagtctctgaagatctcctgtacggcctccggatacaactttgccagcta ctggatcggctgggtgcgccagatgcccgggcaaggcctggagtggatgggatcatctatcctggtgactctgataccagatacagtccgtcct tccaaggccaggtcaccatctcagccgacaagtccatcagcaccgcctacctgcagtggagcagcctgaaggcctcggacaccgccacgtattac tgtgtgagacgggtcccctctacactaacaaccactaccttgactattggggccagggcacccctggtcaccgtctcctcaggcggcggcggctc tggcggaggtggcagcggcggtggcggatccgccatccagatgacccagtctccatcctcactgtctgcatctgtaggagacagagtcaccatca cttgtcgggcaagtcagggcattagcaatatttagcctggtttcagcagaaaccagggaaagcctaagctcctgatctatgctgcatccagt ttgcaaagtggggtcccatcaaggttcagcggcagtggatctgggacagatttcactctcaccatcagcagcctgcagcctgaagattttgcaac ttattactgccaacagtataagagttaccccctcactttcggcggagggaccaaggtggagatcaaa (SEQ ID NO: 62) |
| AP3-3 | gaggtgcagctggtgcagtctggggctgaagtgaagaagcctggggcctcagtgaaggtttcctgtaaggcatctggatacaccttcagcgacta ctttatgcactgggtgcgacaggcccctggacaaagggcttgagtggatgggataaccaactggtggttccacaacctacgcacagaagct tccagggcagagtcaccatgaccagagacacgtccacgagcatagtctacatggagctgagcagcctgagatctgaagacacggccgtgtactac tgtacgcgagtcggctactacggtatggacgtctggggccaagggaccctggtcaccgtctcctcaggcggcggcggctctggcggaggtggcag cggcggtggcggatccgacatcgtgatgacccagtctccatccaccctgtctgcatctgtaggagacagagtcaccatcacttgccgggcaagtc agagcactagcaggttttttaaattggtatcagcagaaacctgggaaagcccctaaactcctgatctatgctgcatccagtttgcatagtggcgtc ccatcaaggttcagtggcagtggatctgggacagatttcactctcaccatcagcagtctgcaacctgaagattttgcaacttactactgtcaaca |

-continued

Nucleic Acids Encoding the Human scFvs

| Antibody | Variable Heavy Chain |
|---|---|
| | gacttccagttaccctctcactttcggcggagggaccaaggtggaaatcaaacgtggcctcggggggcctggtcgactacaaagatgacgatgacaaa (SEQ ID NO: 63) |
| AP3-5 | caggtccagctggtacagtctggggggaggcgtggtccaggttgggaggtccctgagactttcctgtgcggcctctggattcaccttcacaaactttggcatgcactgggtccgccaggctccaggcaaggggctggagtgggtggcactcatctcatctgatggatatagacaggcctatgcagactccgtgaagggccggttcaccatctccggagacaactccaagaacacagtgtatctgcaaatgaacagcctgacaagtgaggacacggctgtttattactgtgccatcatacccctgtattacggattttttgattggggaatttgactactggggccagggaaccctggtcaccgtctcctcaggcggcggcggctctggcggaggtggcagcggcggtggcggatccgaaacgacactcacgcagtctccaggcaccctgtctttgtctccaggggaaagagccaccctctcctgcagggccagtcagagtgtttccagcccctacttagcctggtaccagcagaaacctggccaggctcccaggctcctcatttatggtgcatctaacagggccactggcatcccagacaggtcagtggcagtgggtctgggacagacttcactctcaccatcagcagcctgcaggctgaagatgaggcagtttattactgtcagcaatactacaatactccgctcactttcggcggagggaccaaggtggaaatcaaacgtggcctcggggggcctggtcgactacaaagatgacgatgacaaa (SEQ ID NO: 64) |
| AP3-6 | caggtgcagctacagcagtggggcgcaggcctgttgaagccttcggagaccctgtccctcacctgcgctgtctatagtgggtcttttactcgtgactactggggctggatccgccagcccccgggaagggctggagtggattggggaaatcaatcatagtggaagcaccaactacaaccgtccctcaagagtcgagtcaccacgtcggtagacaagtccaagaatcagttctccctgaagttgacctctgtgaccgccgcggacacggctgtctattactgtgcgagagccggctttctagcgaccctcttcatgcgggggggttggcgtatggacgtctgggccaaggcaccctggtcaccgtctcctcaggccggcggctctggcggaggtggcagcggcggtggcggatctgatattgtgatgacccagactccaggcaccctgtcttcgtctccaggggaaagagccacccctctcctgcagggccagtcagggtgttagcagcaacttagcctggtaccagcagaaacctggccaggctcccaggctcctcatctatgatgcatccaacagggccactggcatcccactcaggttcagtggcagtgggtctgggacagacttcactctcaccatcagcagactggaacctgaagattttgcagtgtattactgtcaccagtatggtagctcaccgtacacctttggccaggggaccaaggtggaaatcaaacgtggcctcggggggcctggtcgactacaaagatgacgatgacaaa (SEQ ID NO: 65) |
| AP3-8 | gaggtgcagctggtgcagtctggagctgaggtgaagaagcctggggcctcagtgaaggtctcctgcaaggcttctggttacacctttaccagctatggtatcagctgggtgcgacaggcctctggacaaggcctgagtggatggggatggatcagcgcttacaatggtaacacaaactatgcacagaagctccagggcagagtcaccatgaccacagacacatccacgagcagcgctacatggagctgaggagcctgagatctgacgacacggccgtgtattactgtgcgagagtaccccgatatttttgactggttattatacggagcgactactttgactactggggccagggaacccggtcaccgtctcctcaggcggcggcggctctggcggaggtggcagcagcggtggcggatccgacatccagatgacccagtctccttccaccctgtctgtatctgtaggagacagagtcaccatcacttgtcgggcgagtcagggtattagcagctggttagcctggtatcagcagaaaccagggaaagcccctaagctcctgatctatgctgcatccagttttgcaaagtggggtcccatcaaggttcagcggcagtggatctgggacagatttcactctcactatcagcagcctgcagcctgaagattttgcaacttactattgtcaacaggctaacagtttccgctcactttcggcggagggaccaagctggagatcaaacgtggcctcggggggcctggtcgactacaaagatgacgatgacaaa (SEQ ID NO: 66) |
| AP3-10 | caggtgcagctggtgcaatctggagctgaggtgaaggagcctgggtcctcggtgaaggtctcctgcaaggcttctggaggcaccttcagcagctatgctatctactgggtgcgacaggcccctggacaaggccttgagtggatgggatggatcatccctatccttggtatagcaaactacgcacagaagttccagggcagagtcacgattaccgcggacaaatccacgagcacagcctacatggagctgagcagcctgagatctgaggacacggccgtgtattactgtgcgagagctgccggtcatagtactaactactactactacggtatggacgtctggggccaagggaccctggtcaccgtctcctcaggcggcggcggctctggcggaggtggcagcggcggtggcggatcccaacctgtgctgactcagccgccctccgtgtctgggtccctggggcagagggtcaccatctcacctgtggctccaggcactggagtcgtcaccagtggtcattatcccactggttccagcagaagcctggccaagccccaggacactgatttatgatacaagcaacaaacactcctgaccccgtgcccggttctcaggctccccttgggggcaaagctgccctgaccctttcgggtgcgcagcctgaggatgaggctgagtattactgcttgctctcctatagtggtactcgggtgttcggcggagggaccaagctgaccgtcctaggt (SEQ ID NO: 67) |
| AP3-13 | gaggtgcagctggtgcagtctggggctgaggtgaagaagcctggggcctcagtgaaggtttcctgcaaggcatctggatacaccttcaccaactactatatgcactgggtgcgacaggcccctggacaagggcttgagtggatgggaataatcaaccctagtggtggtagcacaagctacgcacagaagtccagggcagagtcaccatgactagggacacgtccacgagcacagcctacatggagctgagcagcctgagatctgaggacacggccgtgtattactgtgcgagagatttcaaagagtatagccgtacgggctactttgactactggggccagggcaccctggtcaccgtctcctcaggcggcggcggctctggcggaggtggcagcagcggtggcggatcctcctatgagctgatgcagccatcctcagtgtcagtgtctccgggacagacagccaggatcacctgctcaggagatgtactggcaaaaaatgtgctcggtggttccagcagaagccaggccaggcccctgtgctggtgatttataaagacagtgagcggccctcagggatccctgagcgattctccggctccagctcagggacacagtcaccttgaccatcagcggggcccaggttgaggatgaggctgactattactgttactctgcggctgacaacaacctgggggtgttcggcggagggaccaaggtcaccgtcctaggt (SEQ ID NO: 68) |
| AP3-20 | cagatcaccttgaaggagtctggtcctgcgctggtgaaacccacacagaccctcacgctgacctgcaacttctctgggttctccctcagcacttatggagggggtgtgggctggctccgtcagccccaggaaaggcctggagtggctcgcgtcatttattggagtgatggtaaacgctacagccctctgtaaagaaccggctcaccatcaccaaggacacctccaaaaaccaccagtgtcctgcaatgaccaacatgaccctgtggacacagccaccttattgtgcacaccttatggatacatctattactacccactggttcgaccctgggcccagggaaccctggtcaccgtctcctcaggcggcggcggctctggcggaggtggcagcggcggtggcggatccgccatccggatgacccagtctccatcctccctgtctgcatctgtaggagacagagtcaccatcacttgccgggcgagtcagggcattagcaattatttagcctggtatcagcagaaaccagggaaagttcctaagctcctgatctatgctgcatccactttgcaatcaggggtcccatctcggttcagcggcagtggatctgggacagatttcactctcaccatcagcagcctgcagcctgaagatgttgcaacttattactgtcaaaagtataacagtgcccctgggacgttcggccaagggaccaaggtggagatcaaacgtggcctcggggggcctggtcgactacaaagatgacgatgacaaa (SEQ ID NO: 69) |
| AP4-8 | caggtgcagctggtgcaatctggggctgaggtgaagaagcctggggcctcggtgaaggtttcctgcaaggcatctggatacaccttcaccaactactttatacactgggtgcgacaggcccctggacaagggcttgagtggatggatggtactcaaccctactgatagtggcacactctacgcacagaacttccagggcagaatcaccatgaccagtgacacgtccacaaacacagtctacatggagctgagcagcctgagatctgacgacacggccatgtattactgtgcaagagagggggggccgacactacccgggtccactcttcgtttgactactggggccagggaaccctggtcaccgtctcctcaggcggcggcggctctggcggaggtggcagcagcggtggcggatccccaggctgtgctgactcagccgcctccgtgtcggggtctcctggacagtcgatcaccatctcctgcactggaaccagcagtgacgttgaagcttacaactatgtctcctggtatcaacaacacccaggcaaagcccccaaactcatgatttatgatgtcagtaatcgcccctcaggggtttctaatcgcttctctggctccaagtctggcaacacggcctcctgaccatctctgggctccaggctgaggacgaggctgattattactgcagctcatatacaagcagcagcacttgggtgttcggcggagggaccaaggtcatcgtccta (SEQ ID NO: 70) |
| AP4-14 | caggtgcagctgcaggagtcgggggggaggcttggtacagcctggcaggtccctgagactctcctgtgcagcctctggattcacctttgatgattatgccctccactgggtccggcaagctccagggaagggcctggagtgggtctcaggtattagttggaatagtgttaccgtaaagtatgcggtctctg |

-continued

Nucleic Acids Encoding the Human scFvs

| Anti-body | Variable Heavy Chain |
|---|---|
| | tgaagggccggttcaccatctccagagacaacgccaagaactccctgtttctgcaaatgaacgctctgagatctgaggacacggccttatattac<br>tgtgcaaaagccagaggggccctcttagaagcagctgacacaccatctgacgactggggccagggcaccctggtcaccgtctcctcaggcggcgg<br>cggctctggcggaggtggcagcggcggtggcggatccgacatcgtgatgacccagtctccgtcctccctgtctgcatctgtaggagacagagtca<br>ccatcacttgccgggcaagtcagagcattagcagctatttaaattggtatcagcagaaaccagggaaagcccctaagctcctgatctatgctgca<br>tccagtttgcaaagtggggtcccatcaaggttcagtggcagtggatctgggacagatttcactctcaccatcagcagcctgcagcctgaagatgt<br>tgcaacttattactgtcaaaagtataacagtgccccgtggacgttcggccaagggaccaaagtggatatcaaa (SEQ ID NO: 71) |
| AP4-20 | caggtacagctgcagcagtcaggcgcaggtctattgaggccttcggagaccctgtccctcacctgcggtctctatggtgggtccttcagtggtca<br>ctattggaactggatccgccagtccccagaaaaggggctggtgtggattggggaaatcactcatagtggaaccaccaattacaacccgtccctca<br>agagtcgagtcatcacatcagtagacacgtccaagaatcagtactccctgaagctgagctttgtgacccctgcggacacggccgtgtattactgt<br>gcgagaggtgattactatgggtactggtacttcgatctctggggccgtggcaccctggtcaccgtctcctcaggcggcggcggctctggcggagg<br>tggcagcggcggtggcggatcccagtctgtgttgacgcagccgcctcagttcctgtggcccaggacagaaggtcaccatctcctgctctggaa<br>gcagctccaacattgggaataattatgtatcctggtaccagcagctcccaggaacagcccccaaactcctcatttatgacactaataagcgaccc<br>tcagggattcctgaccgattcgctggctccaagtctggcacgtcagccaccctgggcatcaccggactccagactggggacgaggccgattatta<br>ctgcggaacatgggatagcagcctgagtgctggcgtgttcggcggagggaccaagctgaccgtccta (SEQ ID NO: 72) |

Example 25

Suppression of Hemolysin Expression in RN4850 by an Anti-AIP4 Human scFv, AP4-4-20

Of the 20 clones obtained by panning an antibody-phage display library, the most potent clone AP4-4-20 was expressed as scFv antibody in *E. coli*. The expressed scFv antibody was purified, and evaluated for its ability to suppress hemolysins expression in *S. aureus* RN 4850 as follows.

Figure 11:
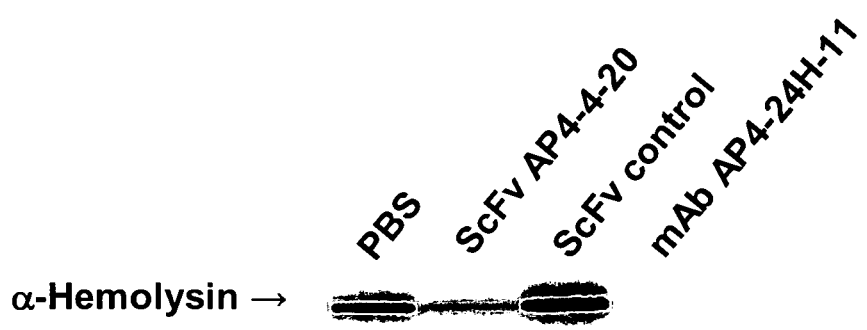
FIG. 11 is the result of a western analysis of the culture supernatants of *S. aureus* RN4850 grown in the presence of the human anti-AIP4 scFv 4-20 antibody for α-hemolysin expression.

*S. aureus* RN4850 was incubated in the presence of scFv AP4-4-20 (2.7 μM) in CYGP medium for 24 hours, and α-hemolysin expression was evaluated by western analysis using *S. aureus* culture supernatants. Results are shown in FIG. 11. The mAb AP4-24H-11 (1.3 μM) and an unrelated scFv antibody control (10 μM) were used as positive and negative controls, respectively. In the presence of the AIP-4 specific antibodies 4-20 and AP4-24H11, a clear reduction in hemolysins secretion is detectable, strongly indicative of inhibition of AIP-dependent QS in *S. aureus*.

Example 26

Figure 12:
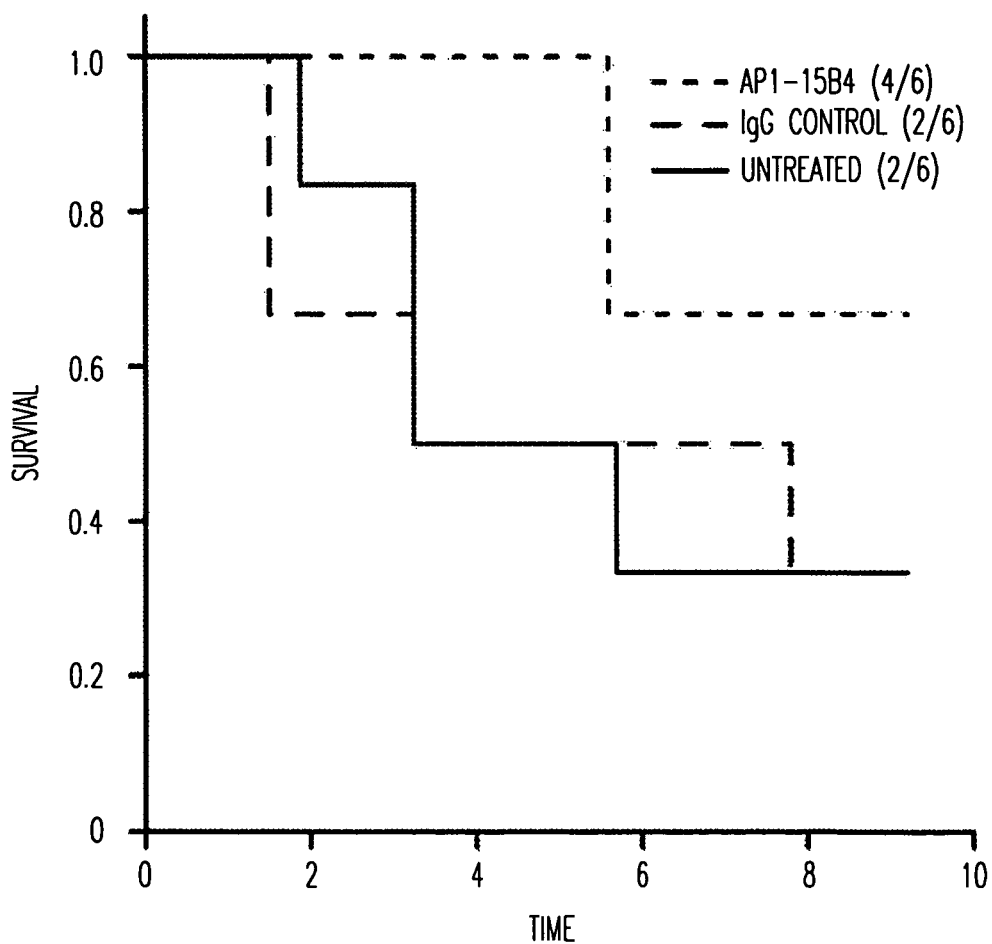
FIG. 12 is the result of an experiment demonstrating the protection of mice from lethal MRSA USA300 challenge by mAb AP1-15B4. Mice were treated with AP1-15B4 (1 mg) or control IgG (1 mg) 2 hours after *S. aureus* injection ($1-3 \times 10^8$ i.p.). The numbers in parenthesis show survivors per group, p=0.02; n=6 for each group.

Anti-AIP1 mAb AP1-15B4 Protects Mice from Lethal Systemic MRSA USA300 Challenge in Postexposure Therapy The effectiveness of our passive immunization approach was demonstrated in a postexposure scenario using mAb AP1-15B4 in a lethal *S. aureus* challenge mouse model. C57BL/6 mice received 1 mg of AP1-15B4 (i.p.), isotype control IgG or PBS 2 hours after they had been infected with at least $1 \times 10^8$ *S. aureus* USA300, an agr I MRSA strain. See Diep et al., *Lancet* 2006, 367, (9512), 731-739. USA300 is in fact one of the most common community-acquired MRSA (CA-MRSA) strains and represents an increasing threat for civilians and military personnel. Hageman et al., *Diagn Microbiol Infect Dis* 2008; James et al., *Arch Dis Child Fetal Neonatal Ed* 2008, 93, (1), F40-4; Tenover et al., *J Clin Microbiol* 2006, 44, (1), 108-18; Beilman et al., *Surg Infect (Larchmt)* 2005, 6, (1), 87-92. As shown in FIG. 12, 4 out of 6 mice receiving AP1-15B4 survived through the 48-hour observation period. In contrast, only two of the PBS treated control mice (2/6) and 2 of the control IgG treated mice (2/6) survived longer than 24 hours. These data for the first time demonstrate the existence of a therapeutic window for a quorum quenching strategy in *S. aureus*. This further validates our immunopharmacotherapeutic approach for preventing *S. aureus* infections as it shows that our quorum quenching antibodies can be administered after the infection of the patient.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

CITED DOCUMENTS

1. Fuqua, C., Winans, S. C., and Greenberg, E. P. (1996). Census and consensus in bacterial ecosystems: the LuxR-LuxI family of quorum-sensing transcriptional regulators. Annu Rev Microbiol 50, 727-751.
2. Nealson, K. H., Platt, T., and Hastings, J. W. (1970). Cellular control of the synthesis and activity of the bacterial luminescent system. J Bacteriol 104, 313-322.
3. de Kievit, T. R., and Iglewski, B. H. (2000). Bacterial quorum sensing in pathogenic relationships. Infect Immun 68, 4839-4849.
4. Kaplan, H. B., and Greenberg, E. P. (1985). Diffusion of autoinducer is involved in regulation of the *Vibrio fischeri* luminescence system. J Bacteriol 163, 1210-1214.
5. Lazazzera, B. A., and Grossman, A. D. (1998). The ins and outs of peptide signaling. Trends Microbiol 6, 288-294.
6. Novick, R. P. (2003). Autoinduction and signal transduction in the regulation of staphylococcal virulence. Mol Microbiol 48, 1429-1449.
7. Meijler, M. M., Horn, L. G., Kaufmann, G. F., McKenzie, K. M., Sun, C., Moss, J. A., Matsushita, M., and Janda, K. D. (2004). Synthesis and biological validation of a ubiquitous quorum-sensing molecule. Angew Chem Int Ed Engl 43, 2106-2108.
8. Schauder, S., Shokat, K., Surette, M. G., and Bassler, B. L. (2001). The LuxS family of bacterial autoinducers: biosynthesis of a novel quorum-sensing signal molecule. Mol Microbiol 41, 463-476.
9. Gotz, F. (2002). *Staphylococcus* and biofilms. Mol Microbiol 43, 1367-1378.
10. Hall-Stoodley, L., Costerton, J. W., and Stoodley, P. (2004). Bacterial biofilms: from the natural environment to infectious diseases. Nat Rev Microbiol 2, 95-108.
11. Lyon, G. J., and Muir, T. W. (2003). Chemical signaling among bacteria and its inhibition. Chem Biol 10, 1007-1021.
12. Rasmussen, T. B., and Givskov, M. (2006). Quorum sensing inhibitors: a bargain of effects. Microbiology 152, 895-904.
13. Smith, R. S., and Iglewski, B. H. (2003). *P. aeruginosa* quorum-sensing systems and virulence. Curr Opin Microbiol 6, 56-60.
14. Chan, W. C., Coyle, B. J., and Williams, P. (2004). Virulence regulation and quorum sensing in staphylococcal infections: competitive AgrC antagonists as quorum sensing inhibitors. J Med Chem 47, 4633-4641.
15. Geske, G. D., Wezeman, R. J., Siegel, A. P., and Blackwell, H. E. (2005). Small molecule inhibitors of bacterial quorum sensing and biofilm formation. J Am Chem Soc 127, 12762-12763.
16. Lyon, G. J., Mayville, P., Muir, T. W., and Novick, R. P. (2000). Rational design of a global inhibitor of the virulence response in *Staphylococcus aureus*, based in part on localization of the site of inhibition to the receptor-histidine kinase, AgrC. Proc Natl Acad Sci USA 97, 13330-13335.
17. Muh, U., Hare, B. J., Duerkop, B. A., Schuster, M., Hanzelka, B. L., Heim, R., Olson, E. R., and Greenberg, E. P. (2006). A structurally unrelated mimic of a *Pseudomonas aeruginosa* acyl-homoserine lactone quorum-sensing signal. Proc Natl Acad Sci USA 103, 16948-16952.
18. Smith, K. M., Bu, Y., and Suga, H. (2003). Library screening for synthetic agonists and antagonists of a *Pseudomonas aeruginosa* autoinducer. Chem Biol 10, 563-571.
19. Kaufmann, G. F., Sartorio, R., Lee, S. H., Mee, J. M., Altobell, L. J., 3rd, Kujawa, D. P., Jeffries, E., Clapham, B., Meijler, M. M., and Janda, K. D. (2006). Antibody interference with N-acyl homoserine lactone-mediated bacterial quorum sensing. J Am Chem Soc 128, 2802-2803.
20. Miyairi, S., Tateda, K., Fuse, E. T., Ueda, C., Saito, H., Takabatake, T., Ishii, Y., Horikawa, M., Ishiguro, M., Standiford, T. J., and Yamaguchi, K. (2006). Immunization with 3-oxododecanoyl-L-homoserine lactone-protein conjugate protects mice from lethal *Pseudomonas aeruginosa* lung infection. J Med Microbiol 55, 1381-1387.
21. Massey, R. C., Horsburgh, M. J., Lina, G., Hook, M., and Recker, M. (2006). The evolution and maintenance of virulence in *Staphylococcus aureus*: a role for host-to-host transmission? Nat Rev Microbiol 4, 953-958.
22. George, E. A., and Muir, T. W. (2007). Molecular mechanisms of agr quorum sensing in virulent staphylococci. Chembiochem 8, 847-855.
23. Sakoulas, G., Eliopoulos, G. M., Moellering, R. C., Jr., Novick, R. P., Venkataraman, L., Wennersten, C., DeGirolami, P. C., Schwaber, M. J., and Gold, H. S. (2003). *Staphylococcus aureus* accessory gene regulator (agr) group II: is there a relationship to the development of intermediate-level glycopeptide resistance? J Infect Dis 187, 929-938.
24. Wright, J. S., 3rd, Jin, R., and Novick, R. P. (2005). Transient interference with staphylococcal quorum sensing blocks abscess formation. Proc Natl Acad Sci USA 102, 1691-1696.
25. Ji, G., Beavis, R., and Novick, R. P. (1997). Bacterial interference caused by autoinducing peptide variants. Science 276, 2027-2030.
26. Mayville, P., Ji, G., Beavis, R., Yang, H., Goger, M., Novick, R. P., and Muir, T. W. (1999). Structure-activity analysis of synthetic autoinducing thiolactone peptides from *Staphylococcus aureus* responsible for virulence. Proc Natl Acad Sci USA 96, 1218-1223.
27. Shigenaga, A., Moss, J. A., Ashley, F. T., Kaufmann, G. F., Janda, K. D. (2006). Solid-phase synthesis and cyclative cleavage of quorum sensing depsipeptide analogs by acylphenyldiazene activation. SYNLETT 4, 551-554.

28. Kaufmann, G. F., Sartorio, R., Lee, S. H., Rogers, C. J., Meijler, M. M., Moss, J. A., Clapham, B., Brogan, A. P., Dickerson, T. J., and Janda, K. D. (2005). Revisiting quorum sensing: Discovery of additional chemical and biological functions for 3-oxo-N-acylhomoserine lactones. Proc Natl Acad Sci USA 102, 309-314.
29. Vuong, C., Saenz, H. L., Gotz, F., and Otto, M. (2000). Impact of the agr quorum-sensing system on adherence to polystyrene in *Staphylococcus aureus*. J Infect Dis 182, 1688-1693.
30. Harraghy, N., Kerdudou, S., and Herrmann, M. (2007). Quorum-sensing systems in staphylococci as therapeutic targets. Anal Bioanal Chem 387, 437-444.
31. Novick, R. P., Ross, H. F., Projan, S. J., Kornblum, J., Kreiswirth, B., and Moghazeh, S. (1993). Synthesis of staphylococcal virulence factors is controlled by a regulatory RNA molecule. Embo J 12, 3967-3975.
32. Valle, J., Toledo-Arana, A., Berasain, C., Ghigo, J. M., Amorena, B., Penades, J. R., and Lasa, I. (2003). SarA and not sigmaB is essential for biofilm development by *Staphylococcus aureus*. Mol Microbiol 48, 1075-1087.
33. Xiong, Y. Q., Willard, J., Yeaman, M. R., Cheung, A. L., and Bayer, A. S. (2006). Regulation of *Staphylococcus aureus* alpha-toxin gene (hla) expression by agr, sarA, and sae in vitro and in experimental infective endocarditis. J Infect Dis 194, 1267-1275.
34. Jarraud, S., Lyon, G. J., Figueiredo, A. M., Gerard, L., Vandenesch, F., Etienne, J., Muir, T. W., and Novick, R. P. (2000). Exfoliatin-producing strains define a fourth agr specificity group in *Staphylococcus aureus*. J Bacteriol 182, 6517-6522.
35. Balaban, N., Goldkorn, T., Nhan, R. T., Dang, L. B., Scott, S., Ridgley, R. M., Rasooly, A., Wright, S. C., Larrick, J. W., Rasooly, R., and Carlson, J. R. (1998). Autoinducer of virulence as a target for vaccine and therapy against *Staphylococcus aureus*. Science 280, 438-440.
36. Shaw, L. N., Jonnson, L M., Singh, V. K., Tarkowski, A., and Stewart, G. C. (2007). Inactivation of traP has no effect on the Agr quorum sensing system or virulence of *Staphylococcus aureus*. Infect Immun.
37. Tsang, L. H., Daily, S. T., Weiss, E. C., and Smeltzer, M. S. (2007). Mutation of traP in *Staphylococcus aureus* has no impact on expression of agr or biofilm formation. Infect Immun.
38. Bantel, H., Sinha, B., Domschke, W., Peters, G., Schulze-Osthoff, K., and Janicke, R. U. (2001). alpha-Toxin is a mediator of *Staphylococcus aureus*-induced cell death and activates caspases via the intrinsic death pathway independently of death receptor signaling. J Cell Biol 155, 637-648.
39. Casadevall, A., Dadachova, E., and Pirofski, L. A. (2004). Passive antibody therapy for infectious diseases. Nat Rev Microbiol 2, 695-703.
40. Yang, G., Gao, Y., Dong, J., Liu, C., Xue, Y., Fan, M., Shen, B., and Shao, N. (2005). A novel peptide screened by phage display can mimic TRAP antigen epitope against *Staphylococcus aureus* infections. J Biol Chem 280, 27431-27435.
41. Yang, G., Gao, Y., Dong, J., Xue, Y., Fan, M., Shen, B., Liu, C., and Shao, N. (2006). A novel peptide isolated from phage library to substitute a complex system for a vaccine against staphylococci infection. Vaccine 24, 1117-1123.
42. Novick, R. P. (1991). Genetic systems in staphylococci. Methods Enzymol 204, 587-636.
43. O'Toole, G. A., Pratt, L. A., Watnick, P. I., Newman, D. K., Weaver, V. B., and Kolter, R. (1999). Genetic approaches to study of biofilms. Methods Enzymol 310, 91-109.
44. Eleaume, H., and Jabbouri, S. (2004). Comparison of two standardisation methods in real-time quantitative RT-PCR to follow *Staphylococcus aureus* genes expression during in vitro growth. J Microbiol Methods 59, 363-370.
45. DeGrado, W. F.; Kaiser, E. T. Polymer-bound oxime esters as supports for solid-phase peptide synthesis. The preparation of protected peptide fragments. *J. Org. Chem.* 1980, 45, 1295-1300.
46. DeGrado, W. F.; Kaiser, E. T. Solid-phase synthesis of protected peptides on a polymer-bound oxime: preparation of segments comprising the sequence of a cytotoxic 26-peptide analog. *J. Org. Chem.* 1982, 47, 3258-3261.
47. Nakagawa, S. H.; Kaiser, E. T. Synthesis of protected peptide segments and their assembly on a polymer-bound oxime: application to the synthesis of a peptide model for plasma apolipoprotein A-I. *J. Org. Chem.* 1983, 48, 678-685.
48. Nakagawa, S. H.; Lau, H. S.; Kezdy, F. J.; Kaiser, E. T. The use of polymer-bound oximes for the synthesis of large peptides usable in segment condensation: synthesis of a 44 amino acid amphiphilic peptide model of apolipoprotein A-1. *J. Am. Chem. Soc.* 1985, 107, 7087-7092.
49. Kaiser, E. T.; Mihara, H.; Laforet, G. A.; Kelly, J. W.; Walters, L.; Findeis, M. A.; Sasaki, T. Peptide and protein synthesis by segment synthesis-condensation. *Science* 1989, 243, 187-192.
50. Osapay, G.; Taylor, J. W. Multicyclic Polypeptide Model Compounds. 2. Synthesis and Conformational Properties of a Highly α-Helical Uncosapeptide Constrained by Three Side-Chain to Side-Chain Lactam Bridges. *J. Am. Chem. Soc.* 1992, 114, 6966-6973.
51. Taylor, J. W. The Synthesis and Study of Side-Chain Lactam-Bridged Peptides. *Biopolymers* 2002, 66, 49-75.
52. Li, P.; Roller, P. P.; Xu, J. Current Synthetic Approaches to Peptide and Peptidomimetic Cyclization. *Curr. Org. Chem.* 2002, 6, 411-440.
53. Chorev, M. The Partial Retro-Inverso Modification: A Road Traveled Together. *Biopolymers* 2005, 80, 67-84.
54. Vince, R.; Brownell, J. Akella, L. B. Synthesis and activity of γ-(L-γ-azaglutamyl)-S-(p-bromobenzyl)-L-cysteinylglycine: A metabolically stable inhibitor of glyoxalase I. *Bioorg. Med. Chem. Lett.* 1999, 9, 853-856.

What is claimed is:

1. An immunogenic molecular entity comprising at least one hapten covalently linked to a macromolecular carrier, wherein the hapten comprises a cyclic peptide comprising a macrocyclic ring, wherein the cyclic peptide comprises the amino acid sequence of YST($X^{a+2}$)DFIM (SEQ ID: 92); wherein the last amino acid residue is covalently bonded to a group R by a respective carbonyl group; $X^{a+2}$ is any amino acid, a respective carbon atom of which is covalently bonded to R; wherein R comprises —$CH_2O$—, —$CH_2CH_2O$—, —$CH_2CH(CH_3)O$—, —$CH_2$-phenyl-O—, —$CH_2S$—, —$CH_2CH_2S$—, or —$(CH_2)_nNH$—, wherein n is 1 to about 4; the N-terminal amino acid residue of the cyclic peptide is attached to the macromolecular carrier.

2. The immunogenic molecular entity of claim 1, wherein the macromolecular carrier comprises a protein, a polymer or a nanoparticle.

3. The immunogenic molecular entity of claim 2, wherein the macromolecular carrier comprises a protein.

4. The immunogenic molecular entity of claim 1, wherein the cyclic peptide is covalently linked to the macromolecular carrier.

5. An immunogenic molecular entity having the structure:

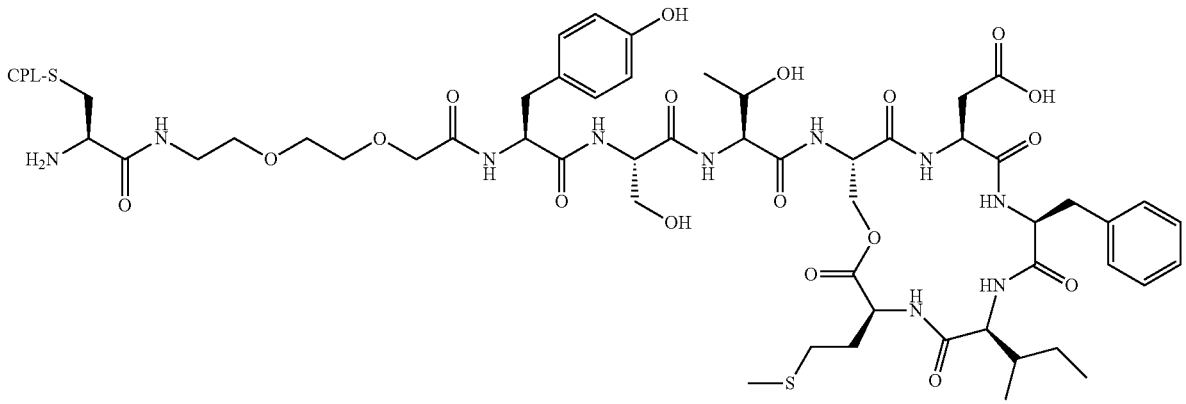

SEQ ID NO: 3 (YSTSDFIM, not including protecting groups),
wherein CPL, is a macromolecular carrier with linker covalently bonded to a cysteine thiol group.

6. A vaccine composition comprising at least one immunogenic molecular entity of claim 1 and a pharmaceutically-acceptable carrier.

7. A method of eliciting an immune response in a mammal comprising administering to the mammal a composition comprising the immunogenic molecular entity of claim 1, in an amount effective to elicit an immune response in the mammal; wherein the mammal is susceptible to infection by *Staphylococcus aureus*.

8. A method of inhibiting quorum sensing in a mammal comprising administering to the mammal the immunogenic molecular entity of claim 1, in an amount effective to elicit an immune response and inhibit the quorum sensing in the mammal.

9. A method for treating infection of a mammal by *Staphylococcus aureus*, comprising administering to the mammal the immunogenic molecular entity of claim 1 in an amount effective to treat infection of the mammal by *Staphylococcus aureus*.

* * * * *

SEQUENCE LISTING

<160> NUMBER OF SEQ ID NOS: 181

<210> SEQ ID NO 1
<211> LENGTH: 8
<212> TYPE: PRT
<213> ORGANISM: Artificial Sequence
<220> FEATURE:
<223> OTHER INFORMATION: a synthetic peptide

```
<400> SEQUENCE: 1

Tyr Ser Thr Ser Tyr Phe Ile Met
 1               5

<210> SEQ ID NO 2
<211> LENGTH: 7
<212> TYPE: PRT
<213> ORGANISM: Artificial Sequence
<220> FEATURE:
<223> OTHER INFORMATION: a synthetic peptide

<400> SEQUENCE: 2

Ile Asn Ser Asp Phe Leu Leu
 1               5

<210> SEQ ID NO 3
<211> LENGTH: 8
<212> TYPE: PRT
<213> ORGANISM: Artificial Sequence
<220> FEATURE:
<223> OTHER INFORMATION: a synthetic peptide

<400> SEQUENCE: 3

Tyr Ser Thr Ser Asp Phe Ile Met
 1               5

<210> SEQ ID NO 4
<211> LENGTH: 9
<212> TYPE: PRT
<213> ORGANISM: Artificial Sequence
<220> FEATURE:
<223> OTHER INFORMATION: a synthetic peptide

<400> SEQUENCE: 4

Gly Val Asn Ala Ser Ser Ser Leu Phe
 1               5

<210> SEQ ID NO 5
<211> LENGTH: 28
<212> TYPE: DNA
<213> ORGANISM: Staphylococcus aureus

<400> SEQUENCE: 5
tggcccaaga ctttagttat cgttatcc                                      28

<210> SEQ ID NO 6
<211> LENGTH: 29
<212> TYPE: DNA
<213> ORGANISM: Staphylococcus aureus

<400> SEQUENCE: 6
tggggaggaa tatttgtagc catacctac                                     29

<210> SEQ ID NO 7
<211> LENGTH: 25
<212> TYPE: DNA
<213> ORGANISM: Staphylococcus aureus

<400> SEQUENCE: 7
gcactgagtc caaggaaact aactc                                         25

<210> SEQ ID NO 8
<211> LENGTH: 24
<212> TYPE: DNA
```

-continued

<213> ORGANISM: Staphylococcus aureus

<400> SEQUENCE: 8
gccatcccaa cttaataacc atgt                                            24

<210> SEQ ID NO 9
<211> LENGTH: 24
<212> TYPE: DNA
<213> ORGANISM: Staphylococcus aureus

<400> SEQUENCE: 9
ctgaaggcca ggctaaacca cttt                                            24

<210> SEQ ID NO 10
<211> LENGTH: 25
<212> TYPE: DNA
<213> ORGANISM: Staphylococcus aureus

<400> SEQUENCE: 10
gaacgaaagg taccattgct ggtca                                           25

<210> SEQ ID NO 11
<211> LENGTH: 24
<212> TYPE: DNA
<213> ORGANISM: Staphylococcus aureus

<400> SEQUENCE: 11
gcgcaacacg atgaagctca acaa                                            24

<210> SEQ ID NO 12
<211> LENGTH: 24
<212> TYPE: DNA
<213> ORGANISM: Staphylococcus aureus

<400> SEQUENCE: 12
acgttagcac tttggcttgg atca                                            24

<210> SEQ ID NO 13
<211> LENGTH: 24
<212> TYPE: DNA
<213> ORGANISM: Staphylococcus aureus

<400> SEQUENCE: 13
gttccgggaa attctggatc aggt                                            24

<210> SEQ ID NO 14
<211> LENGTH: 24
<212> TYPE: DNA
<213> ORGANISM: Staphylococcus aureus

<400> SEQUENCE: 14
gcgcttgaca taattcccaa tacc                                            24

<210> SEQ ID NO 15
<211> LENGTH: 26
<212> TYPE: DNA
<213> ORGANISM: Staphylococcus aureus

<400> SEQUENCE: 15
ctgctttaac aacttgtggt tgtttg                                          26

<210> SEQ ID NO 16
<211> LENGTH: 24

```
<212> TYPE: DNA
<213> ORGANISM: Staphylococcus aureus

<400> SEQUENCE: 16
cgctgtattg acatacatca gcga                                              24

<210> SEQ ID NO 17
<211> LENGTH: 25
<212> TYPE: DNA
<213> ORGANISM: Staphylococcus aureus

<400> SEQUENCE: 17
cgccttaact ttaggtgcag atgac                                             25

<210> SEQ ID NO 18
<211> LENGTH: 24
<212> TYPE: DNA
<213> ORGANISM: Staphylococcus aureus

<400> SEQUENCE: 18
acgcataggg acttcgtgac catt                                              24

<210> SEQ ID NO 19
<211> LENGTH: 120
<212> TYPE: PRT
<213> ORGANISM: Murine

<400> SEQUENCE: 19

Glu Val His Leu Val Glu Ser Gly Gly Asp Leu Val Lys Pro Gly Gly
 1               5                  10                  15

Ser Leu Lys Leu Ser Cys Ala Ala Ser Gly Phe Ala Phe Ser Asp Phe
             20                  25                  30

Ala Met Ser Trp Val Arg Gln Thr Pro Glu Lys Arg Leu Glu Trp Val
         35                  40                  45

Ala Ile Ile Lys Ser Asp Asp Ser Tyr Thr Tyr Tyr Pro Asp Ser Val
     50                  55                  60

Arg Asp Arg Phe Thr Ile Ser Arg Asp Asn Ala Arg Asn Thr Leu Tyr
 65                  70                  75                  80

Leu Gln Met Thr Ser Leu Arg Ser Glu Asp Thr Ala Leu Tyr Tyr Cys
                 85                  90                  95

Thr Lys Ile Tyr Asp Ala Tyr Phe Tyr Ala Met Asp Tyr Trp Gly Gln
            100                 105                 110

Gly Thr Ser Val Thr Val Ser Ser
        115                 120

<210> SEQ ID NO 20
<211> LENGTH: 113
<212> TYPE: PRT
<213> ORGANISM: Murine

<400> SEQUENCE: 20

Glu Val Lys Pro Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asn
             20                  25                  30

Tyr Ala Trp Asn Trp Ile Arg Gln Phe Pro Gly Asn Lys Leu Glu Trp
         35                  40                  45

Met Gly Phe Ile Ser Ser Tyr Gly Thr Thr Thr Tyr Asn Pro Ser Leu
     50                  55                  60
```

-continued

```
Lys Ser Arg Phe Ser Ile Thr Arg Asp Thr Ser Lys Asn Gln Phe Phe
 65                  70                  75                  80

Leu Gln Leu His Ser Val Thr Ile Glu Asp Thr Gly Thr Tyr Phe Cys
                 85                  90                  95

Thr Arg Glu Gly Asp Tyr Trp Gly Gln Gly Thr Leu Thr Val Ser
            100                 105                 110

Ser
```

<210> SEQ ID NO 21
<211> LENGTH: 116
<212> TYPE: PRT
<213> ORGANISM: Murine

<400> SEQUENCE: 21

```
Glu Val Gln Leu Gln Gln Ser Gly Pro Glu Leu Glu Lys Pro Gly Ala
 1               5                  10                  15

Ser Val Lys Ile Ser Cys Lys Ala Ser Gly His Ser Phe Thr Gly Tyr
                 20                  25                  30

Asn Met Asn Trp Val Lys Gln Ser Asn Asp Lys Ser Leu Glu Trp Ile
             35                  40                  45

Gly Asn Ile Ala Pro Tyr Tyr Gly Val Thr Ala Tyr Asn Gln Lys Phe
 50                  55                  60

Lys Gly Lys Ala Thr Leu Thr Gly Asp Lys Ser Ser Ser Thr Ala Tyr
 65                  70                  75                  80

Met Gln Leu Lys Ser Leu Ala Ser Glu Asp Ser Ala Val Tyr Tyr Cys
                 85                  90                  95

Val Leu Asp Thr Ser Gly Tyr Ala Ser Trp Gly Gln Gly Thr Leu Val
            100                 105                 110

Thr Val Ser Ala
        115
```

<210> SEQ ID NO 22
<211> LENGTH: 116
<212> TYPE: PRT
<213> ORGANISM: Murine

<400> SEQUENCE: 22

```
Gln Val Gln Leu Gln Gln Ser Gly Pro Glu Leu Glu Lys Pro Gly Ala
 1               5                  10                  15

Ser Val Lys Ile Ser Cys Lys Ala Ser Gly His Ser Phe Thr Gly Tyr
                 20                  25                  30

Asn Met Asn Trp Val Lys Gln Ser Asn Asp Lys Ser Leu Glu Trp Ile
             35                  40                  45

Gly Asn Ile Ala Pro Tyr Tyr Gly Val Thr Ala Tyr Asn Gln Lys Phe
 50                  55                  60

Lys Gly Lys Ala Thr Leu Thr Gly Asp Lys Ser Ser Ser Thr Ala Tyr
 65                  70                  75                  80

Met Gln Leu Lys Ser Leu Thr Ser Glu Asp Ser Ala Val Tyr Tyr Cys
                 85                  90                  95

Val Leu Asp Thr Ser Gly Tyr Ala Ser Trp Gly Gln Gly Thr Leu Val
            100                 105                 110

Thr Val Ser Ala
        115
```

<210> SEQ ID NO 23
<211> LENGTH: 108
<212> TYPE: PRT

<213> ORGANISM: Murine

<400> SEQUENCE: 23

Gly Gly Asp Leu Val Lys Pro Gly Gly Ser Leu Lys Leu Ser Cys Ala
1               5                   10                  15

Ala Ser Gly Phe Ala Phe Ser Asp Phe Ala Met Ser Trp Val Arg Gln
            20                  25                  30

Thr Pro Glu Lys Arg Leu Glu Trp Val Ala Ile Ile Lys Ser Asp Asp
        35                  40                  45

Ser Tyr Thr Tyr Tyr Pro Asp Ser Val Arg Asp Arg Phe Thr Ile Ser
    50                  55                  60

Arg Asp Asn Ala Arg Asn Thr Leu Tyr Leu Gln Met Thr Ser Leu Arg
65                  70                  75                  80

Ser Glu Asp Thr Ala Leu Tyr Tyr Cys Thr Lys Ile Tyr Asp Ala Tyr
                85                  90                  95

Phe Tyr Ala Met Asp Tyr Trp Gly Gln Gly Thr Ser
            100                 105

<210> SEQ ID NO 24
<211> LENGTH: 101
<212> TYPE: PRT
<213> ORGANISM: Murine

<400> SEQUENCE: 24

Gly Pro Gly Leu Val Lys Pro Ser Gln Ser Leu Ser Leu Thr Cys Thr
1               5                   10                  15

Val Thr Gly Tyr Ser Ile Thr Ser Asn Tyr Ala Trp Asn Trp Ile Arg
            20                  25                  30

Gln Phe Pro Gly Asn Lys Leu Glu Trp Met Gly Phe Ile Ser Ser Tyr
        35                  40                  45

Gly Thr Thr Thr Tyr Asn Pro Ser Leu Lys Ser Arg Phe Ser Ile Thr
    50                  55                  60

Arg Asp Thr Ser Lys Asn Gln Phe Phe Leu Gln Leu His Ser Val Thr
65                  70                  75                  80

Ile Glu Asp Thr Gly Thr Tyr Phe Cys Thr Arg Glu Gly Asp Tyr Trp
                85                  90                  95

Gly Gln Gly Thr Thr
            100

<210> SEQ ID NO 25
<211> LENGTH: 104
<212> TYPE: PRT
<213> ORGANISM: Murine

<400> SEQUENCE: 25

Gly Pro Glu Leu Glu Lys Pro Gly Ala Ser Val Lys Ile Ser Cys Lys
1               5                   10                  15

Ala Ser Gly His Ser Phe Thr Gly Tyr Asn Met Asn Trp Val Lys Gln
            20                  25                  30

Ser Asn Asp Lys Ser Leu Glu Trp Ile Gly Asn Ile Ala Pro Tyr Tyr
        35                  40                  45

Gly Val Thr Ala Tyr Asn Gln Lys Phe Lys Gly Lys Ala Thr Leu Thr
    50                  55                  60

Gly Asp Lys Ser Ser Thr Ala Tyr Met Gln Leu Lys Ser Leu Ala
65                  70                  75                  80

Ser Glu Asp Ser Ala Val Tyr Tyr Cys Val Leu Asp Thr Ser Gly Tyr
                85                  90                  95

Ala Ser Trp Gly Gln Gly Thr Leu
            100

<210> SEQ ID NO 26
<211> LENGTH: 104
<212> TYPE: PRT
<213> ORGANISM: Murine

<400> SEQUENCE: 26

Gly Pro Glu Leu Glu Lys Pro Gly Ala Ser Val Lys Ile Ser Cys Lys
 1               5                  10                  15

Ala Ser Gly His Ser Phe Thr Gly Tyr Asn Met Asn Trp Val Lys Gln
            20                  25                  30

Ser Asn Asp Lys Ser Leu Glu Trp Ile Gly Asn Ile Ala Pro Tyr Tyr
        35                  40                  45

Gly Val Thr Ala Tyr Asn Gln Lys Phe Lys Gly Lys Ala Thr Leu Thr
    50                  55                  60

Gly Asp Lys Ser Ser Ser Thr Ala Tyr Met Gln Leu Lys Ser Leu Thr
65                  70                  75                  80

Ser Glu Asp Ser Ala Val Tyr Tyr Cys Val Leu Asp Thr Ser Gly Tyr
                85                  90                  95

Ala Ser Trp Gly Gln Gly Thr Leu
            100

<210> SEQ ID NO 27
<211> LENGTH: 360
<212> TYPE: DNA
<213> ORGANISM: Murine

<400> SEQUENCE: 27
gaggtgcacc tggtggagtc tgggggagac ttagtgaagc ctgggggtc cctcaaactc        60 tcctgtgcag cctctggatt cgctttcagt gactttgcca tgtcttgggt tcgccagact      120
ccggagaaga ggctggagtg ggtcgcaatc attaaaagtg atgattctta cacctactat      180
ccagacagtg tgagggaccg attcaccatc tccagagaca tgccaggaa caccctttac       240 ctgcaaatga ccagtctgag gtctgaagac acggccttgt attactgtac aaaaatctat      300
gatgcttact ctatgctat ggactactgg ggtcaaggaa cctcagtcac cgtctcctcg       360

<210> SEQ ID NO 28
<211> LENGTH: 339
<212> TYPE: DNA
<213> ORGANISM: Murine

<400> SEQUENCE: 28
gaggtgaagc tcaggagtc aggacctggc ctggtgaaac cttctcagtc tctgtccctc        60
acctgcactg tcactggcta ctcaatcacc agtaattatg cctggaactg gatccggcag      120
tttccaggaa acaaactgga gtggatgggc ttcataagtt cctatggaac cactacctac      180
aacccttctc tcaaaagtcg attctctatc actcgagaca catccaagaa ccagttcttc      240
ctgcaattgc attctgtgac tattgaggac acaggcacat atttctgtac aagagagggt      300
gactactggg gccaaggcac cactctcaca gtctcctca                             339

<210> SEQ ID NO 29
<211> LENGTH: 348
<212> TYPE: DNA
<213> ORGANISM: Murine

<400> SEQUENCE: 29

```
gaggtccagc tgcaacagtc cggacctgag ctggagaagc ctggcgcttc agtgaagata      60
tcctgcaagg cttctggtca ttcattcact ggctacaaca tgaactgggt gaagcagagc     120
aatgacaaga gccttgagtg gattggaaat attgctcctt actatggtgt tactgcctac    180
aaccagaagt tcaagggcaa ggccacattg actggagaca atcctccag cactgcctac     240
atgcagctca agagcctggc atctgaggac tctgcagtct attactgtgt cctagacacc    300
tcgggctacg cttcctgggg ccaagggact ctggtaactg tctctgca                 348
```

<210> SEQ ID NO 30
<211> LENGTH: 348
<212> TYPE: DNA
<213> ORGANISM: Murine

<400> SEQUENCE: 30

```
caggtccagc tgcagcagtc tgggcctgag ctggagaagc ctggcgcttc agtgaagata      60
tcctgcaagg cttctggtca ttcattcact ggctacaaca tgaactgggt gaagcagagc     120
aatgacaaga gccttgagtg gattggaaat attgctcctt actatggtgt tactgcctac    180
aaccagaagt tcaagggcaa ggccacattg actggagaca atcctccag cactgcctac     240
atgcagctca agagcctgac atctgaggac tctgcagtct attactgtgt cctagacacc    300
tcgggctacg cttcctgggg ccaagggact ctggtcactg tctctgca                 348
```

<210> SEQ ID NO 31
<211> LENGTH: 324
<212> TYPE: DNA
<213> ORGANISM: Murine

<400> SEQUENCE: 31

```
gggggagact tagtgaagcc tggggggtcc ctcaaactct cctgtgcagc ctctggattc      60
gctttcagtg actttgccat gtcttgggtt cgccagactc cggagaagag ctggagtgg     120
gtcgcaatca ttaaaagtga tgattcttac acctactatc agacagtgt gagggaccga    180
ttcaccatct ccagagacaa tgccaggaac acccttacc tgcaaatgac cagtctgagg    240
tctgaagaca cggccttgta ttactgtaca aaaatctatg atgcttactt ctatgctatg    300
gactactggg gtcaaggaac ctca                                           324
```

<210> SEQ ID NO 32
<211> LENGTH: 303
<212> TYPE: DNA
<213> ORGANISM: Murine

<400> SEQUENCE: 32

```
ggacctggcc tggtgaaacc ttctcagtct ctgtccctca cctgcactgt cactggctac      60
tcaatcacca gtaattatgc ctggaactgg atccggcagt ttccaggaaa caaactggag     120
tggatgggct tcataagttc ctatggaacc actacctaca accttctct caaaagtcga    180
ttctctatca ctcgagacac atccaagaac cagttcttcc tgcaattgca ttctgtgact    240
attgaggaca caggcacata tttctgtaca agagagggtg actactgggg ccaaggcacc    300
act                                                                  303
```

<210> SEQ ID NO 33
<211> LENGTH: 312
<212> TYPE: DNA
<213> ORGANISM: Murine

<400> SEQUENCE: 33

```
ggacctgagc tggagaagcc tggcgcttca gtgaagatat cctgcaaggc ttctggtcat      60
tcattcactg gctacaacat gaactgggtg aagcagagca atgacaagag ccttgagtgg     120
attggaaata ttgctcctta ctatggtgtt actgcctaca accagaagtt caagggcaag     180
gccacattga ctggagacaa atcctccagc actgcctaca tgcagctcaa gagcctggca     240
tctgaggact ctgcagtcta ttactgtgtc ctagacacct cgggctacgc ttcctggggc     300
caagggactc tg                                                         312
```

<210> SEQ ID NO 34
<211> LENGTH: 312
<212> TYPE: DNA
<213> ORGANISM: Murine

<400> SEQUENCE: 34

```
gggcctgagc tggagaagcc tggcgcttca gtgaagatat cctgcaaggc ttctggtcat      60
tcattcactg gctacaacat gaactgggtg aagcagagca atgacaagag ccttgagtgg     120
attggaaata ttgctcctta ctatggtgtt actgcctaca accagaagtt caagggcaag     180
gccacattga ctggagacaa atcctccagc actgcctaca tgcagctcaa gagcctgaca     240
tctgaggact ctgcagtcta ttactgtgtc ctagacacct cgggctacgc ttcctggggc     300
caagggactc tg                                                         312
```

<210> SEQ ID NO 35
<211> LENGTH: 251
<212> TYPE: PRT
<213> ORGANISM: Homo sapiens

<400> SEQUENCE: 35

```
Gln Val Gln Leu Val Gln Ser Gly Ala Glu Val Lys Lys Pro Gly Glu
 1               5                  10                  15
Ser Leu Arg Ile Ser Cys Lys Gly Ser Gly Tyr Ser Phe Thr Ser His
            20                  25                  30
Trp Ile Ser Trp Val Arg Gln Met Pro Gly Lys Gly Leu Glu Trp Met
        35                  40                  45
Gly Arg Ile Asp Pro Ser Asp Ser Tyr Ser Asn Tyr Ser Pro Ser Phe
    50                  55                  60
Gln Gly His Val Ile Ile Ser Val Asp Lys Ser Ile Ser Thr Ala Tyr
65                  70                  75                  80
Leu Gln Trp Ser Ser Leu Lys Ala Ser Asp Thr Ala Ile Tyr Tyr Cys
                85                  90                  95
Ala Arg Gln Leu Ile Val Val Val Pro Ala Ala Pro Tyr Tyr Tyr Tyr
            100                 105                 110
Tyr Tyr Gly Met Asp Val Trp Gly Gln Gly Thr Leu Val Thr Val Ser
        115                 120                 125
Ser Gly Gly Gly Gly Ser Gly Gly Gly Gly Ser Gly Gly Gly Gly Ser
    130                 135                 140
Glu Ile Val Leu Thr Gln Ser Pro Gly Thr Leu Ser Leu Ser Pro Gly
145                 150                 155                 160
Glu Arg Ala Thr Leu Ser Cys Arg Ala Ser Gln Thr Val Asn Ser Tyr
                165                 170                 175
Leu Ala Trp Tyr Gln Lys Pro Gly Gln Ala Pro Arg Leu Leu Ile Tyr
            180                 185                 190
```

```
Gly Ala Ser Ser Arg Ala Thr Gly Ile Pro Asp Arg Phe Ser Gly Ser
            195                 200                 205

Gly Ser Gly Thr Asp Phe Thr Leu Thr Ile Ser Arg Leu Glu Pro Glu
    210                 215                 220

Asp Phe Ala Val Tyr Tyr Cys Gln Gln Tyr Gly Ser Ser His Pro Trp
225                 230                 235                 240

Thr Phe Gly Gln Gly Thr Lys Val Glu Ile Lys
                245                 250
```

<210> SEQ ID NO 36
<211> LENGTH: 252
<212> TYPE: PRT
<213> ORGANISM: Homo sapiens

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Val Phe Gly Ser Glu Ser Gln Asp Pro Ser Asp Ile Trp Ser
            100                 105                 110

Gly Tyr Tyr Gly Met Glu Val Trp Gly Gln Gly Thr Leu Val Thr Val
        115                 120                 125

Ser Ser Gly Gly Gly Gly Ser Gly Gly Gly Gly Ser Gly Gly Gly Gly
    130                 135                 140

Ser Asp Ile Gln Met Thr Gln Ser Pro Ser Ser Val Ser Ala Ser Val
145                 150                 155                 160

Gly Asp Arg Val Thr Ile Thr Cys Arg Ala Ser Gln Gly Ile Ser Ser
                165                 170                 175

Trp Leu Ala Trp Tyr Gln Gln Lys Pro Gly Lys Ala Pro Lys Leu Leu
            180                 185                 190

Ile Tyr Ala Ala Ser Ser Leu Gln Ser Arg Val Pro Ser Arg Phe Ser
        195                 200                 205

Gly Ser Gly Ser Gly Thr Asp Phe Thr Leu Thr Ile Ser Ser Leu Gln
    210                 215                 220

Pro Glu Asp Phe Ala Thr Tyr Tyr Cys Gln Gln Ala Asn Ser Phe Pro
225                 230                 235                 240

Tyr Thr Phe Gly Gln Gly Thr Lys Leu Glu Ile Lys
                245                 250
```

<210> SEQ ID NO 37
<211> LENGTH: 243
<212> TYPE: PRT
<213> ORGANISM: Homo sapiens

<400> SEQUENCE: 37

```
Gln Val Gln Leu Val Glu Ser Gly Ala Glu Ala Lys Lys Pro Gly Ser
1               5                   10                  15
```

```
Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Ile Thr Gly Thr Thr Ala Pro Pro Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Val Ile Trp Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Arg Lys Pro
                165                 170                 175

Gly Lys Ala Pro Lys Leu Leu Ile Tyr Ala Ala Ser Ser Leu Gln Ser
            180                 185                 190

Gly Val Thr Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Thr Pro Pro Thr Phe Gly Gln Gly Thr Lys Leu
225                 230                 235                 240

Glu Ile Lys

<210> SEQ ID NO 38
<211> LENGTH: 249
<212> TYPE: PRT
<213> ORGANISM: Homo sapiens

<400> SEQUENCE: 38

Gln Val Gln Leu Val Gln Ser Gly Ser Glu Leu Lys Lys Pro Gly Ala
1               5                   10                  15

Ser Val Lys Leu Ser Cys Arg Ala Ser Gly Tyr Thr Phe Thr Ser Tyr
            20                  25                  30

Ser Met Val Trp Val Arg Gln Ala Pro Gly Glu Gly Leu Glu Trp Met
        35                  40                  45

Gly Gly Ile Asn Thr Asn Thr Gly Asn Pro Thr Tyr Ala Gln Gly Phe
    50                  55                  60

Thr Glu Arg Phe Val Phe Ser Phe Asp Ser Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Trp Ala Tyr Ser Gly Ser Trp Pro Leu Gly Gln Asn Pro
            100                 105                 110

Ser Asp His Trp Gly Gln Gly Thr Leu Val Thr Val Ser Ser Gly Gly
        115                 120                 125

Gly Gly Ser Gly Gly Gly Gly Ser Gly Gly Gly Ser Glu Ile Val
    130                 135                 140
```

```
Met Thr Gln Ser Pro Ala Thr Leu Ser Val Ser Pro Gly Glu Arg Ala
145                 150                 155                 160

Thr Leu Ser Cys Arg Ala Ser Gln Ser Val Ser Arg Asn Leu Ala Trp
                165                 170                 175

Tyr Gln Gln Lys Pro Gly Gln Ala Pro Arg Leu Leu Ile Tyr Asp Thr
            180                 185                 190

Ser Thr Arg Ala Thr Gly Ile Pro Ala Arg Phe Ser Gly Ser Gly Ser
        195                 200                 205

Gly Thr Glu Phe Thr Leu Thr Ile Ser Ser Leu Gln Ser Glu Asp Ser
    210                 215                 220

Ala Val Tyr Tyr Cys Gln Gln Tyr Asn Ile Trp Pro Pro Leu Thr Phe
225                 230                 235                 240

Gly Gly Gly Thr Lys Val Glu Ile Lys
                245

<210> SEQ ID NO 39
<211> LENGTH: 242
<212> TYPE: PRT
<213> ORGANISM: Homo sapiens

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Arg Thr Trp Ile Arg Gln Ser Pro Val Lys Gly Leu Glu Trp Ile
        35                  40                  45

Gly Glu Val Asn Asp Arg Gly Ser Pro Asn Tyr Asn Pro Ser Phe Lys
    50                  55                  60

Ser Arg Leu Thr Ile Ser Ile Asp Thr Ser Lys Asn Leu Ser Leu Lys
65                  70                  75                  80

Leu Arg Phe Met Thr Ala Ala Asp Thr Ala Val Tyr Ser Cys Ala Arg
                85                  90                  95

Ile Arg Pro Arg Tyr Gly Met Asp Val Trp Gly Gln Gly Thr Met Val
            100                 105                 110

Thr Val Ser Ser Gly Gly Gly Ser Gly Gly Gly Ser Ser Gly
        115                 120                 125

Gly Gly Ser Asp Ile Val Met Thr Gln Thr Pro Leu Ser Ser Pro Val
    130                 135                 140

Thr Leu Gly Gln Pro Ala Ser Ile Ser Cys Arg Ser Ser Gln Ser Leu
145                 150                 155                 160

Val His Ser Asp Gly Asn Thr Tyr Leu Thr Trp Phe His Gln Arg Pro
                165                 170                 175

Gly Gln Pro Pro Arg Val Leu Ile His Lys Val Ser Asn Leu Phe Ser
            180                 185                 190

Gly Val Pro Asp Arg Phe Ser Gly Ser Gly Ala Gly Thr Asp Phe Thr
        195                 200                 205

Leu Lys Ile Ser Arg Val Glu Ala Glu Asp Val Gly Val Tyr Tyr Cys
    210                 215                 220

Met Gln Ala Thr Gln Leu Tyr Thr Phe Gly Gln Gly Thr Lys Val Glu
225                 230                 235                 240

Ile Lys

<210> SEQ ID NO 40
<211> LENGTH: 245
```

```
<212> TYPE: PRT
<213> ORGANISM: Homo sapiens

<400> SEQUENCE: 40

Glu Val Gln Leu Val Gln Ser Gly Ala Glu Val Lys Lys Pro Gly Ala
  1               5                  10                  15

Ser Val Lys Val Ser Cys Lys Val Ser Gly Tyr Thr Leu Thr Glu Leu
                 20                  25                  30

Ser Met His Trp Val Arg Gln Ala Pro Gly Lys Gly Leu Glu Trp Met
             35                  40                  45

Gly Gly Phe Asp Pro Glu Asp Gly Glu Thr Ile Ser Ala Gln Lys Phe
         50                  55                  60

Gln Gly Arg Val Thr Met Thr Glu Asp Thr Ser Thr Asp Thr Ala Tyr
 65                  70                  75                  80

Met Asp Leu Ser Ser Leu Arg Ser Glu Asp Thr Ala Val Tyr Tyr Cys
                 85                  90                  95

Ala Thr Gln Arg Leu Cys Ser Gly Gly Arg Cys Tyr Ser His Phe Asp
                100                 105                 110

Tyr Trp Gly Gln Gly Thr Thr Val Thr Val Ser Ser Gly Gly Gly Gly
            115                 120                 125

Ser Gly Gly Gly Gly Ser Gly Gly Gly Gly Ser Glu Thr Thr Leu Thr
        130                 135                 140

Gln Ser Pro Ala Ile Met Ser Ala Ser Pro Gly Glu Arg Val Thr Met
145                 150                 155                 160

Thr Cys Ser Ala Ser Ser Ser Ile Arg Tyr Ile Tyr Trp Tyr Gln Gln
                165                 170                 175

Lys Pro Gly Ser Ser Pro Arg Leu Leu Ile Tyr Asp Thr Ser Asn Val
            180                 185                 190

Ala Pro Gly Val Pro Phe Arg Phe Ser Gly Ser Gly Ser Gly Thr Ser
        195                 200                 205

Tyr Ser Leu Thr Ile Asn Arg Met Glu Ala Glu Asp Ala Ala Thr Tyr
    210                 215                 220

Tyr Cys Gln Glu Trp Ser Gly Tyr Pro Tyr Thr Phe Gly Gly Gly Thr
225                 230                 235                 240

Lys Val Glu Ile Lys
            245

<210> SEQ ID NO 41
<211> LENGTH: 244
<212> TYPE: PRT
<213> ORGANISM: Homo sapiens

<400> SEQUENCE: 41

Gln Met Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Thr Tyr
                 20                  25                  30

Val Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95
```

Ala Arg Val Trp Ser Pro Leu Asp Tyr Trp Gly Gln Gly Thr Leu Val
          100                 105                 110

Thr Val Ser Ser Gly Gly Gly Gly Ser Gly Gly Gly Gly Ser Gly Gly
        115                 120                 125

Gly Gly Ser Asp Ile Val Met Thr Gln Ser Pro Asp Ser Leu Ala Val
        130                 135                 140

Ser Leu Gly Glu Arg Ala Thr Ile Asn Cys Lys Ser Ser Gln Ser Val
145                 150                 155                 160

Leu Tyr Ser Ser Asn Asn Met Asn Tyr Leu Ala Trp Tyr Gln Gln Lys
                165                 170                 175

Pro Gly Gln Pro Pro Lys Leu Leu Ile Tyr Trp Ala Ser Thr Arg Glu
            180                 185                 190

Ser Gly Val Pro Asp Arg Phe Ser Gly Ser Gly Ser Gly Thr Asp Phe
        195                 200                 205

Thr Leu Thr Ile Ser Ser Leu Gln Ala Glu Asp Ala Ala Val Tyr Tyr
    210                 215                 220

Cys Gln Gln Tyr Tyr Ser Thr Pro Pro Thr Phe Gly Gly Gly Thr Lys
225                 230                 235                 240

Leu Glu Ile Lys

<210> SEQ ID NO 42
<211> LENGTH: 246
<212> TYPE: PRT
<213> ORGANISM: Homo sapiens

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Gly Tyr
            20                  25                  30

Tyr Met His Trp Val Pro Gln Ala Pro Gly Gln Gly Leu Glu Trp Met
        35                  40                  45

Gly Trp Ile Asn Pro Asn Asn Gly Gly Thr Asn Tyr Asp Gln Lys Phe
    50                  55                  60

Gln Gly Arg Val Ala Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asn Gly Arg Val Thr Thr Gly Gly Tyr Trp Gly Gln Gly
            100                 105                 110

Thr Leu Val Thr Val Ser Ser Gly Gly Gly Gly Ser Gly Gly Gly Gly
        115                 120                 125

Ser Ser Gly Gly Gly Ser Gln Ser Val Leu Thr Gln Pro Pro Ser Leu
    130                 135                 140

Ser Gly Ala Pro Gly Gln Ser Val Thr Ile Ser Cys Ala Gly Thr Ser
145                 150                 155                 160

Ser Ser Ile Gly Ala Gly Tyr Asp Val Gln Trp Tyr Gln Gln Leu Pro
                165                 170                 175

Gly Lys Thr Pro Lys Leu Leu Ile Tyr Gly Asn Asp Asn Arg Pro Ser
            180                 185                 190

Gly Val Pro Asp Arg Phe Ser Gly Ser Arg Ser Tyr Thr Ser Ala Ser
        195                 200                 205

Leu Val Ile Thr Arg Val Gln Ile Glu Asp Glu Ala Asp Tyr Tyr Cys
    210                 215                 220

```
Gln Ser Tyr Asp Ser Ser Leu Ile Gly Pro Gln Phe Gly Gly Gly Thr
225                 230                 235                 240

Lys Leu Thr Val Leu Gly
                245

<210> SEQ ID NO 43
<211> LENGTH: 244
<212> TYPE: PRT
<213> ORGANISM: Homo sapiens

<400> SEQUENCE: 43

Gln Val Gln Leu Val Gln Ser Gly Ala Glu Val Lys Lys Pro Gly Glu
1               5                   10                  15

Ser Leu Lys Ile Ser Cys Thr Ala Ser Gly Tyr Asn Phe Ala Ser Tyr
                20                  25                  30

Trp Ile Gly Trp Val Arg Gln Met Pro Gly Gln Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Thr Tyr Tyr Cys
                85                  90                  95

Val Arg Arg Val Pro Leu Tyr Thr Asn Asn His Tyr Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Ala Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Gly Ile Ser Asn Tyr Leu Ala Trp Phe Gln Gln Lys
                165                 170                 175

Pro Gly Lys Ala Pro Lys Ser Leu Ile Tyr Ala Ala Ser Ser Leu Gln
            180                 185                 190

Ser Gly Val Pro Ser Lys Tyr Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Tyr Lys Ser Tyr Pro Leu Thr Phe Gly Gly Gly Thr Lys
225                 230                 235                 240

Val Glu Ile Lys

<210> SEQ ID NO 44
<211> LENGTH: 239
<212> TYPE: PRT
<213> ORGANISM: Homo sapiens

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Phe Met His Trp Val Arg Gln Ala Pro Gly Gln Gly Leu Glu Trp Met
            35                  40                  45

Gly Val Ile Asn Pro Thr Gly Gly Ser Thr Thr Tyr Ala Gln Ser Phe
```

```
                    50                  55                  60
Gln Gly Arg Val Thr Met Thr Arg Asp Thr Ser Thr Ser Ile Val Tyr
 65                  70                  75                  80

Met Glu Leu Ser Ser Leu Arg Ser Glu Asp Thr Ala Val Tyr Tyr Cys
                     85                  90                  95

Thr Arg Val Gly Tyr Tyr Gly Met Asp Val Trp Gly Gln Gly Thr Leu
                100                 105                 110

Val Thr Val Ser Ser Gly Gly Gly Ser Gly Gly Gly Gly Ser Gly
            115                 120                 125

Gly Gly Gly Ser Asp Ile Val Met Thr Gln Ser Pro Ser Thr Leu Ser
130                 135                 140

Ala Ser Val Gly Asp Arg Val Thr Ile Thr Cys Arg Ala Ser Gln Ser
145                 150                 155                 160

Thr Ser Arg Phe Leu Asn Trp Tyr Gln Gln Lys Pro Gly Lys Ala Pro
                165                 170                 175

Lys Leu Leu Ile Tyr Ala Ala Ser Ser Leu His Ser Gly Val Pro Ser
                180                 185                 190

Arg Phe Ser Gly Ser Gly Ser Gly Thr Asp Phe Thr Leu Thr Ile Ser
                195                 200                 205

Ser Leu Gln Pro Glu Asp Phe Ala Thr Tyr Tyr Cys Gln Gln Thr Ser
            210                 215                 220

Ser Tyr Pro Leu Thr Phe Gly Gly Gly Thr Lys Val Glu Ile Lys
225                 230                 235

<210> SEQ ID NO 45
<211> LENGTH: 246
<212> TYPE: PRT
<213> ORGANISM: Homo sapiens

<400> SEQUENCE: 45

Gln Val Gln Leu Val Gln Ser Gly Gly Gly Val Val Gln Val Gly Arg
  1               5                  10                  15

Ser Leu Arg Leu Ser Cys Ala Ala Ser Gly Phe Thr Phe Thr Asn Phe
                 20                  25                  30

Gly Met His Trp Val Arg Gln Ala Pro Gly Lys Gly Leu Glu Trp Val
             35                  40                  45

Ala Leu Ile Ser Ser Asp Gly Tyr Arg Gln Ala Tyr Ala Asp Ser Val
 50                  55                  60

Lys Gly Arg Phe Thr Ile Ser Gly Asp Asn Ser Lys Asn Thr Val Tyr
 65                  70                  75                  80

Leu Gln Met Asn Ser Leu Thr Ser Glu Asp Thr Ala Val Tyr Tyr Cys
                 85                  90                  95

Ala Ile Ile Pro Pro Val Leu Arg Ile Phe Asp Trp Glu Phe Asp Tyr
                100                 105                 110

Trp Gly Gln Gly Thr Leu Val Thr Val Ser Ser Gly Gly Gly Gly Ser
             115                 120                 125

Gly Gly Gly Gly Ser Gly Gly Gly Gly Ser Glu Thr Thr Leu Thr Gln
130                 135                 140

Ser Pro Gly Thr Leu Ser Leu Ser Pro Gly Glu Arg Ala Thr Leu Ser
145                 150                 155                 160

Cys Arg Ala Ser Gln Ser Val Ser Ser Pro Tyr Leu Ala Trp Tyr Gln
                165                 170                 175

Gln Lys Pro Gly Gln Ala Pro Arg Leu Leu Ile Tyr Gly Ala Ser Asn
                180                 185                 190
```

```
Arg Ala Thr Gly Ile Pro Asp Arg Phe Ser Gly Ser Gly Ser Gly Thr
        195                 200                 205
Asp Phe Thr Leu Thr Ile Ser Ser Leu Gln Ala Glu Asp Glu Ala Val
210                 215                 220
Tyr Tyr Cys Gln Gln Tyr Tyr Asn Thr Pro Leu Thr Phe Gly Gly Gly
225                 230                 235                 240
Thr Lys Val Glu Ile Lys
                245

<210> SEQ ID NO 46
<211> LENGTH: 247
<212> TYPE: PRT
<213> ORGANISM: Homo sapiens

<400> SEQUENCE: 46

Gln Val Gln Leu Gln Gln Trp Gly Ala Gly Leu Leu Lys Pro Ser Glu
1               5                   10                  15
Thr Leu Ser Leu Thr Cys Ala Val Tyr Ser Gly Ser Phe Thr Arg Asp
            20                  25                  30
Tyr Trp Gly Trp Ile Arg Gln Pro Pro Gly Lys Gly Leu Glu Trp Ile
        35                  40                  45
Gly Glu Ile Asn His Ser Gly Ser Thr Asn Tyr Asn Pro Ser Leu Lys
    50                  55                  60
Ser Arg Val Thr Thr Ser Val Asp Lys Ser Lys Asn Gln Phe Ser Leu
65                  70                  75                  80
Lys Leu Thr Ser Val Thr Ala Ala Asp Thr Ala Val Tyr Tyr Cys Ala
                85                  90                  95
Arg Arg Arg Leu Ser Ser Asp Leu Phe Met Arg Gly Val Gly Gly Met
            100                 105                 110
Asp Val Trp Gly Gln Gly Thr Leu Val Thr Val Ser Ser Gly Gly Gly
        115                 120                 125
Gly Ser Gly Gly Gly Gly Ser Gly Gly Gly Gly Ser Asp Ile Val Met
    130                 135                 140
Thr Gln Thr Pro Gly Thr Leu Ser Ser Ser Pro Gly Glu Arg Ala Thr
145                 150                 155                 160
Leu Ser Cys Arg Ala Ser Gln Gly Val Ser Ser Asn Leu Ala Trp Tyr
                165                 170                 175
Gln Gln Lys Pro Gly Gln Ala Pro Arg Leu Leu Ile Tyr Asp Ala Ser
            180                 185                 190
Asn Arg Ala Thr Gly Ile Pro Leu Arg Phe Ser Gly Ser Gly Ser Gly
        195                 200                 205
Thr Asp Phe Thr Leu Thr Ile Ser Arg Leu Glu Pro Glu Asp Phe Ala
    210                 215                 220
Val Tyr Tyr Cys His Gln Tyr Gly Ser Ser Pro Tyr Thr Phe Gly Gln
225                 230                 235                 240
Gly Thr Lys Val Glu Ile Lys
                245

<210> SEQ ID NO 47
<211> LENGTH: 248
<212> TYPE: PRT
<213> ORGANISM: Homo sapiens

<400> SEQUENCE: 47

Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
             20                  25                  30

Gly Ile Ser Trp Val Arg Gln Ala Ser Gly Gln Gly Leu Glu Trp Met
         35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Val Pro Arg Tyr Phe Asp Trp Leu Leu Tyr Gly Ser Asp Tyr
                100                 105                 110

Phe Asp Tyr Trp Gly Gln Gly Thr Leu Val Thr Val Ser Ser Gly Gly
            115                 120                 125

Gly Gly Ser Gly Gly Gly Ser Ser Gly Gly Gly Ser Asp Ile Gln
        130                 135                 140

Met Thr Gln Ser Pro Ser Thr Leu Ser Val Ser Val Gly Asp Arg Val
145                 150                 155                 160

Thr Ile Thr Cys Arg Ala Ser Gln Gly Ile Ser Ser Trp Leu Ala Trp
                165                 170                 175

Tyr Gln Gln Lys Pro Gly Lys Ala Pro Lys Leu Leu Ile Tyr Ala Ala
                180                 185                 190

Ser Ser Leu Gln Ser Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Ala Asn Ser Phe Pro Leu Thr Phe Gly
225                 230                 235                 240

Gly Gly Thr Lys Leu Glu Ile Lys
                245

<210> SEQ ID NO 48
<211> LENGTH: 249
<212> TYPE: PRT
<213> ORGANISM: Homo sapiens

<400> SEQUENCE: 48

Gln Val Gln Leu Val Gln Ser Gly Ala Glu Val Lys Glu Pro Gly Ser
  1               5                  10                  15

Ser Val Lys Val Ser Cys Lys Ala Ser Gly Gly Thr Phe Ser Ser Tyr
             20                  25                  30

Ala Ile Tyr Trp Val Arg Gln Ala Pro Gly Gln Gly Leu Glu Trp Met
         35                  40                  45

Gly Trp Ile Ile Pro Ile Leu Gly Ile Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Ala Gly His Ser Thr Asn Tyr Tyr Tyr Gly Met Asp
                100                 105                 110

Val Trp Gly Gln Gly Thr Leu Val Thr Val Ser Ser Gly Gly Gly
            115                 120                 125

Ser Gly Gly Gly Gly Ser Ser Gly Gly Gly Ser Gln Thr Val Val Thr
        130                 135                 140
```

```
Gln Glu Pro Ser Leu Thr Val Ser Leu Gly Gly Val Thr Leu Thr
145                 150                 155                 160

Cys Gly Ser Ser Thr Gly Ala Val Thr Ser Gly His Tyr Pro Tyr Trp
                165                 170                 175

Phe Gln Gln Lys Pro Gly Gln Ala Pro Arg Thr Leu Ile Tyr Asp Thr
            180                 185                 190

Ser Asn Lys His Ser Trp Thr Pro Ala Arg Phe Ser Gly Ser Leu Leu
        195                 200                 205

Gly Gly Lys Ala Ala Leu Thr Leu Ser Gly Ala Gln Pro Glu Asp Glu
    210                 215                 220

Ala Glu Tyr Tyr Cys Leu Leu Ser Tyr Ser Gly Thr Arg Val Phe Gly
225                 230                 235                 240

Gly Gly Thr Lys Leu Thr Val Leu Gly
                245

<210> SEQ ID NO 49
<211> LENGTH: 245
<212> TYPE: PRT
<213> ORGANISM: Homo sapiens

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Phe Lys Glu Tyr Ser Arg Thr Gly Tyr Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Ser Gly Gly Gly Ser Ser Tyr Glu Leu Met Gln Pro
    130                 135                 140

Ser Ser Val Ser Val Ser Pro Gly Gln Thr Ala Arg Ile Thr Cys Ser
145                 150                 155                 160

Gly Asp Val Leu Ala Lys Lys Cys Ala Arg Trp Phe Gln Gln Lys Pro
                165                 170                 175

Gly Gln Ala Pro Val Leu Val Ile Tyr Lys Asp Ser Glu Arg Pro Ser
            180                 185                 190

Gly Ile Pro Glu Arg Phe Ser Gly Ser Ser Ser Gly Thr Thr Val Thr
        195                 200                 205

Leu Thr Ile Ser Gly Ala Gln Val Glu Asp Glu Ala Asp Tyr Tyr Cys
    210                 215                 220

Tyr Ser Ala Ala Asp Asn Asn Leu Gly Val Phe Gly Gly Gly Thr Lys
225                 230                 235                 240

Val Thr Val Leu Gly
                245
```

<210> SEQ ID NO 50
<211> LENGTH: 246
<212> TYPE: PRT
<213> ORGANISM: Homo sapiens

<400> SEQUENCE: 50

```
Gln Ile Thr Leu Lys Glu Ser Gly Pro Ala Leu Val Lys Pro Thr Gln
 1               5                  10                  15

Thr Leu Thr Leu Thr Cys Asn Phe Ser Gly Phe Ser Leu Ser Thr Tyr
             20                  25                  30

Gly Gly Gly Val Gly Trp Leu Arg Gln Pro Pro Gly Lys Ala Leu Glu
         35                  40                  45

Trp Leu Ala Val Ile Tyr Trp Ser Asp Gly Lys Arg Tyr Ser Pro Ser
 50                  55                  60

Val Lys Asn Arg Leu Thr Ile Thr Lys Asp Thr Ser Lys Asn His Val
 65                  70                  75                  80

Val Leu Thr Met Thr Asn Met Asp Pro Val Asp Thr Ala Thr Tyr Tyr
                 85                  90                  95

Cys Ala His Leu Met Met Asp Thr Ser Ile Thr Thr His Trp Phe Asp
            100                 105                 110

Pro Trp Gly Gln Gly Thr Leu Val Thr Val Ser Ser Gly Gly Gly Gly
        115                 120                 125

Ser Gly Gly Gly Gly Ser Gly Gly Gly Gly Ser Ala Ile Arg Met Thr
130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Asn Tyr Leu Ala Trp Tyr Gln
            165                 170                 175

Gln Lys Pro Gly Lys Val Pro Lys Leu Leu Ile Tyr Ala Ala Ser Thr
        180                 185                 190

Leu Gln Ser Gly Val Pro Ser Arg Phe Ser Gly Ser Gly Ser Gly Thr
    195                 200                 205

Asp Phe Thr Leu Thr Ile Ser Ser Leu Gln Pro Glu Asp Val Ala Thr
210                 215                 220

Tyr Tyr Cys Gln Lys Tyr Asn Ser Ala Pro Gly Thr Phe Gly Gln Gly
225                 230                 235                 240

Thr Lys Val Glu Ile Lys
                245
```

<210> SEQ ID NO 51
<211> LENGTH: 249
<212> TYPE: PRT
<213> ORGANISM: Homo sapiens

<400> SEQUENCE: 51

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
             20                  25                  30

Phe Ile His Trp Val Arg Gln Ala Pro Gly Gln Gly Leu Glu Trp Met
         35                  40                  45

Gly Leu Leu Asn Pro Thr Asp Ser Gly Thr Leu Tyr Ala Gln Asn Phe
 50                  55                  60

Gln Gly Arg Ile Thr Met Thr Ser Asp Thr Ser Thr Asn Thr Val Tyr
 65                  70                  75                  80

Met Glu Leu Ser Ser Leu Arg Ser Asp Asp Thr Ala Met Tyr Tyr Cys
```

```
                85                  90                  95
Ala Arg Glu Gly Gly Ala Asp Thr Thr Arg Val His Ser Ser Phe Asp
            100                 105                 110

Tyr Trp Gly Gln Gly Thr Leu Val Thr Val Ser Ser Gly Gly Gly
            115                 120                 125

Ser Gly Gly Gly Ser Ser Gly Gly Ser Gln Ala Val Leu Thr
130                 135                 140

Gln Pro Pro Ser Val Ser Gly Ser Pro Gly Gln Ser Ile Thr Ile Ser
145                 150                 155                 160

Cys Thr Gly Thr Ser Ser Asp Val Glu Ala Tyr Asn Tyr Val Ser Trp
                165                 170                 175

Tyr Gln Gln His Pro Gly Lys Ala Pro Lys Leu Met Ile Tyr Asp Val
            180                 185                 190

Ser Asn Arg Pro Ser Gly Val Ser Asn Arg Phe Ser Gly Ser Lys Ser
        195                 200                 205

Gly Asn Thr Ala Ser Leu Thr Ile Ser Gly Leu Gln Ala Glu Asp Glu
    210                 215                 220

Ala Asp Tyr Tyr Cys Ser Ser Tyr Thr Ser Ser Arg Thr Trp Val Phe
225                 230                 235                 240

Gly Gly Gly Thr Lys Val Ile Val Leu
                245

<210> SEQ ID NO 52
<211> LENGTH: 246
<212> TYPE: PRT
<213> ORGANISM: Homo sapiens

<400> SEQUENCE: 52

Gln Val Gln Leu Gln Glu Ser Gly Gly Gly Leu Val Gln Pro Gly Arg
 1                   5                  10                  15

Ser Leu Arg Leu Ser Cys Ala Ala Ser Gly Phe Thr Phe Asp Asp Tyr
                20                  25                  30

Ala Leu His Trp Val Arg Gln Ala Pro Gly Lys Gly Leu Glu Trp Val
            35                  40                  45

Ser Gly Ile Ser Trp Asn Ser Val Thr Val Lys Tyr Ala Val Ser Val
    50                  55                  60

Lys Gly Arg Phe Thr Ile Ser Arg Asp Asn Ala Lys Asn Ser Leu Phe
65                  70                  75                  80

Leu Gln Met Asn Ala Leu Arg Ser Glu Asp Thr Ala Leu Tyr Tyr Cys
                85                  90                  95

Ala Lys Ala Arg Gly Ala Leu Leu Glu Ala Ala Asp Thr Pro Ser Asp
            100                 105                 110

Asp Trp Gly Gln Gly Thr Leu Val Thr Val Ser Ser Gly Gly Gly Gly
            115                 120                 125

Ser Gly Gly Gly Gly Ser Gly Gly Gly Ser Asp Ile Val Met Thr
130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Ser Ser Tyr Leu Asn Trp Tyr Gln
                165                 170                 175

Gln Lys Pro Gly Lys Ala Pro Lys Leu Leu Ile Tyr Ala Ala Ser Ser
            180                 185                 190

Leu Gln Ser Gly Val Pro Ser Arg Phe Ser Gly Ser Gly Ser Gly Thr
        195                 200                 205
```

```
Asp Phe Thr Leu Thr Ile Ser Ser Leu Gln Pro Glu Asp Val Ala Thr
    210                 215                 220

Tyr Tyr Cys Gln Lys Tyr Asn Ser Ala Pro Trp Thr Phe Gly Gln Gly
225                 230                 235                 240

Thr Lys Val Asp Ile Lys
                245

<210> SEQ ID NO 53
<211> LENGTH: 244
<212> TYPE: PRT
<213> ORGANISM: Homo sapiens

<400> SEQUENCE: 53

Gln Val Gln Leu Gln Gln Ser Gly Ala Gly Leu Leu Arg Pro Ser Glu
1               5                   10                  15

Thr Leu Ser Leu Thr Cys Gly Leu Tyr Gly Ser Phe Ser Gly His
            20                  25                  30

Tyr Trp Asn Trp Ile Arg Gln Ser Pro Glu Lys Gly Leu Val Trp Ile
            35                  40                  45

Gly Glu Ile Thr His Ser Gly Thr Thr Asn Tyr Asn Pro Ser Leu Lys
    50                  55                  60

Ser Arg Val Ile Thr Ser Val Asp Thr Ser Lys Asn Gln Tyr Ser Leu
65                  70                  75                  80

Lys Leu Ser Phe Val Thr Pro Ala Asp Thr Ala Val Tyr Tyr Cys Ala
                85                  90                  95

Arg Gly Asp Tyr Tyr Gly Tyr Trp Tyr Phe Asp Leu Trp Gly Arg Gly
                100                 105                 110

Thr Leu Val Thr Val Ser Ser Gly Gly Gly Ser Gly Gly Gly Gly
            115                 120                 125

Ser Gly Gly Gly Gly Ser Gln Ser Val Leu Thr Gln Pro Pro Ser Val
    130                 135                 140

Pro Val Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Ala Pro Lys Leu Leu Ile Tyr Asp Thr Asn Lys Arg Pro Ser Gly
                180                 185                 190

Ile Pro Asp Arg Phe Ala Gly Ser Lys Ser Gly Thr Ser Ala Thr Leu
            195                 200                 205

Gly Ile Thr Gly Leu Gln Thr Gly Asp Glu Ala Asp Tyr Tyr Cys Gly
    210                 215                 220

Thr Trp Asp Ser Ser Leu Ser Ala Gly Val Phe Gly Gly Gly Thr Lys
225                 230                 235                 240

Leu Thr Val Leu

<210> SEQ ID NO 54
<211> LENGTH: 801
<212> TYPE: DNA
<213> ORGANISM: Homo sapiens

<400> SEQUENCE: 54
caggtgcagc tggtgcagtc tggagcagag gtgaaaaagc ccggggagtc tctgaggatc      60
tcctgcaagg gttctggata cagctttacc agccactgga tcagctgggt gcgccagatg     120
cccgggaaag gcctggagtg gatggggagg attgatccta gtgactctta tagcaactac     180
agcccctcct tccaaggcca cgtcatcatc tcagttgaca gtccatcag cactgcctac     240
```

```
ttgcagtgga gcagcctgaa ggcctcggac accgccatat attactgtgc gagacagctc    300
attgtagtag taccagctgc tccctattac tactactact acggtatgga cgtctggggc    360
caaggaaccc tggtcaccgt ctcctcaggc ggcggcggct ctggcggagg tggcagcagc    420
ggtggcggat ccgaaattgt gttgacgcag tctccaggca ccctgtcttt gtctccaggg    480
gaaagagcca ccctctcctg cagggccagt cagactgtta acagctactt agcctggtac    540
cagtagaaac ctggccaggc tcccaggctc ctcatctatg gtgcatccag cagggccact    600
ggcatcccag acaggttcag tggcagtggg tctgggacag acttcactct caccatcagc    660
agactggagc tgaagatttt gcagtgtatt actgtcagca gtatggtagc tcacatccg     720 tggacgttcg gccaagggac caaggtggag atcaaacgtg gcctcggggg cctggtcgac    780
tacaaagatg acgatgacaa a                                             801

<210> SEQ ID NO 55
<211> LENGTH: 801
<212> TYPE: DNA
<213> ORGANISM: Homo sapiens

<400> SEQUENCE: 55
caggttcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac     180
gcacagaagt tccagggcag agtcacgatt accgcggacg aatccacgag cacagcctac    240
atggagctga gcagcctgag atctgaggac acggccatat attactgtgc gagagtctttt    300 ggttccgagt cgcaagatcc gtccgatatt tggagtggtt attacggtat ggaagtctgg    360
ggccaaggaa ccctggtcac cgtctcctca ggcggtggcg gctctggcgg aggtggcagc    420
ggcggtggcg gatccgacat ccagatgacc cagtctccgt cttccgtgtc tgcatctgta    480
ggagacagag tcaccatcac ttgtcgggcg agtcaggta ttagcagctg gttagcctgg      540
tatcagcaga aaccagggaa agcccctaag ctcctgatct atgctgcatc cagtttgcaa    600
agtagggtcc catcaaggtt cagcggcagt ggatctggga cagattttcac tctcaccatc    660 agcagcctgc agcctgaaga ttttgcaact tactattgtc aacaggctaa cagtttcccg    720 tacactttg gccagggggac caagctggag atcaaacgtg gcctcgggg cctggtcgac    780 tacaaagatg acgatgacaa a                                            801

<210> SEQ ID NO 56
<211> LENGTH: 729
<212> TYPE: DNA
<213> ORGANISM: Homo sapiens

<400> SEQUENCE: 56
caggtgcagc tggtggagtc tggggctgag gcgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagccggt    300
ataactggaa ctacggctcc cccagactac tggggccagg gcaccctggt caccgtctcc    360
tcaggcggcg gcggctccgg cggaggtggc agcggcggtg gcggatccgt catctggatg    420
```

```
acccagtctc catcctccct gtctgcatct gtaggagaca gagtcaccat cacttgccgg      480
gcaagtcaga gcattagcag ctatttaaat tggtatcagc ggaaaccagg aaagcccct       540 aagctcctga tctatgctgc atccagtttg caaagtgggg tcacatcaag gttcagtggc      600
agtggatctg ggacagattt cactctcacc atcagcagtc tgcaacctga agattttgca      660
acttactact gtcaacagag ttacagtacc cctccgacgt tcggccaagg gaccaagctg      720
gagatcaaa                                                              729
```

<210> SEQ ID NO 57
<211> LENGTH: 792
<212> TYPE: DNA
<213> ORGANISM: Homo sapiens

<400> SEQUENCE: 57

```
caggtgcagc tggtgcagtc cggatctgag ttaaagaagc ctggggcctc agtgaagctt       60
tcctgcaggg cttctggata cacattcact agttattcca tggtttgggt gcgacaggcc      120
cctggagaag ggcttgagtg gatgggaggg atcaacacca cacactggaa cccaacgtat      180
gcccagggct tcacagaacg gtttgtcttc tccttcgaca gctctgtcag cacggcatat      240
ctgcaaatca gcagcctaaa ggctgaggac actgccgtgt attactgtgc gagagattgg      300
gcgtatagcg gcagctggcc cttaggccag aacccttctg accactgggg ccagggcacc      360
ctggtcaccg tctcctcagg cggcggcggc tctggcggag gtggcagcgg cggtggcgga      420
tccgaaatag tgatgacgca gtctccagcc accctgtctg tgtctccagg ggaaagagcc      480
accctctcct gcagggccag tcagagtgtt agccgcaact tagcctggta ccagcagaaa      540
cctggccagg ctcccaggct cctcatctat gatacatcca ccagggccac tggtatccca      600
gccaggttca gtggcagtgg gtctgggaca gagttcactc tcaccatcag cagcctgcag      660
tctgaagatt ctgcagttta ttactgtcag cagtataata tctggcctcc actcactttc      720
ggcggaggga ccaaggtgga gatcaaacgt ggcctcgggg cctggtcga ctacaaagat      780 gacgatgaca aa                                                          792
```

<210> SEQ ID NO 58
<211> LENGTH: 774
<212> TYPE: DNA
<213> ORGANISM: Homo sapiens

<400> SEQUENCE: 58

```
caggtgcagc tacagcagtg gggcgcagga ttgttgaagc cttcggagac cctgtccctc       60
acctgcgctg tctatggtgg gtccttcagt ggttactacc ggacctggat ccgccagtcc      120
ccagtgaagg ggctggagtg gattggggaa gtcaatgatc gtggaagccc caactacaac      180
ccgtccttca gagtcgact caccatatca atcgacacgt ccaagaacta gttatccctg      240
aagttgagat ttatgaccgc cgcggacacg gctgtatatt cgtgtgcgag aattaggcct      300
aggtacggta tggacgtctg ggccagggg acaatggtca ccgtctcctc aggcggcggc      360
ggctctggcg gaggtggcag cagcggtggc ggatccgata ttgtgatgac ccagactcca      420
ctctcctcac ctgtcaccct tggacagccg gcctccatct cctgcaggtc tagtcaaagc      480
ctcgtacaca gtgatggaaa cacctacttg acttggtttc accagaggcc aggccagcct      540
ccaagagtcc tcattcataa ggtttctaac ctgttctctg ggtcccaga cagattcagt      600 ggcagtgggg cagggacaga tttcacactg aaaatcagca gggtggaagc tgaggatgtc      660
ggggtttatt actgcatgca agctacacaa ttgtacactt ttggccaggg gaccaaggtg      720
```

```
gaaatcaaac gtggcctcgg gggcctggtc gactacaaag atgacgatga caaa        774
```

<210> SEQ ID NO 59
<211> LENGTH: 735
<212> TYPE: DNA
<213> ORGANISM: Homo sapiens

<400> SEQUENCE: 59

```
gaggtccagc tggtacagtc tggggctgag gtgaagaagc ctggggcctc agtgaaggtc    60
tcctgcaagg tttccggata caccctcact gaattatcca tgcactgggt gcgacaggct   120
cctggaaaag ggcttgagtg gatgggaggt tttgatcctg aagatggtga acaatctcc   180
gcgcagaagt tccagggcag agtcaccatg accgaggaca catctacaga cacagcctac   240
atggatctga gcagcctgag atctgaggac acggccgttt attactgtgc aacgcagcgc   300
ttgtgtagtg gtggtcgctg ctactcccac tttgactact ggggccaggg caccacggtc   360
accgtctcct caggcggcgg cggctctggc ggaggtggca gcggcggtgg cggatccgaa   420
acgacactca cgcagtctcc agcaatcatg tctgcatctc aggggagag ggtcaccatg    480
acctgcagtg ccagctcaag tatacgttac atatattggt accaacagaa gcctggatcc   540
tcccccagac tcctgattta tgacacatcc aacgtggctc ctggagtccc ttttcgcttc   600
agtggcagtg gtctgggac ctcttattct ctcacaatca accgaatgga ggctgaggat   660
gctgccactt attactgcca ggagtggagt ggttatccgt acacgttcgg agggggggacc  720
aaggtggaga tcaaa                                                   735
```

<210> SEQ ID NO 60
<211> LENGTH: 777
<212> TYPE: DNA
<213> ORGANISM: Homo sapiens

<400> SEQUENCE: 60

```
cagatgcagc tggtgcagtc tggggctgag gtgaagaagc ctgggtcctc ggtgaaggtc    60
tcctgcaagg cttctggagg caccttcaac acctatgtta tcagttgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagtttgg   300
agtccccttg actactgggg ccagggcacc ctggtcaccg tctcctcagg cggcggtggc   360
tctgcggag gtgcagcgg cggtggcgga tccgacatcg tgatgaccca gtctccagac   420
tccctggctg tgtctctggg cgagagggcc accatcaact gcaagtccag ccagagtgtt   480
ttatacagct ccaacaatat gaactactta gcttggtacc agcagaaacc aggacagcct   540
cctaagctgc tcatttactg ggcatctacc cgggaatccg gggtccctga ccgattcagt   600
ggcagcgggt ctgggacaga tttcactctc accatcagca gcctgcaggc tgaagatgcg   660
gcagtttatt actgtcagca gtattatagt actcctccga cgttcggcca agggaccaag   720
ctggagatca acgtggcct cgggggcctg gtcgactaca agatgacga tgacaaa       777
```

<210> SEQ ID NO 61
<211> LENGTH: 783
<212> TYPE: DNA
<213> ORGANISM: Homo sapiens

<400> SEQUENCE: 61

| | |
|---|---|
| caggtgcagc tggtgcaatc tggggctgag gtgaagaagc ctggggcctc agtgaaggtc | 60 |
| tcctgcaagg gttctggata caccttcacc ggctactata tgcactgggt gccacaggcc | 120 |
| cctggacaag ggcttgagtg gatgggatgg atcaaccta acaatggtgg cacaaactat | 180 |
| gaccagaagt ttcagggcag ggtcgccatg accaggaca cgtccatctc cacagcctac | 240 |
| atggagctga gcaggctgag atctgacgac actgccgtgt attactgtgc gagagataat | 300 |
| gggagggtga ccacaggggg ctactggggc cagggcaccc tggtcaccgt ctcctcaggc | 360 |
| ggcggcggct ctggcggagg tggcagcagc ggtggcggat cccagtctgt gttgacgcag | 420 |
| cctcctcat tgtctgggc cccgggacag agtgtcacca tctcctgcgc tgggaccagt | 480 |
| tccagcatcg gggcaggtta cgatgtacag tggtaccagc aacttccagg aaaaaccccc | 540 |
| aaactcctca tctacgggaa tgataatcgg ccctcagggg tccctgaccg attctctgga | 600 |
| tccaggtctt acacctcagc ctccctggtc atcactagag tccagattga ggatgaggct | 660 |
| gattattact gccagtcgta tgacagcagt ctcattggtc ctcaattcgg cgggggacc | 720 |
| aagctgaccg tcctaggtgg cctcggggc ctggtcgact acaaagatga ccatgacaaa | 780 |
| tac | 783 |

<210> SEQ ID NO 62
<211> LENGTH: 732
<212> TYPE: DNA
<213> ORGANISM: Homo sapiens

<400> SEQUENCE: 62

| | |
|---|---|
| caggtgcagc tggtgcaatc tggggctgag gtgaaaaagc ccggggagtc tctgaagatc | 60 |
| tcctgtacgg cctccggata caactttgcc agctactgga tcggctgggt gcgccagatg | 120 |
| cccgggcaag gcctggagtg gatggggatc atctatcctg gtgactctga taccagatac | 180 |
| agtccgtcct tccaaggcca ggtcaccatc tcagccgaca agtccatcag caccgcctac | 240 |
| ctgcagtgga gcagcctgaa ggcctcggac accgccacgt attactgtgt gagacgggtc | 300 |
| cccctctaca ctaacaacca ctaccttgac tattggggcc agggcaccct ggtcaccgtc | 360 |
| tcctcaggcg gcggcggctc tggcggaggt ggcagcggcg gtggcggatc cgccatccag | 420 |
| atgacccagt ctccatcctc actgtctgca tctgtaggag acagagtcac catcacttgt | 480 |
| cgggcgagtc agggcattag caattattta gcctggtttc agcagaaacc agggaaagcc | 540 |
| cctaagtccc tgatctatgc tgcatccagt ttgcaaagtg gggtcccatc aaagtacagc | 600 |
| ggcagtggat ctgggacaga tttcactctc accatcagca gcctgcagcc tgaagatttt | 660 |
| gcaacttatt actgccaaca gtataagagt taccccctca ctttcggcgg agggaccaag | 720 |
| gtggagatca aa | 732 |

<210> SEQ ID NO 63
<211> LENGTH: 762
<212> TYPE: DNA
<213> ORGANISM: Homo sapiens

<400> SEQUENCE: 63

| | |
|---|---|
| gaggtgcagc tggtgcagtc tggggctgaa gtgaagaagc ctggggcctc agtgaaggtt | 60 |
| tcctgtaagg catctggata caccttcagc gactacttta tgcactgggt gcgacaggcc | 120 |
| cctggacaag ggcttgagtg gatgggagta atcaacccaa ctggtggttc cacaacctac | 180 |
| gcacagagct ccagggcag agtcaccatg accagagaca cgtccacgag catagtctac | 240 |
| atggagctga gcagcctgag atctgaagac acggccgtgt actactgtac gcgagtcggc | 300 |

```
tactacggta tggacgtctg gggccaaggc accctggtca ccgtctcctc aggcggcggc    360
ggctctggcg gaggtggcag cggcggtggc ggatccgaca tcgtgatgac ccagtctcca    420
tccaccctgt ctgcatctgt aggagacaga gtcaccatca cttgccgggc aagtcagagc    480
actagcaggt ttttaaattg gtatcagcag aaacctggga agcccctaa actcctgatc      540 tatgctgcat ccagtttgca tagtggcgtc ccatcaaggt tcagtggcag tggatctggg    600
acagatttca ctctcaccat cagcagtctg caacctgaag attttgcaac ttactactgt    660
caacagactt ccagttaccc tctcactttc ggcggaggga ccaaggtgga atcaaacgt    720 ggcctcgggg gcctggtcga ctacaaagat gacgatgaca aa                        762

<210> SEQ ID NO 64
<211> LENGTH: 783
<212> TYPE: DNA
<213> ORGANISM: Homo sapiens

<400> SEQUENCE: 64
caggtccagc tggtacagtc tgggggaggc gtggtccagg ttgggaggtc cctgagactt    60
tcctgtgcgg cctctggatt caccttcaca aactttggca tgcactgggt ccgccaggct   120
ccaggcaagg ggctggagtg ggtggcactc atctcatctg atggatatag acaggcctat   180
gcagactccg tgaagggccg gttcaccatc tccggagaca actccaagaa cacagtgtat   240
ctgcaaatga acagcctgac aagtgaggac acggctgttt attactgtgc catcataccc   300
cctgtattac ggattttga ttgggaattt gactactggg gccagggaac cctggtcacc    360
gtctcctcag gcggcggcgg ctctggcgga ggtggcagcg gcggtggcgg atccgaaacg   420
acactcacgc agtctccagg caccctgtct ttgtctccag gggaaagagc caccctctcc   480
tgcagggcca gtcagagtgt tccagccccc tacttagcct ggtaccagca gaaacctggc   540
caggctccca ggctcctcat ttatggtgca tctaacaggg ccactggcat cccagacagg   600
ttcagtggca gtgggtctgg gacagacttc actctcacca tcagcagcct gcaggctgaa   660
gatgaggcag tttattactg tcagcaatac tacaatactc cgctcacttt cggcggaggg   720
accaaggtgg aaatcaaacg tggcctcggg ggcctggtcg actacaaaga tgacgatgac   780
aaa                                                                 783

<210> SEQ ID NO 65
<211> LENGTH: 786
<212> TYPE: DNA
<213> ORGANISM: Homo sapiens

<400> SEQUENCE: 65
caggtgcagc tacagcagtg gggcgcaggc ctgttgaagc cttcggagac cctgtccctc    60
acctgcgctg tctatagtgg gtctttact cgtgactact ggggctggat ccgccagccc   120
cccgggaagg ggctggagtg gattggggaa atcaatcata gtggaagcac caactacaac   180
ccgtccctca gagtcgagt caccacgtcg gtagacaagt ccaagaatca gttctccctg   240
aagttgacct ctgtgaccgc cgcggacacg gctgtctatt actgtgcgag acgccggctt   300
tctagcgacc tcttcatgcg ggggtttggc ggtatggacg tctggggcca aggcaccctg   360
gtcaccgtct cctcaggcgg cggcggctct ggcggaggtg gcagcggcgg tggcggatct   420
gatattgtga tgacccagac tccaggcacc ctgtcttcgt ctccagggga aagagccacc   480
ctctcctgca gggccagtca gggtgttagc agcaacttag cctggtacca gcagaaacct   540
```

```
ggccaggctc ccaggctcct catctatgat gcatccaaca gggccactgg catcccactc     600
aggttcagtg gcagtgggtc tgggacagac ttcactctca ccatcagcag actggaacct     660
gaagattttg cagtgtatta ctgtcaccag tatggtagct caccgtacac ctttggccag     720
gggaccaagg tggaaatcaa acgtggcctc gggggcctgg tcgactacaa agatgacgat     780
gacaaa                                                                786

<210> SEQ ID NO 66
<211> LENGTH: 789
<212> TYPE: DNA
<213> ORGANISM: Homo sapiens

<400> SEQUENCE: 66
gaggtgcagc tggtgcagtc tggagctgag gtgaagaagc ctggggcctc agtgaaggtc      60
tcctgcaagg cttctggtta cacctttacc agctatggta tcagctgggt gcgacaggcc     120
tctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagtaccc     300
cgatattttg actggttatt atacgggagc gactactttg actactgggg ccaggaaacc     360
ctggtcaccg tctcctcagg cggcggcggc tctggcggag gtggcagcag cggtggcgga     420
tccgacatcc agatgaccca gtctccttcc accctgtctg tatctgtagg agacagagtc     480
accatcactt gtcgggcgag tcagggtatt agcagctggt tagcctggta tcagcagaaa     540
ccagggaaag cccctaagct cctgatctat gctgcatcca gtttgcaaag tggggtccca     600
tcaaggttca gcggcagtgg atctgggaca gatttcactc tcactatcag cagcctgcag     660
cctgaagatt ttgcaactta ctattgtcaa caggctaaca gtttcccgct cacttttcggc    720 ggagggacca agctggagat caaacgtggc ctcgggggcc tggtcgacta caaagatgac     780
gatgacaaa                                                             789

<210> SEQ ID NO 67
<211> LENGTH: 747
<212> TYPE: DNA
<213> ORGANISM: Homo sapiens

<400> SEQUENCE: 67
caggtgcagc tggtgcaatc tggagctgag gtgaaggagc ctgggtcctc ggtgaaggtc      60
tcctgcaagg cttctggagg caccttcagc agctatgcta tctactgggt gcgacaggcc     120
cctggacaag ggcttgagtg gatgggatgg atcatcccta tccttggtat agcaaactac     180
gcacagaagt tccagggcag agtcacgatt accgcggaca atccacgag cacagcctac       240 atggagctga gcagcctgag atctgaggac acggccgtgt attactgtgc gagagctgcc     300
ggtcatagta ctaactacta ctactacggt atggacgtct ggggccaagg caccctggtc     360
accgtctcct caggcggcgg cggctctggc ggaggtggca gcggtgg cggatcccag        420 actgtggtga cccaggagcc ctcactgact gtgtccctag gagggacagt cactctcacc     480 tgtgctcca gcactggagc tgtcaccagt ggtcattatc cctactggtt ccagcagaag      540
cctggccaag cccccaggac actgatttat gatacaagca caaacactc ctggacccct      600 gcccggttct caggctccct ccttggggc aaagctgccc tgacctttc gggtgcgcag       660 cctgaggatg aggctgagta ttactgcttg ctctcctata gtggtactcg ggtgttcggc     720
ggagggacca agctgaccgt cctaggt                                         747
```

<210> SEQ ID NO 68
<211> LENGTH: 735
<212> TYPE: DNA
<213> ORGANISM: Homo sapiens

<400> SEQUENCE: 68

| | | | | | |
|---|---|---|---|---|---|
| gaggtgcagc | tggtgcagtc | tggggctgag | gtgaagaagc | ctggggcctc | agtgaaggtt | 60 |
| tcctgcaagg | catctggata | caccttcacc | aactactata | tgcactgggt | gcgacaggcc | 120 |
| cctggacaag | gcttgagtg | gatgggaata | atcaaccta | gtggtggtag | cacaagctac | 180 |
| gcacagaagt | tccagggcag | agtcaccatg | actaggaca | cgtccacgag | cacagtctac | 240 |
| atggagctga | gcagcctgag | atctgaggac | acggccgtgt | attactgtgc | gagagatttc | 300 |
| aaagagtata | gccgtacggg | ctactttgac | tactggggcc | agggcaccct | ggtcaccgtc | 360 |
| tcctcaggcg | gcggcggctc | tggcggaggt | ggcagcagcg | gtggcggatc | ctcctatgag | 420 |
| ctgatgcagc | catcctcagt | gtcagtgtct | ccgggacaga | cagccaggat | cacctgctca | 480 |
| ggagatgtac | tggcaaaaaa | atgtgctcgg | tggttccagc | agaagccagg | ccaggcccct | 540 |
| gtgctggtga | tttataaaga | cagtgagcgg | ccctcaggga | tccctgagcg | attctccggc | 600 |
| tccagctcag | gaccacagt | caccttgacc | atcagcgggg | cccaggttga | ggatgaggct | 660 |
| gactattact | gttactctgc | ggctgacaac | aacctggggg | tgttcggcgg | agggaccaag | 720 |
| gtcaccgtcc | taggt | | | | | 735 |

<210> SEQ ID NO 69
<211> LENGTH: 783
<212> TYPE: DNA
<213> ORGANISM: Homo sapiens

<400> SEQUENCE: 69

| | | | | | |
|---|---|---|---|---|---|
| cagatcacct | tgaaggagtc | tggtcctgcg | ctggtgaaac | ccacacagac | cctcacgctg | 60 |
| acctgcaact | tctctgggtt | ctccctcagc | acttatggag | ggggtgtggg | ctggctccgt | 120 |
| cagcccccag | gaaaggccct | ggagtggctt | gccgtcattt | attggagtga | tggtaaacgc | 180 |
| tacagcccct | ctgtaaagaa | ccggctcacc | atcaccaagg | acacctccaa | aaaccacgtg | 240 |
| gtcctgacaa | tgaccaacat | ggaccctgtg | gacacagcca | cctattattg | tgcacacctt | 300 |
| atgatggata | catctattac | tacccactgg | ttcgacccct | ggggccaggg | aaccctggtc | 360 |
| accgtctcct | caggcggcgg | cggctctggc | ggaggtggca | gcggcggtgg | cggatccgcc | 420 |
| atccggatga | cccagtctcc | atcctccctg | tctgcatctg | taggagacag | agtcaccatc | 480 |
| acttgccggg | cgagtcaggg | cattagcaat | tatttagcct | ggtatcagca | gaaaccaggg | 540 |
| aaagttccta | agctcctgat | ctatgctgca | tccactttgc | aatcaggggt | cccatctcgg | 600 |
| ttcagcggca | gtggatctgg | gacagatttc | actctcacca | tcagcagcct | gcagcctgaa | 660 |
| gatgttgcaa | cttattactg | tcaaaagtat | aacagtgccc | ctgggacgtt | cggccaaggg | 720 |
| accaaggtgg | agatcaaacg | tggcctcggg | ggcctggtcg | actacaaaga | tgacgatgac | 780 |
| aaa | | | | | | 783 |

<210> SEQ ID NO 70
<211> LENGTH: 747
<212> TYPE: DNA
<213> ORGANISM: Homo sapiens

<400> SEQUENCE: 70

| | |
|---|---|
| caggtgcagc tggtgcaatc tgggctgag gtgaagaagc tgggtcctc ggtgaaggtt | 60 |
| tcctgcaagg catctggata caccttcacc aactacttta tacactgggt gcgacaggcc | 120 |
| cctggacaag ggcttgagtg gatgggacta ctcaaccta ctgatagtgg cacactctac | 180 |
| gcacagaact tccagggcag aatcaccatg accagtgaca cgtccacaaa cacagtctac | 240 |
| atggagctga gcagcctgag atctgacgac acggccatgt attactgtgc aagagagggg | 300 |
| ggggccgaca ctacccgggt ccactcttcg tttgactact ggggccaggg aaccctggtc | 360 |
| accgtctcct caggcggcgg cggctctggc ggaggtggca gcagcggtgg cggatcccag | 420 |
| gctgtgctga ctcagccgcc ttccgtgtcg gggtctcctg gacagtcgat caccatctcc | 480 |
| tgcactggaa ccagcagtga cgttgaagct acaactatg tctcctggta tcaacaacac | 540 |
| ccaggcaaag cccccaaact catgatttat gatgtcagta atcggccctc agggggttct | 600 |
| aatcgcttct ctggctccaa gtctggcaac acggcctccc tgaccatctc tgggctccag | 660 |
| gctgaggacg aggctgatta ttactgcagc tcatatacaa gcagcagcac ttgggtgttc | 720 |
| ggcggaggga ccaaggtcat cgtccta | 747 |

<210> SEQ ID NO 71
<211> LENGTH: 738
<212> TYPE: DNA
<213> ORGANISM: Homo sapiens

<400> SEQUENCE: 71

| | |
|---|---|
| caggtgcagc tgcaggagtc ggggggaggc ttggtacagc ctggcaggtc cctgagactc | 60 |
| tcctgtgcag cctctggatt caccttgat gattatgccc tccactgggt ccggcaagct | 120 |
| ccagggaagg gcctggagtg gtctcaggt attagttgga atagtgttac cgtaaagtat | 180 |
| gcggtctctg tgaagggccg gttcaccatc tccagagaca cgccaagaa ctccctgttt | 240 |
| ctgcaaatga acgctctgag atctgaggac acggcttat attactgtgc aaaagccaga | 300 |
| ggggccctct tagaagcagc tgacacacca tctgacgact ggggccaggg caccctggtc | 360 |
| accgtctcct caggcggcgg cggctctggc ggaggtggca gcggcggtgg cggatccgac | 420 |
| atcgtgatga cccagtctcc gtcctccctg tctgcatctg taggagacag agtcaccatc | 480 |
| acttgccggg caagtcagag cattagcagc tatttaaatt ggtatcagca gaaaccaggg | 540 |
| aaagccccta agctcctgat ctatgctgca tccagtttgc aaagtggggt cccatcaagg | 600 |
| ttcagtggca gtggatctgg gacagatttc actctcacca tcagcagcct gcagcctgaa | 660 |
| gatgttgcaa cttattactg tcaaaagtat aacagtgccc cgtggacgtt cggccaaggg | 720 |
| accaaagtgg atatcaaa | 738 |

<210> SEQ ID NO 72
<211> LENGTH: 732
<212> TYPE: DNA
<213> ORGANISM: Homo sapiens

<400> SEQUENCE: 72

| | |
|---|---|
| caggtacagc tgcagcagtc aggcgcaggt ctattgaggc cttcggagac cctgtccctc | 60 |
| acctgcggtc tctatggtgg gtccttcagt ggtcactatt ggaactggat ccgccagtcc | 120 |
| ccagaaaagg ggctggtgtg gattgggaa atcactcata gtggaaccac caattacaac | 180 |
| ccgtccctca gagtcgagt catcacatca gtagacacgt ccaagaatca gtactccctg | 240 |
| aagctgagct ttgtgacccc tgcggacacg gccgtgtatt actgtgcgag aggtgattac | 300 |
| tatgggtact ggtacttcga tctctggggc cgtggcaccc tggtcaccgt ctcctcaggc | 360 |

```
ggcggcggct ctggcggagg tggcagcggc ggtggcggat cccagtctgt gttgacgcag    420
ccgccctcag ttcctgtggc cccaggacag aaggtcacca tctcctgctc tggaagcagc    480
tccaacattg gaataatta tgtatcctgg taccagcagc tcccaggaac agccccaaa     540 ctcctcattt atgacactaa taagcgaccc tcagggattc ctgaccgatt cgctggctcc    600
aagtctggca cgtcagccac cctgggcatc accggactcc agactgggga cgaggccgat    660
tattactgcg aacatggga tagcagcctg agtgctggcg tgttcggcgg agggaccaag    720
ctgaccgtcc ta                                                        732

<210> SEQ ID NO 73
<211> LENGTH: 369
<212> TYPE: DNA
<213> ORGANISM: Homo sapiens

<400> SEQUENCE: 73
gaaattgtgt tgacgcagtc tccaggcacc ctgtctttgt ctccagggga aagagccacc     60
ctctcctgca gggccagtca gactgttaac agctacttag cctggtacca gtagaaacct    120
ggccaggctc ccaggctcct catctatggt gcatccagca gggccactgg catcccagac    180
aggttcagtg gcagtgggtc tgggacagac ttcactctca ccatcagcag actggagcct    240
gaagattttg cagtgtatta ctgtcagcag tatggtagct cacatccgtg acgttcggc     300 caagggacca aggtggagat caaacgtggc ctcgggggcc tggtcgacta caaagatgac    360
gatgacaaa                                                            369

<210> SEQ ID NO 74
<211> LENGTH: 366
<212> TYPE: DNA
<213> ORGANISM: Homo sapiens

<400> SEQUENCE: 74
gacatccaga tgacccagtc tccgtcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaagtag ggtcccatca    180
aggttcagcg gcagtggatc tgggacagat ttcactctca ccatcagcag cctgcagcct    240
gaagattttg caacttacta ttgtcaacag gctaacagtt cccgtacac ttttggccag     300 gggaccaagc tggagatcaa acgtggcctc gggggcctgg tcgactacaa agatgacgat    360
gacaaa                                                               366

<210> SEQ ID NO 75
<211> LENGTH: 366
<212> TYPE: DNA
<213> ORGANISM: Homo sapiens

<400> SEQUENCE: 75
gtcatctgga tgacccagtc tccatcctcc ctgtctgcat ctgtaggaga cagagtcacc     60
atcacttgcc gggcaagtca gagcattagc agctatttaa attggtatca gcggaaacca    120
gggaaagccc ctaagctcct gatctatgct gcatccagtt tgcaaagtgg ggtcacatca    180
aggttcagtg gcagtggatc tgggacagat ttcactctca ccatcagcag tctgcaacct    240
gaagattttg caacttacta ctgtcaacag agttacagta cccctccgac gttcggccaa    300
gggaccaagc tggagatcaa acgtggcctc gggggcctgg tcgactacaa agatgacgat    360
``` gacaaa                                                               366

<210> SEQ ID NO 76
<211> LENGTH: 369
<212> TYPE: DNA
<213> ORGANISM: Homo sapiens

<400> SEQUENCE: 76
gaaatagtga tgacgcagtc tccagccacc ctgtctgtgt ctccagggga aagagccacc    60
ctctcctgca gggccagtca gagtgttagc cgcaacttag cctggtacca gcagaaacct   120
ggccaggctc ccaggctcct catctatgat acatccacca gggccactgg tatcccagcc   180
aggttcagtg gcagtgggtc tgggacagag ttcactctca ccatcagcag cctgcagtct   240
gaagattctg cagtttatta ctgtcagcag tataatatct ggcctccact cactttcggc   300
ggagggacca aggtggagat caaacgtggc ctcggggggcc tggtcgacta caaagatgac   360
gatgacaaa                                                           369

<210> SEQ ID NO 77
<211> LENGTH: 333
<212> TYPE: DNA
<213> ORGANISM: Homo sapiens

<400> SEQUENCE: 77
gatattgtga tgacccagac tccactctcc tcacctgtca cccttggaca gccggcctcc    60
atctcctgca ggtctagtca aagcctcgta cacagtgatg gaaacaccta cttgacttgg   120
tttcaccaga ggccaggcca gcctccaaga gtcctcattc ataaggtttc taacctgttc   180
tctggggtcc cagacagatt cagtggcagt ggggcaggga cagatttcac actgaaaatc   240
agcagggtgg aagctgagga tgtcgggggt tattactgca tgcaagctac acaattgtac   300
acttttggcc aggggaccaa ggtggaaatc aaa                                333

<210> SEQ ID NO 78
<211> LENGTH: 363
<212> TYPE: DNA
<213> ORGANISM: Homo sapiens

<400> SEQUENCE: 78
gaaacgacac tcacgcagtc tccagcaatc atgtctgcat ctccagggga gagggtcacc    60
atgacctgca gtgccagctc aagtatacgt tacatatatt ggtaccaaca gaagcctgga   120
tcctccccca gactcctgat ttatgacaca tccaacgtgg ctcctggagt cccttttcgc   180
ttcagtggca gtgggtctgg gacctcttat tctctcacaa tcaaccgaat ggaggctgag   240
gatgctgcca cttattactg ccaggagtgg agtggttatc cgtacacgtt cggagggggg   300
accaaggtgg agatcaaacg tggcctcggg ggcctggtcg actacaaaga tgacgatgac   360
aaa                                                                 363

<210> SEQ ID NO 79
<211> LENGTH: 384
<212> TYPE: DNA
<213> ORGANISM: Homo sapiens

<400> SEQUENCE: 79
gacatcgtga tgacccagtc tccagactcc ctggctgtgt ctctgggcga gagggccacc    60
atcaactgca agtccagcca gagtgtttta tacagctcca acaatatgaa ctacttagct   120
tggtaccagc agaaaccagg acagcctcct aagctgctca tttactgggc atctacccgg   180

```
gaatccgggg tccctgaccg attcagtggc agcgggtctg ggacagattt cactctcacc      240
atcagcagcc tgcaggctga agatgcggca gtttattact gtcagcagta ttatagtact      300
cctccgacgt tcggccaagg gaccaagctg gagatcaaac gtggcctcgg gggcctggtc      360
gactacaaag atgacgatga caaa                                             384

<210> SEQ ID NO 80
<211> LENGTH: 333
<212> TYPE: DNA
<213> ORGANISM: Homo sapiens

<400> SEQUENCE: 80
cagtctgtgt tgacgcagcc tccctcattg tctggggccc cgggacagag tgtcaccatc       60
tcctgcgctg ggaccagttc cagcatcggg gcaggttacg atgtacagtg gtaccagcaa      120
cttccaggaa aaccccccaa actcctcatc tacgggaatg ataatcggcc ctcaggggtc      180
cctgaccgat tctctggatc caggtcttac acctcagcct ccctggtcat cactagagtc      240
cagattgagg atgaggctga ttattactgc cagtcgtatg acagcagtct cattggtcct      300
caattcggcg gggggaccaa gctgaccgtc cta                                   333

<210> SEQ ID NO 81
<211> LENGTH: 321
<212> TYPE: DNA
<213> ORGANISM: Homo sapiens

<400> SEQUENCE: 81
gccatccaga tgacccagtc tccatcctca ctgtctgcat ctgtaggaga cagagtcacc       60
atcacttgtc gggcgagtca gggcattagc aattatttag cctggtttca gcagaaacca      120
gggaaagccc ctaagtccct gatctatgct gcatccagtt tgcaaagtgg ggtcccatca      180
aagtacagcg gcagtggatc tgggacagat ttcactctca ccatcagcag cctgcagcct      240
gaagattttg caacttatta ctgccaacag tataagagtt accccctcac tttcggcgga      300
gggaccaagg tggagatcaa a                                                321

<210> SEQ ID NO 82
<211> LENGTH: 321
<212> TYPE: DNA
<213> ORGANISM: Homo sapiens

<400> SEQUENCE: 82
gacatcgtga tgacccagtc tccatccacc ctgtctgcat ctgtaggaga cagagtcacc       60
atcacttgcc gggcaagtca gagcactagc aggttttaa attggtatca gcagaaacct      120
gggaaagccc ctaaactcct gatctatgct gcatccagtt tgcatagtgg cgtcccatca      180
aggttcagtg gcagtggatc tgggacagat ttcactctca ccatcagcag tctgcaacct      240
gaagattttg caacttacta ctgtcaacag acttccagtt accctctcac tttcggcgga      300
gggaccaagg tggaaatcaa a                                                321

<210> SEQ ID NO 83
<211> LENGTH: 324
<212> TYPE: DNA
<213> ORGANISM: Homo sapiens

<400> SEQUENCE: 83
gaaacgacac tcacgcagtc tccaggcacc ctgtctttgt ctccagggga aagagccacc       60
```

```
ctctcctgca gggccagtca gagtgtttcc agcccctact tagcctggta ccagcagaaa    120
cctggccagg ctcccaggct cctcatttat ggtgcatcta acagggccac tggcatccca    180
gacaggttca gtggcagtgg gtctgggaca gacttcactc tcaccatcag cagcctgcag    240
gctgaagatg aggcagttta ttactgtcag caatactaca atactccgct cactttcggc    300
ggagggacca aggtggaaat caaa                                           324
```

<210> SEQ ID NO 84
<211> LENGTH: 321
<212> TYPE: DNA
<213> ORGANISM: Homo sapiens

<400> SEQUENCE: 84

```
gatattgtga tgacccagac tccaggcacc ctgtcttcgt ctccagggga aagagccacc     60
ctctcctgca gggccagtca gggtgttagc agcaacttag cctggtacca gcagaaacct    120
ggccaggctc ccaggctcct catctatgat gcatccaaca gggccactgg catcccactc    180
aggttcagtg gcagtgggtc tgggacagac ttcactctca ccatcagcag actggaacct    240
gaagattttg cagtgtatta ctgtcaccag tatggtagct caccgtacac ctttggccag    300
gggaccaagg tggaaatcaa a                                              321
```

<210> SEQ ID NO 85
<211> LENGTH: 321
<212> TYPE: DNA
<213> ORGANISM: Homo sapiens

<400> SEQUENCE: 85

```
gacatccaga tgacccagtc tccttccacc ctgtctgtat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ctatcagcag cctgcagcct    240
gaagattttg caacttacta ttgtcaacag gctaacagtt cccgctcac tttcggcgga    300 gggaccaagc tggagatcaa a                                              321
```

<210> SEQ ID NO 86
<211> LENGTH: 327
<212> TYPE: DNA
<213> ORGANISM: Homo sapiens

<400> SEQUENCE: 86

```
cagactgtgg tgacccagga gccctcactg actgtgtccc taggagggac agtcactctc     60
acctgtggct ccagcactgg agctgtcacc agtggtcatt atcccactg gttccagcag    120 aagcctggcc aagcccccag gacactgatt tatgataaa gcaacaaaca ctcctggacc    180
cctgcccggt tctcaggctc cctccttggg ggcaaagctg ccctgaccct ttcgggtgcg    240
cagcctgagg atgaggctga gtattactgc ttgctctcct atagtggtac tcgggtgttc    300
ggcggaggga ccaagctgac cgtccta                                        327
```

<210> SEQ ID NO 87
<211> LENGTH: 321
<212> TYPE: DNA
<213> ORGANISM: Homo sapiens

<400> SEQUENCE: 87

```
tcctatgagc tgatgcagcc atcctcagtg tcagtgtctc cgggacagac agccaggatc     60
```

```
acctgctcag gagatgtact ggcaaaaaaa tgtgctcggt ggttccagca gaagccaggc      120
caggcccctg tgctggtgat ttataaagac agtgagcggc cctcagggat ccctgagcga      180
ttctccggct ccagctcagg gaccacagtc accttgacca tcagcggggc ccaggttgag      240
gatgaggctg actattactg ttactctgcg gctgacaaca acctgggggt gttcggcgga      300
gggaccaagg tcaccgtcct a                                                321
```

<210> SEQ ID NO 88
<211> LENGTH: 321
<212> TYPE: DNA
<213> ORGANISM: Homo sapiens

<400> SEQUENCE: 88

```
gccatccgga tgacccagtc tccatcctcc ctgtctgcat ctgtaggaga cagagtcacc       60
atcacttgcc gggcgagtca gggcattagc aattatttag cctggtatca gcagaaacca      120
gggaaagttc ctaagctcct gatctatgct gcatccactt tgcaatcagg ggtcccatct      180
cggttcagcg gcagtggatc tgggacagat ttcactctca ccatcagcag cctgcagcct      240
gaagatgttg caacttatta ctgtcaaaag tataacagtg cccctgggac gttcggccaa      300
gggaccaagg tggagatcaa a                                                321
```

<210> SEQ ID NO 89
<211> LENGTH: 330
<212> TYPE: DNA
<213> ORGANISM: Homo sapiens

<400> SEQUENCE: 89

```
caggctgtgc tgactcagcc gccttccgtg tcggggtctc ctggacagtc gatcaccatc       60
tcctgcactg gaaccagcag tgacgttgaa gcttacaact atgtctcctg gtatcaacaa      120
cacccaggca aagccccaa actcatgatt tatgatgtca gtaatcggcc ctcagggggtt      180 tctaatcgct tctctggctc caagtctggc aacacggcct ccctgaccat ctctgggctc      240
caggctgagg acgaggctga ttattactgc agctcatata caagcagcag cacttgggtg      300
ttcggcggag ggaccaaggt catcgtccta                                       330
```

<210> SEQ ID NO 90
<211> LENGTH: 321
<212> TYPE: DNA
<213> ORGANISM: Homo sapiens

<400> SEQUENCE: 90

```
gacatcgtga tgacccagtc tccgtcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag cctgcagcct      240
gaagatgttg caacttatta ctgtcaaaag tataacagtg ccccgtggac gttcggccaa      300
gggaccaaag tggatatcaa a                                                321
```

<210> SEQ ID NO 91
<211> LENGTH: 330
<212> TYPE: DNA
<213> ORGANISM: Homo sapiens

<400> SEQUENCE: 91

```
cagtctgtgt tgacgcagcc gccctcagtt cctgtggccc caggacagaa ggtcaccatc    60
tcctgctctg gaagcagctc caacattggg aataattatg tatcctggta ccagcagctc   120
ccaggaacag ccccccaaact cctcatttat gacactaata agcgaccctc agggattcct   180
gaccgattcg ctggctccaa gtctggcacg tcagccaccc tgggcatcac cggactccag   240
actggggacg aggccgatta ttactgcgga acatgggata gcagcctgag tgctggcgtg   300
ttcggcggag ggaccaagct gaccgtccta                                    330

<210> SEQ ID NO 92
<211> LENGTH: 8
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 4
<223> OTHER INFORMATION: Xaa = Ser, Tyr, Cys, Lys or an amino acid with
      a chemically modified side chain

<400> SEQUENCE: 92

Tyr Ser Thr Xaa Asp Phe Ile Met
1               5

<210> SEQ ID NO 93
<211> LENGTH: 8
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 4
<223> OTHER INFORMATION: Xaa = Ser, Tyr, Cys, Lys or an amino acid with
      a chemically modified side chain

<400> SEQUENCE: 93

Tyr Ser Thr Xaa Tyr Phe Ile Met
1               5

<210> SEQ ID NO 94
<211> LENGTH: 7
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 3
<223> OTHER INFORMATION: Xaa = Ser, Tyr, Cys, Lys or an amino acid with
      a chemically modified side chain

<400> SEQUENCE: 94

Ile Asn Xaa Asp Phe Leu Leu
1               5

<210> SEQ ID NO 95
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain
```

```
<400> SEQUENCE: 95

Gly Val Asn Ala Xaa Ser Ser Leu Phe
  1               5

<210> SEQ ID NO 96
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 96

Gly Val Asn Pro Xaa Gly Gly Trp Phe
  1               5

<210> SEQ ID NO 97
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 97

Lys Ala Lys Thr Xaa Thr Val Leu Tyr
  1               5

<210> SEQ ID NO 98
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 98

Lys Thr Lys Thr Xaa Thr Val Leu Tyr
  1               5

<210> SEQ ID NO 99
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain
<220> FEATURE:
<221> NAME/KEY: MOD_RES
<222> LOCATION: 6
<223> OTHER INFORMATION: Xaa = Orn

<400> SEQUENCE: 99

Gly Ala Asn Pro Xaa Xaa Leu Tyr Tyr
```

```
<210> SEQ ID NO 100
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 100

Gly Ala Asn Pro Xaa Ala Leu Tyr Tyr
1               5

<210> SEQ ID NO 101
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 101

Gly Tyr Ser Thr Xaa Ser Tyr Tyr Phe
1               5

<210> SEQ ID NO 102
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 102

Gly Tyr Arg Thr Xaa Asn Thr Tyr Phe
1               5

<210> SEQ ID NO 103
<211> LENGTH: 8
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 4
<223> OTHER INFORMATION: Xaa = Ser, Tyr, Cys, Lys or an amino acid with
      a chemically modified side chain

<400> SEQUENCE: 103

Tyr Asn Pro Xaa Val Gly Tyr Phe
1               5

<210> SEQ ID NO 104
<211> LENGTH: 9
<212> TYPE: PRT
<213> ORGANISM: Artificial Sequence
```

```
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 104

Gly Gly Lys Val Xaa Ser Ala Tyr Phe
 1               5

<210> SEQ ID NO 105
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 105

Ser Val Lys Pro Xaa Thr Gly Phe Ala
 1               5

<210> SEQ ID NO 106
<211> LENGTH: 8
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 4
<223> OTHER INFORMATION: Xaa = Ser, Tyr, Cys, Lys or an amino acid with
      a chemically modified side chain

<400> SEQUENCE: 106

Asp Ser Val Xaa Ala Ser Tyr Phe
 1               5

<210> SEQ ID NO 107
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 107

Lys Tyr Asn Pro Xaa Ser Asn Tyr Leu
 1               5

<210> SEQ ID NO 108
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain
```

<400> SEQUENCE: 108

Lys Tyr Asn Pro Xaa Ala Ser Tyr Leu
 1               5

<210> SEQ ID NO 109
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 109

Lys Tyr Asn Pro Xaa Ala Asn Tyr Leu
 1               5

<210> SEQ ID NO 110
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 110

Arg Ile Pro Thr Xaa Thr Gly Phe Phe
 1               5

<210> SEQ ID NO 111
<211> LENGTH: 7
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 3
<223> OTHER INFORMATION: Xaa = Ser, Tyr, Cys, Lys or an amino acid with
      a chemically modified side chain

<400> SEQUENCE: 111

Asp Ile Xaa Asn Ala Tyr Phe
 1               5

<210> SEQ ID NO 112
<211> LENGTH: 7
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 3
<223> OTHER INFORMATION: Xaa = Ser, Tyr, Cys, Lys or an amino acid with
      a chemically modified side chain

<400> SEQUENCE: 112

Asp Met Xaa Asn Gly Tyr Phe
 1               5

```
<210> SEQ ID NO 113
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 113

Lys Tyr Asn Pro Xaa Leu Gly Phe Leu
 1               5

<210> SEQ ID NO 114
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 114

Lys Tyr Tyr Pro Xaa Phe Gly Tyr Phe
 1               5

<210> SEQ ID NO 115
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 115

Gly Ala Arg Pro Xaa Gly Gly Phe Phe
 1               5

<210> SEQ ID NO 116
<211> LENGTH: 9
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 5
<223> OTHER INFORMATION: Xaa = Ser, Tyr, Cys, Lys or an amino acid with
      a chemically modified side chain

<400> SEQUENCE: 116

Gly Ala Lys Pro Xaa Gly Gly Phe Phe
 1               5

<210> SEQ ID NO 117
<211> LENGTH: 8
<212> TYPE: PRT
<213> ORGANISM: Artificial Sequence
<220> FEATURE:
<223> OTHER INFORMATION: a synthetic peptide
<220> FEATURE:
```

```
<221> NAME/KEY: VARIANT
<222> LOCATION: 4
<223> OTHER INFORMATION: Xaa = Ser, Tyr, Cys, Lys or an amino acid with
      a chemically modified side chain

<400> SEQUENCE: 117

Tyr Ser Pro Xaa Thr Asn Phe Phe
1               5

<210> SEQ ID NO 118
<211> LENGTH: 7
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 4
<223> OTHER INFORMATION: Xaa = Ser, Tyr, Cys, Lys or an amino acid with
      a chemically modified side chain

<400> SEQUENCE: 118

Tyr Ser Pro Xaa Thr Asn Phe
1               5

<210> SEQ ID NO 119
<211> LENGTH: 11
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 3
<223> OTHER INFORMATION: Xaa = Ser, Tyr, Cys, Lys or an amino acid with
      a chemically modified side chain

<400> SEQUENCE: 119

Gln Asn Xaa Pro Asn Ile Phe Gly Gln Trp Met
1               5                   10

<210> SEQ ID NO 120
<211> LENGTH: 8
<212> TYPE: PRT
<213> ORGANISM: Staphylococcus aureus

<400> SEQUENCE: 120

Tyr Ser Thr Cys Asp Phe Ile Met
1               5

<210> SEQ ID NO 121
<211> LENGTH: 9
<212> TYPE: PRT
<213> ORGANISM: Staphylococcus aureus

<400> SEQUENCE: 121

Gly Val Asn Ala Cys Ser Ser Leu Phe
1               5

<210> SEQ ID NO 122
<211> LENGTH: 7
<212> TYPE: PRT
<213> ORGANISM: Staphylococcus aureus

<400> SEQUENCE: 122

Ile Asn Cys Asp Phe Leu Leu
1               5
```

<210> SEQ ID NO 123
<211> LENGTH: 8
<212> TYPE: PRT
<213> ORGANISM: Staphylococcus aureus

<400> SEQUENCE: 123

Tyr Ser Thr Cys Tyr Phe Ile Met
1               5

<210> SEQ ID NO 124
<211> LENGTH: 9
<212> TYPE: PRT
<213> ORGANISM: Staphylococcus arlettae

<400> SEQUENCE: 124

Gly Val Asn Pro Cys Gly Gly Trp Phe
1               5

<210> SEQ ID NO 125
<211> LENGTH: 9
<212> TYPE: PRT
<213> ORGANISM: Staphylococcus auricularis

<400> SEQUENCE: 125

Lys Ala Lys Thr Cys Thr Val Leu Tyr
1               5

<210> SEQ ID NO 126
<211> LENGTH: 9
<212> TYPE: PRT
<213> ORGANISM: Staphylococcus auricularis

<400> SEQUENCE: 126

Lys Thr Lys Thr Cys Thr Val Leu Tyr
1               5

<210> SEQ ID NO 127
<211> LENGTH: 9
<212> TYPE: PRT
<213> ORGANISM: Staphylococcus capitis
<220> FEATURE:
<221> NAME/KEY: MOD_RES
<222> LOCATION: 6
<223> OTHER INFORMATION: Xaa = Orn

<400> SEQUENCE: 127

Gly Ala Asn Pro Cys Xaa Leu Tyr Tyr
1               5

<210> SEQ ID NO 128
<211> LENGTH: 9
<212> TYPE: PRT
<213> ORGANISM: Staphylococcus capitis

<400> SEQUENCE: 128

Gly Ala Asn Pro Cys Ala Leu Tyr Tyr
1               5

<210> SEQ ID NO 129
<211> LENGTH: 9
<212> TYPE: PRT
<213> ORGANISM: Staphylococcus caprae

<400> SEQUENCE: 129

Gly Tyr Ser Thr Cys Ser Tyr Tyr Phe

<210> SEQ ID NO 130
<211> LENGTH: 9
<212> TYPE: PRT
<213> ORGANISM: Staphylococcus caprae

<400> SEQUENCE: 130

Gly Tyr Arg Thr Cys Asn Thr Tyr Phe
1               5

<210> SEQ ID NO 131
<211> LENGTH: 8
<212> TYPE: PRT
<213> ORGANISM: Staphylococcus carnosus

<400> SEQUENCE: 131

Tyr Asn Pro Cys Val Gly Tyr Phe
1               5

<210> SEQ ID NO 132
<211> LENGTH: 9
<212> TYPE: PRT
<213> ORGANISM: Staphylococcus cohnii

<400> SEQUENCE: 132

Gly Gly Lys Val Cys Ser Ala Tyr Phe
1               5

<210> SEQ ID NO 133
<211> LENGTH: 9
<212> TYPE: PRT
<213> ORGANISM: Staphylococcus cohnii

<400> SEQUENCE: 133

Ser Val Lys Pro Cys Thr Gly Phe Ala
1               5

<210> SEQ ID NO 134
<211> LENGTH: 8
<212> TYPE: PRT
<213> ORGANISM: Staphylococcus epidermis

<400> SEQUENCE: 134

Asp Ser Val Cys Ala Ser Tyr Phe
1               5

<210> SEQ ID NO 135
<211> LENGTH: 9
<212> TYPE: PRT
<213> ORGANISM: Staphylococcus epidermis

<400> SEQUENCE: 135

Lys Tyr Asn Pro Cys Ser Asn Tyr Leu
1               5

<210> SEQ ID NO 136
<211> LENGTH: 9
<212> TYPE: PRT
<213> ORGANISM: Staphylococcus epidermis

<400> SEQUENCE: 136

Lys Tyr Asn Pro Cys Ala Ser Tyr Leu
1               5

<210> SEQ ID NO 137
<211> LENGTH: 9
<212> TYPE: PRT
<213> ORGANISM: Staphylococcus epidermis

<400> SEQUENCE: 137

Lys Tyr Asn Pro Cys Ala Asn Tyr Leu
1               5

<210> SEQ ID NO 138
<211> LENGTH: 9
<212> TYPE: PRT
<213> ORGANISM: Staphylococcus intermedius

<400> SEQUENCE: 138

Arg Ile Pro Thr Ser Thr Gly Phe Phe
1               5

<210> SEQ ID NO 139
<211> LENGTH: 7
<212> TYPE: PRT
<213> ORGANISM: Staphylococcus lugdunensis

<400> SEQUENCE: 139

Asp Ile Cys Asn Ala Tyr Phe
1               5

<210> SEQ ID NO 140
<211> LENGTH: 7
<212> TYPE: PRT
<213> ORGANISM: Staphylococcus lugdunensis

<400> SEQUENCE: 140

Asp Met Cys Asn Gly Tyr Phe
1               5

<210> SEQ ID NO 141
<211> LENGTH: 9
<212> TYPE: PRT
<213> ORGANISM: Staphylococcus simulans

<400> SEQUENCE: 141

Lys Tyr Asn Pro Cys Leu Gly Phe Leu
1               5

<210> SEQ ID NO 142
<211> LENGTH: 9
<212> TYPE: PRT
<213> ORGANISM: Staphylococcus simulans

<400> SEQUENCE: 142

Lys Tyr Tyr Pro Cys Phe Gly Tyr Phe
1               5

<210> SEQ ID NO 143
<211> LENGTH: 10
<212> TYPE: PRT
<213> ORGANISM: Staphylococcus gallinarum

<400> SEQUENCE: 143

Val Gly Ala Arg Pro Cys Gly Gly Phe Phe
1               5                   10

<210> SEQ ID NO 144

```
<211> LENGTH: 9
<212> TYPE: PRT
<213> ORGANISM: Staphylococcus xylosus

<400> SEQUENCE: 144

Gly Ala Lys Pro Cys Gly Gly Phe Phe
1               5

<210> SEQ ID NO 145
<211> LENGTH: 8
<212> TYPE: PRT
<213> ORGANISM: Staphylococcus warneri

<400> SEQUENCE: 145

Tyr Ser Pro Cys Thr Asn Phe Phe
1               5

<210> SEQ ID NO 146
<211> LENGTH: 11
<212> TYPE: PRT
<213> ORGANISM: Enterococcus faecalis

<400> SEQUENCE: 146

Gln Asn Ser Pro Asn Ile Phe Gly Gln Trp Met
1               5                   10

<210> SEQ ID NO 147
<211> LENGTH: 111
<212> TYPE: PRT
<213> ORGANISM: Murine

<400> SEQUENCE: 147

Asp Ile Val Arg Thr Gln Ser Pro Leu Ser Leu Ser Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ile Leu Glu Ala Glu Asp Leu Gly Ile Tyr Phe Cys Ser Gln Ser
                85                  90                  95

Thr His Phe Pro Thr Phe Gly Gly Gly Thr Lys Leu Glu Ile Lys
            100                 105                 110

<210> SEQ ID NO 148
<211> LENGTH: 112
<212> TYPE: PRT
<213> ORGANISM: Murine

<400> SEQUENCE: 148

Asp Ile Val Met Thr Gln Ala Thr Leu Ser Leu Pro Val Ser Leu Gly
1               5                   10                  15

Asp Gln Ala Ser Ile Ser Cys Arg Ser Ser Gln Arg Leu Val Pro Ser
            20                  25                  30

Asn Gly Asn Ile Tyr Leu His Trp Phe Leu Gln Lys Pro Gly Gln Ser
        35                  40                  45

Pro Lys Leu Leu Ile Tyr Lys Leu Ser Ser Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ser Glu Asp Leu Gly Ile Tyr Phe Cys Ser Gln Thr
                 85                  90                  95

Thr His Val Pro Tyr Thr Phe Gly Gly Gly Thr Lys Leu Glu Ile Lys
            100                 105                 110
```

<210> SEQ ID NO 149
<211> LENGTH: 111
<212> TYPE: PRT
<213> ORGANISM: Murine

<400> SEQUENCE: 149

```
Asp Ile Val Met Thr Gln Ala Thr Ala Ser Leu Thr Val Ser Leu Gly
 1               5                  10                  15

Gln Arg Ala Thr Ile Ser Cys Arg Ala Ser Lys Ser Val Ser Thr Ser
             20                  25                  30

Gly Tyr Ser Tyr Met His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Val Pro Tyr Thr Phe Gly Gly Gly Thr Lys Leu Glu Leu Lys
            100                 105                 110
```

<210> SEQ ID NO 150
<211> LENGTH: 111
<212> TYPE: PRT
<213> ORGANISM: Murine

<400> SEQUENCE: 150

```
Asp Ile Glu Met Thr Gln Ile Thr Ala Ser Leu Thr Val Ser Leu Gly
 1               5                  10                  15

Gln Arg Ala Thr Ile Ser Cys Arg Ala Ser Lys Ser Val Ser Thr Ser
             20                  25                  30

Gly Tyr Ser Tyr Met His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Val Pro Tyr Thr Phe Gly Gly Gly Thr Lys Leu Glu Leu Lys
            100                 105                 110
```

<210> SEQ ID NO 151
<211> LENGTH: 99
<212> TYPE: PRT
<213> ORGANISM: Murine

<400> SEQUENCE: 151

```
Pro Leu Ser Leu Ser Val Ser Leu Gly Asp Gln Ala Ser Ile Ser Cys
 1               5                  10                  15
```

Arg Ser Ser Gln Ser Leu Leu His Ser Asn Gly Asn Thr Tyr Leu His
            20                  25                  30

Trp Tyr Leu Gln Lys Pro Gly Gln Ser Pro Lys Leu Leu Ile Tyr Lys
            35                  40                  45

Val Ser Asn Arg Phe Ser Gly Val Pro Asp Arg Phe Ser Gly Ser Gly
        50                  55                  60

Ser Gly Thr Asp Phe Thr Leu Lys Ile Ser Ile Leu Glu Ala Glu Asp
65                  70                  75                  80

Leu Gly Ile Tyr Phe Cys Ser Gln Ser Thr His Phe Pro Thr Phe Gly
                85                  90                  95

Gly Gly Thr

<210> SEQ ID NO 152
<211> LENGTH: 100
<212> TYPE: PRT
<213> ORGANISM: Murine

<400> SEQUENCE: 152

Thr Leu Ser Leu Pro Val Ser Leu Gly Asp Gln Ala Ser Ile Ser Cys
1               5                   10                  15

Arg Ser Ser Gln Arg Leu Val Pro Ser Asn Gly Asn Ile Tyr Leu His
            20                  25                  30

Trp Phe Leu Gln Lys Pro Gly Gln Ser Pro Lys Leu Leu Ile Tyr Lys
            35                  40                  45

Leu Ser Ser Arg Phe Ser Gly Val Pro Asp Arg Phe Ser Gly Ser Gly
        50                  55                  60

Ser Gly Thr Asp Phe Thr Leu Lys Ile Ser Arg Val Glu Ser Glu Asp
65                  70                  75                  80

Leu Gly Ile Tyr Phe Cys Ser Gln Thr Thr His Val Pro Tyr Thr Phe
                85                  90                  95

Gly Gly Gly Thr
            100

<210> SEQ ID NO 153
<211> LENGTH: 99
<212> TYPE: PRT
<213> ORGANISM: Murine

<400> SEQUENCE: 153

Thr Ala Ser Leu Thr Val Ser Leu Gly Gln Arg Ala Thr Ile Ser Cys
1               5                   10                  15

Arg Ala Ser Lys Ser Val Ser Thr Ser Gly Tyr Ser Tyr Met His Trp
            20                  25                  30

Tyr Gln Gln Lys Pro Gly Gln Pro Pro Lys Leu Leu Ile Tyr Leu Ala
            35                  40                  45

Ser Asn Leu Glu Ser Gly Val Pro Ala Arg Phe Ser Gly Ser Gly Ser
        50                  55                  60

Gly Thr Asp Phe Thr Leu Asn Ile His Pro Val Glu Glu Glu Asp Ala
65                  70                  75                  80

Ala Thr Tyr Tyr Cys Gln His Ser Arg Glu Val Pro Tyr Thr Phe Gly
                85                  90                  95

Gly Gly Thr

<210> SEQ ID NO 154
<211> LENGTH: 99
<212> TYPE: PRT
<213> ORGANISM: Murine

<400> SEQUENCE: 154

Thr Ala Ser Leu Thr Val Ser Leu Gly Gln Arg Ala Thr Ile Ser Cys
1               5                   10                  15

Arg Ala Ser Lys Ser Val Ser Thr Ser Gly Tyr Ser Tyr Met His Trp
            20                  25                  30

Tyr Gln Gln Lys Pro Gly Gln Pro Pro Lys Leu Leu Ile Tyr Leu Ala
        35                  40                  45

Ser Asn Leu Glu Ser Gly Val Pro Ala Arg Phe Ser Gly Ser Gly Ser
    50                  55                  60

Gly Thr Asp Phe Thr Leu Asn Ile His Pro Val Glu Glu Asp Ala
65                  70                  75                  80

Ala Thr Tyr Tyr Cys Gln His Ser Arg Glu Val Pro Tyr Thr Phe Gly
                85                  90                  95

Gly Gly Thr

<210> SEQ ID NO 155
<211> LENGTH: 333
<212> TYPE: DNA
<213> ORGANISM: Murine

<400> SEQUENCE: 155
gacattgtga ggacacagtc tccactctcc ctgtctgtca gtcttggaga tcaagcctcc     60
atctcttgta gatctagtca gagccttta cacagtaatg gaaacaccta tttacattgg    120
tacctgcaga agccaggcca gtctccaaaa ctcctgatct acaaagtttc caaccgattt    180
tctggggtcc cagacaggtt cagtggcagt ggatcaggga cagatttcac actcaagatc    240
agcatattgg aggctgagga tctgggaatt tatttctgct ctcaaagtac acattttccg    300
acgttcggtg gaggcaccaa gctggaaata aaa                                 333

<210> SEQ ID NO 156
<211> LENGTH: 336
<212> TYPE: DNA
<213> ORGANISM: Murine

<400> SEQUENCE: 156
gacattgtga tgactcaggc tacactctcc ctgcctgtca gtcttggaga ccaagcctcc     60
atctcttgca gatccagtca gcgccttgtt cccagtaatg gaaacattta tttacattgg    120
ttcctgcaga agccaggcca gtctccaaag ctcctgatct acaaactttc cagtcgattt    180
tctggggtcc cagacaggtt cagtggcagt ggatcaggga cagatttcac actcaagatc    240
agcagagtgg agtctgagga tctgggaatt tatttctgct ctcaaactac acatgttcca    300
tacacgttcg gaggggggac caagctggaa atcaaa                              336

<210> SEQ ID NO 157
<211> LENGTH: 333
<212> TYPE: DNA
<213> ORGANISM: Murine

<400> SEQUENCE: 157
gacattgtga tgactcaggc tactgcttcc ttaactgtat ctctggggca gagggccacc     60
atctcatgca gggccagcaa aagtgtcagt acatctggct atagttatat gcactggtac    120
caacagaaac caggacagcc acccaaactc ctcatctatc ttgcatccaa cctagaatct    180
ggggtccctg ccaggttcag tggcagtggg tctgggacag acttcaccct caacatccat    240

```
cctgtggagg aggaggatgc tgcaacctat tactgtcagc acagtaggga ggttccgtac    300
acgttcggag gggggaccaa gctggagctg aaa                                 333

<210> SEQ ID NO 158
<211> LENGTH: 333
<212> TYPE: DNA
<213> ORGANISM: Murine

<400> SEQUENCE: 158
gacattgaga tgacccagat tactgcttcc ttaactgtat ctctgggca gagggccacc     60 atctcatgca gggccagcaa aagtgtcagt acatctggct atagttatat gcactggtac   120
caacagaaac caggacagcc acccaaactc ctcatctatc ttgcatccaa cctagaatct   180
ggggtccctg ccaggttcag tggcagtggg tctgggacag acttcaccct caacatccat   240
cctgtggagg aggaggatgc tgcaacctat tactgtcagc acagtaggga ggttccgtac   300
acgttcggag gggggaccaa gctggagctg aaa                                 333

<210> SEQ ID NO 159
<211> LENGTH: 297
<212> TYPE: DNA
<213> ORGANISM: Murine

<400> SEQUENCE: 159
ccactctccc tgtctgtcag tcttggagat caagcctcca tctcttgtag atctagtcag    60
agccttttac acagtaatgg aaacacctat ttacattggt acctgcagaa gccaggccag   120
tctccaaaac tcctgatcta caagtttcc aaccgatttt ctgggtccc agacaggttc    180 agtggcagtg gatcagggac agatttcaca ctcaagatca gcatattgga ggctgaggat   240
ctgggaattt atttctgctc tcaaagtaca cattttccga cgttcggtgg aggcacc      297

<210> SEQ ID NO 160
<211> LENGTH: 300
<212> TYPE: DNA
<213> ORGANISM: Murine

<400> SEQUENCE: 160
acactctccc tgcctgtcag tcttggagac caagcctcca tctcttgcag atccagtcag    60
cgccttgttc ccagtaatgg aaacatttat ttacattggt cctgcagaa gccaggccag   120 tctccaaagc tcctgatcta caaactttcc agtcgatttt ctgggtccc agacaggttc    180 agtggcagtg gatcagggac agatttcaca ctcaagatca gcagagtgga gtctgaggat   240
ctgggaattt atttctgctc tcaaactaca catgttccat acacgttcgg agggggggacc 300

<210> SEQ ID NO 161
<211> LENGTH: 297
<212> TYPE: DNA
<213> ORGANISM: Murine

<400> SEQUENCE: 161
actgcttcct taactgtatc tctggggcag agggccacca tctcatgcag ggccagcaaa    60
agtgtcagta catctggcta tagttatatg cactggtacc aacagaaacc aggacagcca   120
cccaaactcc tcatctatct tgcatccaac ctagaatctg ggtccctgc caggttcagt   180 ggcagtgggt ctgggacaga cttcaccctc aacatccatc ctgtggagga ggaggatgct   240
gcaacctatt actgtcagca cagtagggag gttccgtaca cgttcggagg ggggacc      297
```

<210> SEQ ID NO 162
<211> LENGTH: 297
<212> TYPE: DNA
<213> ORGANISM: Murine

<400> SEQUENCE: 162

```
actgcttcct taactgtatc tctggggcag agggccacca tctcatgcag ggccagcaaa      60
agtgtcagta catctggcta tagttatatg cactggtacc aacagaaacc aggacagcca     120
cccaaactcc tcatctatct tgcatccaac ctagaatctg gggtccctgc caggttcagt     180
ggcagtgggt ctgggacaga cttcaccctc aacatccatc ctgtggagga ggaggatgct     240
gcaacctatt actgtcagca cagtagggag gttccgtaca cgttcggagg ggggacc        297
```

<210> SEQ ID NO 163
<211> LENGTH: 387
<212> TYPE: DNA
<213> ORGANISM: Homo sapiens

<400> SEQUENCE: 163

```
caggtgcagc tggtgcagtc tggagcagag gtgaaaaagc ccggggagtc tctgaggatc      60
tcctgcaagg gttctggata cagctttacc agccactgga tcagctgggt gcgccagatg     120
cccgggaaag gcctggagtg gatggggagg attgatccta gtgactctta tagcaactac     180
agcccctcct ccaaggcca cgtcatcatc tcagttgaca gtccatcag cactgcctac       240
ttgcagtgga gcagcctgaa ggcctcggac accgccatat attactgtgc gagacagctc     300
attgtagtag taccagctgc tccctattac tactactact acggtatgga cgtctggggc     360
caaggaaccc tggtcaccgt ctcctca                                         387
```

<210> SEQ ID NO 164
<211> LENGTH: 390
<212> TYPE: DNA
<213> ORGANISM: Homo sapiens

<400> SEQUENCE: 164

```
caggttcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tctttggtac agcaaactac       180
gcacagaagt tccagggcag agtcacgatt accgcggacg aatccacgag cacagcctac     240
atggagctga gcagcctgag atctgaggac acggccatat attactgtgc gagagtcttt     300
ggttccgagt cgcaagatcc gtccgatatt tggagtggtt attacggtat ggaagtctgg     360
ggccaaggaa ccctggtcac cgtctcctca                                       390
```

<210> SEQ ID NO 165
<211> LENGTH: 363
<212> TYPE: DNA
<213> ORGANISM: Homo sapiens

<400> SEQUENCE: 165

```
caggtgcagc tggtggagtc tggggctgag gcgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tctttggtac agcaaactac       180
gcacagaagt tccagggcag agtcacgatt accgcggacg aatccacgag cacagcctac     240
atggagctga gcagcctgag atctgaggac acggccgtgt attactgtgc gagagccggt     300
```

```
ataactggaa ctacggctcc cccagactac tggggccagg gcaccctggt caccgtctcc    360
tca                                                                  363

<210> SEQ ID NO 166
<211> LENGTH: 378
<212> TYPE: DNA
<213> ORGANISM: Homo sapiens

<400> SEQUENCE: 166
caggtgcagc tggtgcagtc cggatctgag ttaaagaagc ctggggcctc agtgaagctt     60
tcctgcaggg cttctggata cacattcact agttattcca tggtttgggt gcgacaggcc    120
cctggagaag ggcttgagtg gatgggaggg atcaacacca cactgggaa cccaacgtat    180 gcccagggct tcacagaacg gtttgtcttc ccttcgaca gctctgtcag cacggcatat    240
ctgcaaatca gcagcctaaa ggctgaggac actgccgtgt attactgtgc gagagattgg    300
gcgtatagcg gcagctggcc cttaggccag aacccttctg accactgggg ccagggcacc    360
ctggtcaccg tctcctca                                                  378

<210> SEQ ID NO 167
<211> LENGTH: 366
<212> TYPE: DNA
<213> ORGANISM: Homo sapiens

<400> SEQUENCE: 167
caggtgcagc tacagcagtg gggcgcagga ttgttgaagc cttcggagac cctgtccctc     60
acctgcgctg tctatggtgg gtccttcagt ggttactacc ggacctggat ccgccagtcc    120
ccagtgaagg ggctggagtg gattgggaa gtcaatgatc gtggaagccc caactacaac    180
ccgtccttca agagtcgact caccatatca atcgacacgt ccaagaacta gttatccctg    240
aagttgagat ttatgaccgc cgcggacacg gctgtatatt cgtgtgcgag aattaggcct    300
aggtacggta tggacgtctg gggccagggg acaatggtca ccgtctcctc aggcggcggc    360
ggctct                                                               366

<210> SEQ ID NO 168
<211> LENGTH: 372
<212> TYPE: DNA
<213> ORGANISM: Homo sapiens

<400> SEQUENCE: 168
gaggtccagc tggtacagtc tggggctgag gtgaagaagc ctggggcctc agtgaaggtc     60
tcctgcaagg tttccggata cacctcact gaattatcca tgcactgggt gcgacaggct    120
cctggaaaag ggcttgagtg gatgggaggt tttgatcctg aagatggtga acaatctcc    180 gcgcagaagt tccagggcag agtcaccatg accgaggaca catctacaga cacagcctac    240
atggatctga gcagcctgag atctgaggac acggccgttt attactgtgc aacgcagcgc    300
ttgtgtagtg gtggtcgctg ctactcccac tttgactact ggggccaggg caccacggtc    360
accgtctcct ca                                                        372

<210> SEQ ID NO 169
<211> LENGTH: 348
<212> TYPE: DNA
<213> ORGANISM: Homo sapiens

<400> SEQUENCE: 169
cagatgcagc tggtgcagtc tggggctgag gtgaagaagc ctgggtcctc ggtgaaggtc     60
```

```
tcctgcaagg cttctggagg caccttcaac acctatgtta tcagtttggg gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagtttgg    300
agtccccttg actactgggg ccagggcacc ctggtcaccg tctcctca                 348
```

<210> SEQ ID NO 170
<211> LENGTH: 357
<212> TYPE: DNA
<213> ORGANISM: Homo sapiens

<400> SEQUENCE: 170

```
caggtgcagc tggtgcaatc tggggctgag gtgaagaagc ctggggcctc agtgaaggtc    60
tcctgcaagg gttctggata caccttcacc ggctactata tgcactgggt gccacaggcc    120
cctggacaag ggcttgagtg gatgggatgg atcaaccctaa acaatggtgg cacaaactat   180
gaccagaagt tccagggcag ggtcgccatg accagggaca cgtccatctc cacagcctac    240
atggagctga gcaggctgag atctgacgac actgccgtgt attactgtgc gagagataat    300
gggagggtga ccacaggggg ctactgggc cagggcaccc tggtcaccgt ctcctca        357
```

<210> SEQ ID NO 171
<211> LENGTH: 366
<212> TYPE: DNA
<213> ORGANISM: Homo sapiens

<400> SEQUENCE: 171

```
caggtgcagc tggtgcaatc tggggctgag gtgaaaaagc ccggggagtc tctgaagatc    60
tcctgtacgg cctccggata caactttgcc agctactgga tcggctgggt gcgccagatg    120
cccgggcaag gcctggagtg gatggggatc atctatcctg gtgactctga taccagatac    180
agtccgtcct tccaaggcca ggtcaccatc tcagccgaca gtccatcag caccgcctac    240 ctgcagtgga gcagcctgaa ggcctcggac accgccacgt attactgtgt gagacgggtc    300
cccctctaca ctaacaacca ctaccttgac tattggggcc agggcaccct ggtcaccgtc    360
tcctca                                                              366
```

<210> SEQ ID NO 172
<211> LENGTH: 351
<212> TYPE: DNA
<213> ORGANISM: Homo sapiens

<400> SEQUENCE: 172

```
gaggtgcagc tggtgcagtc tggggctgaa gtgaagaagc ctggggcctc agtgaaggtt    60
tcctgtaagg catctggata caccttcagc gactactta tgcactgggt gcgacaggcc    120
cctggacaag ggcttgagtg gatgggagta atcaacccaa ctggtggttc cacaacctac    180
gcacagagct ccagggcag agtcaccatg accagagaca cgtccacgag catagtctac    240
atggagctga gcagcctgag atctgaagac acggccgtgt actactgtac gcgagtcggc    300
tactacggta tggacgtctg ggggccaaggc accctggtca ccgtctcctc a            351
```

<210> SEQ ID NO 173
<211> LENGTH: 369
<212> TYPE: DNA
<213> ORGANISM: Homo sapiens

<400> SEQUENCE: 173

```
caggtccagc tggtacagtc tgggggaggc gtggtccagg ttggGaggtc cctgagactt      60
tcctgtgcgg cctctggatt caccttcaca aactttggca tgcactgggt ccgccaggct     120
ccaggcaagg ggctggagtg gtggcactc atctcatctg atggatatag acaggcctat     180
gcagactccg tgaagggccg gttcaccatc tccggagaca actccaagaa cacagtgtat     240
ctgcaaatga acagcctgac aagtgaggac acggctgttt attactgtgc catcataccc     300
cctgtattac ggattttga ttgggaattt gactactggg gccagggaac cctggtcacc     360
gtctcctca                                                             369
```

<210> SEQ ID NO 174
<211> LENGTH: 375
<212> TYPE: DNA
<213> ORGANISM: Homo sapiens

<400> SEQUENCE: 174

```
caggtgcagc tacagcagtg gggcgcaggc ctgttgaagc cttcggagac cctgtccctc      60
acctgcgctg tctatagtgg gtctttact cgtgactact ggggctggat ccgccagccc     120
cccgggaagg ggctggagtg gattgggGaa atcaatcata gtggaagcac caactacaac     180
ccgtccctca agagtcgagt caccacgtcg tagacaagt ccaagaatca gttctccctg     240
aagttgacct ctgtgaccgc cgcggacacg gctgtctatt actgtgcgag acgcggcttt     300
tctagcgacc tcttcatgcg gggggttggc ggtatggacg tctggggcca aggcaccctg     360
gtcaccgtct cctca                                                     375
```

<210> SEQ ID NO 175
<211> LENGTH: 378
<212> TYPE: DNA
<213> ORGANISM: Homo sapiens

<400> SEQUENCE: 175

```
gaggtgcagc tggtgcagtc tggagctgag gtgaagaagc ctggggcctc agtgaaggtc      60
tcctgcaagg cttctggtta cacctttacc agctatggta tcagctgggt gcgacaggcc     120
tctggacaag ggcttgagtg gatgggatgg atcagcgctt acaatggtaa cacaaactat     180
gcacagaagt tccagggcag agtcaccatg accacagaca catccacgag cacagcctac     240
atggagctga ggagcctgag atctgacgac acggccgtgt attactgtgc gagagtaccc     300
cgatattttg actggttatt atacgggagc gactactttg actactgggg ccagggaacc     360
ctggtcaccg tctcctca                                                   378
```

<210> SEQ ID NO 176
<211> LENGTH: 372
<212> TYPE: DNA
<213> ORGANISM: Homo sapiens

<400> SEQUENCE: 176

```
caggtgcagc tggtgcaatc tggagctgag gtgaaggagc ctgggtcctc ggtgaaggtc      60
tcctgcaagg cttctggagg caccttcagc agctatgcta tctactgggt gcgacaggcc     120
cctggacaag ggcttgagtg gatgggatgg atcatcccta tccttggtat agcaaactac     180
gcacagaagt tccagggcag agtcacgatt accgcggaca atccacgag cacagcctac     240
atggagctga gcagcctgag atctgaggac acggccgtgt attactgtgc gagagctgcc     300
ggtcatagta ctaactacta ctactacggt atggacgtct ggggccaagg caccctggtc     360
```
accgtctcct ca                                                            372

<210> SEQ ID NO 177
<211> LENGTH: 366
<212> TYPE: DNA
<213> ORGANISM: Homo sapiens

<400> SEQUENCE: 177
gaggtgcagc tggtgcagtc tggggctgag gtgaagaagc ctggggcctc agtgaaggtt      60
tcctgcaagg catctggata caccttcacc aactactata tgcactgggt gcgacaggcc     120
cctggacaag gcttgagtg gatgggaata atcaacccta gtggtggtag cacaagctac      180
gcacagaagt tccagggcag agtcaccatg actagggaca cgtccacgag cacagtctac     240
atggagctga gcagcctgag atctgaggac acggccgtgt attactgtgc gagagatttc     300
aaagagtata gccgtacggg ctactttgac tactggggcc agggcaccct ggtcaccgtc     360
tcctca                                                                  366

<210> SEQ ID NO 178
<211> LENGTH: 372
<212> TYPE: DNA
<213> ORGANISM: Homo sapiens

<400> SEQUENCE: 178
cagatcacct tgaaggagtc tggtcctgcg ctggtgaaac ccacacagac cctcacgctg      60
acctgcaact tctctgggtt ctccctcagc acttatggag gggtgtggg ctggctccgt      120 cagcccccag gaaaggccct ggagtggctt gccgtcattt attggagtga tgttaaacgc     180
tacagcccct ctgtaaagaa ccggctcacc atcaccaagg acacctccaa aaaccacgtg    240
gtcctgacaa tgaccaacat ggaccctgtg gacacagcca ctattattg tgcacacctt     300 atgatggata catctattac tacccactgg ttcgacccct ggggccaggg aaccctggtc     360
accgtctcct ca                                                            372

<210> SEQ ID NO 179
<211> LENGTH: 372
<212> TYPE: DNA
<213> ORGANISM: Homo sapiens

<400> SEQUENCE: 179
caggtgcagc tggtgcaatc tggggctgag gtgaagaagc ctgggtcctc ggtgaaggtt      60
tcctgcaagg catctggata caccttcacc aactacttta tacactgggt gcgacaggcc    120
cctggacaag gcttgagtg gatgggacta ctcaacccta ctgatagtgg cacactctac     180
gcacagaact tccagggcag aatcaccatg accagtgaca cgtccacaaa cacagtctac    240
atggagctga gcagcctgag atctgacgac acggccatgt attactgtgc aagagagggg    300
ggggccgaca ctacccgggt ccactcttcg tttgactact ggggccaggg aaccctggtc    360
accgtctcct ca                                                            372

<210> SEQ ID NO 180
<211> LENGTH: 372
<212> TYPE: DNA
<213> ORGANISM: Homo sapiens

<400> SEQUENCE: 180
caggtgcagc tgcaggagtc gggggagggc ttggtacagc ctggcaggtc cctgagactc     60

```
tcctgtgcag cctctggatt cacctttgat gattatgccc tccactgggt ccggcaagct      120
ccagggaagg gcctggagtg ggtctcaggt attagttgga atagtgttac cgtaaagtat      180
gcggtctctg tgaagggccg gttcaccatc tccagagaca acgccaagaa ctccctgttt      240
ctgcaaatga acgctctgag atctgaggac acggccttat attactgtgc aaaagccaga      300
ggggccctct tagaagcagc tgacacacca tctgacgact ggggccaggg caccctggtc      360
accgtctcct ca                                                          372

<210> SEQ ID NO 181
<211> LENGTH: 357
<212> TYPE: DNA
<213> ORGANISM: Homo sapiens

<400> SEQUENCE: 181
caggtacagc tgcagcagtc aggcgcaggt ctattgaggc cttcggagac cctgtccctc       60
acctgcggtc tctatggtgg gtccttcagt ggtcactatt ggaactggat ccgccagtcc      120
ccagaaaagg ggctggtgtg gattggggaa atcactcata gtggaaccac caattacaac      180
ccgtccctca agagtcgagt catcacatca gtagacacgt ccaagaatca gtactccctg      240
aagctgagct ttgtgacccc tgcggacacg gccgtgtatt actgtgcgag aggtgattac      300
tatgggtact ggtacttcga tctctggggc cgtggcaccc tggtcaccgt ctcctca        357
```